US012186371B2

(12) United States Patent
Wagner

(10) Patent No.: US 12,186,371 B2
(45) Date of Patent: Jan. 7, 2025

(54) BIOMARKERS AND TREATMENT METHODS FOR TRAUMATIC BRAIN INJURY-ASSOCIATED IMPAIRMENTS

(71) Applicant: UNIVERSITY OF PITTSBURGH—OF THE COMMONWEALTH SYSTEM OF HIGHER EDUCATION, Pittsburgh, PA (US)

(72) Inventor: Amy Kathleen Wagner, Pittsburgh, PA (US)

(73) Assignee: UNIVERSITY OF PITTSBURGH—OF THE COMMONWEALTH SYSTEM OF HIGHER EDUCATION, Pittsburgh, PA (US)

(*) Notice: Subject to any disclaimer, the term of this patent is extended or adjusted under 35 U.S.C. 154(b) by 1016 days.

(21) Appl. No.: 17/135,970

(22) Filed: Dec. 28, 2020

(65) Prior Publication Data

US 2021/0196797 A1 Jul. 1, 2021

Related U.S. Application Data

(63) Continuation of application No. PCT/US2019/039879, filed on Jun. 28, 2019.

(60) Provisional application No. 62/692,364, filed on Jun. 29, 2018.

(51) Int. Cl.
*A61K 38/20* (2006.01)
*C07K 16/24* (2006.01)
*G01N 33/68* (2006.01)

(52) U.S. Cl.
CPC ........ *A61K 38/2046* (2013.01); *C07K 16/241* (2013.01); *G01N 33/6896* (2013.01); *G01N 2333/70578* (2013.01); *G01N 2800/28* (2013.01); *G01N 2800/52* (2013.01)

(58) Field of Classification Search
None
See application file for complete search history.

(56) References Cited

U.S. PATENT DOCUMENTS

| 9,808,523 B2* | 11/2017 | Tobinick | A61K 9/0085 |
|---|---|---|---|
| 2002/0009444 A1 | 1/2002 | Grillo-Lopez | |
| 2015/0079086 A1 | 3/2015 | Tobinick | |
| 2016/0178643 A1 | 6/2016 | Everett et al. | |

FOREIGN PATENT DOCUMENTS

| WO | WO 2010/008594 A1 | 1/2010 |
|---|---|---|
| WO | WO 2012/061289 A2 | 5/2012 |
| WO | WO 2015/081166 A1 | 6/2015 |

OTHER PUBLICATIONS

Skolnick et al (Trends Biotechnol. Jan. 2000;18(1):34-9) (Year: 2000).*
Burgess et al. (J. Cell Biol. 111:2129-2138, 1990) (Year: 1990).*
Lazar et al. (Mol. Cell. Biol., 8:1247-1252, 1988) (Year: 1988).*
Miosge (Proc Natl Acad Sci U S A. Sep. 15, 2015;112(37):E5189-98) (Year: 2015).*
Bork (Genome Research, 2000, 10:398-400) (Year: 2000).*
Kulmanov et al (Bioinformatics, 34(4), 2018, 660-668) (Year: 2018).*
Vajdos et al. (J Mol Biol. Jul. 5, 2002;320(2):415-28) (Year: 2002).*
Brown et al. (J Immunol. May 1996;156(9):3285-91) (Year: 1996).*
Aagaard et al (Advanced Drug Delivery Reviews 59 (2007) 75-86) (Year: 2007).*
Warzocha et al (Leukemia and Lymphoma (1997) vol. 24. pp. 267-281) (Year: 1997).*
McKeague et al (J Nucleic Acids. 2012;2012:748913. Epub Oct. 24, 2012) (Year: 2012).*
Guido et al (Curr Med Chem. 2008;15(1):37-46) (Year: 2008).*
Clark et al (J. Med. Chem., 2014, 57 (12), pp. 5023-5038) (Year: 2014).*
Cronstein et al (Clin Adv Hematol Oncol. Oct. 2015;13(10):639-41) (Year: 2015).*
Kirchhoff (Biotechnol Bioeng. Dec. 2017;114(12):2696-2705. Epub Sep. 19, 2017) (Year: 2017).*
Waiker et al (J Am Soc Nephrol. Jan. 2012; 23(1): 13-21) (Year: 2012).*
Mayeux (NeuroRx. Apr. 2004;1(2):182-8) (Year: 2004).*
McBride et al (Cureus 15(6): e40417; (Jun. 14, 2023)) (Year: 2023).*
Maier (Shock, vol. 26, No. 2, pp. 122Y127, 2006) (Year: 2006).*
Santarsieri (Brain Behav Immun. Mar. 2015 ; 45: 15-27) (Year: 2015).*
Aimaretti et al., "Residual Pituitary Function after Brain Injury-Induced Hypopituitarism: A Prospective 12-Month Study," J. Clin. Endocrinol. Metab. 90, 6085-6092 (2005).
Asadullah et al., "Very low monocytic HLA-DR expression indicates high risk of infection—immunomonitoring for patients after neurosurgery and patients during high dose steroid therapy," Eur J Emerg Med., 184-190 (1995).
Aspinall et al., "Cellular signalling pathways in immune aging and regeneration," Biochem. Soc. Trans. 42, 651-656 (2014).
Avery et al., "IL-21-Induced Isotype Switching to IgG and IgA by Human Naive B Cells Is Differentially Regulated by IL-4[1]," The Journal of Immunology, 181, 1767-1779 (2008).

(Continued)

*Primary Examiner* — Brian Gangle
*Assistant Examiner* — Andrea K McCollum
(74) *Attorney, Agent, or Firm* — Baker Botts L.L.P.

(57) ABSTRACT

The present disclosure relates to methods, compositions, and kits for treating traumatic brain injury (TBI) and TBI-associated impairments in a subject. The methods include administering to the subject an interleukin-7 (IL-7) or IL-7 agonist, a tumor necrosis factor alpha (TNFα) inhibitor, or both. The present disclosure also relates to methods of using biomarkers for identifying a subject that is likely to respond to a treatment for TBI-associated impairments, and monitoring the subject's response to such treatment.

11 Claims, 127 Drawing Sheets

(56) References Cited

OTHER PUBLICATIONS

Baker et al., "The injury severity score: a method for describing patients with multiple injuries and evaluating emergency care," J Trauma, 14:187-196 (1974).
Baron et al., "The moderator-mediator variable distinction in social psychological research: Conceptual, strategic, and statistical considerations," Journal of Personality and Social Psychology, vol. 51(6), 1173-1182 (1986).
Barton et al., "Persistent hypogonadotropic hypogonadism in men after severe traumatic brain injury: temporal hormone profiles and outcome prediction," J Head Trauma Rehabil., 31(4):277-287 (2016).
Baumgarth et al., "Inherent specificities in natural antibodies: a key to immune defense against pathogen invasion," Springer Semin. Immunopathol. 26, 347-362 (2005).
Bazan et al., "A new class of membrane-bound chemokine with a CX 3 C motif," Nature 385, 640-644 (1997).
Berger et al., "Trajectory Analysis of Serum Biomarker Concentrations Facilitates Outcome Prediction after Pediatric Traumatic and Hypoxemic Brain Injury," Dev Neurosci., 32: 396-405; p. 399, col. 1, paragraph 1; DOI: 10.1159/000316803 (2010).
Boes et al., "A critical role of natural immunoglobulin M in immediate defense against systemic bacterial infection," J. Exp. Med. 188, 2381-2386 (1998).
Bondanelli et al., "Anterior pituitary function may predict functional and cognitive outcome in patients with traumatic brain injury undergoing rehabilitation," J. Neurotrauma 24, 1687-1697 (2007).
Brait et al., "Importance of T lymphocytes in brain injury, immunodeficiency, and recovery after cerebral ischemia," J Cereb Blood Flow Metab., 32, 598-611 (2012).
Brait et al., "Mechanisms contributing to cerebral infarct size after stroke: gender, reperfusion, T lymphocytes, and Nox2-derived superoxide," J Cereb Blood Flow Metab., 30, 1306-1317 (2010).
Burton et al., "Inhibition of interleukin-6 trans-signaling in the brain facilitates recovery from lipopolysaccharide-induced sickness behavior," J Neuroinflammation. 8:54 (2011).
Buttram et al., "Multiplex Assessment of Cytokine and Chemokine Levels in Cerebrospinal Fluid following Severe Pediatric Traumatic Brain Injury: Effects of Moderate Hypothermia," J Neurotrauma., 24, 1707-1717 (2007).
Campbell et al., "Protection from collagen-induced arthritis in granulocyte-macrophage colony-stimulating factor-deficient mice," J. Immunol. 161, 3639-3644 (1998).
Campbell et al., "Immunomodulatory effects of etanercept in a model of brain injury act through attenuation of the acute-phase response," J Neurochem., 103, 2245-2255 (2007).
Capitini et al., "Cytokines as adjuvants for vaccine and cellular therapies for cancer," Am J Immunol., 65-83 (2009).
Carlozzi et al., "Traumatic Brain Injury Patient-Reported Outcome Measure: Identification of Health-Related Quality-of-Life Issues Relevant to Individuals With Traumatic Brain Injury," Arch Phys Med Rehabil, 92(10 Suppl):S52-60 (2011).
Carlson et al., "Hypogonadism on admission to acute rehabilitation is correlated with lower functional status at admission and discharge," Brain Inj. 23, 336-344 (2009).
Chen et al., "Regulation of Dendritic Cells and Macrophages by an Anti-Apoptotic Cell Natural Antibody that Suppresses TLR Responses and Inhibits Inflammatory Arthritis," J Immunol, 183:1346-1359 (2009).
Chen et al., "IgM Antibodies to Apoptosis-Associated Determinants Recruit C1q and Enhance Dendritic Cell Phagocytosis of Apoptotic Cells1," J Immunol, 182:6031-6043 (2009).
Chen et al., "Neutrophil to Lymphocyte Ratio as a Novel Predictor of Outcome in Patients with Severe Traumatic Brain Injury," J Head Trauma Rehabil, pp. 1-7, (2017) DOI: 10.1097/HTR.0000000000000320.
Chen et al., "Neutrophil to Lymphocyte Ratio as a Novel Predictor of Outcome in Patients With Severe Traumatic Brain Injury," J Head Trauma Rehabil., 33(1):E53-E59 (2018).
Chen et al., "Peak Neutrophil-to-Lymphocyte Ratio Correlates with Clinical Outcomes in Patients with Severe Traumatic Brain Injury," Neurocrit Care, 30, 334-339 (2019) DOI https://doi.org/10.1007/s12028-018-0622-9.
Chio et al., "Therapeutic evaluation of etanercept in a model of traumatic brain injury," J. Neurochem., 115, 921-929 (2010).
Chodobski et al., "Blood-brain barrier pathophysiology in traumatic brain injury," Transl Stroke Res. 2(4): 492-516 (2011).
Chrousos et al., "The hypothalamic-pituitary-adrenal axis and immune-mediated inflammation," N Engl J Med., 332(20):1351-1362 (1995).
Cook et al., "Using Functional Independence Measure profiles as an index of outcome in the rehabilitation of brain-injured patients," Arch Phys Med Rehabil, 75, 390-393 (1994).
Cope et al., "Soluble TNF receptor production by activated T lymphocytes: differential effects of acute and chronic exposure to TNF," Immunology, 84, 21-30 (1995).
Crompton, "Hypothalamic lesions following closed head injury," Brain, 165-172 (1971).
Cuesta et al., "Symptoms of gonadal dysfunction are more predictive of hypopituitarism than nonspecific symptoms in screening for pituitary dysfunction following moderate or severe traumatic brain injury," Clin. Endocrinol. (Oxf.) 84, 92-98 (2016).
Daniel et al., "Traumatic infarction of the anterior lobe of the pituitary gland," Lancet Lond. Engl. 2, 927-931 (1959).
Decaroli et al., "Aging and sex hormones in males," Virulence, 8(5), 545-570 (2016).
DeCathelineau et al., "The final step in programmed cell death: phagocytes carry apoptotic cells to the grave," Essays Biochem, 39: 105-117 (2003).
Donders et al., "Clinical utility of the patient health Questionnaire-9 in the assessment of major depression after broad-spectrum traumatic brain injury," Arch Phys Med Rehabil. 98(12):2514-2519 (2017).
Dubourg et al., "Sports-related chronic repetitive head trauma as a cause of pituitary dysfunction," Neurosurg Focus, 31 (5):E2 (2011).
Dukhinova et al., "Platelets mediate protective neuroinflammation and promote neuronal plasticity at the site of neuronal injury," Brain, Behavior, and Immunity, 74, 7-27 (2018).
Dunn, "Multiple Comparisons Using Rank Sums," Technometrics 6, 241-252 (1964).
Elenkov et al., "The sympathetic nerve—an integrative interface between two supersystems: the brain and the immune system," Pharmacol Rev, 52:595-638 (2000).
Engelhardt et al., "The movers and shapers in immune privilege of the CNS," Nat. Immunol., 18, 123-131 (2017).
Eriksson et al., "Low levels of antibodies against phosphorylcholine in Alzheimer's disease," J. Alzheimer's Dis. JAD 21, 577-584 (2010).
Ernst et al., "The peptide ligands mediating positive selection in the thymus control T cell survival and homeostatic proliferation in the periphery," Immunity, 11(2):173-181 (1999).
Fernandez-Rodriguez et al., "Hypopituitarism following traumatic brain injury: determining factors for diagnosis," Front. Endocrinol. 2:25 (2011).
Feuerstein et al., "The role of cytokines in the neuropathology of stroke and neurotrauma," Neuroimmunomodulation, 5:143-159 (1998).
Fiskesund et al., "Low levels of antibodies against phosphorylcholine predict development of stroke in a population-based study from northern Sweden," Stroke 41, 607-612 (2010).
Francois et al., "Interleukin-7 restores lymphocytes in septic shock: the IRIS-7 randomized clinical trial," JCI Insight., 3(5) (2018).
Frasca et al., "Humoral immune response and B-cell functions including immunoglobulin class switch are downregulated in aged mice and humans," Semin. Immunol. 17, 378-384 (2005).
Fry et al., "Interleukin-7: from bench to clinic," Blood, 99(11):3892-3904 (2002).
Ghigo et al., "Consensus guidelines on screening for hypopituitarism following traumatic brain injury," Brain Injury, 19, 711-724 (2005).
Glance et al., "Increases in Mortality, Length of Stay, and Cost Associated With Hospital-Acquired Infections in Trauma Patients," Archives of Surgery, 146(7):794-801 (2011).

(56) References Cited

OTHER PUBLICATIONS

Goldrath et al., "Low-affinity ligands for the TCR drive proliferation of mature $CD8^+$ T cells in lymphopenic hosts," Immunity 11, 183-190 (1999).
Gonzalez-Juarrero et al., "Disruption of granulocyte macrophage-colony stimulating factor production in the lungs severely affects the ability of mice to control *Mycobacterium tuberculosis* infection," J. Leukoc. Biol. 77, 914-922 (2005).
Gorst-Rasmussen et al., "tt: Treelet transform with Stata," The Stata Journal, 12(1):130-146 (2012).
Gorst-Rasmussen et al., "Exploring Dietary Patterns By Using the Treelet Transform," Am J Epidemiol., 173(10):1097-1104 (2011).
Goyal et al., "S100b as a prognostic biomarker in outcome prediction for patients with severe traumatic brain injury," J. Neurotrauma 30, 946-957 (2013).
Graber et al., "Protective Autoimmunity in the Nervous System," Pharmacol. Ther. 121, 147-159 (2009).
Gray et al., "Apoptotic cells protect mice from autoimmune inflammation by the induction of regulatory B cells," PNAS, 104, 14080-14085 (2007).
Gregory et al., "Interleukin 7 receptor αchain (IL7R) shows allelic and functional association with multiple sclerosis," Nature Genetics, 39(9):1083-1091 (2007).
Griesbach et al., "Effects of acute restraint-induced stress on glucocorticoid receptors and brain-derived neurotrophic factor after mild traumatic brain injury," Neuroscience, 210:393-402 (2012).
Grönwall et al., "Protective roles of natural IgM antibodies," Front. Immunol. 3, 66, 10 pages (2012).
Guaraldi et al., "Hypothalamic-pituitary autoimmunity and traumatic brain injury," J. Clin. Med., 4, 1025-1035 (2015).
Guimond et al., "Interleukin 7 signaling in dendritic cells regulates the homeostatic proliferation and niche size of CD4+ T cells," Nature Immunology, 10 (2):149-157 (2009).
Haas et al., "B-1a and B-1b cells exhibit distinct developmental requirements and have unique functional roles in innate and adaptive immunity to S. pneumoniae," Immunity 23, 7-18 (2005).
Harman et al., "Longitudinal effects of aging on serum total and free testosterone levels in healthy men," J. Clin. Endocrinol. Metab. 86, 724-731 (2001).
Harrison et al., "Role for neuronally derived fractalkine in mediating interactions between neurons and CX3CR1-expressing microglia," Proc. Natl. Acad. Sci. USA. 95, 10896-10901 (1998).
Hay et al., "Blood-brain barrier disruption is an early event that may persist for many years after traumatic brain injury in humans," J. Neuropathol. Exp. Neurol. 74, 1147-1157 (2015).
Hazeldine et al., "Traumatic brain injury and peripheral immune suppression: primer and prospectus," Front Neurol. 6:235 (2015).
Hedegaard et al., "Autoantibodies to myelin basic protein (MBP) in healthy individuals and in patients with multiple sclerosis: a role in regulating cytokine responses to MBP," Immunology 128, e451-e461 (2009).
Hensler et al., "Association between Injury Pattern of Patients with Multiple Injuries and Circulating Levels of Soluble Tumor Necrosis Factor Receptors, Interleukin-6 and Interleukin-10, and Polymorphonuclear Neutrophil Elastase," J Trauma, 52(5):962-970 (2002).
Holmin et al., "Intracerebral Inflammation After Human Brain Contusion," Neurosurgery 42, 291-298 (1998).
Holzmacher et al., "Platelet transfusion does not improve outcomes in patients with brain injury on antiplatelet therapy," Brain Injury, 32(3), 325-330 (2018).
Huynh et al., "Phosphatidylserine-dependent ingestion of apoptotic cells promotes TGF-β1 secretion and the resolution of inflammation," J Clin Invest., 109, 41-50 (2002).
Imai et al., "Identification and molecular characterization of fractalkine receptor CX3CR1, which mediates both leukocyte migration and adhesion," Cell 91, 521-530 (1997).
International Search Report and Written Opinion dated Sep. 10, 2019 in corresponding International Patent Application No. PCT/US2019/039879.

Jassam et al., "Neuroimmunology of traumatic brain injury: time for a paradigm shift," Neuron 95, 1246-1265 (2017).
Jennett et al., "Assessment of outcome after severe brain damage: a practical scale," The Lancet, 305(7905):480-484 (1975).
Jeong et al., "Brain inflammation and microglia: facts and misconceptions," Exp Neurobiol. 22:59-67 (2013).
Johnson et al., "Inflammation and white matter degeneration persist for years after a single traumatic brain injury," Brain, 136(1):28-42 (2013).
Jones et al., "Antagonism of the interleukin-1 receptor following traumatic brain injury in the mouse reduces the number of nitric oxide synthase-2-positive cells and improves anatomical and functional outcomes," European Journal of Neuroscience, 22, 72-78 (2005).
Joseph et al., "The significance of platelet count in traumatic brain injury patients on antiplatelet therapy," The Journal of Trauma and Acute Care Surgery, 77(3), 417-421 (2014).
Juengst et al., "Development and content validity of the behavioral assessment screening tool (BASTβ)," Disabil Rehabil. 41(10):1200-1206 (2019).
Kasturi et al., "Traumatic Brain Injury Causes Long-Term Reduction in Serum Growth Hormone and Persistent Astrocytosis in the Cortico-Hypothalamusuitary Axis of Adult Male Rats," J. Neurotrauma 26, 1315-1324 (2009).
Kenne et al., "Neutrophil depletion reduces edema formation and tissue loss following traumatic brain injury in mice," Journal of Neuroinflammation, 9:17 (2012).
Kenney et al., "Autonomic Nervous System and Immune System Interactions," Compr Physiol. 4(3): 1177-1200 (2014).
Kesinger et al., "Hospital Acquired Pneumonia is an Independent Predictor of Poor Global Outcome in Severe Traumatic Brain Injury up to 5 Years after Discharge: HAP Predicts Poor Outcomes 5 years post TBI," J Trauma Acute Care Surg. 78(2), 396-402 (2015).
Khaled et al., "Death and Baxes: mechanisms of lymphotrophic cytokines," Immunol Rev. 193:48-57 (2003).
Kjaer et al., "Toward a structure-based comprehension of the lectin pathway of complement," Mol. Immunol. 56, 413-422 (2013).
Klimas et al., "Biomarkers for chronic fatigue," Brain Behav Immun. 26(8): 1202-1210 (2012).
Knoblach et al., "Early neuronal expression of tumor necrosis factor-a after experimental brain injury contributes to neurological impairment," Journal of Neuroimmunology, 95(1), 115-125 (1999).
Kobeissy et al., "Assessing neuro-systemic & behavioral components in the pathophysiology of blast-related brain injury," Front. Neurol. 4, 186 (2013).
Kopczak et al., "Screening for hypopituitarism in 509 patients with traumatic brain injury or subarachnoid hemorrhage," J. Neurotrauma 31:99-107 (2014).
Krawczenko et al., "The biological role and potential therapeutic application of interleukin 7," Arch Immunol Ther Exp, 53:518-525 (2005).
Kumar et al., "Acute CSF interleukin-6 trajectories after TBI: associations with neuroinflammation, polytrauma, and outcome," Brain Behav Immun. 45:253-262 (2015).
Kumar et al., "Biomarkers of traumatic brain injury: temporal changes in body fluids," J Head Trauma Rehabil. 30(6):369-381 (2015).
Kumar et al., "Epidemiology of Comorbid Conditions Among Adults 50 Years and Older With Traumatic Brain Injury," J Head Trauma Rehabil. 33(1):15-24 (2018).
Lachman et al., "Monitoring Cognitive Functioning: Psychometric Properties of the Brief Test of Adult Cognition by Telephone," Assessment, 21(4):404-417 (2014).
Lattanzi et al., "Neutrophil-to-lymphocyte ratio predicts the outcome of acute intracerebral hemorrhage," Stroke, 47(6):1654-1657 (2016).
Lee et al., "Treelets—A Tool for Dimensionality Reduction and Multi-Scale Analysis of Unstructured Data," (2014).
Levine et al., "Molecular mechanisms of soluble cytokine receptor generation," J Biol Chem, 283(21):14177-14181 (2008).
Lévy et al., "Effects of Recombinant Human Interleukin 7 on T-Cell Recovery and Thymic Output in HIV-Infected Patients Receiving

(56) References Cited

OTHER PUBLICATIONS

Antiretroviral Therapy: Results of a Phase I/IIa Randomized, Placebo-Controlled, Multicenter Study," Clinical Infectious Diseases, 55(2):291-300 (2012).
Liao et al., "Oxidative Burst of Circulating Neutrophils Following Traumatic Brain Injury in Human," PLoS ONE, 8(7) e68963 (2013).
Liesz et al., "Acquired Immunoglobulin G deficiency in stroke patients and experimental brain ischemia," Experimental Neurology, 271:46-52 (2015).
Lobo et al., "Naturally Occurring IgM Anti-Leukocyte Autoantibodies Inhibit T-Cell Activation and Chemotaxis," J Clin Immunol., 30(Suppl 1): S31-36 (2010).
Louveau et al., "Structural and functional features of central nervous system lymphatics," Nature 523, 337-341 (2015).
Louveau et al., "Revisiting the concept of CNS immune privilege," Trends Immunol., 36(10): 569-577 (2015).
Lozano et al., "Neuroinflammatory responses to traumatic brain injury: etiology, clinical consequences, and therapeutic opportunities," Neuropsychiatr Dis Treat., 11:97-106 (2015).
Lü et al., "Effects of autoimmunity on recovery of function in adult rats following spinal cord injury," Brain, Behavior, and Immunity, 22(8):1217-1230 (2008).
Lucin, et al., "Stress hormones collaborate to induce lymphocyte apoptosis after high level spinal cord injury," J. Neurochem. 110, 1409-1421 (2009).
Lundström et al., "IL-7 in Human Health and Disease," Semin Immunol, 24(3): 218-224 (2012).
Lundström et al., "Soluble IL7Rα potentiates IL-7 bioactivity and promotes autoimmunity," P.N.A.S., 110(19):E1761-E1770 (2013).
Machlus et al., "CCL5 derived from platelets increases megakaryocyte proplatelet formation," Blood, 127(7), 921-926 (2016).
Mackall et al., "Harnessing the biology of IL-7 for therapeutic application," Nat Rev Immunol, 11(5): 330-342 (2011).
Maier et al., "Delayed Elevation of Soluble Tumor Necrosis Factor Receptors P75 and P55 In Cerebrospinal Fluid and Plasma after Traumatic Brain Injury," Shock, vol. 26, No. 2; pp. 122-127 (2006) DOI: 10.1097/01.shk.0000223127.41641.f4.
Malek et al., "Interleukin-2 Receptor Signaling: At the Interface between Tolerance and Immunity," Immunity 33, 153-165 (2010).
Martin et al., "Microvesicles generated following traumatic brain injury induce platelet dysfunction via adenosine diphosphate receptor," J Trauma Acute Care Surg, 86(4):592-600 (2019).
Masel et al., "Chronic Endocrinopathies in Traumatic Brain Injury Disease," Journal of Neurotrauma 32, 1902-1910 (2014).
Mazzucchelli et al., "Interleukin-7 receptor expression: intelligent design," Nat Rev Immunol., 7, 144-154 (2007).
McAlister et al., "Protective anti-donor IgM production after crossmatch positive liver-kidney transplantation," Liver Transpl., 10(2):315-319 (2004).
McKee et al., "Emerging Roles for the Immune System in Traumatic Brain Injury," Front Immunol., 7:556 (2016).
Mikolajczyk et al., "Role of chemokine RANTES in the regulation of perivascular inflammation, T-cell accumulation, and vascular dysfunction in hypertension," FASEB J: Off Publ Fed Am Soc Exp Biol., 30(5):1987-1999 (2016) doi:10.1096/fj.201500088R.
Morgan et al., "Selective in vitro growth of T lymphocytes from normal human bone marrows," Science, 193, 1007-1008 (1976).
Morganti-Kossmann et al., "Modulation of immune response by head injury," Injury, Int. J. Care Injured, 38, 1392-1400 (2007).
Mrakovcic-Sutic et al., "Early Changes in Frequency of Peripheral Blood Lymphocyte Subpopulations in Severe Traumatic Brain-Injured Patients," Scandinavian Journal of Immunology, 72, 57-65 (2010).
Muñoz et al., "Cerebrospinal Fluid Cortisol Mediates Brain-Derived Neurotrophic Factor Relationships to Mortality after Severe TBI: A Prospective Cohort Study," Front. Mol. Neurosci., 10:44 (2017).
Nagin, "Group-Based Trajectory Modeling: An Overview," Ann Nutr Metab, 65:205-210 (2014).

Narayan et al., "Clinical Trials in Head Injury," Journal of Neurotrauma, 19(5), 503-557, (2002) DOI: 10.1089/089771502753754037.
Nasi et al., "Thymic output and functionality of the IL-7/IL-7 receptor system in centenarians: implications for the neolymphogenesis at the limit of human life," Aging Cell, 5, 167-175 (2006).
Nguyen et al., "Polymorphonuclear leukocytes promote neurotoxicity through release of matrix metalloproteinases, reactive oxygen species, and TNF-α," Journal of Neurochemistry, 102, 900-912 (2007).
Nielsen et al., "Natural autoantibodies and complement promote the uptake of a self antigen, human thyroglobulin, by B cells and the proliferation of thyroglobulin-reactive CD4+ T cells in healthy individuals," Eur. J. Immunol. 31, 2660-2668 (2001).
Niyonkuru et al., "Group-Based Trajectory Analysis Applications for Prognostic Biomarker Model Development in Severe TBI: A Practical Example," Journal of Neurotrauma, 30:938-945 (2013).
Notley et al., "Natural IgM Is Required for Suppression of Inflammatory Arthritis by Apoptotic Cells," J. Immunol. Baltim. Md 1950, 186, 4967-4972 (2011).
O'Connor et al., "Myelin basic protein-reactive autoantibodies in the serum and cerebrospinal fluid of multiple sclerosis patients are characterized by low-affinity interactions," Journal of Neuroimmunology, 136, 140-148 (2003).
O'Neil et al., "Complications of Mild Traumatic Brain Injury in Veterans and Military Personnel: A Systematic Review," VA Evidence-based Synthesis Program Reports (2013).
Otte et al., "A meta-analysis of cortisol response to challenge in human aging: importance of gender," Psychoneuroendocrinology, 30, 80-91 (2005).
Pandey et al., "Divergent Roles for p55 and p75 TNF-α Receptors in the Induction of Plasminogen Activator Inhibitor-1," Am J Pathol., 162(3):933-941 (2003).
Peck et al., "The impact of preinjury anticoagulants and prescription antiplatelet agents on outcomes in older patients with traumatic brain injury," The Journal of Trauma and Acute Care Surgery, 76(2), 431-436 (2014).
Perales et al., "Recombinant human interleukin-7 (CYT107) promotes T-cell recovery after allogeneic stem cell transplantation," Blood, 120(24):4882-4891 (2012).
Pereira et al., "Convergence of Innate and Adaptive Immunity during Human Aging," Front. Immunol., 7, 445 (2016).
Petrone et al., "Immune biomarkers for the diagnosis of mild traumatic brain injury," NeuroRehabilitation, 40(4): 501-508 (2017) DOI: 10.3233/NRE-171437.
Plummer et al., "Screening for anxiety disorders with the GAD-7 and GAD-2: a systematic review and diagnostic metaanalysis," Gen Hosp Psychiatry., 39:24-31 (2016).
Popovic et al., "Hypopituitarism as a consequence of traumatic brain injury (TBI) and its possible relation with cognitive disabilities and mental distress," J Endocrinol Invest., 27: 1048-1054 (2004).
Prass et al., "Stroke-induced Immunodeficiency Promotes Spontaneous Bacterial Infections and Is Mediated by Sympathetic Activation Reversal by Poststroke T Helper Cell Type 1-like Immunostimulation," J Exp Med, 198 (5): 725-736 (2003).
Probert et al., "TNF and its receptors in the CNS: The essential, the desirable and the deleterious effects," Neuroscience, 302, 2-22 (2015).
Quattrocchi et al., "Severe head injury: effect upon cellular immune function," Neurological Research, 13(1), 13-20 (1991).
Rath et al., "TNF-Induced Signaling in Apoptosis," J Clin Immunol 19: 350-364 (1999).
Rappaport et al., "Evaluation of Coma and Vegetative States," Arch Phys Med Rehabil., 73(7):628-634 (1992).
Rappaport et al., "Disability Rating Scale for Severe Head Trauma: Coma to Community," Archives of Physical Medicine and Rehabilitation, 63, 118-123 (1982).
Riegger et al., "Immune depression syndrome following human spinal cord injury (SCI): a pilot study," Neuroscience, 158(3):1194-1199 (2009).
Rivest, "Regulation of innate immune responses in the brain," Nat Rev Immunol., 9(6):429-439 (2009).

(56) References Cited

OTHER PUBLICATIONS

Rovlias et al., "The blood leukocyte count and its prognostic significance in severe head injury," Surg Neurol., 55(4):190-196 (2001).

Salonia et al., "Endothelin-1 Is Increased in Cerebrospinal Fluid and Associated with Unfavorable Outcomes in Children after Severe Traumatic Brain Injury," J. Neurotrauma 27, 1819-1825 (2010).

Saltzman et al., "Neurotoxic or Neuroprotective? Current Controversies in SCI-Induced Autoimmunity," Curr Phys Med Rehabil Rep, 174-177 (2013).

Santarsieri et al., "Variable neuroendocrine-immune dysfunction in individuals with unfavorable outcome after severe traumatic brain injury," Brain Behav Immun., 45:15-27 (2015).

Santarsieri et al., "Cerebrospinal Fluid Cortisol and Progesterone Profiles and Outcomes Prognostication after Severe Traumatic Brain Injury," J Neurotrauma., 31:699-712 (2014).

Santucci et al., "Leukocytosis as a Predictor of Severe Injury in Blunt Trauma," Western Journal of Emergency Medicine, 9(2), 81-85 (2008).

Scherbel et al., "Differential acute and chronic responses of tumor necrosis factor-deficient mice to experimental brain injury," Proc. Natl. Acad. Sci. USA, 96, 8721-8726 (1999).

Scholz et al., "Neutrophils and the blood-brain barrier dysfunction after trauma*," Medicinal Research Reviews, 27(3), 401-416 (2007).

Schluns et al., "Interleukin-7 mediates the homeostasis of naïve and memory CD8 T cells in vivo," Nat Immunol., 1, 426-432 (2000).

Schneider et al., "Pituitary imaging abnormalities in patients with and without hypopituitarism after traumatic brain injury," J. Endocrinol. Invest., 30: RC9-RC12 (2007).

Schneider et al., "Hypothalamusry Dysfunction Following Traumatic Brain Injury and Aneurysmal Subarachnoid Hemorrhage: A Systematic Review," JAMA 298, 1429-1438 (2007).

Schwartz et al., "Protective autoimmunity: regulation and prospects for vaccination after brain and spinal cord injuries," Trends in Molecular Medicine, 7(6):252-258 (2001).

Schwartz et al., "Protective autoimmunity and neuroprotection in inflammatory and noninflammatory neurodegenerative diseases," J Neurol Sci., 233, 163-166 (2005).

Schwartz et al., "Protective Autoimmunity: A Unifying Model for the Immune Network Involved in CNS Repair," 2014, Neuroscientist. 20, 4, p. 343-358 (2014).

Schwartz et al., "Breaking peripheral immune tolerance to CNS antigens in neurodegenerative diseases: Boosting autoimmunity to fight-off chronic neuroinflammation," Journal of Autoimmunity, 54, 8-14 (2014).

Scott et al., "Etanercept: A Review of Its Use in Autoimmune Inflammatory Diseases," Drugs, 74:1379-1410 (2014).

Sedger et al., "TNF and TNF-receptors: From mediators of cell death andinflammation to therapeutic giants—past, present and future," Cytokine Growth Factor Reviews, 25, 453-72 (2014).

Seo et al., "Crucial Roles of Interleukin-7 in the Development of T Follicular Helper Cells and in the Induction of Humoral Immunity," J Virol., 88(16):8998-9009 (2014).

Sereti et al., "IL-7 administration drives T cell-cycle entry and expansion in HIV-1 infection," Blood, 113(25):6304-6314 (2009).

Sheikh et al., "Administration of interleukin-7 increases CD4 T cells in idiopathic CD4 lymphocytopenia," Blood, 127(8):977-988 (2016).

Shi et al., "Granulocyte-macrophage colony-stimulating factor (GM-CSF) and T-cell responses: what we do and don't know," Cell Research, 16, 126-133 (2006).

Shin, et al. "DNA Methylation Regulates the Differential Expression of CX3CR1 on Human IL-7Rαlowand IL-7RαhighEffector Memory CD8+T Cells with Distinct Migratory Capacities to the Fractalkine," The Journal of Immunology, 195(6), 2861-2869 (2015) doi:10.4049/jimmunol.1500877.

Shindo et al., "Interleukin 7 and anti-programmed cell death 1 antibody have differing effects to reverse sepsis-induced immunosuppression," Shock, 43(4):334-343 (2015).

Simon et al., "The far-reaching scope of neuroinflammation after traumatic brain injury," Nat Rev Neurol., 13, 171-191 (2017).

Singhal et al., "Association between Cerebrospinal Fluid Interleukin-6 Concentrations and Outcome after Severe Human Traumatic Brain Injury," J Neurotrauma, 19(8):929-937 (2002).

Skrombolas et al., "Challenges and developing solutions for increasing the benefits of IL-2 treatment in tumor therapy," Expert Review of Clinical Immunology, 10(2): 207-217 (2014).

Sorrells et al., "An Inflammatory Review of Glucocorticoid Actions in the CNS," Brain Behav Immun., 21(3): 259-272 (2007).

Stein et al., "Circulating Autoantibodies Recognize and Bind Dying Neurons Following Injury to the Brain," J. Neuropathol. Exp. Neurol., 61, 1100-1108 (2002).

Sutton et al., "Interleukin-1 and IL-23 Induce Innate IL-17 Production from γδ T Cells, Amplifying Th17 Responses and Autoimmunity," Immunity, 31, 331-341 (2009).

Suvannavejh et al., "Divergent Roles for p55 and p75 Tumor Necrosis Factor Receptors in the Pathogenesis of $MOG_{35-55}$-Induced Experimental Autoimmune Encephalomyelitis," Cellular Immunology, 205, 24-33 (2000).

Szmydynger-Chodobska et al., "The role of the choroid plexus in neutrophil invasion after traumatic brain injury," J Cereb Blood Flow Metab., 29, 1503-1516 (2009).

Szmydynger-Chodobska et al., "The Involvement of Pial Microvessels in Leukocyte Invasion after Mild Traumatic Brain Injury," PLoS ONE 11(12): e0167677 (2016) doi:10.1371/journal.pone.0167677.

Szondy et al., "Transmembrane TNF-alpha reverse signaling leading to TGF-beta production is selectively activated by TNF targeting molecules: Therapeutic implications," Pharmacol. Res., 115, 124-132 (2017).

Tanriverdi et al., "Antipituitary antibodies after traumatic brain injury: is head trauma-induced pituitary dysfunction associated with autoimmunity?" Eur. J. Endocrinol. Eur. Fed. Endocr. Soc. 159, 7-13 (2008).

Tanriverdi et al., "Persistent Neuroinflammation May Be Involved in the Pathogenesis of Traumatic Brain Injury (TBI)-Induced Hypopituitarism: Potential Genetic and Autoimmune Factors," J. Neurotrauma 27:301-302 (2010).

Tanriverdi et al., "Investigation of antihypothalamus and antipituitary antibodies in amateur boxers: is chronic repetitive head trauma-induced pituitary dysfunction associated with autoimmunity?" Eur J Endocrinol., 162, 861-867 (2010).

Tanriverdi et al., "A Five Year Prospective Investigation of Anterior Pituitary Function after Traumatic Brain Injury: Is Hypopituitarism Long-Term after Head Trauma Associated with Autoimmunity?" J. Neurotrauma 30:1426-1433 (2013).

Tanriverdi et al., "Pituitary Dysfunction After Traumatic Brain Injury: A Clinical and Pathophysiological Approach," Endocr. Rev. 36(3):305-342 (2015).

Tanriverdi et al., "Classical and non-classical causes of GH deficiency in adults," Best Pract. Res. Clin. Endocrinol. Metab. 31(1), 3-11 (2017).

Tao et al., "Clinical Value of Neutrophil to Lymphocyte and Platelet to Lymphocyte Ratio After Aneurysmal Subarachnoid Hemorrhage," Neurocritical Care, 26, 393-401 (2017).

Taylor et al., "Traumatic Brain Injury-Related Emergency Department Visits, Hospitalizations, and Deaths—United States, 2007 and 2013," US Department of Health and Human Services/Centers for Disease Control and Prevention, MMWR, 66:9 (2017).

Thelin et al., "Elucidating Pro-Inflammatory Cytokine Responses after Traumatic Brain Injury in a Human Stem Cell Model," J Neurotrauma, 35:341-352 (2018) DOI: 10.1089/neu.2017.5155.

Thomson, "Etanercept in psoriasis: the evidence of its therapeutic impact," Core Evid., 2(1): 51-62 (2007).

Tuttolomondo et al., "Studies of selective TNF inhibitors in the treatment of brain injury from stroke and trauma: a review of the evidence to date," Drug Des Devel Ther., 8: 2221-2239 (2014).

Tulsky et al., "TBI-QOL: Development and Calibration of Item Banks to Measure Patient Reported Outcomes Following Traumatic Brain Injury," J Head Trauma Rehabil., 31(1):40-51 (2016).

Vas et al., "Fundamental roles of the innate-like repertoire of natural antibodies in immune homeostasis," Front Immunol (2013) 4:4 (2013) doi:10.3389/fimmu.2013.00004.

(56) References Cited

OTHER PUBLICATIONS

Vezzani, "On Demand Up-regulation of Therapeutic Genes in the Brain: Fiction or Reality?" Epilepsy Curr. 7(3): 88-90 (2007) doi: 10.1111/j.1535-7511.2007.00182.x.
Waage et al., "Tumor necrosis factor receptors in chronic lymphocytic leukemia," Leukemia and Lymphoma 13, 41-46 (1994).
Waetzig et al., "Soluble tumor necrosis factor (TNF) receptor-1 induces apoptosis via reverse TNF signaling and autocrine transforming growth factor-β1," The FASEB Journal, 19(1), 91-93 (2004).
Wagner et al., "Intentional Traumatic Brain Injury: Epidemiology, Risk Factors, and Associations with Injury Severity and Mortality," J Trauma 49, 404-410 (2000).
Wagner, "TBI translational rehabilitation research in the $21^{st}$ Century: exploring a Rehabilomics research model," Eur J Phys Rehabil Med, 46, 549-555 (2010).
Wagner et al., "Acute Serum Hormone Levels: Characterization and Prognosis after Severe Traumatic Brain Injury," J Neurotrauma, 28:871-888 (2011).
Wagner et al., "CSF Bcl-2 and cytochrome C temporal profiles in outcome prediction for adults with severe TBI," J. Cereb. Blood Flow Metab., 31, 1886-1896 (2011).
Wagner et al., "Persistent hypogonadism influences estradiol synthesis, cognition and outcome in males after severe TBI," Brain Injury, 26(10): 1226-1242 (2011).
Wagner et al., "A Rehabilomics focused perspective on molecular mechanisms underlying neurological injury, complications, and recovery after severe TBI," Pathophysiology 20, 39-48 (2013).
Wagner et al., "Rehabilomics Research. A Model for Translational Rehabilitation and Comparative Effectiveness Rehabilitation Research," American Journal of Physical Medicine & Rehabilitation, 93:913-916 (2014).

Wang et al., "Plasma Anti-Glial Fibrillary Acidic Protein Autoantibody Levels during the Acute and Chronic Phases of Traumatic Brain Injury: A Transforming Research and Clinical Knowledge in Traumatic Brain Injury Pilot Study," J Neurotrauma, 33(13), 1270-1277 (2016).
Wang et al., "An update on diagnostic and prognostic biomarkers for traumatic brain injury," Expert Rev. Mol. Diagn. 18(2), 165-180 (2018).
Woiciechowsky et al., "Sympathetic activation triggers systemic interleukin-10 release in immunodepression induced by brain injury," Nature Medicine, 4(7):808-813 (1998).
Yang et al., "Role of TNF-TNF Receptor 2 Signal in Regulatory T Cells and Its Therapeutic Implications," Front Immunol, 9 (2018).
Yang et al., "Autoimmunity and Traumatic Brain Injury," Curr Phys Med Rehabil Rep 5:22-29 (2017).
Zaloshnja et al., "Prevalence of Long-Term Disability From Traumatic Brain Injury in the Civilian Population of the United States, 2005," J Head Trauma Rehabil, 23, 394-400 (2008).
Zhang et al., "Human Traumatic Brain Injury Induces Autoantibody Response against Glial Fibrillary Acidic Protein and Its Breakdown Products," PLoS One, 9(3), e92698 (2014).
Zhou et al., "Erythropoietin regulates immune/inflammatory reaction and improves neurological function outcomes in traumatic brain injury," Brain and Behavior, 7(11), e00827 (2017).
Ziebell et al., "Involvement of Pro- and Anti-Inflammatory Cytokines and Chemokines in the Pathophysiology of Traumatic Brain Injury," Neurotherapeutics, 7, 22-30 (2010).
Brain Trauma Foundation, "Guidelines for the Management of Severe Traumatic Brain Injury," $3^{rd}$ Edition J Neurotrauma. 24(Suppl 1): S1-S106 (2007).

* cited by examiner

Demographic and Clinical Information on Cohort (APA IgM/IgG)

| | APA IgM Low TRAJ | APA IgM Medium TRAJ | APA IgM High TRAJ | P-value | | APA IgG Low TRAJ | APA IgG Medium TRAJ | APA IgG High TRAJ | P-value |
|---|---|---|---|---|---|---|---|---|---|
| Age, Mean (SE) | 40.95 (3.968) | 39.85 (2.808) | 33.76 (1.815) | p=0.217 | Age, Mean (SE) | 36.72 (2.913) | 37.38 (2.237) | 36.97 (2.824) | p=0.890 |
| Sex, Male n (%) | 18, (90.0) | 40, (85.1) | 46, (74.2) | p=0.240 | Sex, Male n (%) | 32 (88.9) | 45 (75.0) | 27 (81.8) | p=0.264 |
| GCS (Best in 24) Median (IQR) | 7.50 (3.50) | 7.00 (4.00) | 7.00 (4.00) | p=0.741 | GCS (Best in 24) Median (IQR) | 8.00 (4.00) | 7.00 (4.00) | 7.00 (4.00) | p=0.448 |
| ISS, Mean (SE) | 25.61 (4.379) | 12.41 (2.748) | 22.74 (2.470) | p=0.016 | ISS, Mean (SE) | 20.26 (3.178) | 19.18 (2.633) | 19.31 (3.659) | p=0.988 |
| IL-7 (pmol/L) Mean (SE) | 49.04 (7.75) | 50.96 (3.18) | 67.64 (3.94) | p=0.002 | IL-7 (pmol/L) Mean (SE) | 53.17 (5.83) | 57.44 (3.34) | 66.95 (5.11) | p=0.06 |
| IL-7 (4 Hours) Mean (SE) | 61.93 (14.37) | 58.43 (5.79) | 70.48 (5.45) | p=0.073 | IL-7 (4 Hours) Mean (SE) | 54.91 (8.77) | 60.28 (5.04) | 83.06 (8.90) | p=0.013 |
| IL-7 (7-Days) Mean (SE) | 61.75 (14.46) | 52.99 (5.92) | 76.00 (8.24) | p=0.114 | IL-7 (7-Days) Mean (SE) | 44.18 (8.61) | 60.22 (5.55) | 84.38 (10.33) | p=0.004 |

FIG. 1

Demographic and Clinical Information on Cohort (AHA IgM/IgG)

| | AHA IgM Low Tril | AHA IgM Medium Tril | AHA IgM High Tril | P-value | AHA IgG Low Tril | AHA IgG Medium Tril | AHA IgG High Tril | P-value |
|---|---|---|---|---|---|---|---|---|
| Age, Mean (SE) | 45.00 (3.264) | 34.81 (1.829) | 34.17 (3.349) | p=0.02 | 4.087 (2.722) | 33.50 (2.046) | 40.05 (2.944) | p=0.031 |
| Sex, Male (%) | 24 (83.0) | 64 (82.7) | 13 (72.2) | p=0.368 | 34 (73.9) | 52 (81.3) | 18 (94.7) | p=0.158 |
| BMI (Ref: Median n=24), Median (IQR) | 7.50 (4.00) | 7.00 (4.00) | 8.00 (6.50) | p=0.891 | 8.00 (3.75) | 7.00 (3.00) | 8.00 (5.00) | p=0.085 |
| LOS, Mean (SE) | 13.65 (4.967) | 21.51 (2.097) | 18.06 (3.607) | p=0.079 | 16.45 (2.913) | 22.30 (2.615) | 18.00 (3.772) | p=0.311 |
| IL-7 (Pretx Infection), Mean (SE) | 53.23 (5.75) | 59.38 (3.28) | 64.59 (6.50) | p=0.257 | 50.92 (3.85) | 64.24 (3.87) | 58.77 (7.11) | p=0.030 |
| IL-7 (Pretx Graft), Mean (SE) | 52.05 (8.92) | 66.59 (5.02) | 75.86 (11.82) | p=0.070 | 53.59 (5.37) | 70.06 (6.46) | 73.29 (12.30) | p=0.148 |
| IL-7 (Pretx Tumor), Mean (SE) | 48.13 (8.40) | 66.81 (5.74) | 69.77 (15.02) | p=0.129 | 47.15 (4.34) | 72.45 (7.55) | 74.08 (15.01) | p=0.022 |

APA IgM 4-6 months post injury

| Interaction Model | Point Estimate (95%CI) | p-value |
|---|---|---|
| Age | 7.078 (1.462, 34.255) | p=0.0150 |
| IL-7 | 1.004 (0.990, 1.018) | p=0.5974 |
| Age*IL-7 Interaction | 0.978 (0.957, 0.999) | p=0.0423 |

APA IgM 7-12 months post injury

| Interaction Model | Point Estimate (95%CI) | p-value |
|---|---|---|
| Age | 5.873 (0.800, 43.093) | p=0.0817 |
| IL-7 | 1.001 (0.983, 1.018) | p=0.9395 |
| Age*IL-7 Interaction | 0.974 (0.946, 1.003) | p=0.0836 |

Fig. 4

Ordinal Logistic Regression Results: AHA IgM/IgG

AHA IgM 4-6 months post-injury

| Main Effects Model | Point Estimate (95%CI) | P value |
|---|---|---|
| Age | 2.173 (0.896, 5.271) | 0.0860 |
| IL-7 | 0.989 (0.978, 1.001) | 0.0643 |

AHA IgG 7-12 months post-injury

| Main Effects Model | Point Estimate (95%CI) | P value |
|---|---|---|
| Age | 0.728 (0.280, 1.895) | 0.5157 |
| IL-7 | 0.983 (0.970, 0.997) | 0.0155 |

AHA IgM 7-12 months post-injury

| Main Effects Model | Point Estimate (95%CI) | P value |
|---|---|---|
| Age | 2.445 (0.827, 7.223) | 0.1058 |
| IL-7 | 0.986 (0.971, 1.001) | 0.0713 |

IL-7 was independently associated with AHA IgG production 7-12 months post-injury (p=0.0155)

A

B

| Demographic Information | APA LGG Low TRA | APA LGG Moderate TRA | APA LGG High TRA | P-value | APA LGG Low TRA | APA LGG Moderate TRA | APA LGG High TRA | P-value |
|---|---|---|---|---|---|---|---|---|
| Age at injury, Mean (SE) | 42.77 (3.72) | 36.66 (2.68) | 33.61 (2.12) | p=0.1647 | 45.03 (3.29) | 34.27 (1.91) | 31.65 (3.56) | p=0.0133 |
| Sex, Men n (%) | 28 (17.50) | 49 (33.63) | 54 (33.75) | p=0.1148 | 33 (20.63) | 84 (52.50) | 14 (8.75) | p=0.3309 |
| Best in 24 GCS, Median (IQR) | 8.00 (4.00) | 7.00 (3.00) | 7.00 (4.00) | p=0.4314 | 8.00 (4.00) | 7.00 (4.00) | 7.00 (4.00) | p=0.9432 |
| ISS, Mean (SE) | 30.82 (2.67) | 30.58 (2.21) | 34.05 (1.58) | p=0.1955 | 33.42 (5.17) | 32.85 (1.23) | 27.91 (2.16) | p=0.2171 |
| | APA LGG Low TRA | APA LGG Moderate TRA | APA LGG High TRA | P-value | APA LGG Low TRA | APA LGG Moderate TRA | APA LGG High TRA | P-value |
| Age at injury, Mean (SE) | 37.57 (2.93) | 37.12 (2.39) | 34.70 (2.89) | p=0.8483 | 39.29 (2.56) | 33.68 (2.28) | 40.20 (3.53) | p=0.0841 |
| Sex, Men n (%) | 43 (26.88) | 57 (35.63) | 31 (19.38) | p=0.3962 | 46 (28.75) | 64 (40.00) | 21 (13.13) | p=0.3703 |
| Best in 24 GCS, Median (IQR) | 8.00 (3.00) | 7.00 (4.00) | 7.00 (4.00) | p=0.3930 | 8.00 (7.00) | 7.00 (3.00) | 8.00 (4.00) | p=0.0548 |
| ISS, Mean (SE) | 30.63 (2.09) | 33.13 (1.77) | 33.56 (2.31) | p=0.0913 | 31.00 (2.08) | 34.47 (1.72) | 28.00 (1.94) | p=0.2130 |

Fig. 9

Ordinal Logistic Regression Results: APA and AHA IgM AAbs

APA IgM TRAJ and IL-7 Levels 2 weeks-6 months post TBI (N=117)

| Main Effects Model | Odds Ratios | P value |
|---|---|---|
| Age Dichotomized | 1.680 (0.826, 3.417) | p=0.1521 |
| IL-7 | 0.929 (0.895, 0.964) | p=0.0001 |

AHA IgM TRAJ and IL-7 Levels 2weeks-6 months post TBI (N=117)

| Main Effects Model | Odds Ratio | P value |
|---|---|---|
| Age Dichotomized | 2.916 (1.341, 6.340) | p=0.0069 |
| IL-7 | 0.939 (0.907, 0.971) | p=0.0003 |

Ordinal Logistic Regression Results: APA and AHA IgG AAbs

| | APA IgG TRAJ and IL-7 Levels 2 weeks-6 months post TBI (N=117) | | AHA IgG TRAJ and IL-7 Levels 2 weeks-6 months post TBI (N=117) | |
|---|---|---|---|---|
| Interaction Model | Odds Ratios | P value | Odds Ratios | P value |
| Age Dichotomized | 13.916 (2.035, 95.168) | p=0.0073 | 4.952 (0.750, 32.690) | p=0.0967 |
| IL-7 | 1.053 (0.992, 1.117) | p=0.0922 | 1.018 (0.959, 1.080) | p=0.5571 |
| Age Dichotomized IL-7 Interaction | 0.897 (0.835, 0.964) | p=0.0030 | 0.949 (0.886, 1.017) | p=0.1368 |

Fig. 29

Linear Regression: APA IgM:IgG Ratio (0-3mo.) mean Levels

| Interaction Model | Beta | p-value |
|---|---|---|
| IL-7 TRAJ (1) | -0.69 | 0.0439 |
| IL-7 TRAJ (2) | -0.37 | 0.2141 |
| PHH status | -0.22 | 0.6107 |
| IL-7 TRAJ 1*PHH | -0.10 | 0.8652 |
| IL-7 TRAJ 2*PHH | 0.15 | 0.7812 |

Reference Group: IL-7 TRAJ 3
Sample size: $n=94$

Fig. 30

Ordinal Logistic Regression: APA IgM Male TRAJ

| Interaction Model | p-value |
|---|---|
| IL-7 TRAJ (1) | 0.0002 |
| IL-7 TRAJ (2) | 0.9004 |
| PHH (1) | 0.1011 |
| IL-7 TRAJ (1)*PHH | 0.6810 |
| IL-7 TRAJ (2)*PHH | 0.3652 |

Reference Groups: IL-7 TRAJ 3, No PHH
Sample size: $n=94$

Fig. 31

Ordinal Logistic Regression: APA IgM Male TRAJ

|  | Point Estimate (CI) | p-value |
|---|---|---|
| IL-7 TRAJ (2) | 3.64 (0.78,16.81) | 0.0478 |
| IL-7 TRAJ (3) | 1.11 (0.18,7.07) | 0.4885 |
| PHH (1) | 0.46 (0.19,1.14) | 0.0933 |
| TC1 score | 0.64 (0.21,1.94) | 0.4294 |
| IL-7*TC1 score | 1.70 (1,2.85) | 0.0466 |

Reference Groups: IL-7 TRAJ 1, No PHH
Sample size: $n=94$

Acute and Chronic Phenomena Event Rate (% of TRAJ)

*Signifies significant difference in event rate between low & high TRAJs

|  | Stratified Inflammatory Profiles | Low IL-7 TRAJ | High IL-7 TRAJ | Low sTNFR-I TRAJ | High sTNFR-I TRAJ |
|---|---|---|---|---|---|
| ACUTE PHENOMENA | Lymphopenia *(Low Lymphocyte TRAJ)* | 41.9 | 29.4 | * 25 | 43.5 |
| | Neutrophilia *(High Neutrophil TRAJ)* | 49.38 | 60 | * 44.07 | 60.92 |
| | Lymphopenia + Neutrophilia *(High NLR TRAJ)* | 29.6 | 30.9 | * 18.3 | 38.2 |
| | Acute Hospital-Acquired Infection | 50.8 | 56.7 | 50.8 | 55.1 |
| CHRONIC PHENOMENA | Persistent Hypogonadotropic Hypogonadism | * 42.5 | 29.1 | * 24.5 | 46.5 |
| | Post-traumatic Depression *(6mo.)* | 27.9 | 32.8 | 28.6 | 31.7 |
| | Cognitive Impairment *(6mo. Overall)* | 47.5 | 50.9 | 45.9 | 52.7 |
| | Headache *(Chronic Headache Trajectory)* | 40.48 | 37.5 | 38.46 | 40.74 |
| | Seizure Incidence | 24.1 | 24.7 | * 17.33 | 29.6 |
| OVERALL OUTCOME | Unfavorable GOS Score *(6mo. Score=2,3)* | 40 | 40.3 | * 23.1 | 53.7 |
| | DRS Score *(6mo. Moderate to Severe Disability)* | 33.3 | 42.2 | * 28.1 | 45 |

Leverage chronic sTNFR-I profiles as:
(1) indicator of perpetuating cell death cascades
(2) chronic outcome prognosticator sTNFR-I has greater capacity than IL-7 alone for chronic outcome differentiation

| Auto-antibody Levels 0-6mo. Mean, SE | Low IL-7 TRAJ | High IL-7 TRAJ | p-value |
|---|---|---|---|
| AHA IgM | 6.37 (0.5) | 8.18 (0.7) | 0.0075 |
| APA IgM | 0.56 (0.1) | 1.32 (0.2) | <0.0001 |
| GFAP IgM | 8.6 (0.6) | 11.82 (0.7) | 0.0002 |
| AHA IgG | 6.21 (0.5) | 8.26 (0.8) | 0.0494 |
| APA IgG | 0.94 (0.1) | 1.6 (0.2) | 0.0009 |
| GFAP IgG | 39.34 (2.0) | 39.2 (2.5) | 0.616 |
| AHA IgM:IgG | 1.77 (0.2) | 2.27 (0.3) | 0.5613 |
| APA IgM:IgG | 0.94 (0.1) | 1.41 (0.2) | 0.0098 |
| GFAP IgM:IgG | 0.28 (0.02) | 0.44 (0.1) | 0.0003 |

| Stratified Inflammatory Profiles | Low IL-7 Low sTNFRI | Low IL-7 High sTNFRI | High IL-7 High sTNFRI | High IL-7 Low sTNFRI |
|---|---|---|---|---|
| ACUTE PHENOMENA | | | | |
| * Lymphopenia (Low Lymphocyte TRAJ) | 32.4 | 46.7 | 39 | 15.4 |
| * Neutrophilia (High Neutrophil TRAJ) | 35.3 | 59.57 | 62.5 | 56 |
| * Lymphopenia + Neutrophilia (High NLR TRAJ) | 20.6 | 35.6 | 41.5 | 15.4 |
| Acute Hospital-Acquired Infection | 52.9 | 48.9 | 61.9 | 48 |
| CHRONIC PHENOMENA | | | | |
| * Persistent Hypogonadotropic Hypogonadism | 28.1 | 51.4 | 30.3 | 14.3 |
| Post-traumatic Depression (6mo.) | 30.3 | 25 | 34.3 | 26.1 |
| Cognitive Impairment (6mo. Overall) | 47.2 | 48 | 56.7 | 44 |
| Headache (Chronic Headache Trajectory) | 40 | 40.91 | 40 | 36.84 |
| Seizure Incidence | 17.1 | 30.4 | 29.8 | 17.6 |
| OVERALL OUTCOME | | | | |
| * Unfavorable GOS Score (6mo. Score=2,3) | 21.1 | 56.4 | 50 | 25.9 |
| * DRS Score (6mo. Moderate to Severe Disability) | 26.3 | 40 | 50 | 30.8 |
| | Low dose rIL-7 | Higher dose rIL-7 + TNF-α inhibitor | TNF-α inhibitor | NO Treatment Ideal Inflammatory Profile |

*Stars denote outcomes that were differentiated by grid membership with at least trending concordance/significance (p<0.1)

|  | LOW sTNFRI TRAJ | HIGH sTNFRI TRAJ |
|---|---|---|
| LOW IL-7 TRAJ | Single therapy (low rIL-7)<br>• Mean age 32<br>• Predominantly male (82%)<br>• 30% exhibit signs of acute lymphopenia<br>• Earliest time to first hospital-acquired infection | DUAL therapy (higher rIL-7 + TNFa inhibitor)<br>• Mean age 44<br>• Predominantly male (81%)<br>• High rates of acute lymphopenia and neutrophilia<br>• Less severe neurological injuries and polytrauma (GCS, ISS, non-head ISS scores) |
| HIGH IL-7 TRAJ | No treatment<br>• Mean age 32<br>• Greater female proportion (nearly 40%) | Single therapy (TNF-a inhibitor)<br>• Mean age 38<br>• Slightly more females (nearly 25%)<br>• Exhibit signs of acute lymphopenia and neutrophilia (high NLR)<br>• More severe neurological injuries (GCS and ISS scores) and greater polytrauma (non-head ISS score) |

Fig. 39

|  | Post-TBI Condition/Outcome | LOW sTNFRI TRAJ | HIGH sTNFRI TRAJ | Row p-value |
|---|---|---|---|---|
| LOW IL-7 TRAJ | Age<br>Gender, Male<br>Race, White<br>GCS Score: Best in 24hr.<br>ISS<br>Non-head ISS<br>Time to Infection | 32.09 (2.0)<br>37/45 (82.2%)<br>37/41 (90.2%)<br>8 (6-13)<br>26.88 (1.8)<br>11.10 (2.3)<br>4.67 (1.0) | 44.39 (2.9)<br>40/49 (81.6%)<br>40/43 (93.0%)<br>9 (7-11)<br>25.89 (2.2)<br>9.03 (2.4)<br>7.04 (1.0) | $p=0.0058$<br>$X^2=0.0055$, $p=0.9409$<br>$X^2=3.8715$, $p=0.1443$<br>$p=0.4954$<br>$p=0.7172$<br>$p=0.2896$<br>$p=0.0620$ |
| HIGH IL-7 TRAJ | Age<br>Gender, Male<br>Race, White<br>GCS Score: Best in 24hr.<br>ISS<br>Non-head ISS<br>Time to Infection | 32.57 (2.5)<br>22/35 (62.9%)<br>30/32 (88.2%)<br>7.5 (7-10)<br>29.81 (2.2)<br>10.56 (1.8)<br>6.26 (0.85) | 38.3 (2.5)<br>35/47 (74.5%)<br>45/46 (97.8%)<br>7 (6-9)<br>31.28 (1.8)<br>12.86 (1.5)<br>5.38 (0.65) | $p=0.0998$<br>$X^2=1.2761$, $p=0.2586$<br>$X^2=3.2737$, $p=0.1946$<br>$p=0.3743$<br>$p=0.5638$<br>$p=0.3160$<br>$p=0.3992$ |
| Column p-value | Age<br>Gender, Male<br>Race, White<br>GCS Score: Best in 24hr.<br>ISS<br>Non-head ISS<br>Time to Infection | $p=0.9149$<br>$X^2=3.8736$, $p=0.0500$<br>$X^2=1.2316$, $p=0.5402$<br>$p=0.3218$<br>$p=0.2245$<br>$p=0.7988$<br>$p=0.0063$ | $p=0.2391$<br>$X^2=0.7206$, $p=0.3960$<br>$X^2=2.1955$, $p=0.3336$<br>$p=0.0077$<br>$p=0.0441$<br>$p=0.0193$<br>$p=0.3047$ |  |

| | Stratified Inflammatory Profiles | Low NLR | High NLR |
|---|---|---|---|
| ACUTE PHENOMENA | Lymphopenia (Low Lymphocyte TRAJ) | 20.19 | 73.33 |
| | Neutrophilia (High Neutrophil TRAJ) | 41.18 | 84.09 |
| | Acute Hospital-Acquired Infection | 42.72 | 77.78 |
| CHRONIC PHENOMENA | Persistent Hypogonadotropic Hypogonadism | 37.14 | 37.14 |
| | Post-traumatic Depression (6mo.) | 25.35 | 48.28 |
| | Cognitive Impairment (6mo. Overall) | 46.58 | 48.15 |
| | Headache (Chronic Headache Trajectory) | 40.54 | 30.77 |
| | Seizure Incidence | 22.22 | 26.19 |
| OVERALL OUTCOME | Unfavorable GOS Score (6mo. Score=2,3) | 36.36 | 55 |
| | DRS Score (6mo. Moderate to Severe Disability) | 35.63 | 50 |

Fig. 45

Acute Immune Cell TRAJS (% of TRAJ reported)

| | Low Neutro | High Neutro | Low Lymph | High Lymph | Low NLR | High NLR |
|---|---|---|---|---|---|---|
| Low sTNFR-I | 49.25 | 32.91 | 27.78 | 47.37 | 47.12 | 24.44 |
| High sTNFR-I | 50.75 | 67.09 | 72.22 | 52.63 | 52.88 | 75.56 |
| | $X^2=4.02, p=0.0449$ | | $X^2=5.49, p=0.0191$ | | $X^2=6.71, p=0.0096$ | |

A

B

A

B

C

D

| Logistic Regression to PHH (n=125) | | |
|---|---|---|
| | OR (95% CI) | p-value |
| Age | 1.027 (1.0, 1.056) | *p=0.0507* |
| GCS Score | 0.912 (0.777, 1.071) | p=0.2622 |
| APA IgM<br>0-6m. mean | 0.426 (0.198, 0.916) | p=0.029 |
| RANTES<br>0-6m. mean (x0.01) | 1.213 (1.018, 1.447) | p=0.031 |
| sTNFRI<br>0-6m. mean (x0.01) | 1.158 (1.053, 1.274) | p=0.0025 |
| IL-7<br>0-6m. mean | 1.006 (0.969, 1.044) | p=0.7676 |
| IL-7*sTNFRI<br>Interaction | 1.013 (1.005, 1.021) | p=0.002 |
| AUC | c=0.795 | |

*Note: interaction graphic refers to month 0–6 mean levels (pg/mL) of IL-7 (not scaled) and sTNFRI (scaled by a factor of 100)

| Endogenous Risk TRAJ Profile | Associated Unfavorable Conditions | Absolute Risk Reduction (ARR) | Numbers Needed to Treat (NNT) |
|---|---|---|---|
| High NLR | Lymphopenia | 53% | n=2 |
| | Neutrophilia | 43% | n=2 |
| | HAI | 35% | n=3 |
| | PTD | 23% | n=4 |
| | Poor GOS | 19% | n=5 |
| High sTNFR-I | Lymphopenia | 19% | n=5 |
| | Neutrophilia | 17% | n=6 |
| | High NLR | 20% | n=5 |
| | PHH | 22% | n=5 |
| | Seizure Incidence | 13% | n=8 |
| | Poor GOS | 31% | n=3 |
| | Mod./Severe DRS | 17% | n=6 |
| Low IL7 | PHH | 13% | n=7 |

0-6 Month Treelet Cluster Score Comparisons
*Unrestricted chronic cohort*

| Unrestricted Treelet Clusters | IL7 TRAJ 1 | | | IL7 TRAJ 2 | | | IL7 TRAJ 3 | | | p-value |
|---|---|---|---|---|---|---|---|---|---|---|
| | Mean | SE | n | Mean | SE | n | Mean | SE | n | |
| TC1 | -1.8297 | 0.13 | 54 | 0.1077 | 0.18 | 65 | 2.0425 | 0.29 | 46 | <0.0001 |
| TC2 | -0.7598 | 0.06 | 54 | -0.3480 | 0.14 | 65 | 1.4272 | 0.46 | 46 | <0.0001 |
| TC3 | 0.1624 | 0.28 | 54 | -0.1768 | 0.16 | 65 | 0.2949 | 0.22 | 46 | 0.2589 |
| TC4 | -0.1802 | 0.15 | 54 | 0.3646 | 0.26 | 65 | -0.1261 | 0.11 | 46 | 0.0004 |
| TC5 | -0.3447 | 0.16 | 54 | 0.0843 | 0.18 | 65 | 0.2959 | 0.16 | 46 | 0.001 |

FIG. 74

Between IL-7 TRAJ Group Comparisons

Markers that did not cluster in unrestricted treelet

| Other Markers | IL-7 TRAJ 1 Mean | SE | IL-7 TRAJ 2 Mean | SE | IL-7 TRAJ 3 Mean | SE | p-value | 1v2 p-value | 1v3 p-value | 2v3 p-value |
|---|---|---|---|---|---|---|---|---|---|---|
| IL_10_m06 | 35.57 | 3.96 | 51.46 | 4.28 | 64.27 | 3.91 | <0.0001 | 0.0014 | <0.0001 | 0.0016 |
| MIP_1a_m06 | 61.41 | 16.18 | 160.78 | 50.45 | 295.54 | 46.90 | <0.0001 | <0.0001 | <0.0001 | 0.0007 |
| IL_17A_m06 | 19.11 | 2.28 | 32.26 | 3.81 | 30.85 | 1.74 | <0.0001 | <0.0001 | <0.0001 | 0.0842 |
| IL_4_m06 | 103.51 | 7.67 | 164.83 | 8.38 | 287.52 | 78.74 | <0.0001 | <0.0001 | <0.0001 | 0.0003 |
| sICAM_1_m06 | 146807.29 | 5889.57 | 157896.13 | 5967.41 | 169978.99 | 8198.80 | 0.0177 | 0.1375 | 0.007 | 0.0811 |
| sIL_6R_m06 | 26389.10 | 866.28 | 26021.56 | 810.72 | 24493.46 | 991.47 | 0.4673 | 0.8733 | 0.25 | 0.3055 |
| sgp130_m06 | 154769.15 | 4256.98 | 161459.21 | 2734.43 | 162269.36 | 4949.73 | 0.5224 | 0.2782 | 0.4127 | 0.9204 |
| sIL_1RII_m06 | 9072.92 | 349.30 | 9334.50 | 269.07 | 9538.10 | 414.63 | 0.7433 | 0.5721 | 0.4634 | 0.8573 |
| NCAM_m06 | 270806.57 | 10172.91 | 287439.99 | 8467.62 | 290427.93 | 12227.00 | 0.1757 | 0.091 | 0.1401 | 0.8843 |
| sCD30_m06 | 32.23 | 4.08 | 38.17 | 3.78 | 56.41 | 14.05 | 0.005 | 0.0401 | 0.0012 | 0.2016 |
| sIL_4R_m06 | 1510.53 | 45.24 | 1605.95 | 47.79 | 1719.90 | 55.42 | 0.003 | 0.0369 | 0.0009 | 0.1225 |
| sIL_1RI_m06 | 21.96 | 5.16 | 13.93 | 3.05 | 36.53 | 7.99 | 0.0229 | 0.1381 | 0.127 | 0.0094 |

FIG. 75

Demographics/Outcomes by IL-7 TRAJ

| Variable | IL-7 TRAJ 1 | IL-7 TRAJ 2 | IL-7 TRAJ 3 | p-value |
|---|---|---|---|---|
| n | 63 | 67 | 45 | |
| Age, Mean (SE) | 39.85 (2.49) | 31.68 (1.59) | 38.06 (2.47) | 0.0721 |
| BMI, Mean (SE) | 27.96 (1.00) | 25.81 (0.75) | 26.57 (0.88) | 0.3047 |
| Sex, Men (%) | 48 (71.64) | 56 (81.16) | 29 (61.70) | |
| Race, Caucasian (%) | 45 (67.16) | 61 (88.40) | 43 (91.49) | |
| Ethnicity, White (%) | 39 (58.21) | 50 (72.46) | 40 (85.10) | |
| Hospital LOS (days), Mean (SE) | 60.33 (36.08) | 20.86 (2.0) | 23.23 (1.76) | 0.4828 |
| ICU LOS (days), Mean (SE) | 16.78 (2.5) | 16.57 (3.13) | 8 (n/a) | 0.6382 |
| Rehab LOS (days), Mean (SE) | 18.5 (8.5) | 23.69 (4.23) | 34.94 (4.44) | 0.0998 |
| GCS Best in 24hr., Mean (SE) | 8.01 (0.66) | 7.92 (0.44) | 7.49 (0.43) | 0.2351 |
| ISS, Mean (SE) | 30.95 (2.61) | 32.19 (1.68) | 33.42 (1.74) | 0.4859 |
| DRS 6mo., Mean (SE) | 4.63 (0.93) | 3.37 (0.70) | 5.73 (0.86) | 0.0171 |
| DRS 12mo., Mean (SE) | 3.53 (0.89) | 2.55 (0.64) | 5.33 (1.01) | 0.0074 |
| GOS 6mo., Mean (SE) | 3.94 (0.14) | 4.11 (0.11) | 3.67 (0.12) | 0.0386 |
| GOS 12mo., Mean (SE) | 4.18 (0.14) | 4.3 (0.10) | 3.88 (0.13) | 0.0312 |

Fig. 83

6 mo. GOS scores by PHH Status
PHH=1, No PHH=0
Unfavorable (GOS=2,3)=0, Favorable (GOS=4,5)=1

| Frequency<br>Percent<br>Row Pct<br>Col Pct | Table of PHH by FavorableGOS_6M | | |
|---|---|---|---|
| | FavorableGOS_6M(FavorableGOS_6M) | | |
| PHH(PHH) | 0 | 1 | Total |
| 0 | 14<br>16.87<br>26.92<br>48.28 | 38<br>45.78<br>73.08<br>70.37 | 52<br>62.65 |
| 1 | 15<br>18.07<br>48.39<br>51.72 | 16<br>19.28<br>51.61<br>29.63 | 31<br>37.35 |
| Total | 29<br>34.94 | 54<br>65.06 | 83<br>100.00 |

| Statistic | DF | Value | Prob |
|---|---|---|---|
| Chi-Square | 1 | 3.9352 | 0.0473 |

Fig. 90

| Marker | HR (95% CI) | p-value |
|---|---|---|
| IL7 TRAJ High vs Low | 0.875 [0.390, 1.962] | 0.7462 |
| IL7 Levels | 0.776 [0.487, 1.238] | 0.2875 |
| sTNFR1 TRAJ High vs Low | 2.863 [1.121, 7.312] | 0.0279 |
| sTNFR1 Levels | 1.737 [1.069, 2.824] | 0.0258 |

| Marker | OR (95% CI) | p-value |
|---|---|---|
| sTNFR1 TRAJ | 3.687 [1.262, 10.769] | 0.0170 |

Fig. 92

| | Logistic Regression to GOS score (6m) | | |
|---|---|---|---|
| | OR (95% CI) | p-value | AUC |
| TC1 – Adaptive | 1.022 [0.836, 1.249] | 0.8342 | 0.731 |
| TC2 – Innate | 1.077 [0.884, 1.313] | 0.4605 | 0.736 |
| TC3 – Allergy | 0.846 [0.557, 1.284] | 0.4321 | 0.737 |
| TC4 – sReceptors | 2.008 [1.337, 2.018] | 0.0008 | 0.799 |
| TC5 – Chemokines | 1.577 [1.054, 2.358] | 0.0266 | 0.751 |

Fig. 93

Disability Categories

| Total DR Score | Level of Disability |
|---|---|
| 0 | None |
| 1 | Mild |
| 2-3 | Partial |
| 4-6 | Moderate |
| 7-11 | Moderately Severe |
| 12-16 | Severe |
| 17-21 | Extremely Severe |
| 22-24 | Vegetative State |
| 25-29 | Extreme Vegetative State |

Fig. 94

| Linear Regression to DRS score (6m) | | |
|---|---|---|
| | Beta | p-value |
| TC1 – Adaptive | -0.0216 | 0.9336 |
| TC2 – Innate | 0.0212 | 0.9313 |
| TC3 – Allergy | -0.0946 | 0.7966 |
| TC4 – sReceptors | 1.8978 | <0.0001 |
| TC5 - Chemokines | 0.4986 | 0.2831 |

| Logistic Regression to GOS score (6m) | | |
|---|---|---|
| | OR (95% CI) | p-value |
| Age | 1.006 (0.984, 1.029) | p=0.57 |
| GCS | 0.765 (0.673, 0.871) | p<0.0001 |
| sTNFRI | 1.056 (1.001, 1.115) | p=0.04 |
| AUC | | c=0.737 |

B

| Linear Regression to DRS score (6m) | | |
|---|---|---|
| | Beta | p-value |
| Age | -0.017 | p=0.5013 |
| GCS | -0.528 | p<0.0001 |
| sTNFRI | 0.187 | p=0.0013 |

Fig. 96

| | Logistic Regression to Unfavorable GOS score (6m) | | | | | |
|---|---|---|---|---|---|---|
| | OR (95% CI) | p-value | OR (95% CI) | p-value | OR (95% CI) | p-value |
| sTNFRI TRAJ<br>*High vs. Low* | 4.4 (1.9-10.2) | 0.0005 | 1.9 (0.7-5.1) | 0.2117 | 1.7 (0.6-4.6) | 0.3178 |
| IL-7 TRAJ<br>*High vs. Low* | 0.5 (0.2-1.1) | 0.0063 | 0.5 (0.2-1.2) | 0.1126 | 0.4 (0.2-1.0) | 0.0637 |
| TC4 – sReceptors<br>*sIL-2Ra, sTNFRII* | - | - | 1.8 (1.1-2.9) | 0.0111 | 1.7 (1.1-2.7) | 0.0283 |
| TC5 – Chemokines<br>*ITAC, RANTES* | - | - | - | - | 1.5 (0.9-2.3) | 0.0855 |
| AUC (c) | 0.79 | | 0.81 | - | 0.82 | - |

|  | APA IgM Low TRAJ | APA IgM Medium TRAJ | APA IgM High TRAJ | p-value |
|---|---|---|---|---|
| Age at injury, Mean (SE) | 41.00 (3.25) | 37.62 (2.36) | 33.62 (1.75) | p=0.1847 |
| Sex | | | | p=0.1053 |
| Men n (%) | 29 (17.90) | 48 (30.25) | 54 (33.33) | |
| Women n (%) | 2 (1.23) | 11 (6.79) | 17 (10.49) | |
| Race n (%) | | | | p=0.6062 |
| Caucasian | 28 (17.61) | 53 (33.33) | 65 (40.98) | |
| African American | 1 (0.63) | 6 (3.77) | 3 (1.89) | |
| Other | 1 (0.63) | 1 (0.63) | 1 (0.63) | |
| Best in 24 GCS, | | | | p=0.4195 |
| Median (IQR) | 8.00 (4.00) | 7.00 (4.00) | 7.00 (4.00) | |
| Non-head ISS, | | | | p=0.2722 |
| Mean (SE) | 14.54 (3.00) | 9.14 (1.58) | 11.48 (1.36) | |
| Length of stay (days), Mean (SE) | | | | p=0.7226 |
|  | 22.71 (3.38) | 23.92 (3.16) | 22.86 (1.50) | |
| Mechanism of injury, n (%) | | | | |
| MVA | 10 (10.99) | 11 (12.09) | 21 (23.08) | |
| Motorcycle | 3 (3.30) | 7 (7.69) | 12 (13.19) | |
| Fall | 7 (7.69) | 3 (3.30) | 4 (4.40) | |
| Assault/fight | 0 (0.00) | 1 (1.10) | 1 (1.10) | |
| Other | 0 (0.00) | 1 (1.10) | 0 (0.00) | |
| Injury type from CT, n (%) | | | | |
| SDH | 15 (16.67) | 14 (15.67) | 30 (33.33) | p=0.5475 |
| SAH | 16 (17.58) | 15 (16.48) | 27 (29.67) | p=0.5652 |
| DAI | 3 (3.33) | 6 (6.67) | 16 (17.78) | p=0.1301 |
| EDH | 2 (2.20) | 2 (2.20) | 9 (9.89) | p=0.2470 |
| Contusion | 8 (8.89) | 6 (6.67) | 18 (20.00) | p=0.3799 |
| IVH | 5 (5.56) | 5 (5.56) | 6 (6.67) | p=0.5966 |
| ICH | 6 (6.67) | 10 (11.11) | 15 (16.67) | p=0.6563 |

Fig. 104B

|  | AHA IgM Low TRAJ | AHA IgM Medium TRAJ | AHA IgM High TRAJ | p-value |
|---|---|---|---|---|
| Age at injury, Mean (SE) | 44.87 (2.88) | 33.95 (1.57) | 32.85 (3.14) | p=0.0049 |
| Sex<br>Men n (%)<br>Women n (%) | 34 (20.99)<br>6 (3.70) | 84 (51.85)<br>18 (11.11) | 14 (8.64)<br>6 (3.70) | p=0.3413 |
| Race n (%)<br>  Caucasian<br>  African American<br>  Other | 35 (22.01)<br>2 (1.26)<br>1 (0.63) | 93 (58.49)<br>6 (3.77)<br>2 (1.26) | 18 (11.32)<br>2 (1.26)<br>0 (0.00) | p=0.8841 |
| Best in 24 GCS, Median (IQR) | 8.00 (4.00) | 7.00 (4.00) | 7.00 (4.00) | p=0.9255 |
| Non-head ISS, Mean (SE) | 11.17 (3.06) | 11.82 (1.12) | 6.67 (1.44) | p=0.2921 |
| Length of stay (days), Mean (SE) | 23.58 (3.53) | 23.89 (1.67) | 17.40 (2.45) | p=0.3668 |
| Mechanism of injury, n (%)<br>  MVA<br>  Motorcycle<br>  Fall<br>  Assault/fight<br>  Other | 3 (3.30)<br>4 (4.40)<br>4 (4.40)<br>0 (0.00)<br>0 (0.00) | 32 (35.16)<br>17 (18.68)<br>8 (8.79)<br>1 (1.10)<br>1 (1.10) | 7 (7.59)<br>1 (1.10)<br>2 (2.20)<br>1 (1.10)<br>0 (0.00) |  |
| Injury type from CT, n (%)<br>  SDH<br>  SAH<br>  DAI<br>  EDH<br>  Contusion<br>  IVH<br>  ICH | 9 (10.00)<br>7 (7.69)<br>3 (3.33)<br>2 (2.20)<br>1 (1.11)<br>4 (4.44)<br>5 (5.56) | 41 (45.56)<br>43 (47.25)<br>18 (20.00)<br>9 (9.89)<br>27 (30.00)<br>10 (11.11)<br>22 (24.44) | 9 (10.00)<br>8 (8.79)<br>4 (4.44)<br>2 (2.20)<br>4 (4.44)<br>2 (2.22)<br>4 (4.44) | p=0.3809<br>p=0.9381<br>p=0.7983<br>p=0.7951<br>*p=0.0939*<br>p=0.3395<br>p=0.8725 |

Fig. 104C

|  | GFAP IgM Low TRAJ | GFAP IgM Medium TRAJ | GFAP IgM High TRAJ | p-value |
|---|---|---|---|---|
| Age at injury, Mean (SE) | 44.52 (4.89) | 38.49 (1.98) | 32.09 (1.70) | p=0.03060 |
| Sex | | | | p=0.0265 |
| Men n (%) | 16 (9.88) | 67 (41.36) | 49 (30.25) | |
| Women n (%) | 3 (1.85) | 8 (4.94) | 19 (11.73) | |
| Race n (%) | | | | p=0.9171 |
|   Caucasian | 16 (10.06) | 69 (43.40) | 61 (38.36) | |
|   African American | 1 (0.63) | 4 (2.52) | 5 (3.14) | |
|   Other | 0 (0.00) | 1 (0.63) | 2 (1.26) | |
| Best in 24 GCS, Median (IQR) | 8.50 (3.00) | 7.00 (4.00) | 7.00 (4.00) | p=0.5004 |
| Non-head ISS, Mean (SE) | 11.00 (3.56) | 11.59 (1.61) | 10.86 (1.35) | p=0.9648 |
| Length of stay (days), Mean (SE) | 20.00 (4.39) | 23.54 (1.95) | 23.05 (2.14) | p=0.9804 |
| Mechanism of injury, n (%) | | | | |
|   MVA | 0 (0.00) | 17 (18.68) | 25 (27.47) | |
|   Motorcycle | 1 (1.10) | 11 (12.09) | 10 (10.99) | |
|   Fall | 1 (1.10) | 10 (10.99) | 3 (3.30) | |
|   Assault/fight | 0 (0.00) | 1 (1.10) | 1 (1.10) | |
|   Other | 0 (0.00) | 1 (1.10) | 0 (0.00) | |
| Injury type from CT, n (%) | | | | |
|   SDH | 4 (4.44) | 28 (31.11) | 27 (30.00) | p=0.9378 |
|   SAH | 3 (3.30) | 28 (30.77) | 27 (29.67) | p=1.0000 |
|   DAI | 1 (1.11) | 12 (13.33) | 12 (13.33) | p=1.0000 |
|   EDH | 0 (0.00) | 8 (8.79) | 5 (5.49) | p=0.6142 |
|   Contusion | 2 (2.22) | 15 (16.67) | 15 (16.67) | p=0.9389 |
|   IVH | 2 (2.22) | 10 (11.11) | 4 (4.44) | p=0.1019 |
|   ICH | 0 (0.00) | 15 (16.67) | 16 (17.78) | p=0.2761 |

Fig. 107A

|     | APA IgM Low TRAJ | APA IgM Medium TRAJ | APA IgM High TRAJ | p value |
| --- | --- | --- | --- | --- |
| TC1 | -1.394 (0.297) | -0.611 (0.254) | 0.853 (0.261) | p=<0.0001 |
| TC2 | -0.526 (0.0587) | -0.491 (0.072) | 0.511 (0.308) | p=0.0004 |
| TC3 | 0.0078 (0.263) | -0.106 (0.259) | -0.110 (0.150) | p=0.4478 |
| TC4 | 0.253 (0.305) | -0.161 (0.192) | -0.097 (0.137) | p=0.3701 |

Fig. 107B

|     | AHA IgM Low TRAJ | AHA IgM Medium TRAJ | AHA IgM High TRAJ | p value |
| --- | --- | --- | --- | --- |
| TC1 | -1.502 (0.256) | 0.196 (0.206) | 1.037 (0.579) | p=<0.0001 |
| TC2 | -0.259 (0.259) | 0.106 (0.214) | -0.277 (0.229) | p=0.0341 |
| TC3 | 0.084 (0.323) | -0.003 (0.147) | -0.816 (0.188) | *p=0.0650* |
| TC4 | -0.230 (0.192) | 0.066 (0.148) | -0.409 (0.050) | p=0.0343 |

Fig. 107C

|     | GFAP IgM Low TRAJ | GFAP IgM Medium TRAJ | GFAP IgM High TRAJ | p value |
| --- | --- | --- | --- | --- |
| TC1 | -1.831 (0.325) | -0.617 (0.234) | 0.794 (0.253) | p=<0.0001 |
| TC2 | -0.631 (0.031) | 0.152 (0.313) | -0.058 (0.156) | *p=0.0537* |
| TC3 | 0.360 (0.633) | 0.114 (0.199) | -0.354 (0.137) | p=0.2824 |
| TC4 | -0.028 (0.332) | 0.0308 (0.175) | -0.139 (0.148) | p=0.2243 |

Fig. 107D

|     | APA IgG Low TRAJ | APA IgG Medium TRAJ | APA IgG High TRAJ | p value |
| --- | --- | --- | --- | --- |
| TC1 | -0.238 (0.340) | -0.246 (0.258) | 0.557 (0.332) | *p=0.0666* |
| TC2 | -0.385 (0.097) | -0.246 (0.142) | 0.871 (0.550) | p=0.0493 |
| TC3 | -0.246 (0.232) | 0.012 (0.197) | -0.097 (0.186) | p=0.4790 |
| TC4 | -0.146 (0.181) | 0.041 (0.181) | -0.141 (0.161) | p=0.4767 |

Fig. 107E

|     | AHA IgG Low TRAJ | AHA IgG Medium TRAJ | AHA IgG High TRAJ | p value |
| --- | --- | --- | --- | --- |
| TC1 | -0.41 (0.298) | 0.032 (0.224) | 0.689 (0.635) | p=0.1619 |
| TC2 | -0.267 (0.136) | -0.091 (0.241) | 1.053 (0.617) | p=0.1285 |
| TC3 | -0.257 (0.230) | 0.002 (0.167) | 0.045 (0.218) | p=0.1184 |
| TC4 | -0.248 (0.143) | 0.010 (0.141) | 0.250 (0.503) | p=0.2027 |

Fig. 107F

|  | GFAP IgG Low TRAJ | GFAP IgG Medium TRAJ | GFAP IgG High TRAJ | p value |
|---|---|---|---|---|
| TC1 | -0.160 (0.345) | 0.013 (0.210) | -1.141 (0.956) | p=0.7035 |
| TC2 | 0.131 (0.448) | -0.064 (0.133) | -0.642 (0.056) | p=0.3111 |
| TC3 | -0.228 (0.225) | -0.013 (0.148) | -1.0673 (0.717) | p=0.3549 |
| TC4 | 0.080 (0.228) | -0.0945 (0.123) | -0.732 (0.0358) | p=0.1360 |

Fig. 108

| APA IgM TRAJ (N=131) | | | |
|---|---|---|---|
| Variable | Odds Ratio (95% Confidence Interval) | p-value | AIC Statistic |
| Age | 0.980 (0.959, 1.002) | p=0.0722 | 324.638 for base model |
| Sex | 0.377 (0.143, 0.993) | p=0.0483 | 236.450 adding TC1 and TC2 weights |
| Best in 24 GCS | 0.988 (0.903, 1.083) | p=0.8029 | |
| TC1 weight | 1.602 (1.236, 2.075) | p=0.0004 | |
| TC2 weight | 1.650 (0.946, 2.880) | p=0.0778 | |

Fig. 109

| AHA IgM TRAJ (N=131) | | | |
|---|---|---|---|
| Variable | Odds Ratio (95% Confidence Interval) | p-value | AIC Statistic |
| Age | 0.966 (0.943, 0.989) | p=0.0048 | 276.044 for base model |
| Sex | 0.615 (0.234, 1.618) | p=0.3249 | 209.660 adding TC1 and TC2 weights |
| Best in 24 GCS | 1.089 (0.988, 1.201) | p=0.0857 | |
| TC1 weight | 1.622 (1.302, 2.021) | p=<0.0001 | |
| TC2 weight | 0.848 (0.682, 1.054) | p=0.1366 | |

Fig. 110

| GFAP IgM TRAJ (N=131) | | | |
|---|---|---|---|
| Variable | Odds Ratio (95% Confidence Interval) | p-value | AIC Statistic |
| Age | 0.975 (0.953, 0.998) | p=0.0325 | 296.766 for base model |
| Sex | 0.350 (0.953, 0.998) | p=0.0420 | 217.050 adding TC1 and TC2 weights |
| Best in 24 GCS | 1.061 (0.964, 1.168) | p=0.2280 | |
| TC1 weight | 1.866 (1.425, 2.450) | p=<0.0001 | |
| TC2 weight | 0.814 (0.650, 1.019) | p=0.0729 | |

Fig. 111

|  |  | PLR TRAJ n (%) | | |
|---|---|---|---|---|
|  |  | Low | Moderate | High |
| NLR TRAJ n (%) | Low | 68 (21.18) | 28 (8.72) | 14 (4.36) |
|  | Moderate | 34 (10.59) | 50 (15.58) | 43 (13.40) |
|  | High | 8 (2.49) | 32 (9.97) | 44 (13.71) |

Fig. 113A

|  | Low NLR TRAJ (n=110) | Moderate NLR TRAJ (n=127) | High NLR TRAJ (n=84) | p-value |
|---|---|---|---|---|
| Age, Mean (SE) | 42.75 (1.6) | 37.87 (1.4) | 40.60 (2.1) | 0.1175 |
| Sex, Male, n (%) | 86 (78.1) | 104 (81.9) | 69 (82.1) | 0.7135 |
| Race, White, n (%) | 96 (91.4) | 110 (90.9) | 75 (91.5) | 0.7249 |
| BMI, Mean (SE) | 26.82 (0.8) | 26.74 (0.5) | 27.19 (0.8) | 0.9916 |
| MOI, n (%) | | | | |
| MVA | 47 (47.47) | 52 (42.98) | 36 (45.57) | |
| Motorcycle | 10 (10.10) | 29 (23.97) | 16 (20.25) | |
| Bicycle/Skateboard | 1 (1.01) | 2 (2.48) | 4 (5.06) | 0.0469 |
| Fall | 28 (28.28) | 23 (19.01) | 21 (26.58) | |
| Assault/Fight | 6 (6.06) | 4 (3.31) | 0 (0) | |
| Other | 7 (7.07) | 10 (8.26) | 2 (2.53) | |
| GCS Score (24hr. best), Mean (SE) | 8.67 (0.4) | 7.76 (0.3) | 7.26 (0.3) | 0.0304 |
| Hospital LOS, Mean (SE) | 17.92 (1.1) | 21.37 (1.3) | 23.94 (1.8) | 0.0061 |
| ICU LOS, Mean (SE) | 12.14 (2.5) | 17.11 (2.0) | 18.22 (2.3) | 0.1132 |
| Rehab LOS, Mean (SE) | 28.40 (4.7) | 20.09 (2.9) | 34.67 (5.2) | 0.0326 |
| Ventilator Days, Mean (SE) | 6.04 (0.5) | 9.40 (0.6) | 10.33 (0.7) | 0.0001 |

Fig. 113B

|  | Low PLR TRAJ (n=111) | Moderate PLR TRAJ (n=110) | High PLR TRAJ (n=101) | p-value |
|---|---|---|---|---|
| Age, Mean (SE) | 44.34 (1.7) | 37.78 (1.5) | 38.50 (1.8) | 0.0084 |
| Sex, Male, n (%) | 79 (71.8) | 88 (80) | 92 (91.1) | 0.0018 |
| Race, White, n (%) | 94 (91.3) | 96 (89.7) | 91 (92.9) | 0.9411 |
| BMI, Mean (SE) | 27.52 (0.8) | 26.69 (0.7) | 26.62 (0.5) | 0.3675 |
| MOI, n (%) |  |  |  |  |
| MVA | 38 (39.18) | 57 (54.81) | 40 (40.82) |  |
| Motorcycle | 12 (12.37) | 19 (18.27) | 24 (24.49) |  |
| Bicycle/Skateboard | 2 (2.06) | 3 (2.88) | 3 (3.06) | 0.1161 |
| Fall | 31 (31.96) | 18 (17.31) | 23 (23.47) |  |
| Assault/Fight | 5 (5.15) | 2 (1.92) | 3 (3.06) |  |
| Other | 9 (9.28) | 5 (4.81) | 5 (5.10) |  |
| GCS Score (24 hr. best), Mean (SE) | 8.25 (0.36) | 7.59 (0.3) | 7.97 (0.3) | 0.5293 |
| Hospital LOS, Mean (SE) | 19.45 (1.5) | 22.67 (1.5) | 20.63 (1.3) | 0.0915 |
| ICU LOS, Mean (SE) | 14.76 (2.2) | 15.50 (2.2) | 17.08 (2.6) | 0.7488 |
| Rehab LOS, Mean (SE) | 28.90 (6.1) | 25.55 (4.2) | 25.47 (3.4) | 0.8301 |
| Ventilator Days, Mean (SE) | 8.24 (0.7) | 8.62 (0.6) | 8.63 (0.6) | 0.7584 |

Fig. 114A

|  | Low NLR TRAJ | Moderate NLR TRAJ | High NLR TRAJ | $X^2$ | p-value |
|---|---|---|---|---|---|
| Positive Infection | 50 (45.45%) | 68 (53.54%) | 51 (60.71%) | 4.5164 | 0.1045 |
| PTD | 12 (24.45%) | 16 (34.78%) | 16 (53.55%) | 6.7924 | 0.0335 |
| Unfavorable GOS | 29 (40.85%) | 62 (60.19%) | 48 (67.61%) | 11.2234 | 0.0037 |

Fig. 114B

|  | Low PLR TRAJ | Moderate PLR TRAJ | High PLR TRAJ | $X^2$ | p-value |
|---|---|---|---|---|---|
| Positive Infection | 56 (50.91%) | 57 (51.82%) | 56 (55.45%) | 0.4809 | 0.7863 |
| PTD | 10 (23.81) | 16 (36.36%) | 18 (46.15%) | 4.4667 | 0.1072 |
| Unfavorable GOS | 42 (53.85%) | 52 (59.77%) | 45 (56.25%) | 0.5994 | 0.7411 |

Fig. 116A

| CT Variable | Low NLR, n (%) | Moderate NLR, n (%) | High NLR, n (%) | $X^2$ | p-value |
|---|---|---|---|---|---|
| SDH | 72 (67.29) | 88 (69.84) | 61 (74.39) | 1.1280 | 0.5689 |
| SAH | 65 (60.75) | 101 (80.16) | 69 (84.15) | 16.8356 | 0.0002 |
| EDH | 17 (15.89) | 27 (21.43) | 14 (17.07) | 1.3149 | 0.5182 |
| IVH | 40 (37.38) | 41 (32.54) | 41 (50) | 6.5055 | 0.0387 |
| IPH | 52 (49.53) | 74 (58.73) | 50 (60.98) | 3.0195 | 0.2210 |
| DAI | 7 (6.54) | 24 (19.05) | 6 (7.32) | 10.8270 | 0.0045 |
| Contusion | 60 (56.07) | 88 (69.84) | 56 (68.29) | 5.4108 | 0.0668 |
| Midline shift | 31 (30.39) | 39 (35.78) | 27 (37.5) | 1.1246 | 0.5699 |
| Extraaxial | 97 (90.65) | 117 (92.86) | 76 (92.68) | 0.4425 | 0.8015 |
| Intraaxial | 86 (80.37) | 110 (87.3) | 76 (92.68) | 6.1288 | 0.0467 |

Fig. 116B

| CT Variable | Low PLR, n (%) | Moderate PLR, n (%) | High PLR, n (%) | $X^2$ | p-value |
|---|---|---|---|---|---|
| SDH | 76 (71.03) | 78 (72.22) | 67 (67) | 0.7248 | 0.6925 |
| SAH | 71 (66.36) | 85 (78.7) | 79 (79) | 5.8207 | 0.0545 |
| EDH | 17 (15.89) | 27 (25) | 14 (14) | 4.8698 | 0.0876 |
| IVH | 39 (36.45) | 43 (39.81) | 40 (40) | 0.3562 | 0.8369 |
| IPH | 54 (50.47) | 61 (56.48) | 62 (62) | 2.7985 | 0.2468 |
| DAI | 11 (10.28) | 13 (12.04) | 13 (13) | 0.3822 | 0.8260 |
| Contusion | 69 (64.49) | 77 (71.3) | 58 (58) | 4.0278 | 0.1335 |
| Midline shift | 31 (30.39) | 31 (32.98) | 35 (40.23) | 2.1222 | 0.3461 |
| Extraaxial | 96 (89.72) | 100 (92.59) | 94 (94) | 1.3591 | 0.5068 |
| Intraaxial | 89 (83.18) | 98 (90.74) | 85 (85) | 2.8346 | 0.2424 |

|  | Low NLR TRAJ | Moderate NLR TRAJ | High NLR TRAJ | p-value |
|---|---|---|---|---|
| Satisfaction with Life Scale Score (6mo.), Mean (SE) | 62.39 (5.4) | 68.60 (3.8) | 78.89 (3.9) | 0.0220 |
| Percent Back to Normal (6mo.), Mean (SE) | 71.82 (3.7) | 68.79 (4.1) | 60.30 (5.1) | 0.0183 |
| PHQ-9 Total Score (6mo.), Mean (SE) | 4.41 (0.7) | 6.09 (0.9) | 7.77 (1.2) | 0.0460 |

FIG. 117A

|  | Low NLR TRAJ | Moderate NLR TRAJ | High NLR TRAJ | p-value |
|---|---|---|---|---|
| Satisfaction with Life Scale Score (6mo.), Mean (SE) | 62.39 (5.4) | 68.60 (3.8) | 78.89 (3.9) | 0.0220 |
| Percent Back to Normal (6mo.), Mean (SE) | 71.82 (3.7) | 68.79 (4.1) | 60.30 (5.1) | 0.0183 |
| PHQ-9 Total Score (6mo.), Mean (SE) | 4.41 (0.7) | 6.09 (0.9) | 7.77 (1.2) | 0.0460 |

|  | Low NLR TRAJ | | | Moderate NLR TRAJ | | | High NLR TRAJ | | | |
| --- | --- | --- | --- | --- | --- | --- | --- | --- | --- | --- |
|  | Mean | SE | n | Mean | SE | n | Mean | SE | n | p-value |
| sIL-6R | 667.11 | 80.32 | 22 | 364.96 | 51.76 | 42 | 549.83 | 83.77 | 22 | 0.0054 |
| sgp130 | 21919.16 | 3158.78 | 22 | 11813.20 | 1681.12 | 42 | 14844.06 | 2268.75 | 22 | 0.0056 |
| sIL-2Ra | 19.16 | 3.93 | 18 | 10.31 | 2.13 | 35 | 14.75 | 4.46 | 20 | 0.0241 |
| sIL-1RII | 309.54 | 51.11 | 16 | 212.02 | 77.31 | 27 | 350.12 | 128.17 | 12 | 0.0275 |
| sTNFRI | 1100.73 | 176.62 | 22 | 606.54 | 79.92 | 42 | 867.80 | 195.04 | 22 | 0.0506 |
| sTNFRII | 2652.17 | 348.52 | 22 | 1657.00 | 170.56 | 42 | 2260.34 | 464.97 | 22 | *0.0741* |
| MIP-3a | 42.87 | 10.01 | 23 | 18.44 | 2.89 | 44 | 34.54 | 10.84 | 23 | 0.0073 |
| NCAM | 57412.92 | 9482.02 | 22 | 32246.70 | 3260.19 | 42 | 36781.18 | 4910.81 | 22 | 0.0139 |
| IL-10 | 20.20 | 3.91 | 18 | 8.73 | 1.75 | 34 | 15.37 | 4.79 | 19 | 0.0157 |
| sICAM-1 | 982.52 | 173.99 | 22 | 532.31 | 81.29 | 42 | 706.57 | 132.50 | 22 | 0.0273 |
| IL-5 | 0.77 | 0.22 | 24 | 0.41 | 0.03 | 44 | 0.49 | 0.07 | 24 | 0.0472 |

Fig. 118B

|  | Low PLR TRAJ | | | Moderate PLR TRAJ | | | High PLR TRAJ | | | |
| --- | --- | --- | --- | --- | --- | --- | --- | --- | --- | --- |
|  | Mean | SE | n | Mean | SE | n | Mean | SE | n | p-value |
| MIP-3a | 40.70 | 9.18 | 24 | 25.63 | 5.15 | 30 | 23.50 | 7.00 | 36 | 0.0067 |
| sICAM-1 | 1022.56 | 192.02 | 24 | 611.11 | 84.03 | 27 | 527.87 | 78.64 | 35 | 0.0589 |
| IL-5 | 0.74 | 0.22 | 25 | 0.49 | 0.05 | 30 | 0.41 | 0.04 | 37 | *0.0908* |
| sIL-6R:IL-6 | 1.70 | 0.41 | 24 | 2.20 | 0.43 | 27 | 3.98 | 1.10 | 35 | *0.1083* | higher in the low NLR TRAJ

Fig. 120A

|  | Low NLR TRAJ | | | Moderate NLR TRAJ | | | High NLR TRAJ | | | |
|---|---|---|---|---|---|---|---|---|---|---|
|  | Mean | SE | n | Mean | SE | n | Mean | SE | n | p-value |
| MIP-1b | 92.92 | 18.58 | 77 | 126.02 | 18.92 | 72 | 109.60 | 26.09 | 46 | 0.0056 |
| IL-8 | 292.54 | 100.95 | 77 | 264.13 | 58.03 | 70 | 483.08 | 151.41 | 46 | *0.1064* |
| sTNFRI | 1350.18 | 92.31 | 77 | 1479.85 | 67.71 | 72 | 1967.81 | 164.03 | 46 | <.0001 |
| sCD30 | 42.39 | 6.38 | 71 | 32.75 | 3.03 | 67 | 71.60 | 17.49 | 40 | 0.0029 |
| sIL-6R | 24311.96 | 768.78 | 77 | 23361.63 | 810.10 | 72 | 27068.20 | 1110.71 | 46 | 0.0245 |
| sTNFRII | 8249.32 | 416.77 | 77 | 9285.70 | 373.23 | 72 | 10994.01 | 828.53 | 46 | 0.0014 |
| sIL-1RII | 9190.23 | 313.95 | 77 | 9700.36 | 432.97 | 72 | 10618.51 | 628.77 | 46 | *0.0638* |
| sTNFRII:sTNFRI | 6.61 | 0.20 | 77 | 6.80 | 0.28 | 72 | 5.95 | 0.23 | 46 | *0.0780* |
| sTNFRI:TNFa | 148.69 | 76.95 | 77 | 75.15 | 4.73 | 72 | 102.58 | 12.29 | 46 | *0.0632* |
| sgp130:sIL6R | 6.86 | 0.28 | 77 | 7.21 | 0.29 | 72 | 6.17 | 0.29 | 46 | 0.0236 |

Fig. 120B

|  | Low PLR TRAJ | | | Moderate PLR TRAJ | | | High PLR TRAJ | | | |
|---|---|---|---|---|---|---|---|---|---|---|
|  | Mean | SE | n | Mean | SE | n | Mean | SE | n | p-value |
| ITAC | 167.94 | 14.26 | 71 | 182.49 | 17.20 | 70 | 269.02 | 33.07 | 55 | 0.0119 |
| MIP-1b | 90.38 | 20.70 | 71 | 135.89 | 23.40 | 70 | 98.27 | 12.26 | 55 | 0.0240 |
| sgp130 | 145666.96 | 4157.63 | 71 | 156778.37 | 3866.05 | 70 | 166611.84 | 4240.87 | 55 | 0.0021 |
| RANTES | 46240.57 | 2926.71 | 71 | 57897.75 | 4316.34 | 70 | 65522.06 | 4638.78 | 55 | 0.0008 |
| NCAM | 252490.87 | 8315.10 | 71 | 284864.14 | 11588.59 | 70 | 279523.38 | 12531.71 | 55 | *0.0858* |

| Model Variable | Model 1 | | | Model 2 | | | Model 3 | | |
|---|---|---|---|---|---|---|---|---|---|
| | OR (CI) | p-value | | OR (CI) | p-value | | OR (CI) | p-value | |
| Age | 1.03 (1.0-1.1) | 0.0004 | | 1.04 (1.0-1.1) | 0.0004 | | 1.0 (0.98-1.1) | 0.3050 | |
| GCS score *(best in 24hr.)* | 0.69 (0.2-0.8) | <0.0001 | | 0.70 (0.6-0.8) | <0.0001 | | 0.75 (0.6-0.9) | 0.0001 | |
| Male vs. Female | 0.32 (0.1-0.7) | 0.0067 | | 0.33 (0.1-0.8) | 0.0088 | | 0.38 (0.1-1.0) | 0.0590 | |
| Positive Infection Status | 1.62 (0.9-2.9) | 0.1161 | | 1.45 (0.8-2.7) | 0.2011 | | 1.33 (0.6-2.9) | 0.4691 | |
| Moderate/High vs. Low PLR TRAJ | 1.54 (0.8-3.0) | 0.2088 | | - | - | | - | - | |
| Moderate/High vs. Low NLR TRAJ | - | - | | 2.66 (1.3-5.3) | 0.0054 | | 2.49 (1.1-5.9) | 0.0398 | |
| sTNFRI *(2-times means, scaled x 0.01)* | - | - | | - | - | | 1.06 (1.0-1.1) | 0.0593 | |
| Area under the curve (AUC); c | 0.79 | | | 0.81 | | | 0.80 | | |

FIG. 122

BIOMARKERS AND TREATMENT METHODS FOR TRAUMATIC BRAIN INJURY-ASSOCIATED IMPAIRMENTS

CROSS-REFERENCE TO RELATED APPLICATIONS

This application is a continuation of International Patent Application No. PCT/US2019/039879, filed on Jun. 28, 2019, which claims priority to U.S. Provisional Application No. 62/692,364, filed on Jun. 29, 2018, the contents of each of which are hereby incorporated by reference in their entireties, and to each of which priority is claimed.

GRANT INFORMATION

This invention was made with government support under 90DP0041 awarded by the Administration for Community Living/National Institute on Disability, Independent Living, and Rehabilitation Research; R49 CE323155 awarded by the Center for Disease Control; and W81XWH-07-1-0701 awarded by the Army/MRMC. The government has certain rights in the invention.

1. TECHNICAL FIELD

The present disclosure relates to methods, compositions, and kits for treating traumatic brain injury (TBI) and TBI-associated impairments in a subject. The methods include administering to the subject an interleukin-7 (IL-7) or IL-7 agonist, a TNFα inhibitor, or both. The present disclosure also relates to methods of using biomarkers for identifying a subject that is likely to respond to a treatment for TBI-associated impairments, and monitoring the subject's response to such treatment.

2. BACKGROUND

Traumatic brain injury (TBI) results in at least 2.5 million visits to hospitals and emergency departments annually in the United States, and the incidence of TBI is increasing (Centers for Disease Control and Prevention, National Center for Injury Prevention and Control, 2016a. TBI. Get the Facts; Centers for Disease Control and Prevention, National Center for Injury Prevention and Control, 2016b. Rates of TBI-related Emergency Department Visits, Hospitalizations, and Deaths by Sex—United States, 2001-2010). The long-term effects of TBI are prevalent and debilitating; it is estimated that 1.1% of Americans live with TBI-related disabilities (Zaloshnja et al., 2008 J. Head Trauma Rehabil. 23, 394-400).

One contributor to post-injury disability is hypogonadotropic hypogonadism (e.g., persistent hypogonadotropic hypogonadism (PHH), which is a well-documented chronic complication of TBI (Masel and Urban, 2014, J. Neurotrauma 32, 1902-1910). In the largest prospective cohort screening study to date, 340 individuals with TBI admitted to inpatient rehabilitation were screened for pituitary hormone deficiencies (Kopczak et al., 2014, J. Neurotrauma 31, 99-107). Thirty-seven percent were noted to have lab values consistent with hypopituitarism, and the most common deficiency was hypogonadism, where 40% of men were deficient in testosterone. Further, symptoms such as fatigue can be manifestations of hypogonadism that directly influence cognitive function. Certain screening consensus for post-traumatic hypopituitarism is based on limited and contradictory evidence on the timeframe in which hypopituitarism develops, with a paucity of evidence on the safety and efficacy of hormone replacement therapy after TBI.

Post-traumatic epilepsy (PTE) negatively impacts recovery of individuals coping with TBI and its comorbidities. PTE accounts for 20% of symptomatic seizures and 5% of all seizures in the general population with higher rates in the military population. The most common comorbid conditions associated with epilepsy in the general population are psychiatric disorders. Health related quality of life (QOL) is often poor among those living with epilepsy, in part due to comorbid disease burden. Further, clear evidence-based guidelines on how to prevent the development of PTE are lacking.

Another contributor to post-injury disability is cognitive deficits due to TBI, which can impair the affect individuals' overall neurorecovery through reduced capacities for activities of daily living, social relationships, recreation, and active participation in the community. Common cognitive impairments following TBI include attention and memory deficits, impaired visual or spatial conceptualization, disturbance of executive function. Disturbances of attention and memory are particularly problematic, as disruption of these primary cognitive functions can cause or exacerbate additional disturbances in executive function, communication, and other relatively more complex cognitive functions.

There have been certain efforts over the last several decades to identify acute neuroprotective treatments for TBI populations. However, mortality rates for severe TBI are largely unchanged over the last decade. There are also still no treatments that have received a Level I recommendation for efficacy in the recent $4^{th}$ edition TBI Guidelines, and no treatments have been approved by the Food and Drug Administration following Phase III trials.

Thus, there remain needs for effective treatments of TBI-associated impairments.

3. SUMMARY

The present disclosure provides methods, compositions, and kits for treating traumatic brain injury (TBI) and TBI-associated impairments (e.g., neuroendocrine dysfunctions, PTE, and deficits to neurorecovery) in a subject. In certain embodiments, treatment methods disclosed herein include administering to the subject an interleukin-7 (IL-7) or IL-7 agonist, and/or a TNFα inhibitor.

The present disclosure also provides biomarkers for use in identifying a subject that is likely to develop a TBI-associated impairment. The biomarkers disclosed herein can also be used for identifying a subject that is likely to respond to a treatment for TBI-associated impairments.

In one aspect, the present disclosure provides a method of treating a TBI, or treating or reducing the risk of a TBI-associated impairment in a subject, including administering to the subject an interleukin-7 (IL-7) or an IL-7 agonist, and/or a TNFα inhibitor.

In certain embodiments, the method improves outcome of TBI in the subject. In certain embodiments, the method reduces long-term disability in the subject. In certain embodiments, the method promotes central nervous system repair, regeneration, and/or remodeling in the subject. In certain embodiments, the method increases a Glasgow Outcome Score of the subject.

In certain embodiments, the method increases serum IgM level in the subject. In certain embodiments, the method increases serum IgM:IgG ratio in the subject. In certain embodiments, the IgM includes anti-pituitary (APA) IgM, anti-hypothalamus (AHA) IgM, or a combination thereof. In certain embodiments, the IgG includes APA IgG, AHA IgG, or a combination thereof. In certain embodiments, the method alters levels of IL-7, TNF-α, soluble receptor proteins (e.g. sTNFR1, sIL-2ra, TNFRII), and chemokines (RANTES, ITAC) in the subject.

In certain embodiments, the TBI-associated impairment is selected from the group consisting of deficits to neurorecovery, PTE, cognitive deficits (e.g., attention deficit, memory deficit, and impaired visual or spatial conceptualization), psychological deficits (e.g., personality changes, mood disturbance, substance abuse), somatic symptoms (e.g., headaches, visual disturbances), emotional symptoms (e.g., irritability), behavioral dysfunctions (e.g., aggression, apathy, impulsivity), physical dysfunctions (e.g., cranial or peripheral nerve damage, impairment in motor functioning, strength and coordination, or impairment in sensation), and hypogonadotropic hypogonadism (e.g., PHH), and other neuroendocrine dysfunction. In certain embodiments, the TBI-associated impairment is a neuroendocrine dysfunction. In certain embodiments, the neuroendocrine dysfunction is selected from pituitary deficiencies, gonadotropin deficiencies, adrenocorticotropic hormone deficiencies, thyroid deficiency, and prolactin deficiencies. In certain embodiments, the neuroendocrine dysfunction is TBI-associated hypogonadotropic hypogonadism. In certain embodiments, the TBI-associated hypogonadotropic hypogonadism is a TBI-associated persistent hypogonadotropic hypogonadism (PHH). In certain embodiments, the TBI-associated impairment is a deficit of neurorecovery. In certain embodiments, the deficit to neurorecovery is post traumatic epilepsy (PTE). In certain embodiments, the deficit to neurorecovery is a cognitive deficit. In certain embodiments, the cognitive deficit is a memory deficit, an attention deficit, or an impaired visual or spatial conceptualization.

In certain embodiments, the IL-7 or the IL-7 agonist, and/or the TNFα inhibitor, is administered to the subject at the post-acute and/or chronic stage of the TBI. In certain embodiments, the IL-7 or the IL-7 agonist, and/or the TNFα inhibitor is administered to the subject between about 24 hours and about 3 days, between about 24 hours and about 3 weeks, between about 24 hours and about 3 months, between 24 hours and about 6 months, between 24 hours and about 8 months, or between 24 hours and 12 months after occurrence of TBI.

In certain embodiments, the IL-7 is a recombinant IL-7. In certain embodiments, the IL-7 is a recombinant human IL-7.

In certain embodiments, the TNFα inhibitor is a monoclonal antibody. In certain embodiments, the TNFα inhibitor is selected from adalimumab (Humira), adalimumab-adbm (Cyltezo), adalimumab-adaz (Hyrimoz), adalimumab-atto (Amjevita), certolizumab pegol (Cimzia), etanercept (Enbrel), eanercept-szzs (Ereizi), golimumab (Simponi, Simponi Aria), infliximab (Remicade), infliximab-abda (Renflexis), infliximab-dyyb (Inflectra), infliximab-qbtx (Ixifi), thalidomide (Immunoprin), lenalidomide (Revlimid), pomalidomide (Pomalyst, Imnovid), xanthine derivatives, pentoxifylline), bupropion, hallucinogens (e.g., (R)-DOI, TCB-2, LSD and LA-SS-Az), biosimilars thereof, and combinations thereof. In certain embodiments, the TNFα inhibitor is etanercept.

In another aspect, the present disclosure provides a method for monitoring a subject's responsiveness to a treatment for a TBI-associated impairment, including: (a) determining the level of a biomarker in a sample obtained from the subject before receiving the treatment; (b) determining the level of the biomarker in a sample obtained from the subject during or after receiving the treatment; and (c) comparing the levels of the biomarker in the samples, where a change of the level of the biomarker during or after the treatment indicates the responsiveness of the subject to the treatment.

In certain embodiments, the method further includes continuing the treatment if the subject is responsive to the treatment. In certain embodiments, the method includes treating the subject with a different treatment for the TBI-associated impairment if the subject is not responsive to the treatment.

In another aspect, the present disclosure provides a method for identifying a subject who has sustained TBI as likely to respond to a treatment for a TBI-associated impairment, including: (a) determining the level of a biomarker in a sample obtained from the subject; (b) comparing the level of the biomarker to a reference level of the biomarker; and (c) identifying the subject as likely to respond to the treatment based on the comparison.

In certain embodiments, the method further includes administering the treatment to the subject that is identified as likely to respond to the treatment.

In certain embodiments, the sample is a blood sample. In certain embodiments, the blood sample is a plasma sample, a serum sample, or a central nervous system (CNS)-derived exosomal fraction of the blood sample.

In certain embodiments, the biomarker is selected from the group consisting of IL-7, soluble tumor necrosis factor receptors (e.g., sTNFRI, and sTNFRII), autoantibodies, hormones, white blood cells indices (e.g., Neutrophil-Lymphocyte Ratio (NLR), absolute lymphocyte counts), TNF-α, BDNF, soluble receptor proteins, chemokines, and combinations thereof. In certain embodiments, the sTNFR is sTNFRI. In certain embodiments, the autoantibody is selected from APA IgM, APA IgG, AHA IgM, AHA IgG, any IgG or IgM autoantibodies, and combinations thereof. In certain embodiments, the hormone is selected from the group consisting of gonadotropins, testosterone, estrogens, progesterone, thyroid hormones, growth hormones, adrenal hormones, prolactin, vasopressin, oxytocin, and combinations thereof. In certain embodiments, the soluble receptor protein includes sIL2Ra. In certain embodiments, the chemokine includes RANTES, ITAC, and combination thereof.

In certain embodiments, the treatment includes administering an IL-7 or an IL-7 agonist, and/or a TNFα inhibitor.

In certain embodiments, the biomarker is sTNFRI, and if the level of sTNFRI is higher than the reference level of sTNFRI, the subject is likely to respond to the treatment including administering the TNFα inhibitor. In certain embodiments, the reference level of sTNFR is about 1500 pg/ml.

In certain embodiments, the biomarker is NLR, and if the level of NLR is higher than the reference level of the NLR, the subject is likely to respond to the treatment including administering the TNFα inhibitor. In certain embodiments, the reference level of the NLR is about 10.

In certain embodiments, the biomarker is IL-7, and if the level of IL-7 is lower than the reference level of the IL-7, the subject is likely to respond to the treatment including administering the IL-7. In certain embodiments, the reference level of IL-7 is about 25 pg/ml.

In another aspect, the present disclosure provides a method for identifying a subject who has sustained TBI as likely to respond to a treatment including an IL-7 or an IL-7 agonist, including: (a) determining the levels of IL-7 in at least two samples obtained from the subject; and (b) assigning a trajectory group membership to the subject based on the levels of IL-7, wherein if the subject is assigned a low IL-7 trajectory group membership, the subject is likely to respond to the treatment.

In certain embodiments, the method further includes administering the treatment to the subject that is identified as likely to respond to the treatment.

In another aspect, the present disclosure provides a method for identifying a subject who has sustained TBI as likely to respond to a treatment including a TNFα inhibitor, including: (a) determining the levels of sTNFR (e.g., sTN-FRI) in at least two samples obtained from the subject; (b) assigning a trajectory group membership to the subject based on the levels of sTNFR, wherein if the subject is assigned a high sTNFR trajectory group membership, the subject is likely to respond to the treatment.

In certain embodiments, the method further includes administering the treatment to the subject that is identified as likely to respond to the treatment.

In another aspect, the present disclosure provides methods for treating a TBI-associated impairment in a subject, including: (a) determining the levels of sTNFR (e.g., sTN-FRI) and the IL-7 in at least two samples obtained from the subject; (b) assigning trajectory group memberships to the subject by assessing the IL-7 and sTNFR levels of the subject in relation to group-based trajectory analyses derived from a population with TBI; and (c-i) treating the subject with an IL-7 or an IL-7 agonist if the subject is assigned a low IL-7 trajectory group membership and a low sTNFR trajectory group membership, (c-ii) treating the subject with an IL-7 or an IL-7 agonist and a TNFα inhibitor if the subject is assigned a low IL-7 trajectory group membership and a high sTNFR trajectory group membership, or (c-iii) treating the subject with a TNFα inhibitor if the subject is assigned a high IL-7 trajectory group membership and a high sTNFR trajectory group membership.

In certain embodiments, the dose of IL-7 or IL-7 agonist is higher in (c-ii) than in (c-i).

In another aspect, the present disclosure provides a method for predicting a subject who has sustained TBI as likely to develop a TBI-associated impairment, including: (a) determining the level of a biomarker in a sample obtained from the subject; (b) comparing the level of the biomarker to a reference level of the biomarker; and (c) predicting the subject as likely to develop the TBI-associated impairment based on the comparison.

In certain embodiments, the biomarker is selected from the group consisting of IL-7, soluble tumor necrosis factor receptors (e.g., sTNFRI, sTNFRII), autoantibodies, hormones, white blood cells indices (e.g., Neutrophil-Lymphocyte Ratio (NLR), absolute lymphocyte counts), TNFα, BDNF, soluble receptors (e.g., sIL-2Ra), chemokines (e.g., RANTES, ITAC), and combinations thereof.

In certain embodiments, the biomarker is sTNFRI, and if the level of sTNFRI is higher than the reference level of sTNFRI, the subject is likely to develop the TBI-associated impairment. In certain embodiments, the reference level of sTNFRI is about 1500 pg/ml.

In certain embodiments, the biomarker is NLR, and if the level of NLR is higher than the reference level of the NLR, the subject is likely to develop the TBI-associated impairment. In certain embodiments, the reference level of NLR is about 10.

In certain embodiments, the biomarker is IL-7, and if the level of IL-7 is lower than the reference level of the IL-7, the subject is likely to develop the TBI-associated impairment. In certain embodiments, the reference level of IL-7 is about 25 pg/ml.

In another aspect, the present disclosure provides a kit for identifying a subject who has sustained TBI as likely to respond to a treatment for a TBI-associated impairment, including a means for detecting a biomarker, wherein the biomarker is selected from the group consisting of IL-7, soluble tumor necrosis factor receptors (e.g., sTNFRI, and sTNFRII), autoantibodies, hormones, white blood cells indices (e.g., Neutrophil-Lymphocyte Ratio (NLR), absolute lymphocyte counts), TNFα, BDNF, soluble receptors (e.g., sIL-2Ra), chemokines (e.g., RANTES, ITAC), and combinations thereof.

In another aspect, the present disclosure provides a kit for monitoring a subject's responsiveness to a treatment for a TBI-associated impairment, including a means for detecting a biomarker, wherein the biomarker is selected from the group consisting of IL-7, soluble tumor necrosis factor receptors (e.g., sTNFRI, and sTNFRII), autoantibodies, hormones, white blood cells indices (e.g., Neutrophil-Lymphocyte Ratio (NLR), absolute lymphocyte counts), TNFα, BDNF, soluble receptors (e.g., sIL-2Ra), chemokines (e.g., RANTES, ITAC), and combinations thereof.

In certain embodiments, the sTNFR is sTNFRI. In certain embodiments, the autoantibody is selected from the group consisting of APA IgM, APA IgG, AHA IgM, AHA IgG, any IgG or IgM autoantibodies, and combinations thereof. In certain embodiments, the hormone is selected from the group consisting of gonadotropins, testosterone, estrogens, progesterone, thyroid hormones, growth hormones, adrenal hormones, prolactin, vasopressin, oxytocin, and combinations thereof.

In one aspect, the present disclosure provides a method of treating a subject that has sustained TBI including administering, to the subject, an IL-7 or an IL-7 agonist.

In another aspect, the present disclosure provides a method of improving outcome in a subject that has sustained TBI including administering, to the subject, an IL-7 or an IL-7 agonist.

In another aspect, the present disclosure provides a method of treating a subject suffering from a TBI-associated impairment including administering to the subject an IL-7 or an IL-7 agonist. In certain embodiments, the TBI-associated impairment is selected from the group consisting of a cognitive deficit, a psychological deficit, a somatic symptom, an emotional symptom, a behavioral dysfunction, a physical dysfunction, and a hypogonadotropic hypogonadism.

In another aspect, the present disclosure provides a method of promoting nerve repair/regeneration/remodeling, including administering, to a subject that has sustained TBI, an IL-7 or an IL-7 agonist. In certain embodiments, the never repair is a central nervous system repair.

In another aspect, the present disclosure provides a method for reducing the risk of TBI-associated hypogonadotropic hypogonadism in a subject suffering from a sustained TBI including administering to the subject an IL-7 or an IL-7 agonist.

In another aspect, the present disclosure provides a method for treating TBI-associated hypogonadotropic hypogonadism in a subject that has sustained TBI, including administering to the subject an IL-7 or an IL-7 agonist. In certain embodiments, the hypogonadotropic hypogonadism is a persistent hypogonadotropic hypogonadism (PHH).

In another aspect, the present disclosure provides a method of treating a TBI-associated cognitive deficit including administering, to a subject that has sustained TBI, an IL-7 or an IL-7 agonist.

In certain embodiments, the TBI-associated cognitive deficit is a memory deficit.

In certain embodiments, the TBI-associated cognitive deficit is an attention deficit. In certain embodiments, the TBI-associated cognitive deficit is an impaired visual or spatial conceptualization.

In another aspect, the present disclosure provides a method of promoting IgM over IgG antibody levels, including anti-pituitary (APA) and anti-hypothalamus (AHA) antibody levels, in a subject that has sustained TBI, including administering, to the subject, an IL-7 or an IL-7 agonist.

In certain embodiments, the IL-7 is a recombinant IL-7. In certain embodiments, the IL-7 is a human recombinant IL-7.

In another aspect, the present disclosure provides a method for identifying a subject that is likely to respond to a treatment for a TBI-associated impairment, where the subject has sustained TBI, including measuring the level of a biomarker in a sample obtained from the subject, where the level of the biomarker indicates the likelihood of the subject to respond to the treatment. In certain embodiments, the method further includes treating the subject that is identified to be likely to respond to the treatment.

In another aspect, the present disclosure provides a method for monitoring a subject's responsiveness to a treatment for a TBI-associated impairment, where the subject has sustained TBI, including measuring a biomarker in a sample obtained from the subject before, during and/or after receiving the treatment, where a change of the level of the biomarker indicates the responsiveness of the subject to the treatment.

In certain embodiments, the TBI-associated impairment is a hypogonadotropic hypogonadism. In certain embodiments, the biomarker is selected from the group consisting of IL-7, APA IgM, AHA IgM, APA IgG, or AHA IgG, gonadotropin and testosterone. In certain embodiments, the treatment is an IL-7 or an IL-7 agonist.

In another aspect, the present disclosure provides a kit for identifying a subject that is likely to respond to a treatment for a TBI-associated impairment, including a means for detection a biomarker that is selected from the group consisting of IL-7, APA IgM, AHA IgM, APA IgG, or AHA IgG, gonadotropin and testosterone.

In another aspect, the present disclosure provides a kit for monitoring a subject's responsiveness to a treatment for a TBI-associated impairment, including a means for detection a biomarker that is selected from the group consisting of IL-7, APA IgM, AHA IgM, APA IgG, or AHA IgG, gonadotropin and testosterone.

In certain embodiments, the subject is a human subject.

4. BRIEF DESCRIPTION OF THE DRAWINGS

FIG. 1 provides demographic and clinical information on cohorts relating to APA IgM/IgG.

FIG. 2 provides demographic and clinical information on cohorts relating to AHA IgM/IgG.

FIG. 3 provides ordinal logistic regression results of APA IgM/IgG.

FIG. 4 provides ordinal logistic regression results of AHA IgM/IgG.

FIG. 5 provides bar figures showing that mean GFAP AAb levels in the first 6 months post injury were associated with PTE rates during the first year of recovery.

FIGS. 6A-6B provide bar figures showing IL-7 levels by APA IgM (6A) and AHA IgM (6B) trajectory group membership.

FIG. 7 provides bar figures showing IL-7 levels by APA IgG TRAJ in subjects older than 31 years old, and in subjects younger than 31 years old.

FIG. 8 provides bar figures showing association of IL-7 with GFAP IgM autoantibodies. For each TRAJ group, the left bar represents measurements from 2 weeks-3 months, the right bar represents measurements from 4-6 months.

FIG. 9 provides demographic information of the enrolled subjects.

FIG. 10 provides ordinal logistic regression results for APA and AHA IgM autoantibodies and IL-7 levels at 2-week to 6-month post TBI.

FIGS. 11A-11B provide bar figures showing that IL-7 levels over a 6-month time period increased from low to high APA IgM TRAJ group membership (11A) and from low to high AHA IgM TRAJ group membership (111B).

FIG. 12 provides ordinal logistic regression results for APA and AHA IgG autoantibodies and IL-7 levels 2-week to 6-month post TBI.

FIG. 13. provides bar figures showing in the low IgG TRAJ group, the group of individuals<age 31 had higher levels of IL-7 up to 6 months post injury than the individuals above the median age. In the high TRAJ group, individuals>age 31 years had higher IL-7 levels up to 6mo post injury than the individuals<age 31 years.

FIGS. 14A-14J provide APA IgM and IgG fluorescence immunohistochemistry staining. Human cadaveric pituitary tissue was stained with control (14 E and 14J) or injured (14A-14D and 14 F-14I) subjects' serum which demonstrated specificity of the APA assay for pituitary tissue. Subjects with higher serum levels of APA demonstrated the highest density staining (+++), and subjects with lower APA levels had less dense staining (+). Uninjured control subject serum had negative staining for APA IgM (14E) but some staining present for APA IgG (14J). (14A) IgM APA staining of TBI subject assigned to high APA IgM group; (14B) IgM APA staining of TBI subject assigned to low APA IgM group; (14C) IgM APA staining of TBI subject assigned to high APA IgM, low IgM/IgG group; (14D) IgM APA staining of TBI subject assigned to low APA IgM, low IgM/IgG group; (14E) IgM APA staining of control subject; (14F) IgG APA staining of TBI subject assigned to high APA IgM group; (14G) IgG APA staining of TBI subject assigned to low APA IgM group; (14H) IgG APA staining of TBI subject assigned to high APA IgM, low IgM/IgG group; (14I) IgG APA staining of TBI subject assigned to low APA IgM, low IgM/IgG group; (14J) IgG APA staining of control subject.

FIGS. 15A-15J provide AHA IgM and IgG fluorescence immune-histochemistry staining. Human cadaveric hypothalamic tissue was stained with control (15E and 15J) or injured (15A-15D and 15 F-15I) subjects' serum which demonstrates specificity of the AHA assay for hypothalamus tissue. Subjects with higher serum levels of AHA demonstrated the highest density staining (+++), and subjects with lower AHA levels had less dense staining (+). Uninjured control subject serum had negative staining for IgM and IgG (15E and 15J). (15A) IgM AHA staining of TBI subject assigned to high AHA IgM group; (15B) IgM AHA staining of TBI subject assigned to low AHA IgM group; (15C) IgM AHA staining of TBI subject assigned to high AHA IgM, low IgM/IgG group; (15D) IgM AHA staining of TBI subject assigned to low AHA IgM, low IgM/IgG group; (15E) IgM AHA staining of control subject; (15F) IgG AHA staining of TBI subject assigned to high AHA IgM group; (15G) IgG AHA staining of TBI subject assigned to low AHA IgM group; (15H) IgG AHA staining of TBI subject assigned to high AHA IgM, low IgM/IgG group; (15I) IgG AHA staining of TBI subject assigned to low AHA IgM, low IgM/IgG group; (15J) IgG AHA staining of control subject.

FIGS. 16A-16H provide mean autoantibody levels, including APA IgM (16A, 16E), APA IgG (16B, 16F), AHA IgM (16C, 16G), AHA IgG (16D, 16H) by PHH status. (16A, 16E) Anti-pituitary autoantibody (APA) IgM concentrations are lower in PHH than in non-PHH group. (16B-16D, 16F-16H) No statistically significant differences existed between PHH and non-PHH groups in APA IgG (p=0.06), AHA IgM (p=0.20), or AHA IgG (p=0.38). All individual values were means of samples collected 2-26 weeks. N=61.

FIGS. 17A-17D provide results of group-based trajectory analysis (TRAJ). TRAJ was performed on APA IgM and AHA IgM separately to identify distinct groups with similar temporal autoantibody level profiles 2-26 weeks post-injury. Three groups were identified in each analysis, which was denoted as low, medium, and high. Autoantibody levels significantly differed at all time points for APA IgM (17A) and AHA IgM (17C) by Kruskal-Wallis tests (p<0.05). APA IgG levels (17B) differed significantly (p<0.05) at weeks 0, 1, 4, 6, 8, 10, 22, and 24. AHA IgG levels were similar at all time points (17D; p>0.05). Dashed lines represent mean control levels (APA IgM, 0.4995 µg/mL; APA IgG, 0.6682 µg/mL; AHA IgM, 6.3073 µg/mL; and AHA IgG, 5.8697 µg/mL).

FIGS. 17E-17H provide group-based trajectory analysis (TRAJ) analysis showing unique clusters of individuals with similar biomarker profiles 6 months post TBI. Two groups were identified, which were denoted as low and high for APA IgM (17E), AHA IgM (17F), APA IgG (17G), and APA IgG (17H).

FIGS. 18A-18B provide testosterone levels by APA and AHA TRAJ groups from week 0 to week 26. Testosterone levels graphed by TRAJ groups for APA IgM (18A) and AHA IgM (18B). Testosterone levels nadir at 1-2 weeks after TBI. (18A) Significant differences were noted in testosterone levels by APA IgM TRAJ group at weeks 8, 16, and 20 (p<0.05). (18B) No significant differences were observed in testosterone levels by AHA IgM TRAJ group at all time points. Dashed lines represent mean control level (11.1 nmol/L).

FIGS. 19A-19B provide autoantibody IgM:IgG ratios graphed by TRAJ groups. (19A) APA ratios differed significantly by APA TRAJ group using Kruskal-Wallis test (p<0.001). Ratios were lowest in the low TRAJ group which differed significantly in pairwise comparisons from the medium (p<0.01) and high (p<0.001) TRAJ groups. (19B) AHA ratios differed by AHA TRAJ group (p=0.006). Pairwise comparisons revealed a higher ratio in the high group relative to the low group (p=0.005). Dashed lines represent healthy control levels (APA, 0.797; AHA, 2.234).

FIG. 20 provides mediation analysis of variables' effect on persistent hypogonadotropic hypogonadism (PHH) outcome. Age and anti-pituitary autoantibody (APA) are associated with PHH among men with severe traumatic brain injury.

FIG. 21A provides spleen lymphocyte group comparison in samples collected on day 21. For each cell group, the left bar represents measurements from CCI Hi Dose group, the middle bar represents measurements from CCI Low Dose group, and the right bar represents measurements from Sham Group.

FIG. 21B provides spleen lymphocyte group comparison in samples collected on day 21. For each cell, the left bar represents measurements from CCI Hi Dose group, the middle bar represents measurements from CCI Low Dose group, and the right bar represents measurements from Sham Group.

FIG. 22A provides post-injury spleen lymphocyte numbers were reduced in samples collected from day 21 low dose IL-7 group when compared with samples collected from day 2 CCI harvest vehicle. Such reduction was partial rescued by high dose rhIL-7 on day 21.

FIG. 22B provides spleen lymphocyte rescue comparison between day 2 and day 27.

FIGS. 23A-23E provide results of novel Object Recognition Test performed on D8 post injury. Entries per cohort (23A, 23D), time per cohort (23B, 23E), and average discrimination index (23C) were measured in each group. (23A, 23B, 23D, 23E) For each group, left bar represents reminder measurements, and right bar represents test measurements.

FIG. 24 provides latency measurements of Morris water maze acquisition trials.

FIG. 25A provides latency measurements of Morris water maze visible platform (VP) trials.

FIG. 25B provides additional latency measurements of Morris water maze visible platform (VP) trials.

FIG. 26A provides peripheral zone time allocation (PZTA) measurements of Morris water maze visible platform (VP) trials.

FIG. 26B provides latency measurements of Morris water maze visible platform (VP) trials.

FIG. 26C provides measurements of Morris water maze visible platform (VP) trials.

FIG. 26D provides peripheral zone time allocation (PZTA) measurements of Morris water maze visible platform (VP) trials.

FIG. 27 provides mean APA IgM (0-3 months) PHH status stratified by IL-7 TRAJ.

FIG. 28 provides mean APA IgM:IgG ratio (0-3 months) PHH status stratified by IL-7 TRAJ.

FIG. 29 provides linear regression of APA IgM:IgG ratio (0-3 months) mean levels.

FIG. 30 provides ordinal logistic regression of APA IgM male TRAJ.

FIG. 31 provides ordinal logistic regression of APA IgM male TRAJ.

FIGS. 32A-32D provide bar figure showing APA IgM (32A), APA IgG (32B), AHA IgM (32C), and AHA IgG (32D) levels. Mean levels were measured in samples collected from 2 weeks to 6 months post-TBI and the mean levels remain stable over time. Thirty-nine males were recruited as controls, and 137 males with moderate to severe TBI were recruited for ALL TBI group.

FIGS. 32E-32T provide APA and AHA IgM and IgG fluorescence immunohistochemistry staining with selected TBI subacute/chronic serum samples.

Human cadaveric pituitary and hypothalamic tissue was stained with subacute-chronic (2-26 weeks) serum samples from four men (subjects 1-4) with severe TBI. Each serum sample was exposed to with human pituitary (APA) and hypothalamic (AHA) tissue sections and then developed with fluorophore-labeled anti-human IgM or IgG (images shown from top to bottom in each column). Arrows point to strongly staining cells. Slides were also counterstained with DNA-dye DAPI. Scale bar in lower right corner represents 50 µm. Individual subject's membership to APA and AHA IgM TRAJ group (high, low) based on ELISA method are shown on top of its IHC images. Representative IHC staining of pituitary and hypothalamic tissue sections with serum samples from 16 TBI subjects were shown. (32E, 32F, 32G,

32H) APA IgM staining; (32I, 32J, 32K, 32L) AHA IgM staining; (32M, 32N, 32O, 32P) APA IgG staining; (32Q, 32R, 32S, and 32T) AHA IgG staining.

FIGS. 32U-32Z provide auto-antibody (AAb) profiles, including APA IgM (32U), APA IgG (32V), AHA IgM (32W), AHA IgG (32X), GFAP IgM (32Y) and GFAP IgG (32Z), in both control and TBI groups.

FIGS. 33A-33B provide group-based trajectory (TRAJ) analysis for IL-7 (33A) and sTNFRI (33B) for a cohort of people with moderate to severe TBI. Levels are compared to levels found in a healthy control group FIG. 34 provides acute and chronic phenomena event rate (% of TRAJ), with significance stars * denoting significant differences among TRAJ groups by TBI related impairment.

FIG. 35A provides mean treelet cluster scores by IL-7 trajectory group membership after TBI.

FIG. 35B provides mean auto-antibody levels for those in the low and high IL-7 TRAJ groups.

FIG. 36 provides patient stratification grid showing individuals that were stratified based on IL-7 and sTNFRI TRAJ memberships (low/high).

FIG. 37 provides table showing acute and chronic phenomena event rate (% of stratified group). *Stars denote significant/trending differences in TBI impairments by TRAJ group membership.

FIG. 38 provides table summarizing metrics of post-acute treatment candidates.

FIG. 39 provides table showing statistical comparison of these variables by stratified TRAJ groups.

FIGS. 40A-40B provide bar figure showing inflammatory profiles associated with psychological assessments. The full cohort number is 106 for percent back to normal test (40A) and the full cohort number is 116 for PHQ-9 total score test (40B).

FIG. 41 provides line figure showing mean NLR by NLR TRAJ group over day 0-20 post-TBI.

FIG. 42 provides mean differences for inflammatory markers among individuals grouped by NLR TRAJ group membership. High NLR was associated with higher levels of sTNFR family expression.

FIG. 43 depicts a basic conceptual model that using NLR as a proxy screening variable for sTNFRI.

FIG. 44 provides table showing acute and chronic event rate (% of TRAJ). * signifies significant difference in event rate between low and high TRAJs. *Stars denote significant/trending differences in TBI impairments by TRAJ group membership.

FIG. 45 provides table showing acute immune cell TRAJs that can be used as proxies for chronic sTNFRI state. A high (and significant) concordance rate was observed between sTNFR1 TRAJ group membership and NLR TRAJ group membership.

FIG. 46A provides chronic inflammation treelet analysis over the first 6 months post-TBI.

FIG. 46B provides chronic inflammation treelet analysis over the first 6 months post-TBI. Inflammatory marker production in serum after TBI clusters into unique patterns after injury that map to 5 main areas of immunity.

FIG. 47 provides bar figure showing mean TC1 scores of the adaptive immunity cluster. IL-7 trajectory group membership strongly associated with adaptive immunity marker expression.

FIG. 48 provides bar figure showing mean TC2 scores of the innate immunity cluster. IL-7 strongly associated with amplified innate immunity marker expression in the context of higher sTNFRI.

FIG. 49 provides bar figure showing mean TC3 scores of the allergy immunity cluster.

FIG. 50 provides bar figure showing mean TC4 scores of the soluble receptor cluster. TNF driven phenomenon of differences in soluble receptor biology.

FIG. 51 provides bar figure showing mean TC5 scores of the chemokine cluster.

Chemokine cluster scores track to both IL-7 and TNF-α receptor levels.

FIGS. 52A-52B provide bar figure showing IgM:IgG ratios of anti-hypothalamic (52A) and anti-GFAP autoantibodies (52B) over 0-6 months post-TBI by stratified patient grid.

FIGS. 53A-53C provide bar figure showing IgM APA (53A), IgG APA (53B), and IgM:IgG ratios (53C) of anti-pituitary autoantibodies over 0-6 months post-TBI by stratified patient grid. Potential treatment responder groups were identified.

FIGS. 54A-54B provide bar figure showing testosterone profiles (54A) and longitudinal hormone profiles (54B) by persistent hypogonadotropic hypogonadism (PHH) status.

FIGS. 55A-55D provide bar figures showing auto-antibody profile, including APA IgM (55A), A1HA 1gM (55B), APA IgG (55C), and AIIA IgG (55D) comparison among control, non-Pill], and PHI groups.

FIG. 56 depicts a multivariate regression based conceptual model for homeostatic disruptions to immunity post-TBI contributing to PHH.

FIGS. 57A-57C provide logistic regression model of PHH outcome on TNFRI and IL-7 interactions. FIG. 57A shows the model variables, and their corresponding odd ratios and p-values. FIG. 57B shows interaction graphic between TNFRI and IL-7. FIG. 57C provides the ROC curves for comparisons. The ROC contrast p values is 0.0044 (+12.5%). The base model: Age, GCS score, and APA IgM (c=0.67). The Final Model: Base Model+IL-7, sTNFRI, RANTES and IL-7*sTNFRI interaction (c=0.7955).

FIGS. 57D-57E provide IL-7× sTNFRI interaction graph. Y axis refers to PHH probability. X axis refers to 0-6 mean IL-7 (centered). Each line represents a different sTNFRI level (centered and scaled×0.01). Groups of individuals within each quadrant of the plot may require unique treatment to address TBI impairment.

FIG. 58 depicts the calculation of absolute risk reduction (ARR) for TBI impairments and neurorecovery.

FIG. 59 provides table showing a summary of parameters of associated unfavorable conditions profile and absolute risk reduction (ARR) profile.

FIG. 60 depicts a temporal scheme for screening and eligibility process for clinical treatment after TBI.

FIGS. 61A-61B provide bar figures showing serum TNFα levels (61A) and serum sTNFRI levels (61B) in biomarkers low sTNFRI TRAJ and high sTNFRI TRAJ groups.

FIG. 62 provides bar figure showing blood lymphocytes at day 21 in CCI mice and sham mice treated with vehicles (VEH), low dose Etanercept (ETN) and high dose Etanercept.

FIG. 63A provides line figure showing anxiety behavior acquired using MWM Visible Platform. Morris Water Maze Acquisition trials were conducted in in CCI mice and sham mice treated with vehicles (VEH), low dose Etanercept (ETN) and high dose Etanercept. Peripheral zone time allocation was measured.

FIG. 63B provides the MWM visible platform trial: latency group comparison.

FIG. 64 provides median serum levels of cytokines by IL-7 treatment group in mice. High IL-6 levels and other markers with high IL-7 treatment supported need for therapy with Etanercept.

FIG. 65 provides median serum levels of cytokines by Etanercept treatment group in mice. Serum reductions in TNFα noted with treatment.

FIG. 66 provides brain and serum TNFα levels in CCI mice treated with treated with vehicles (VEH), low dose Etanercept (ETN) and high dose Etanercept.

Figure 70:
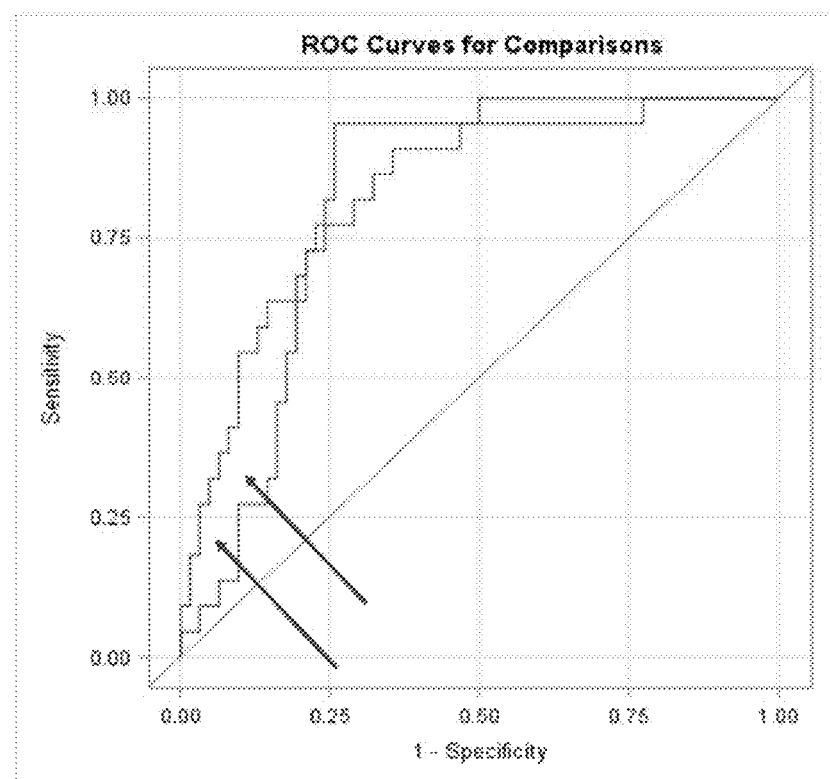

FIG. 70 provides receiver operating characteristic (ROC) curve analysis for APA and AHA TRAJ membership measurements.

Figure 71:
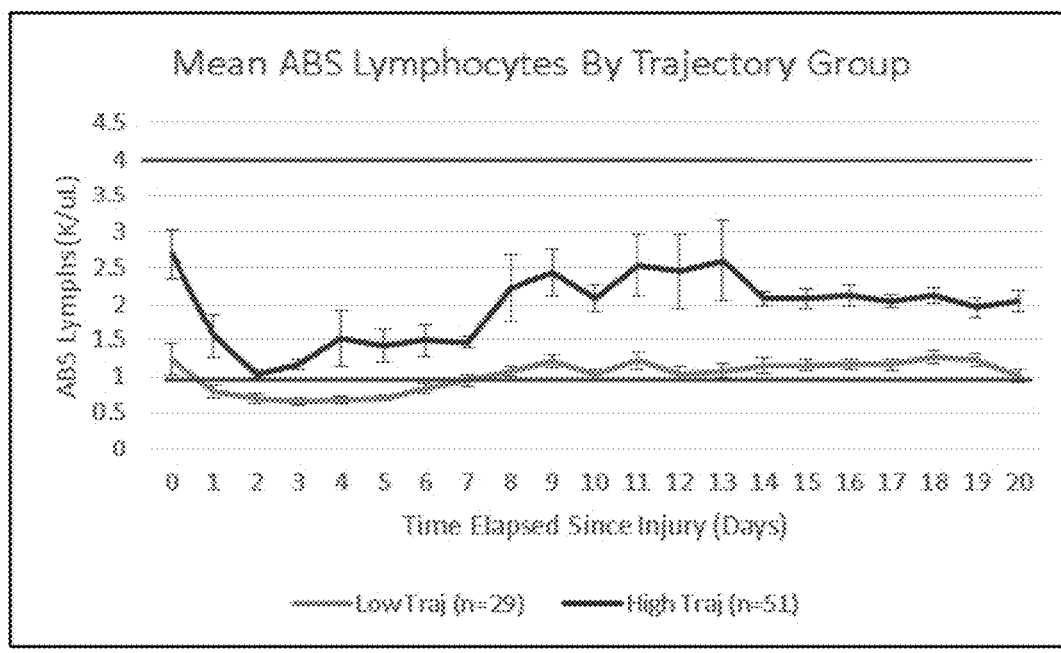

FIG. 71 provides absolute (ABS) lymphocyte counts by trajectory group.

Figure 72:
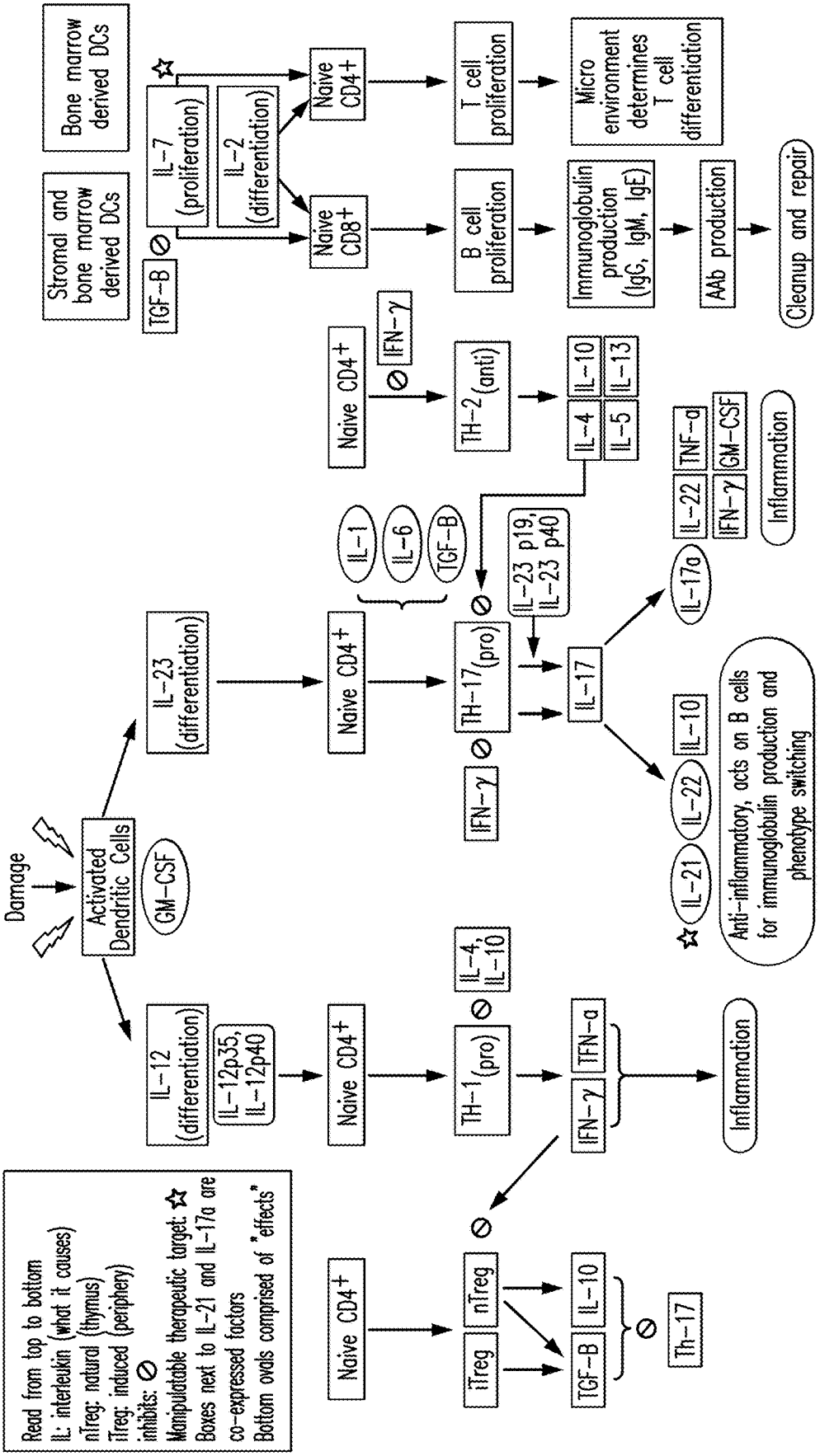

FIG. 72 depicts adaptive immunologic network.

Figure 73:
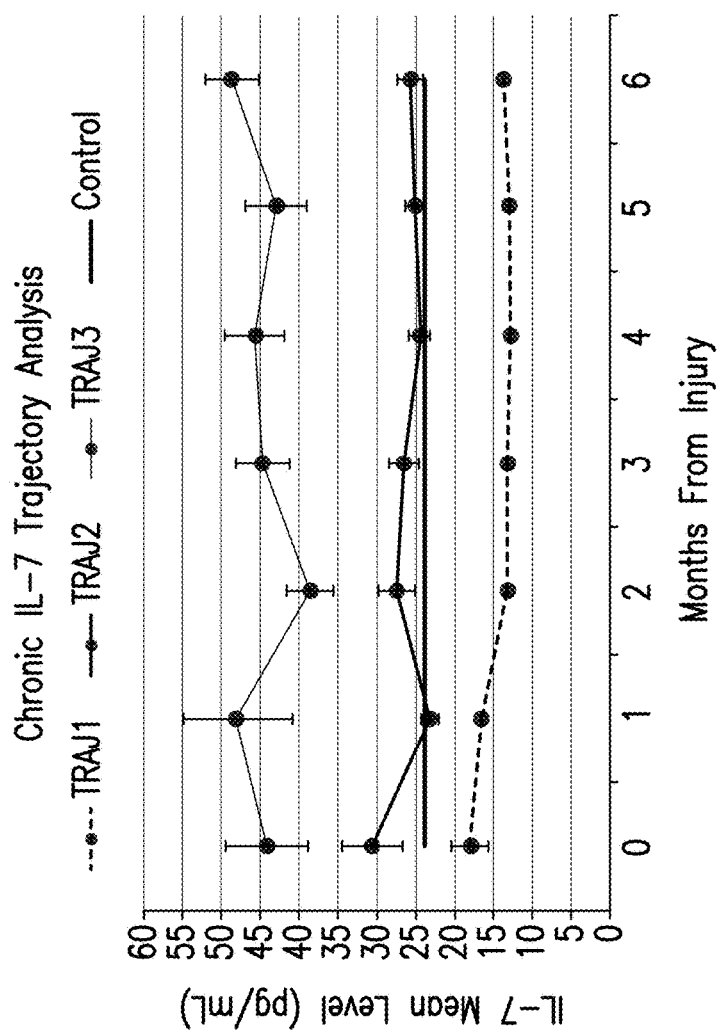

FIG. 73 provides chronic IL-7 trajectory analysis results.

FIG. 74 provides 0-6 month treelet cluster score comparisons.

FIG. 75 provides markers that did not cluster in unrestricted treelet.

Figure 76:
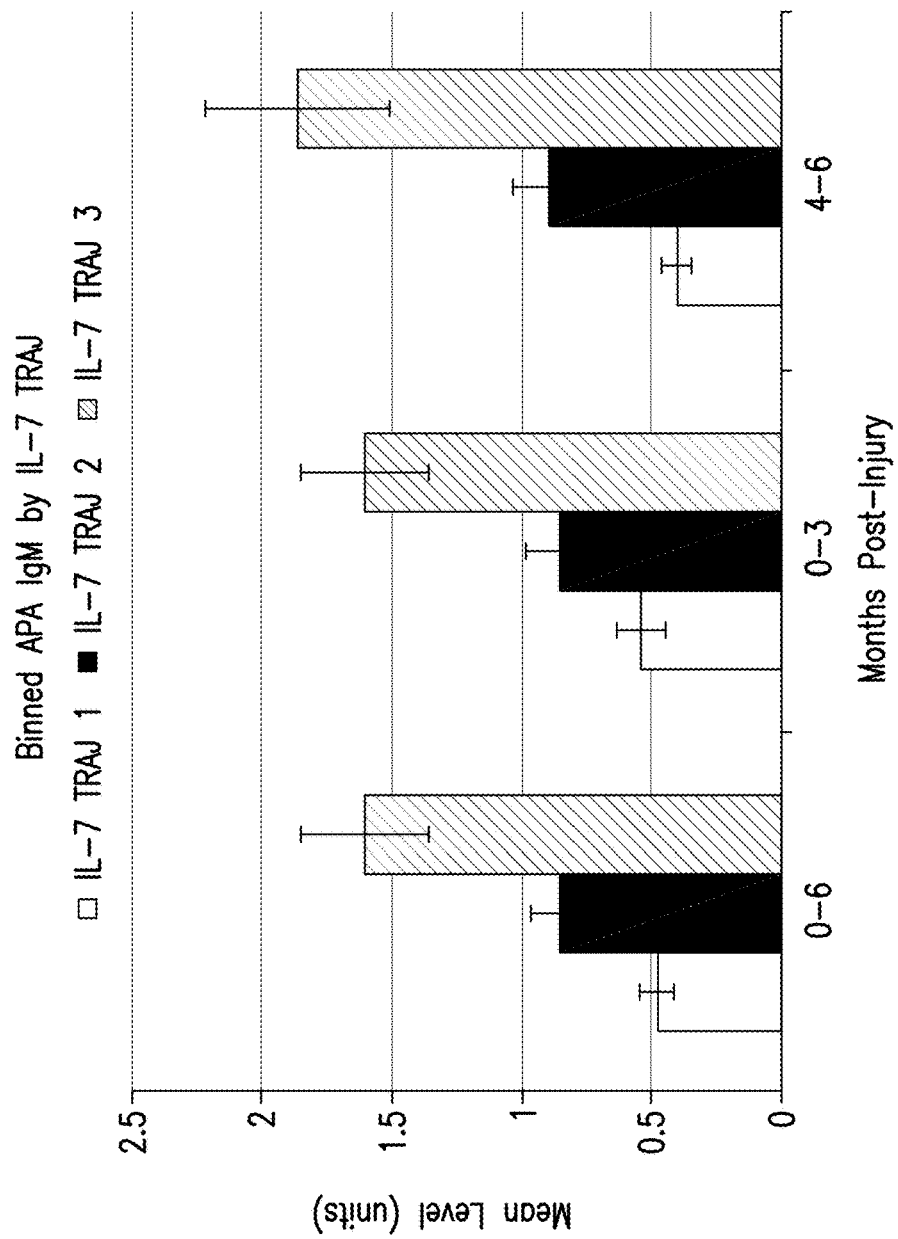

FIG. 76 provides bar figure showing binned APA IgM by IL-7 TRAJ membership.

Figure 77:
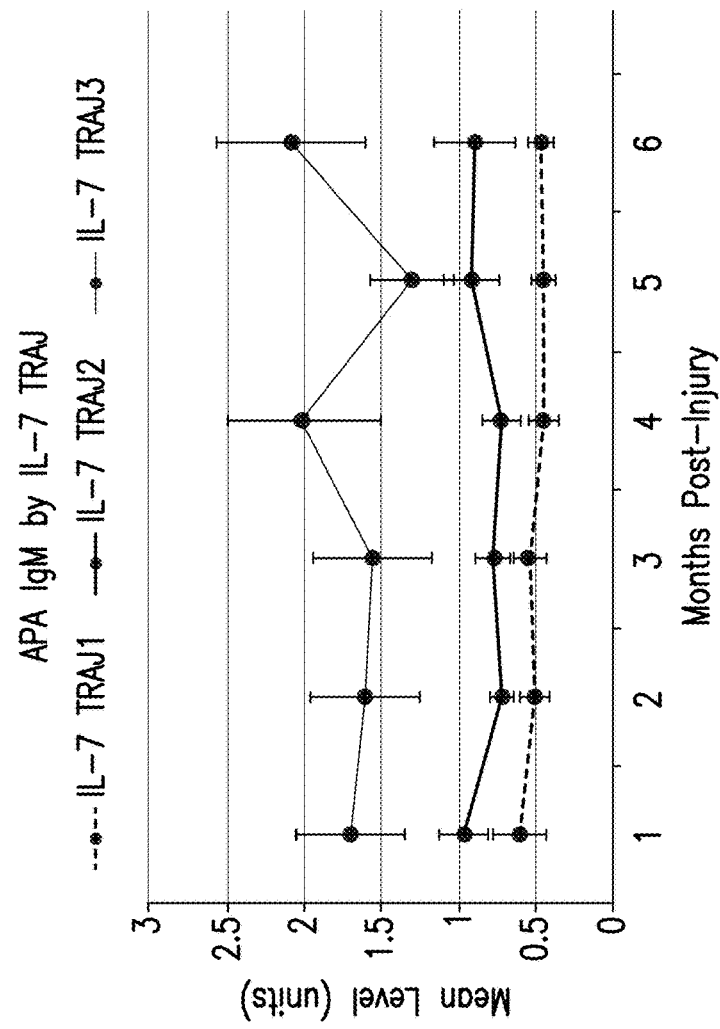

FIG. 77 provides line figure showing APA IgM by IL-7 TRAJ membership.

Figure 78:
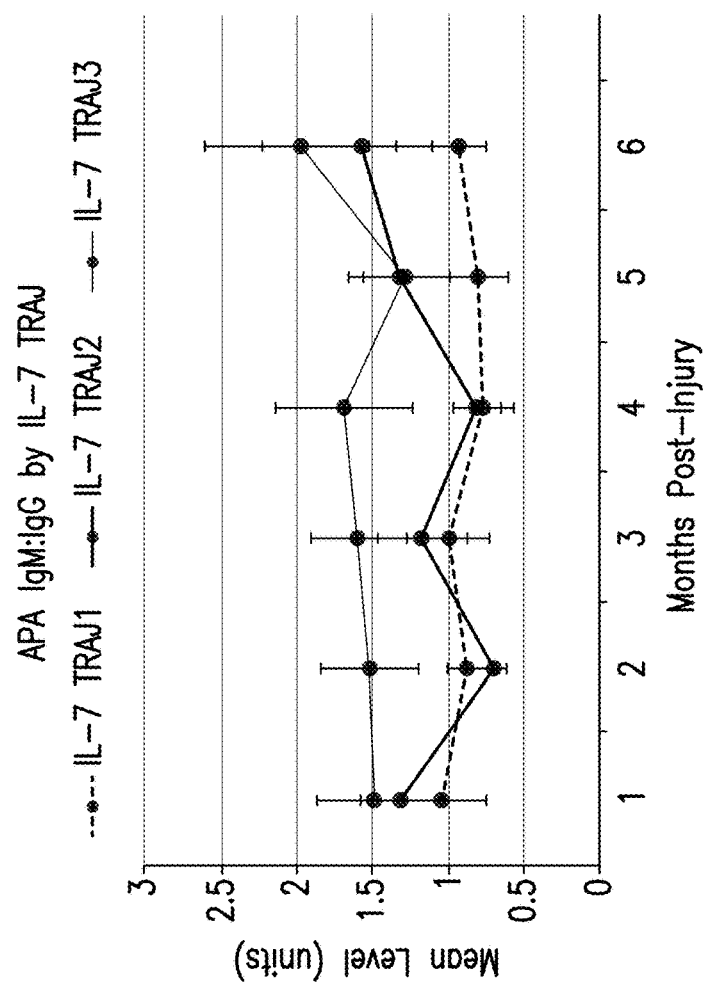

FIG. 78 provides line figures showing APA IgM:IgG ration by IL-7 TRAJ membership.

Figure 79:
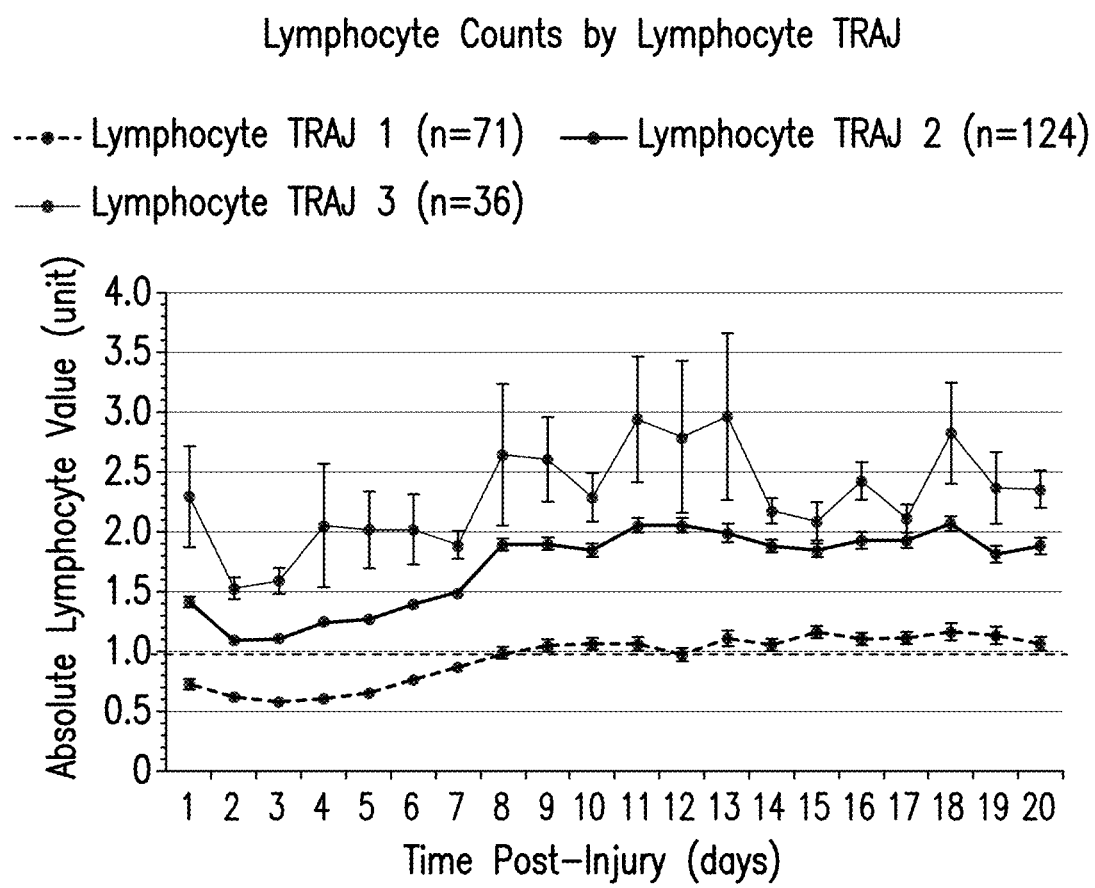

FIG. 79 provides line figure showing group-based TRAJ analysis on lymphocytes.

Figures 80, 81:
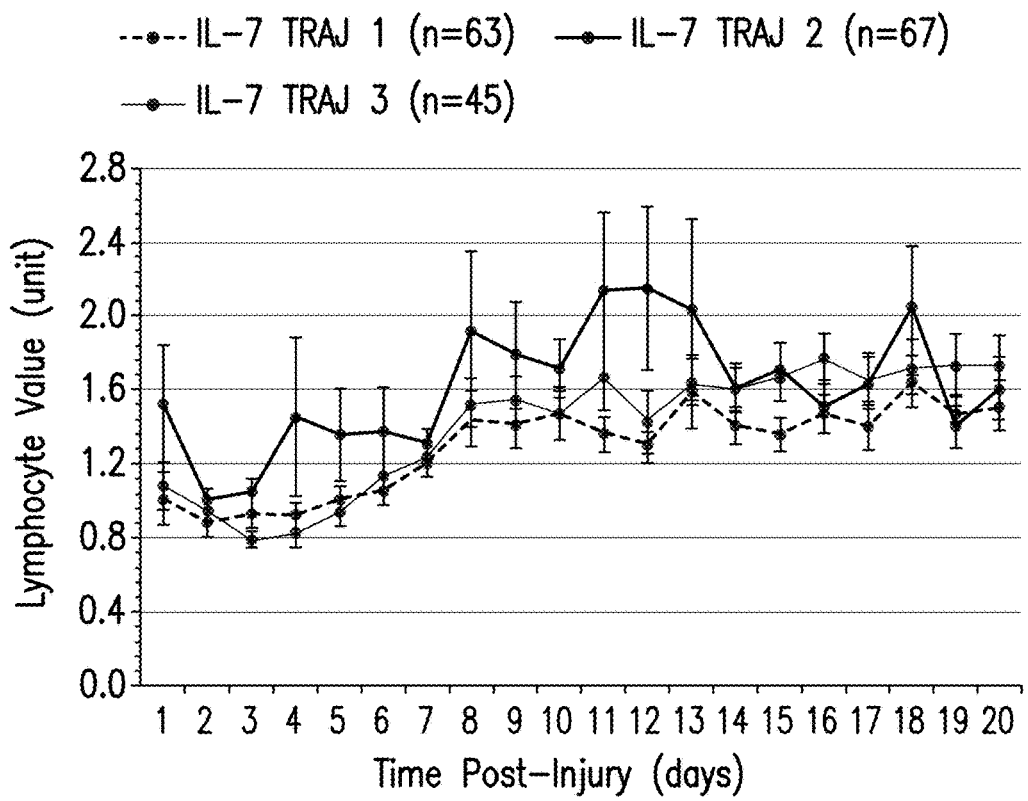

FIG. 80 provides demographics/outcomes by IL-7 TRAJ membership.

FIG. 81 provides line figure showing lymphocyte counts by IL-7 TRAJ membership.

Figure 82:
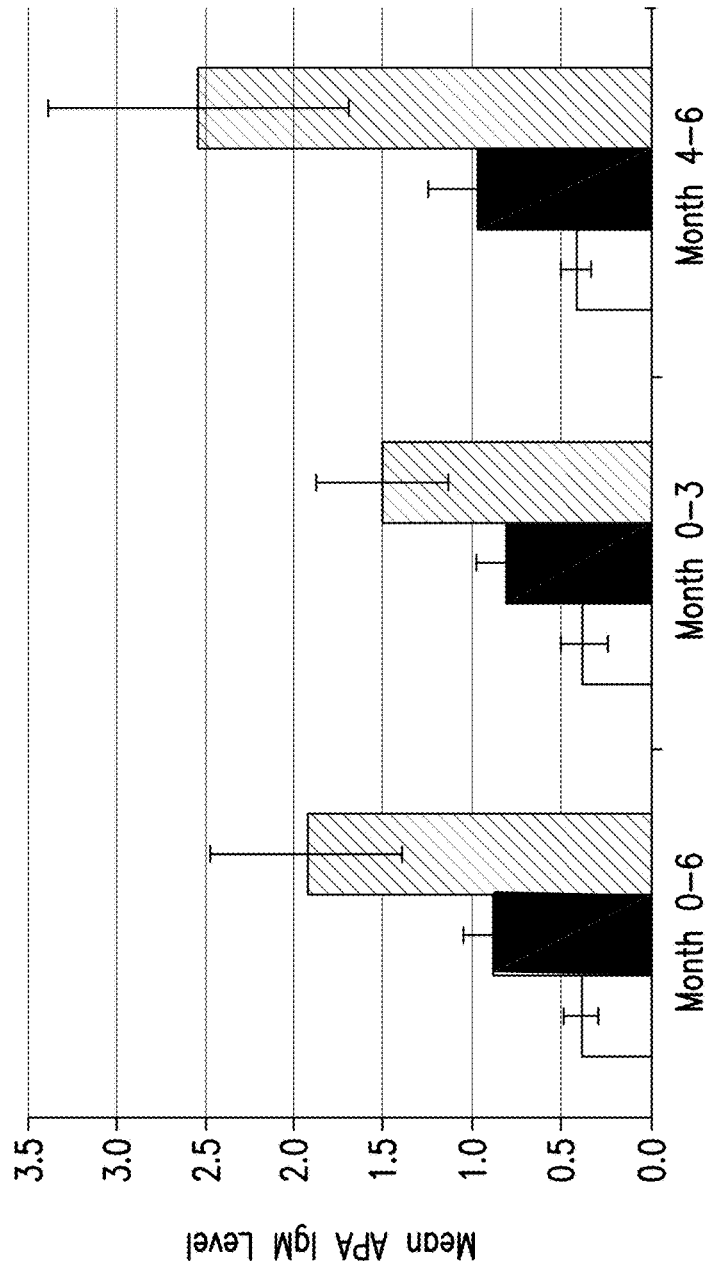

FIG. 82 provides bar figure showing APA IgM by IL-7 TRAJ membership.

FIG. 83 provides table showing 6-month Glasgow Outcome Score (GOS) by PHH status.

Figure 84:
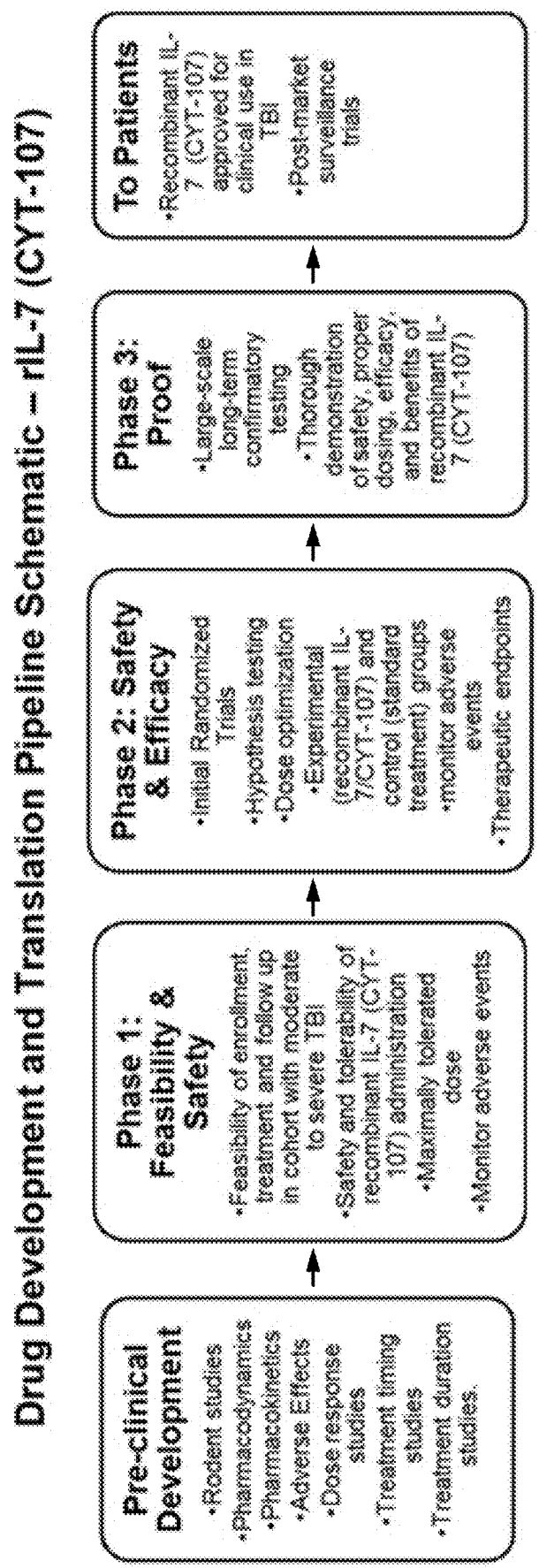

FIG. 84 provides an example drug development and translation pipeline scheme relating to rIL-7 (CYT-107) disclosed herein.

Figure 85:
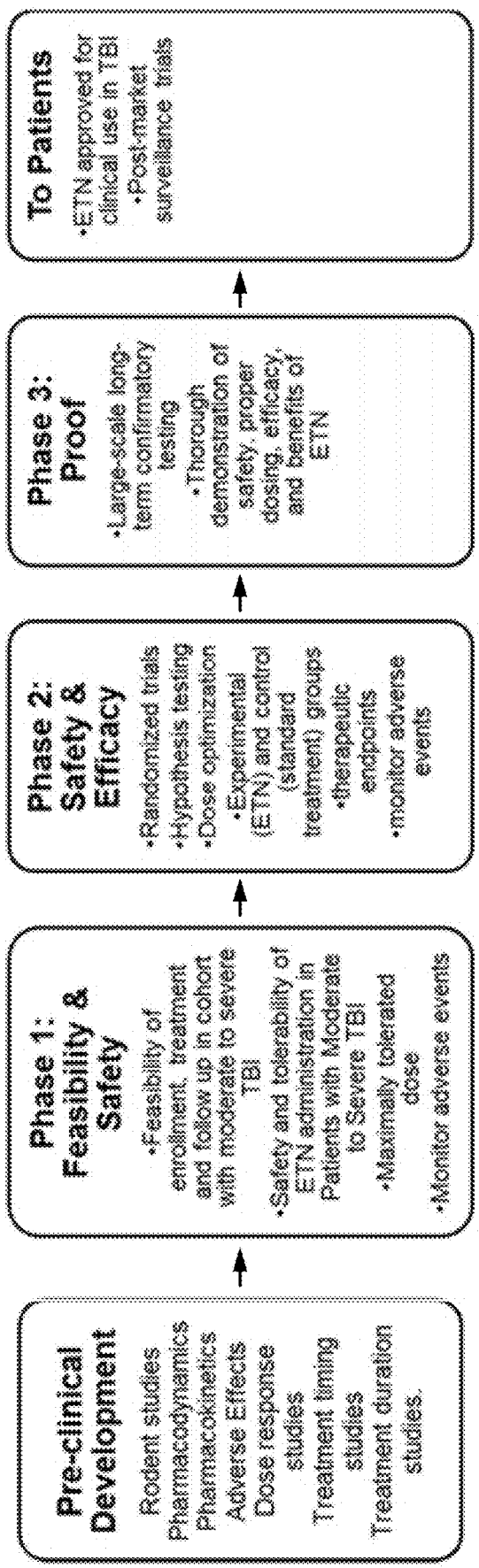

FIG. 85 provides an example drug repurposing and translation pipeline scheme relating to etanercept.

Figure 86:
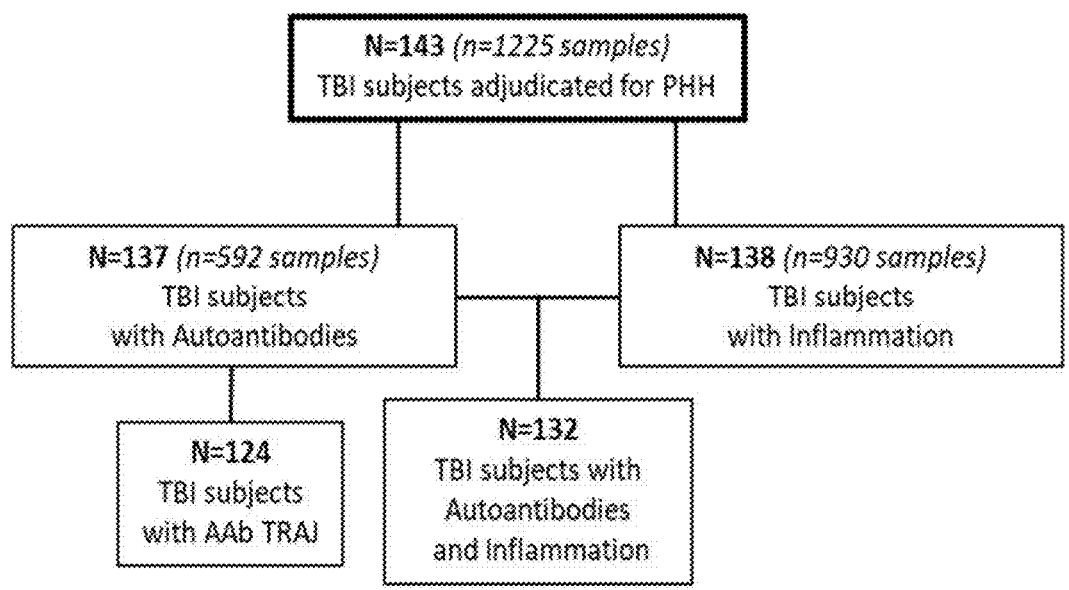

FIG. 86 provides a consort flow chart.

Figure 87B:
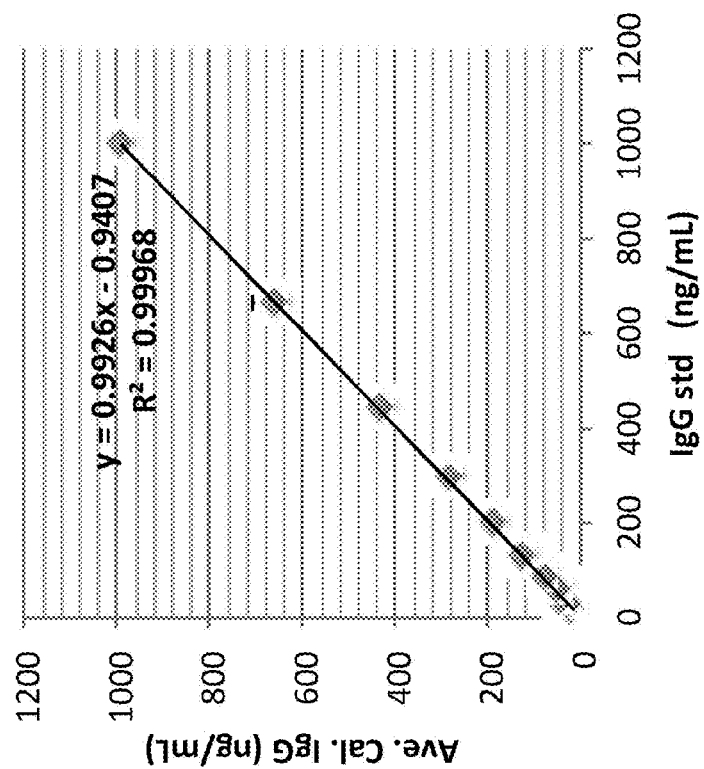
Figure 87A:
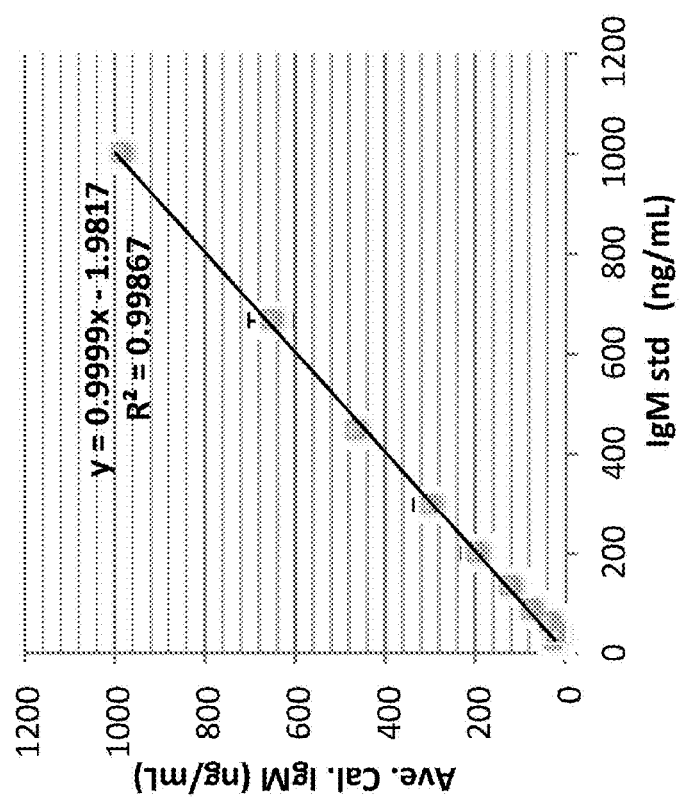

FIGS. 87A-87B provide IgM and IgG autoantibody standard curves: IgM and IgG class autoantibodies ELISA standard curves used to calculate the APA and AHA autoantibody concentrations (titers) in human subject serum. (87A) IgM standard curves, (87B) IgG standard curves. Calculated IgG or IgM concentrations +/−SD from four independent runs were shown. Linear regression fitting results are shown.

Figure 88A:
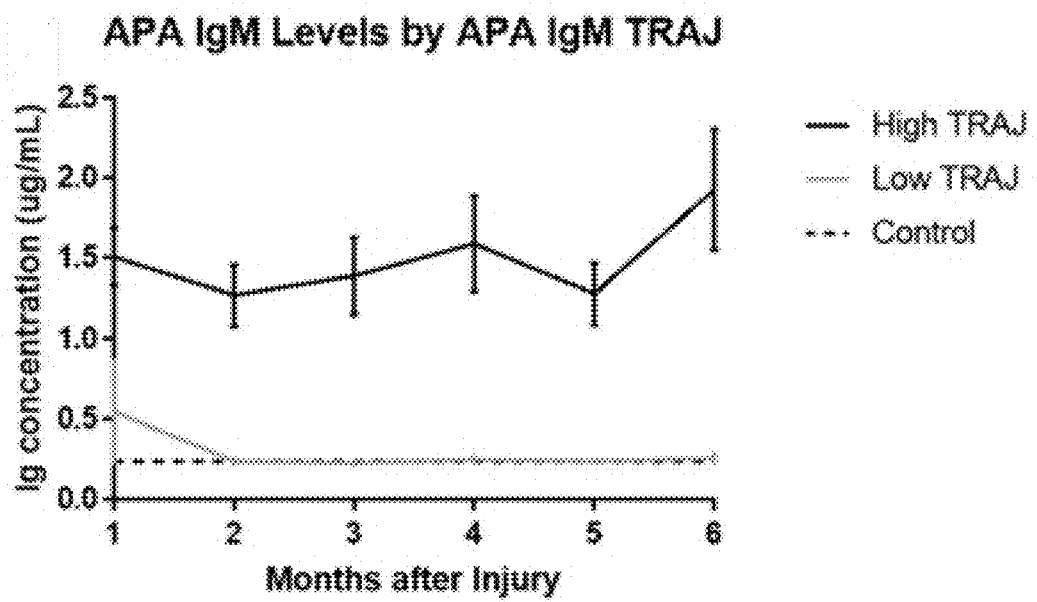
Figure 88B:
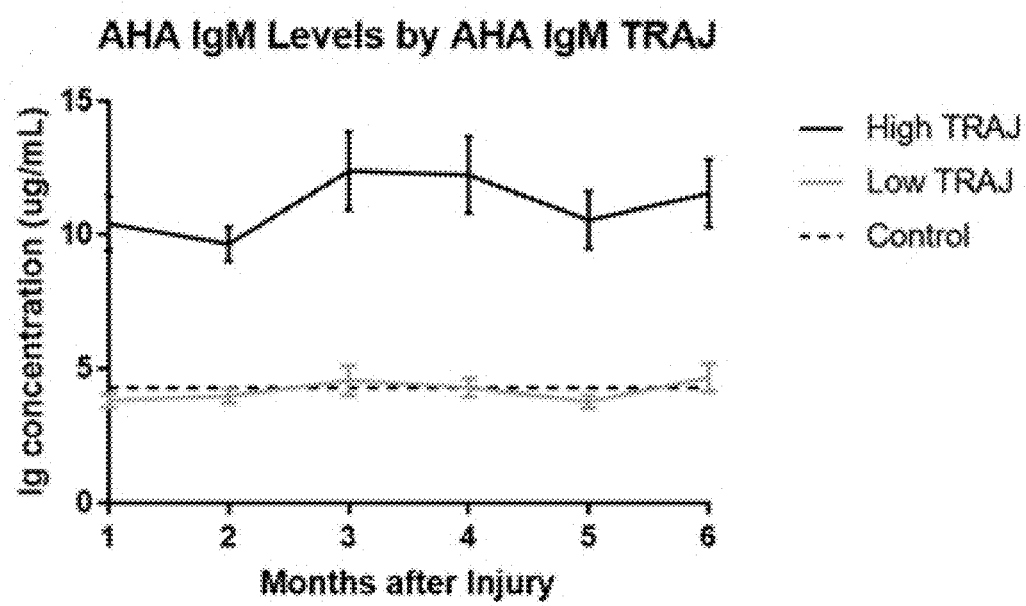

FIGS. 88A-88B provide immunoglobulin levels by TRAJ group membership. APA IgM (88A) and AHA IgM (88B) levels were graphed by the generated TRAJ groups. Dashed lines represent mean control levels (APA IgM, 0.24 pg/mL and AHA IgM, 4.32 pg/mL).

Figure 89:
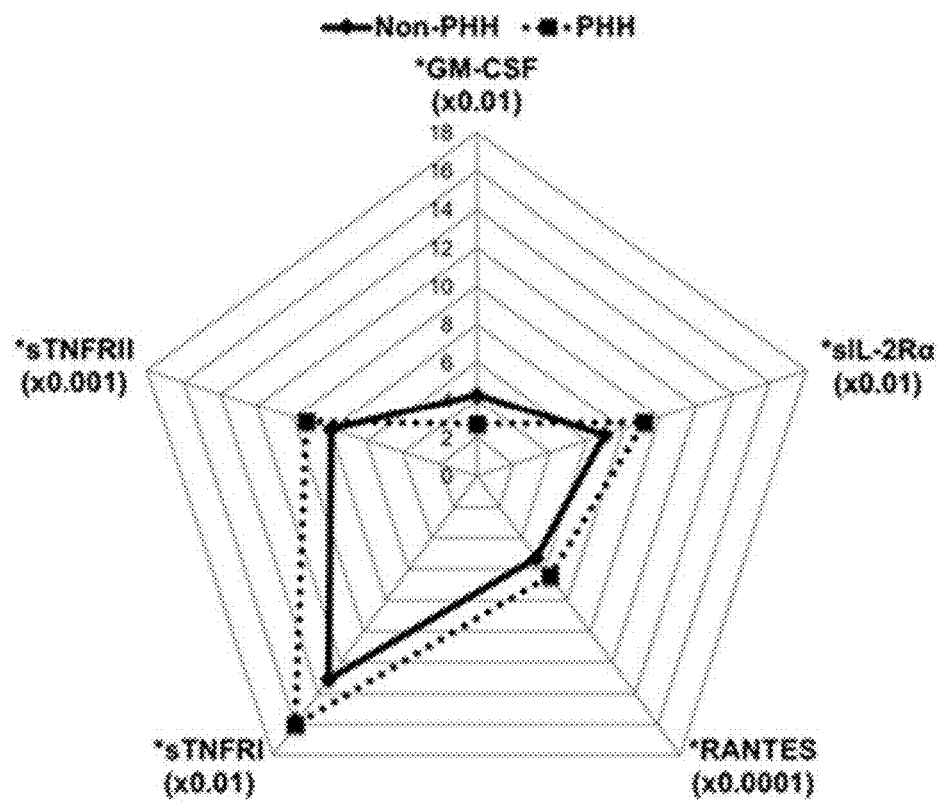

FIG. 89 provides cytokine biomarkers associated with PHH. Of the 33 inflammatory markers assayed, the five graphed above were significantly associated with PHH status ($p<0.05$). Each marker was scaled by a multiple of 10× (indicated in the graph) to fit a 0-20 pg/mL range.

FIG. 90 provides the time to event (first seizure) epilepsy model. It shows the cox proportional hazards regression of IL-7 and sTNFR1 at months 0-6 by time until first seizure through 3-years post-injury. Each row represents an independent model adjusted for covariates.

Figure 91:
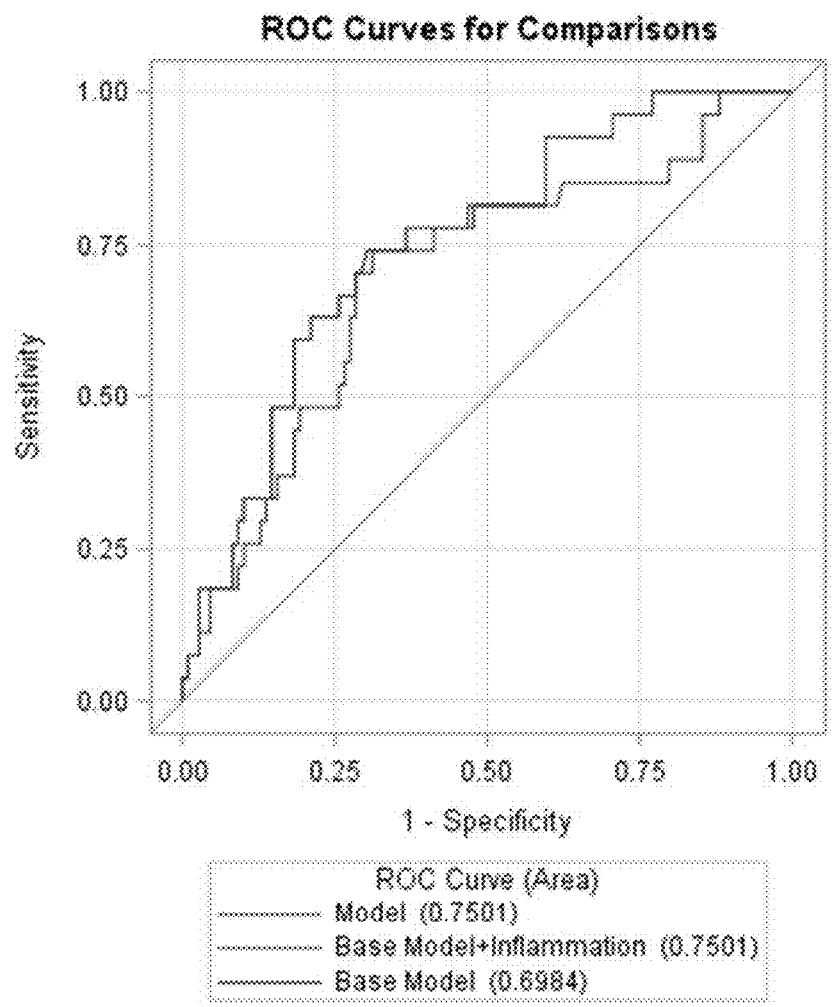

FIG. 91 provides the epilepsy prediction model adjusted for covariates as a part of the base model. TNFR1 values improved ROC Area by 5.6%.

FIG. 92 provides the logistic regression to GOS score. Each line represents an individual model adjusted for covariates including age, sex, and GCS score, modeling towards unfavorable outcome (GOS score=1, 2, 3) wherein treelet clusters were used to predict neuro-recovery (favorable/unfavorable) using the GOS score.

FIG. 93 provides the disability rating scale score overview.

FIG. 94 provides the linear regression to DRS score. Each line represents an individual model adjusted for covariates including age, sex and GCS score, wherein treelet clusters were used to predict neuro-recovery (favorable/unfavorable) using the GOS score.

FIGS. 95A-95B provide the logistic regression to GOS score at 6 month (FIG. 95A) and linear regression to DRS score at 6 months (FIG. 95B).

FIG. 96 provides the logistic regression to unfavorable GOS score at 6 months. Each model adjusted for covariates includes age, sex, and GCS score.

Figure 97A:
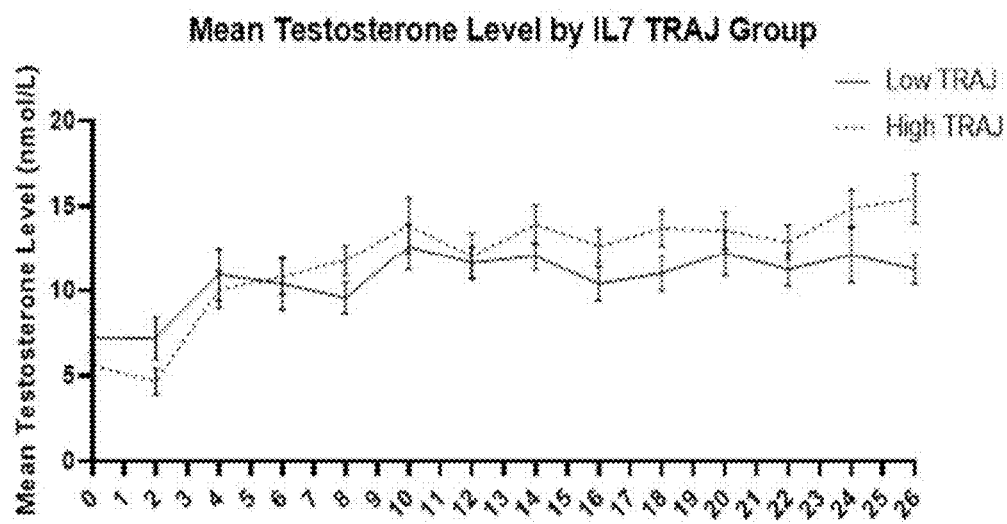
Figure 97B:
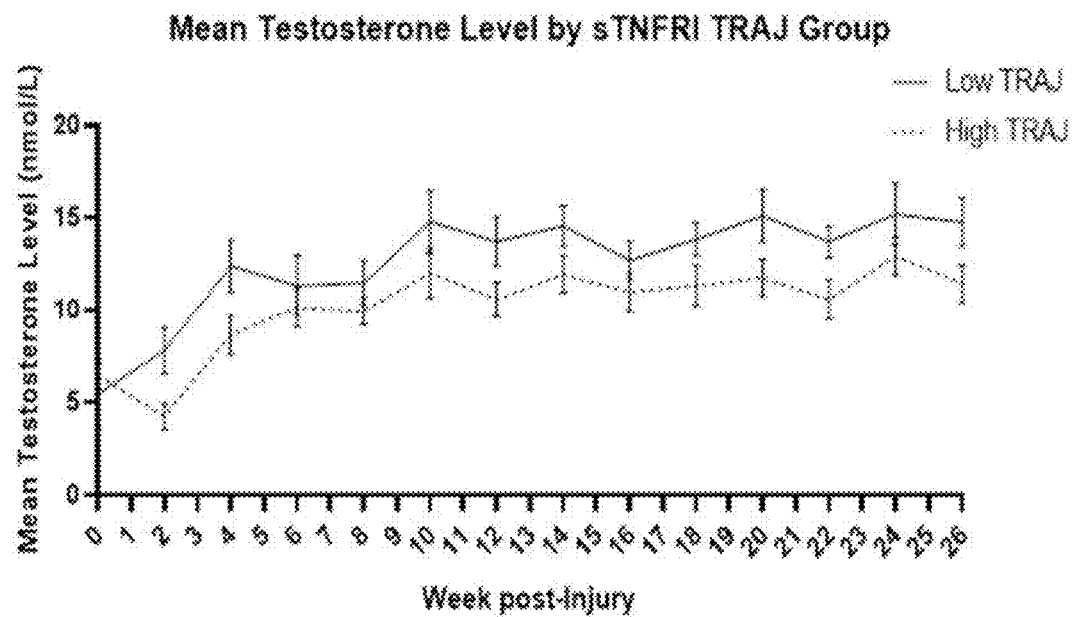

FIGS. 97A-97B provide mean testosterone level by IL-7 TRAJ Group (FIG. 97A) and mean testosterone level by sTNFRI TRAJ Group (FIG. 97B), showing that these autoantibodies directly impacted hormones associated with PHH in men after TBI.

Figure 98A:
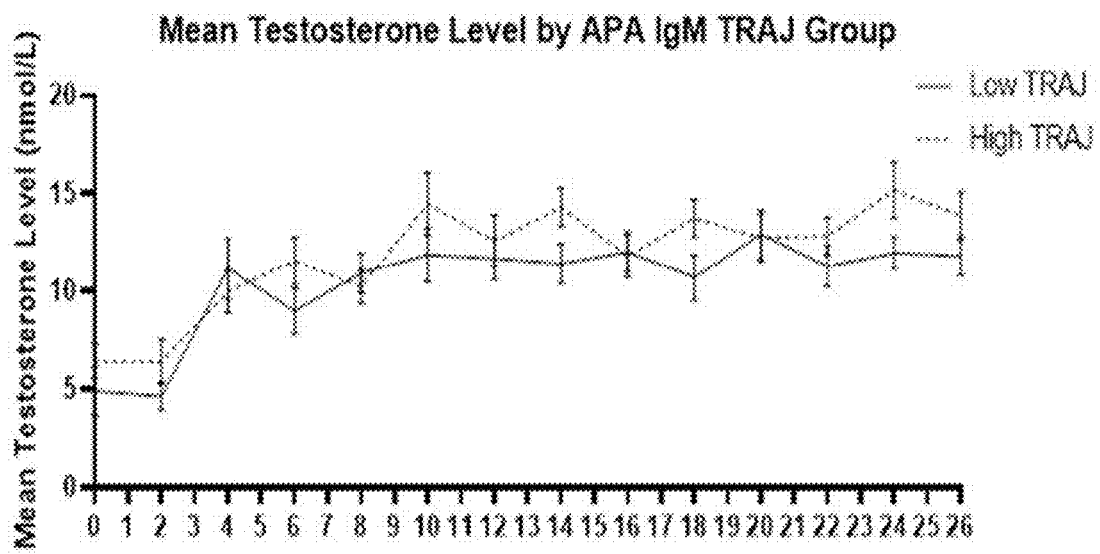
Figure 98B:
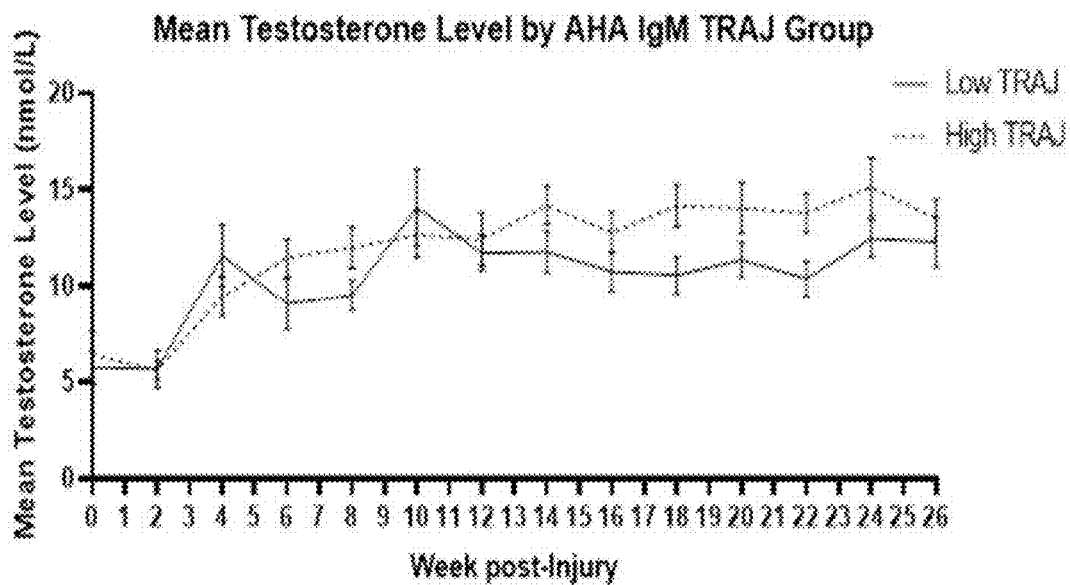

FIGS. 98A-98B provide mean testosterone level by APA IgM TRAJ Group (FIG. 98A) and mean testosterone level by AHA IgM TRAJ Group (FIG. 98B), showing that these inflammatory markers directly impacted hormones associated with PHH in men after TBI.

Figure 99A:
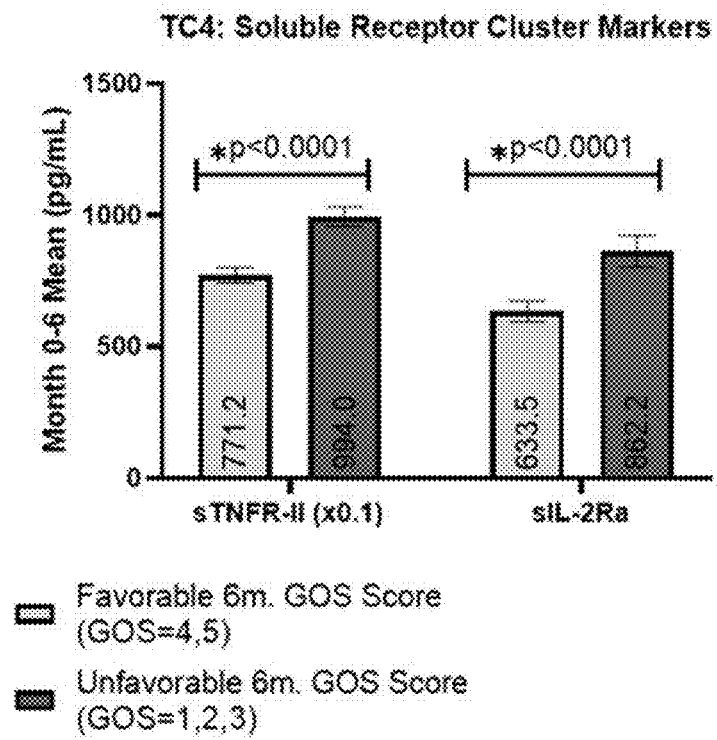
Figure 99B:
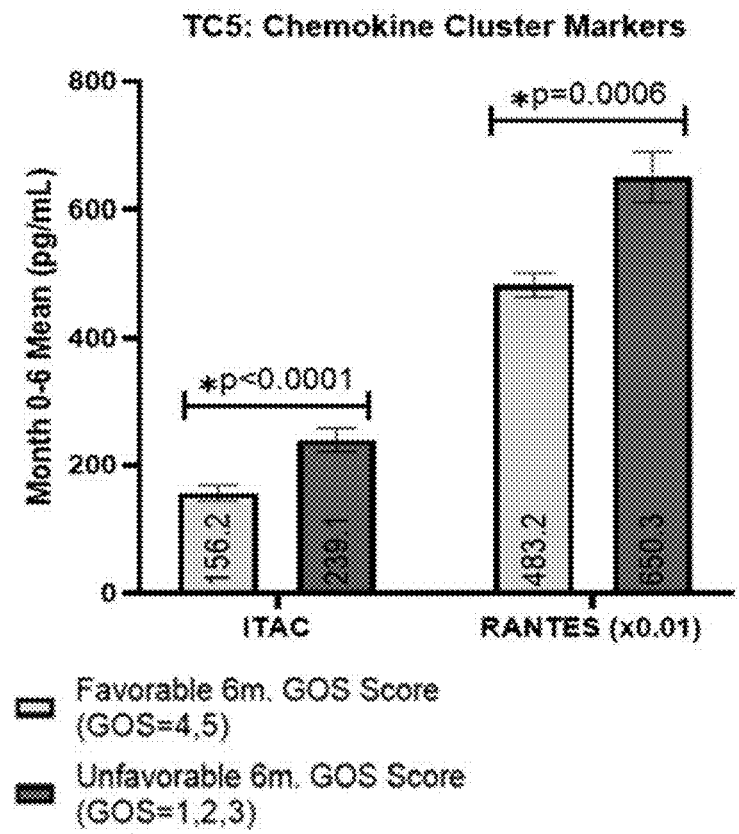

FIGS. 99A-99B provide chronic biological readouts that may inform global recovery using GOS scores and be affected by TNF inhibitor and rh-IL-7 treatment. FIG. 99A provides the readouts of soluble receptors of sTNFR-II and sIL-2Ra. FIG. 99B provides the readouts of chemokines of ITAC and RANTES.

Figure 100A:
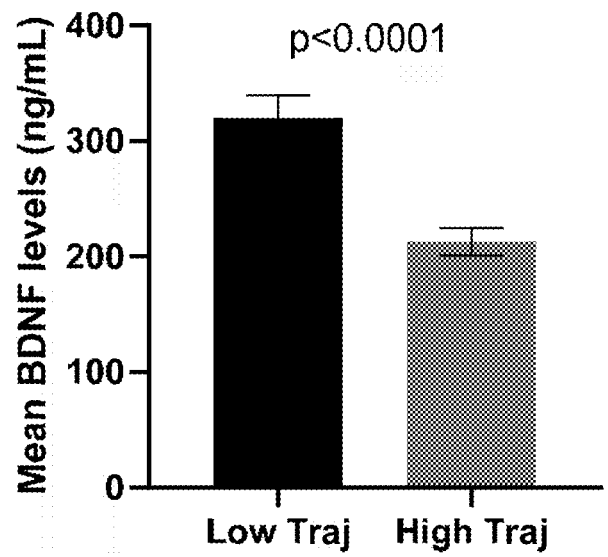
Figure 100B:
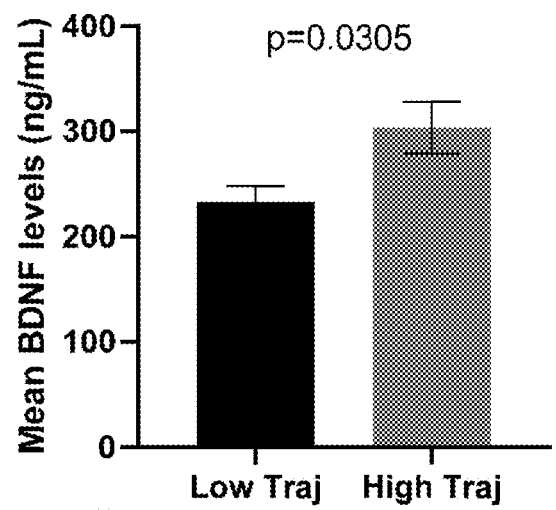

FIGS. 100A-100B provide mean BDNF levels by sTN-FRI TRAJ (FIG. 100A) and mean BDNF levels by APA IgM TRAJ (FIG. 100B).

Figure 101:
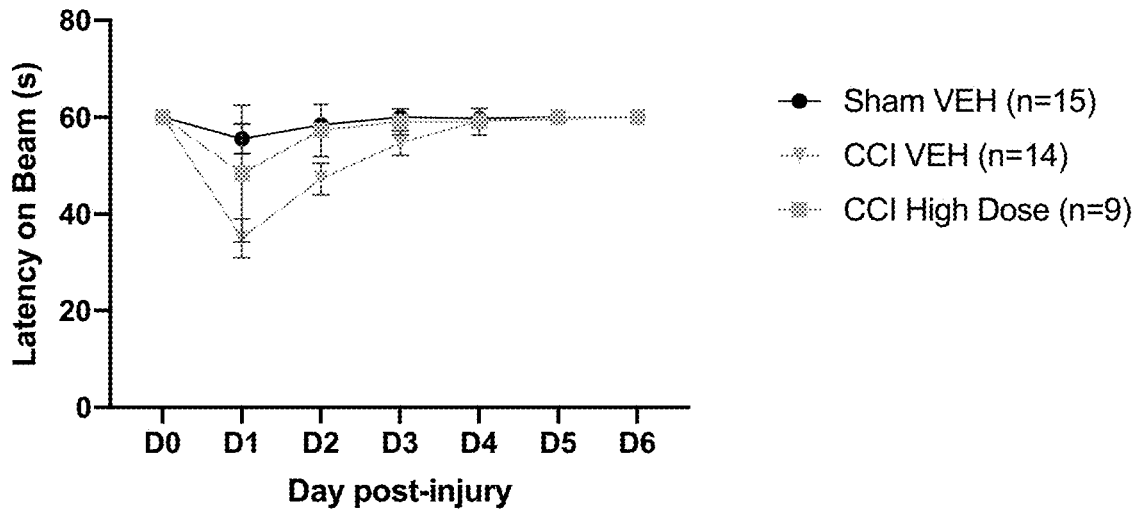

FIG. 101 provides the motor testing of beam balance in rats with experimental TBI (CCI) or sham injury treated with high dose Etanercept.

Figure 102:
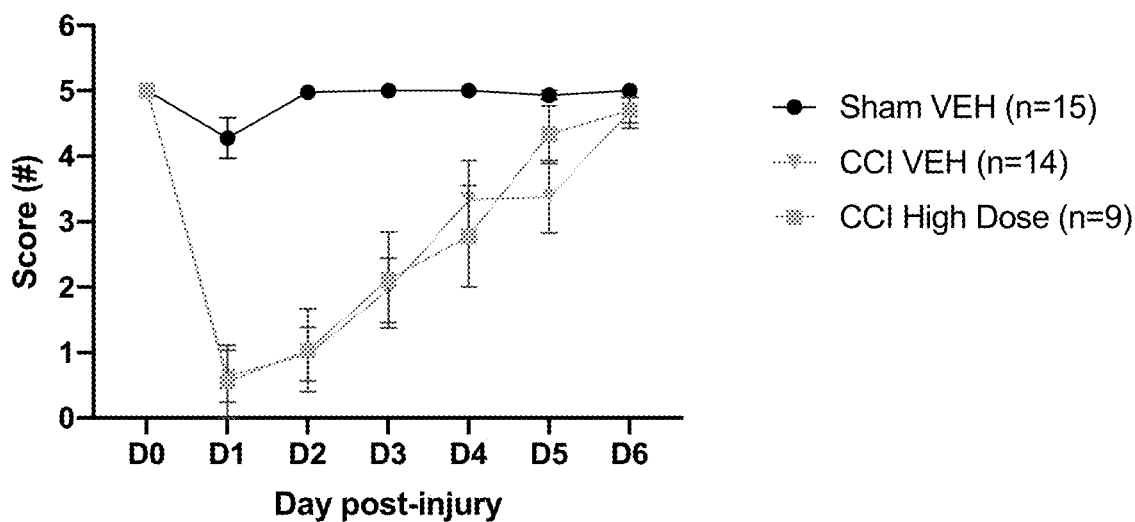

FIG. 102 provides the motor testing of beam walk in rats with experimental TBI (CCI) or sham injury treated with high dose Etanercept.

Figure 103:
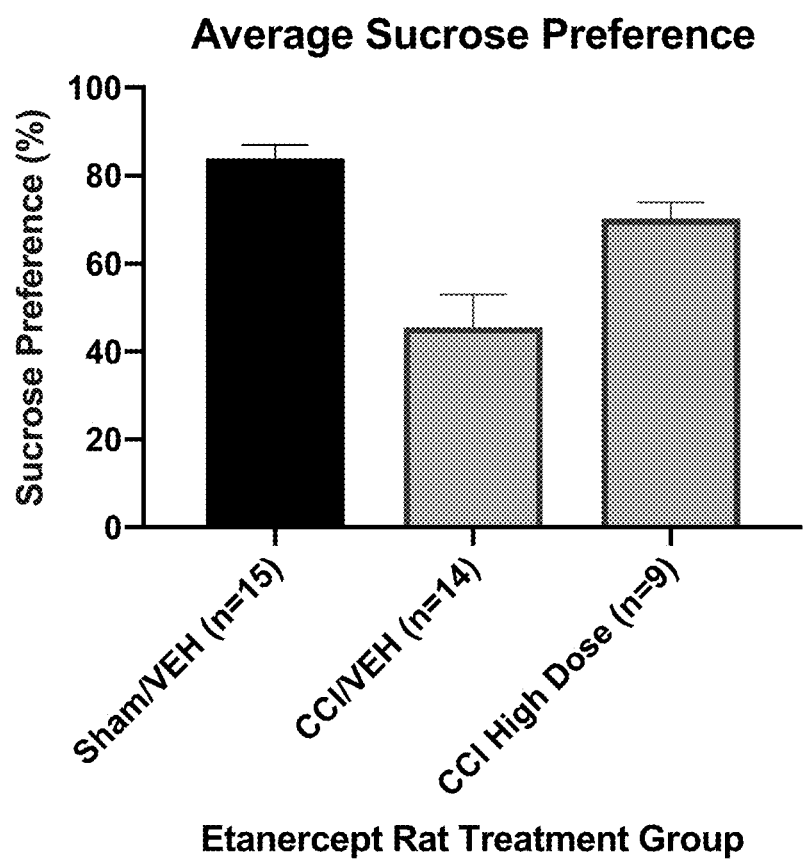

FIG. 103 provides the average sucrose preference in rats and shows treatment effect with Etanercept FIGS. 104A-104C provide demographics and clinical cohort information by IgM TRAJ.

Figure 105A:
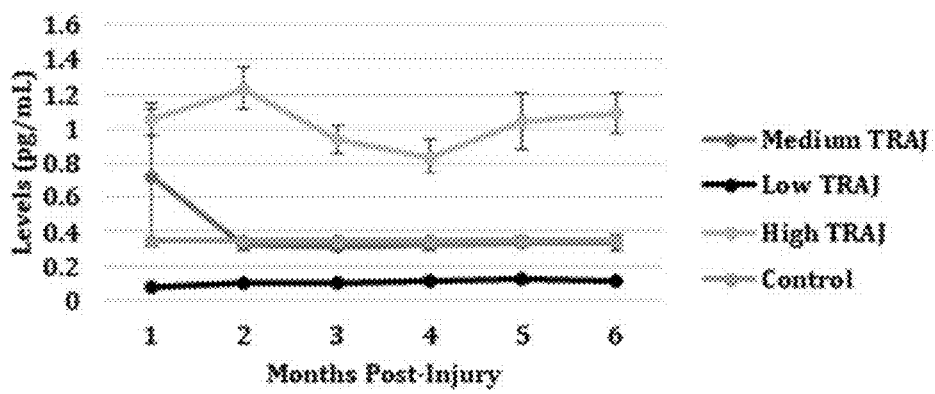
Figure 105B:
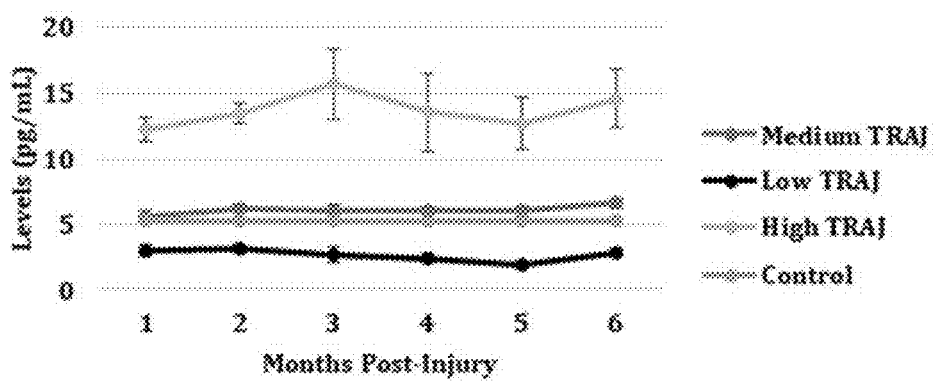
Figure 105C:
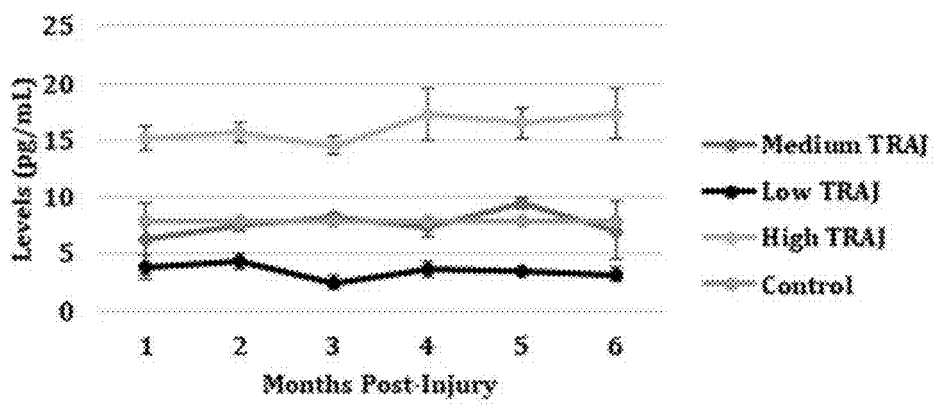

FIGS. 105A-105C provide APA IgM levels by APA IgM TRAJ (FIG. 105A), AHA IgM levels by AHA IgM TRAJ (FIG. 105B), and GFAP IgM levels by GFAP IgM TRAJ (FIG. 105C).

Figure 106:
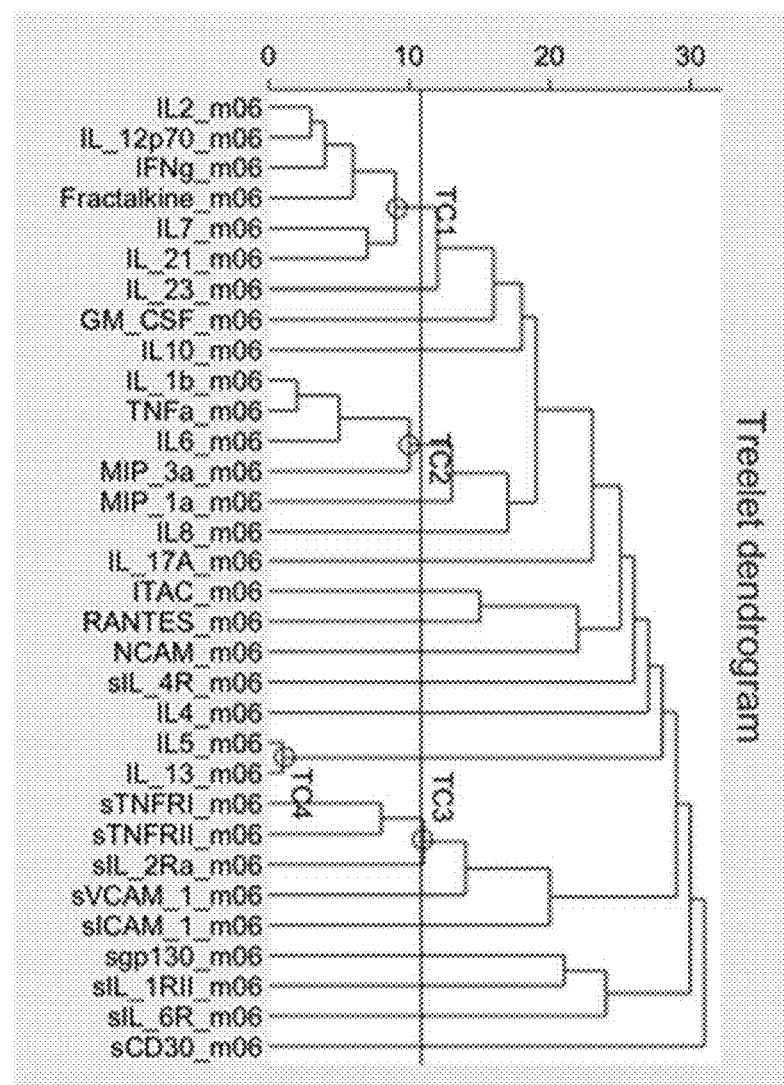

FIG. 106 provides the treelet dendrogram for 32 biological markers.

FIGS. 107A-107F provide the Treelet Cluster (TC) weight associations to TRAJ.

FIG. 108 provides the associations of TC and TC2 to APA IgM TRAJ.

FIG. 109 provides the associations of TC and TC2 to AHA IgM TRAJ.

FIG. 110 provides the associations of TC and TC2 to GFAP IgM TRAJ.

FIG. 111 provides the concordance between NLR TRAJ and PLR TRAJ.

Figure 112A:
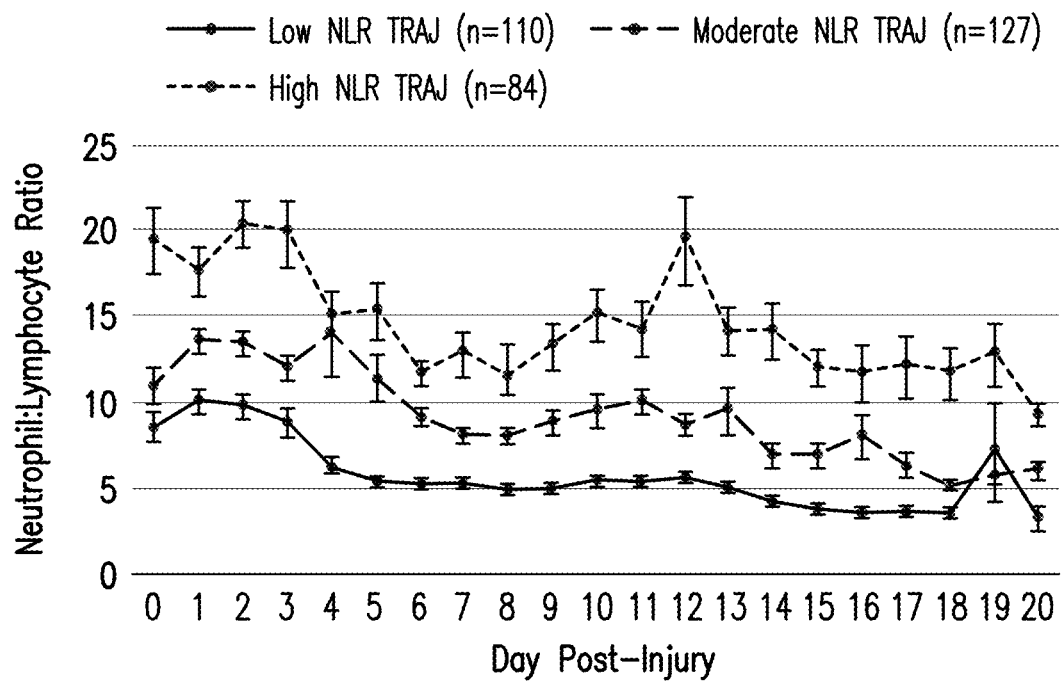

FIG. 112A provides mean NLR Levels by NLR TRAJ. Across all TRAJs, NLR demonstrated a general decrease over the first 21 days post-injury.

Figure 112B:
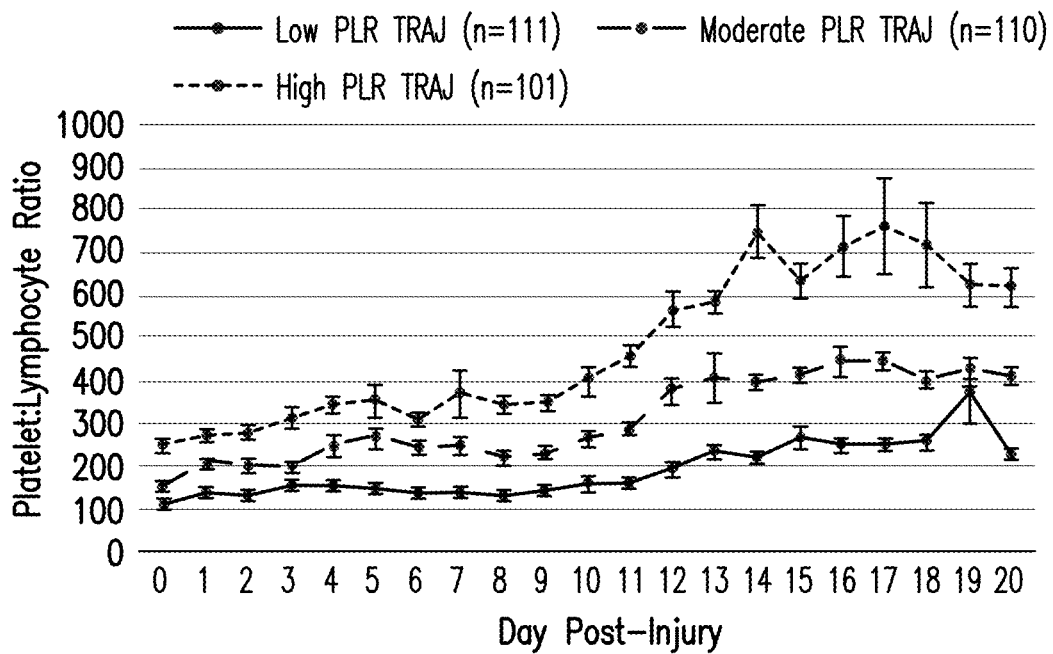

FIG. 112B provides mean PLR Levels by PLR TRAJ. Across all TRAJs, PLR demonstrated a general increase over the first 21 days post-injury.

FIGS. 113A-113B provide clinical and Demographic Associations by NLR TRAJ (FIG. 113A) Clinical and Demographic Associations by PLR TRAJ (FIG. 113B).

FIGS. 114A-114B provide the NLR TRAJ Concordance with Clinical Conditions (FIG. 114A) and PLR TRAJ Concordance with Clinical Conditions (FIG. 114B).

Figure 115A:
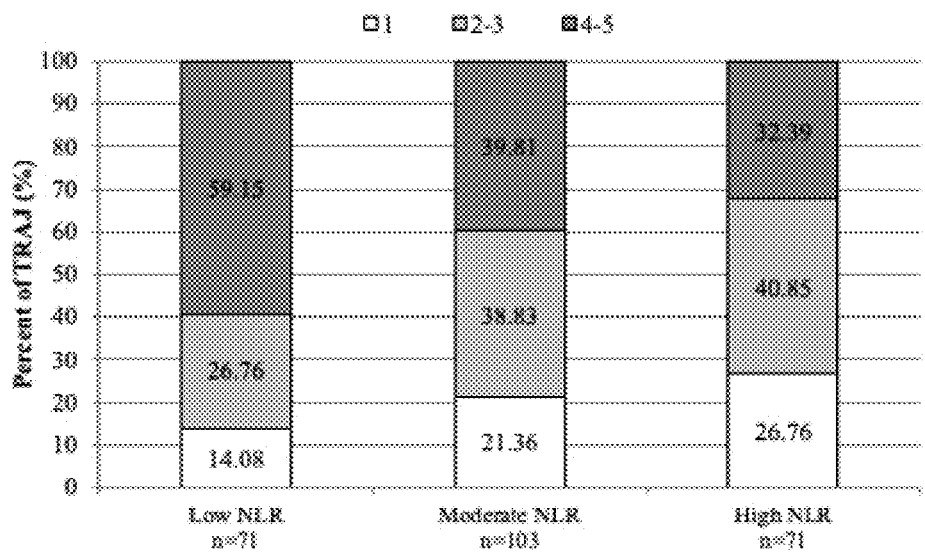

FIG. 115A provides 6-month GOS Scores by NLR TRAJ. The low NLR TRAJ displayed the greatest proportion (59.15%) of individuals demonstrating favorable global functional recovery (GOS Score 4-5) while the high NLR TRAJ had the smallest proportion of favorable outcomes.

Figure 115B:
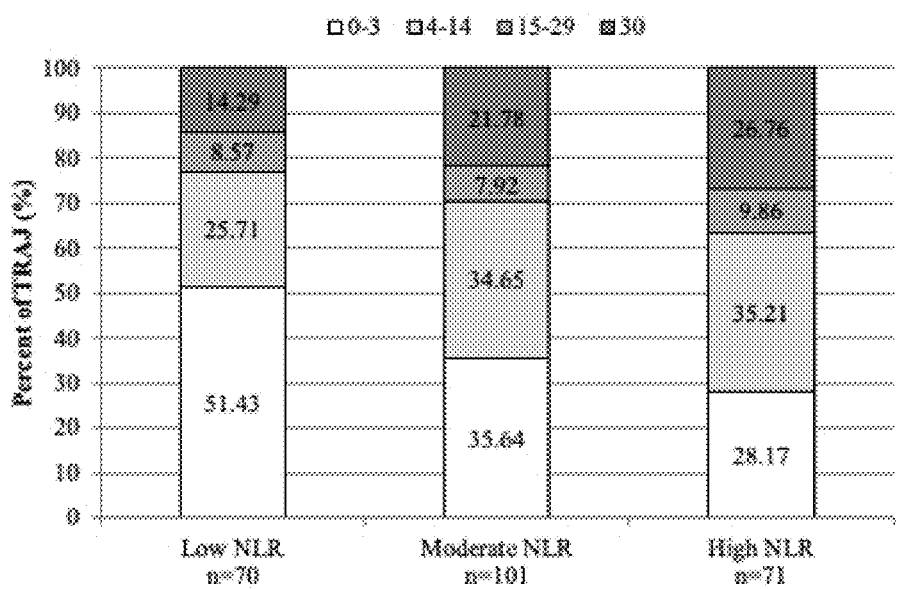

FIG. 115B provides 6-month DRS by NLR TRAJ. The high NLR TRAJ demonstrated the greatest proportion of individuals with severe disability or death at 6-months post-injury.

Figure 115C:
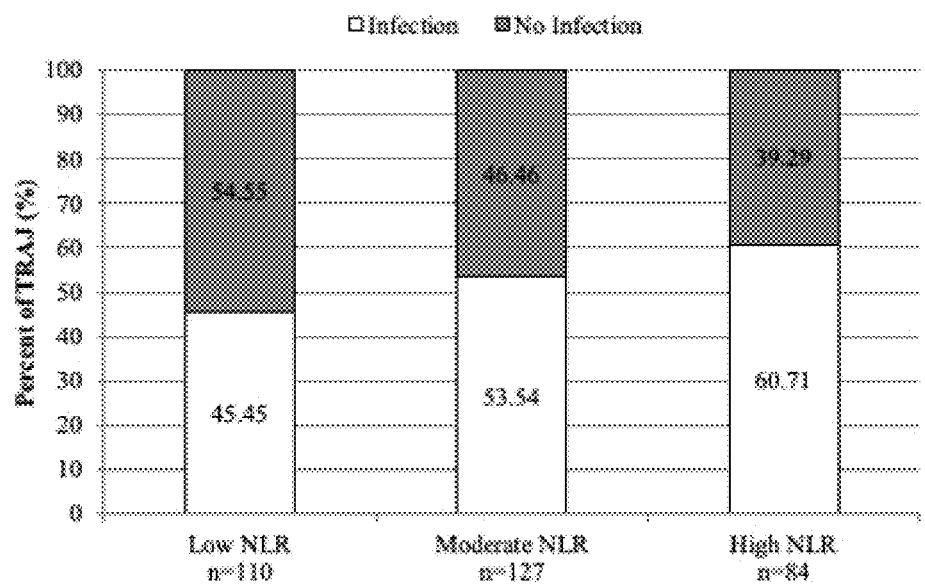

FIG. 115C provides infection status by NLR TRAJ. The high NLR TRAJ demonstrated the greatest proportion of individuals with incidence of acute infection.

Figure 115D:
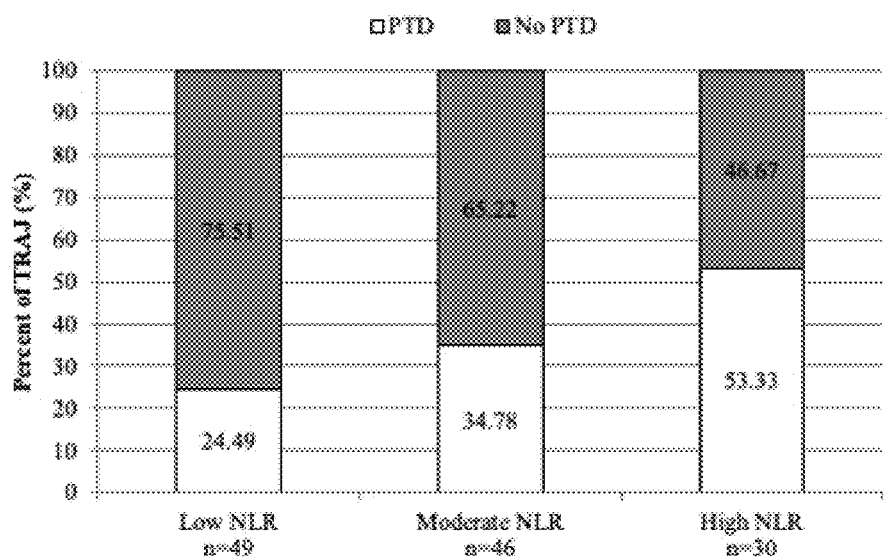

FIG. 115D provides 6-month PTD Prevalence by NLR TRAJ. The high NLR TRAJ demonstrated the greatest proportion of individuals with PTD at 6-months post-injury.

Figure 115E:
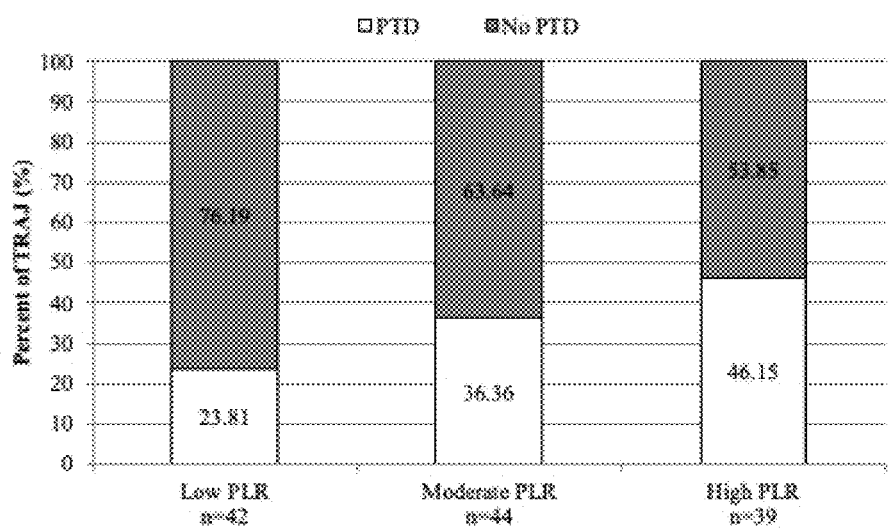

FIG. 115E provides 6-month PTD Prevalence by PLR TRAJ. The high PLR TRAJ demonstrated the greatest proportion of individuals with PTD 6-months after injury.

FIGS. 116A-116B provide the CT Injury incidence by NLR TRAJ (FIG. 116A) and CT Injury Incidence by PLR TRAJ (FIG. 116B).

FIGS. 117A-117B provide behavioral associations by NLR TRAJ (FIG. 117A) and behavioral associations by PLR TRAJ (FIG. 117B).

FIG. 118A provides Mean Soluble Receptor and Cytokine Levels from Day 0 to Day 5 by NLR TRAJ. Significant and trending associations from full panel included.

FIG. 118B provides Day 0-5 Mean Cytokine Levels by PLR TRAJ. Significant and trending associations from full panel included.

Figure 119A:
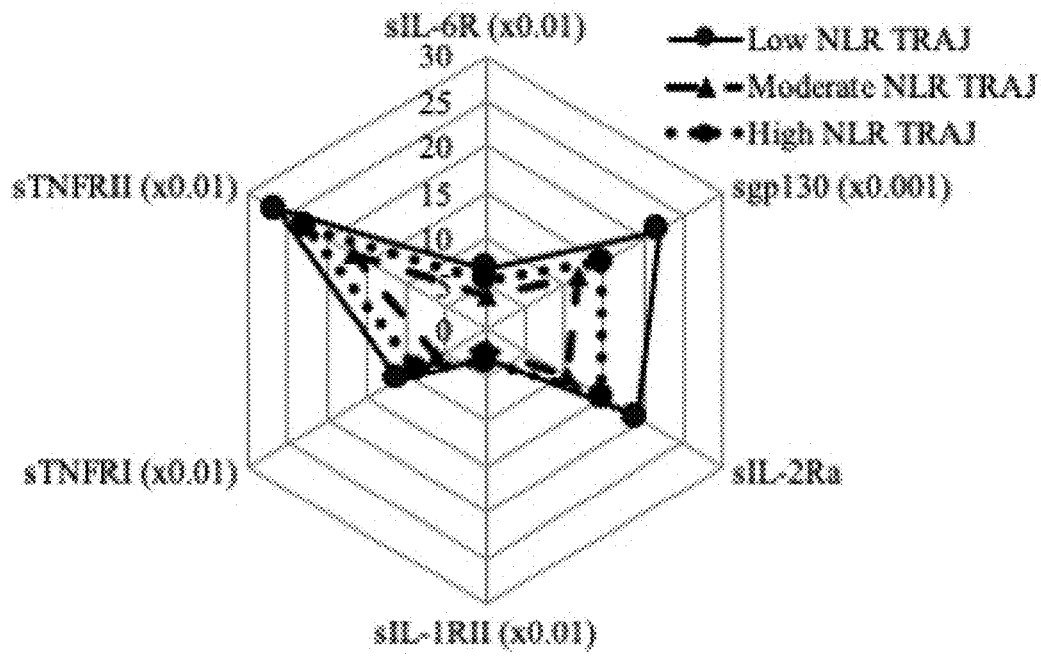

FIG. 119A provides Day 0-5 Mean Soluble Receptor Levels by NLR TRAJ.

Figure 119B:
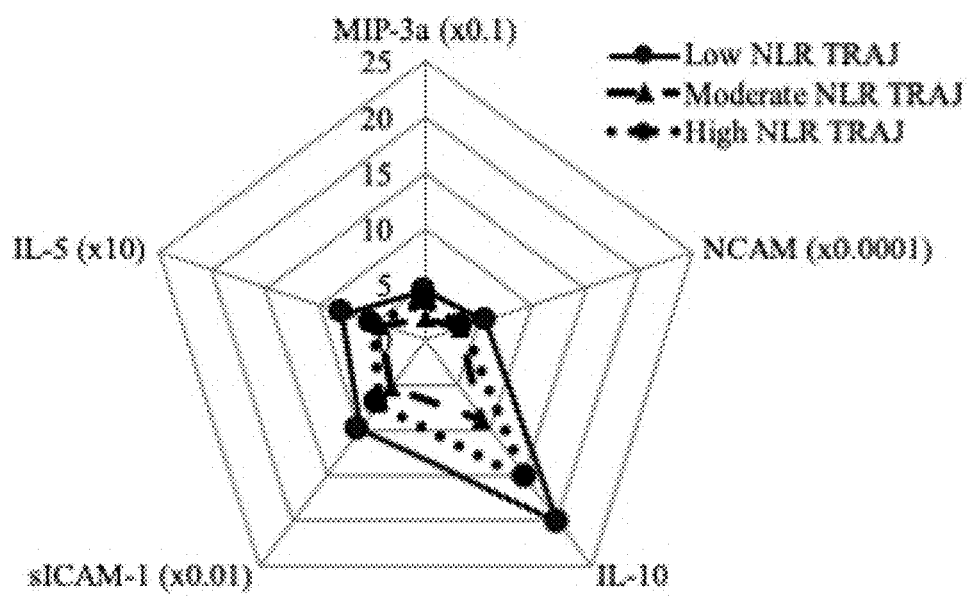

FIG. 119B provides Day 0-5 Mean Cytokine Levels by NLR TRAJ. Trending (p<0.10) markers included due to smaller sample size of acute panel. Marker levels were highest in the low NLR TRAJ, followed by high and moderate groups.

Figure 119C:
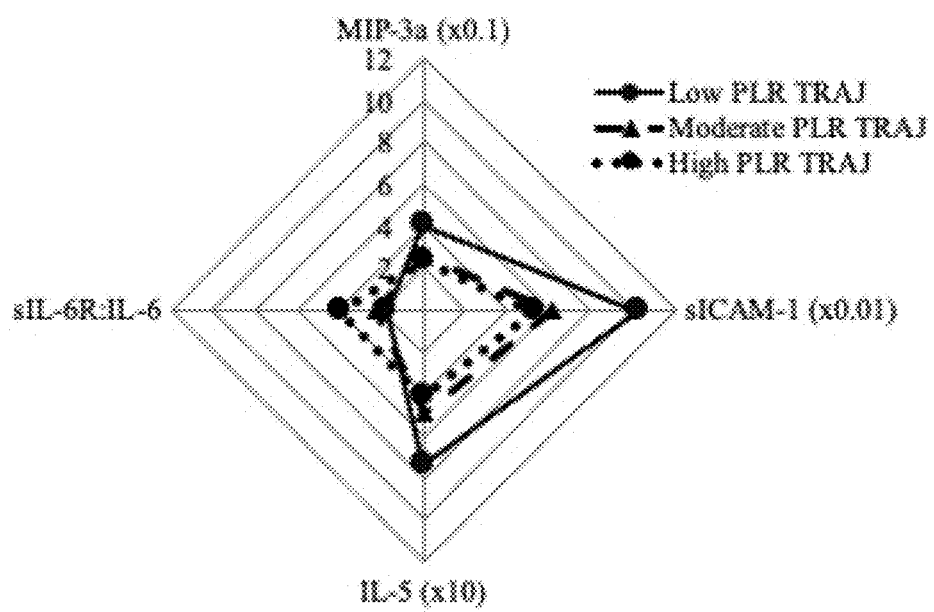

FIG. 119C provides Day 0-5 Mean Cytokine Levels by PLR TRAJ. Trending (p<0.10) markers included due to smaller sample size of acute panel.

FIG. 120A provides Month 0-6 Mean Cytokine Levels by NLR TRAJ. Significant and trending associations from full panel were included.

FIG. 120B provides Month 0-6 Mean Cytokine Levels by PLR TRAJ. Significant and trending associations from full panel included.

Figure 121A:
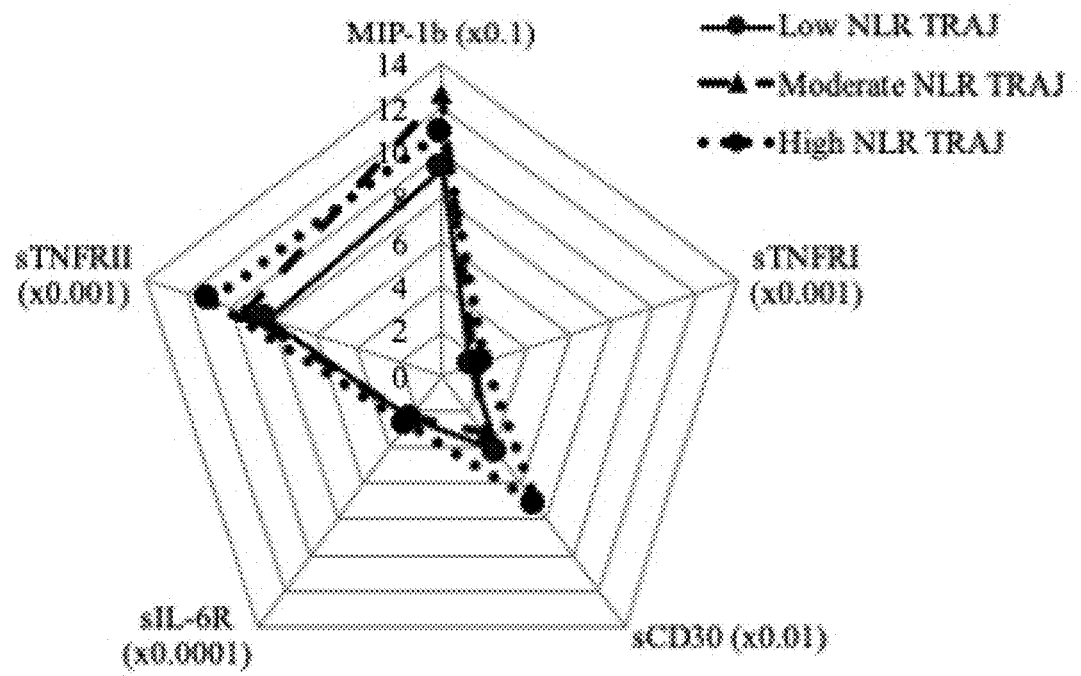

FIG. 121A provides month 0-6 Mean Cytokine Levels by NLR TRAJ.

Figure 121B:
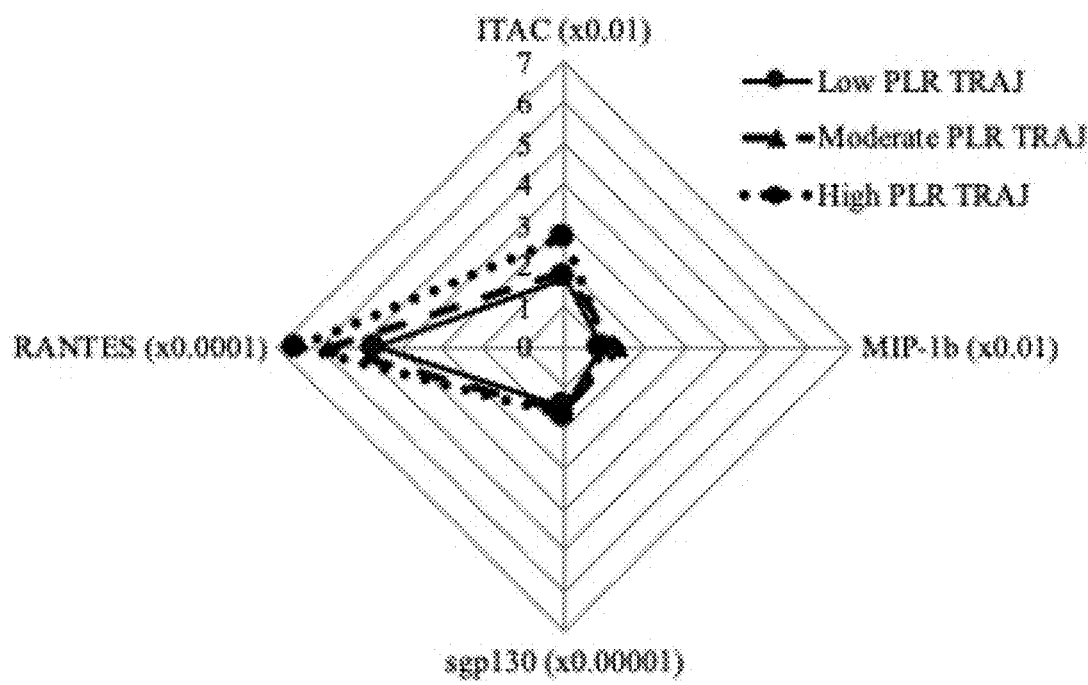

FIG. 121B provides Month 0-6 Mean Cytokine Levels by PLR TRAJ.

FIG. 122 provides Multivariate Models of Unfavorable GOS Score at 6-months post-TBI.

5. DETAILED DESCRIPTION

The present disclosure relates to methods for treating traumatic brain injury (TBI) and TBI-associated impairments (e.g., hypogonadotropic hypogonadism, post traumatic epilepsy (PTE), and deficits to neurorecovery) in a subject. It is based partly on the discovery that administration of IL-7 and/or TNFα can target different immunity domains that contribute to TBI injury response, recovery, and susceptibilities. In certain embodiments, treatment methods disclosed herein include administering to the subject an interleukin-7 (IL-7) or IL-7 agonist, and/or a TNFα inhibitor.

The present disclosure also provides biomarkers for use in identifying a subject that is likely to develop a TBI-associated impairment, and a subject that is likely to respond to a treatment for TBI-associated impairments. The biomarkers disclosed herein include IL-7, autoantibodies, hormones, soluble tumor necrosis factor receptors (e.g., sTNFRI, and sTNFRII), white blood cell indices (e.g., Neutrophil:Lymphocyte ratio (NLR), absolute lymphocyte counts), TNFα, BDNF, soluble receptors (e.g., sIL-2Ra), chemokines (e.g., RANTES, ITAC), and combinations thereof.

Non-limiting embodiments of the present disclosure are described by the present specification and Examples.

For purposes of clarity of disclosure and not by way of limitation, the detailed description is divided into the following subsections:

5.1 Definitions;
5.2 Methods of Treatment;
5.3 Methods of Predicting and Monitoring Responsiveness to Treatments;
and
5.4 Kits.

5.1 Definitions

The terms used in this specification generally have their ordinary meanings in the art, within the context of the present disclosure and in the specific context where each term is used. Certain terms are discussed below, or elsewhere in the specification, to provide additional guidance to the practitioner in describing the compositions and methods of the present disclosure and how to make and use them.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 10% of a given value. Alternatively, particularly with respect to biological systems or processes, the term can mean within an order of magnitude, preferably within 5-fold, and more preferably within 2-fold, of a value.

An "individual" or "subject" herein is a vertebrate, such as a human or non-human animal, for example, a mammal. Mammals include, but are not limited to, humans, non-human primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

As used herein, the term "disease" refers to any condition or disorder that damages or interferes with the normal function of a cell, tissue, or organ.

An "effective amount" of a substance as that term is used herein is that amount sufficient to effect beneficial or desired results, including clinical results, and, as such, an "effective amount" depends upon the context in which it is being applied. An effective amount can be administered in one or more administrations.

As used herein, and as well-understood in the art, "treatment" is an approach for obtaining beneficial or desired results, including clinical results. For purposes of this subject matter, beneficial or desired clinical results include, but are not limited to, alleviation or amelioration of one or more sign or symptoms, diminishment of extent of disease, stabilized (i.e., not worsening) state of disease, prevention of disease, delay or slowing of disease progression, and/or amelioration or palliation of the disease state. The decrease can be a 10-99% (e.g., 10%, 20%, 30%, 40%, 50%, 60%, 70%, 80%, 90%, 95%, 98% or 99%) decrease in severity of complications, impairments, or symptoms. "Treatment" can also mean prolonging survival as compared to expected survival if not receiving treatment.

As used herein, the term "in vitro" refers to an artificial environment and to processes or reactions that occur within an artificial environment. In vitro environments exemplified, but are not limited to, test tubes and cell cultures.

As used herein, the term "in vivo" refers to the natural environment (e.g., an animal or a cell) and to processes or reactions that occur within a natural environment, such as embryonic development, cell differentiation, neural tube formation, etc.

As used herein, the term "TBI-associated impairment" refers to conditions, symptoms, impairments, or any resulting disabilities that are associated with or caused by traumatic brain injuries, including traumas to the head, such as, for example, traumas caused by accidents and/or sports injuries.

As used herein, the term "deficits to neurorecovery" or "poor neurorecovery" refers to acquired impairments relating to neurological system in a subject who has suffered an TBI, where the deficits to neurorecovery includes, but not limited to, cognitive deficits, PTE, mood impairments, and behavioral impairments.

As used herein, the term "cognitive impairment" or "cognitive deficit" refers to an acquired deficit in one or more of memory function, problem solving, orientation, attention, visual conceptualization, spatial conceptualization, executive and/or abstraction that impinges on an individual's ability to function independently.

As used herein, the term "TBI-associated cognitive deficit" or "TBI-associated cognitive impairment" refers to cognitive impairments, as defined herein, that are associated with or caused by traumatic brain injuries, including traumas to the head, such as, for example, traumas caused by accidents and/or sports injuries.

As used herein, the term "neuroendocrine dysfunction" or "NED" refers to a variety of conditions caused by imbalances in the body's hormone production, e.g., hormones produced by hypothalamus and pituitary gland, directly related to the brain. In certain embodiments, neuroendocrine dysfunction includes pituitary deficiencies, gonadotropin deficiencies, adrenocorticotropic hormone deficiencies, thyroid deficiency, prolactin deficiencies.

As used herein, the term "hypogonadism" is used to refer to subjects having a total testosterone level of lower than 12 nmol/L, in certain embodiments of lower than 10 nmol/L, and in further embodiments of lower than 8 nmol/L. In one embodiment, the term "hypogonadism" is used to refer to a male individual having morning serum total testosterone levels below 8 nmol/L.

As used herein, the term "hypogonadotropic" refers to a subject with inappropriately low gonadotropins. In particular, a subject with "inappropriately low gonadotropins" is defined as a subject with (i) luteinizing hormone (LH) levels≤ULN (upper limit of normal) of the respective approved assay, (ii) follicle stimulating hormone (FSH) levels≤ULN. In certain embodiments, the subject is a male subject. In certain embodiments, the subject is a female subject.

As used herein, the term "hypogonadotropic hypogonadism" or "a patient with hypogonadotropic hypogonadism" refers to a subject suffering from hypogonadism as defined herein and being hypogonadotropic as defined herein.

As used herein, the term "TBI-associated hypogonadotropic hypogonadism" refers to hypogonadotropic hypogonadism, as defined herein, that are associated with or caused by traumatic brain injuries, including traumas to the head, such as, for example, traumas caused by accidents and/or sports injuries.

As used herein, the term "persistent hypogonadotropic hypogonadism" or "PHH" refers to hypogonadotropic hypogonadism that lasts for a clinically considered long period of time. In certain embodiments, a subject is designated as having PHH if 50% or more of the samples collected from the subject over such clinically considered long period of time meet the definition of "hypogonadotropic hypogonadism" disclosed herein. In certain embodiments, the clinically considered long period of time is about 3-months, 4-months, 5-months, 6-months, 7-months, 8-months, 9-months, 10-months, 11-months, 1-year, 1.5-years, 2-years, or longer.

As used herein, the term "IL-7 agonist" refers to any molecule that promotes one or more biological activities or increases binding of IL-7 with one or more of its associated molecules and/or target receptor/cellular structures.

As used herein, the term "TNFα inhibitor" refers to any molecule that suppresses the physiologic response to TNFα.

As used herein, the term "biological sample" refers to a sample of biological material obtained from a subject, e.g., a human subject, including a biological fluid, e.g., blood, plasma, serum, urine, sputum, spinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid, bronchoalveolar fluid, biliary fluid and combinations thereof.

5.2 Methods of Treatment

The present disclosure provides methods for treating a TBI in a subject. In certain embodiments, the methods disclosed herein include administering to the subject an IL-7 or an IL-7 agonist. In certain embodiments, the methods disclosed herein include administering to the subject a TNFα inhibitor. In certain embodiments, the methods disclosed herein include administering to the subject a TNFα inhibitor, and an IL-7 or an IL-7 agonist.

In certain embodiments, the subject is a human subject. In certain embodiments, the subject is a non-human subject, such as, but not limited to, a dog, a cat, a horse, a rodent, or a non-human primate. In certain embodiments, the subject is a male subject. In certain embodiments, the subject is a female subject.

In certain embodiments, the methods disclosed herein improve outcome (e.g., reducing long-term disability) of TBI in a subject. In certain embodiments, a good outcome following TBI is associated with one or more of the following: a Glasgow Outcome Scale score of greater than or equal to 4; a Disability Rating Scale (DRS) score of less than 7, or less than 6, or less than 5, or less than 4, or less than or equal to 3; mild or moderate or essentially no post-traumatic epilepsy; mild or moderate or no hypogonadotropic hypogonadism; a Ranchos Los Amigos Scale score of Level VI, Level VII or Level VIII; or mild or moderate presence of one or more of fatigue, headaches, visual disturbances, memory loss, poor attention/concentration, sleep disturbances, dizziness/loss of balance, irritability-emotional disturbances, and/or feelings of depression. A good outcome may be measured at least about 2 months, or at least about 4 months, at least about 6 months, at least about 8 months, at least about 10 months, at least 12 months, at least 14 months, at least 16 months, at least 18 months, at least 20 months, at least 22 months, or at least 24 months, following TBI. In certain embodiments, the methods disclosed herein reduce the extent of disability following TBI. In certain embodiments, the methods disclosed herein increase the likelihood of having a good outcome following TBI.

In certain embodiments, methods disclosed herein improves a Glasgow Outcome Score (GOS) of the subject. GOS is an umbrella metric for cumulative effects of all TBI-associated impairments, including but not limited to cognitive impairments, behavioral impairments, mood impairments, motor impairments, hormonal impairments, epilepsy, etc.

In certain embodiments, the method increases serum 1gM level in the subject. In certain embodiments, the method increases serum 1gM:1gG ratio in the subject. In certain embodiments, the 1gM includes anti-pituitary (APA) 1gM, anti-hypothalamus (AHA) IgM, or a combination thereof. In certain embodiments, the IgG includes APA IgG, AHA IgG, or a combination thereof. In certain embodiments, the method alters levels of IL-7, TNF-α, soluble receptor proteins (e.g. sTNFR1, sIL-2ra, TNFRII), and chemokines (RANTES, ITAC) in the subject.

The present disclosure further provides methods for treating or reducing the risk of developing a TBI-associated impairment (e.g., conditions, symptoms, impairments, and resulting disabilities) in a subject, including administering to the subject an IL-7 or an IL-7 agonist, and/or a TNFα inhibitor.

In certain embodiments, methods disclosed herein treat or reduce the risk of developing a TBI-associated impairment selected from deficits to neurorecovery, PTE, cognitive deficits (e.g., attention deficit, memory deficit, and impaired visual or spatial conceptualization), psychological deficits (e.g., personality changes, mood disturbance, substance abuse), somatic symptoms (e.g., headaches, visual disturbances), emotional symptoms (e.g., irritability), behavioral dysfunctions (e.g., aggression, apathy, impulsivity), physical dysfunctions (e.g., cranial or peripheral nerve damage, impairment in motor functioning, strength and coordination, or impairment in sensation), neuroendocrine dysfunctions (e.g., hypogonadotropic hypogonadism, e.g., PHH), and combinations thereof.

In certain embodiments, the TBI-associated impairment is a neuroendocrine dysfunction. In certain embodiments, the neuroendocrine dysfunction is selected from pituitary deficiencies, gonadotropin deficiencies, adrenocorticotropic hormone deficiencies, thyroid deficiency, and prolactin deficiencies. In certain embodiments, the neuroendocrine dysfunction is TBI-associated hypogonadotropic hypogonadism. In certain embodiments, the TBI-associated hypogonadotropic hypogonadism is TBI-associated persistent hypogonadotropic hypogonadism (PHH). In certain embodiments, the methods disclosed herein for treating or reducing the risk of developing TBI-associated hypogonadotropic hypogonadism increase the total testosterone level in a subject. In certain embodiments, the total testosterone level is increased to about 12 nmol/L or more.

In certain embodiments, the methods disclosed herein alter the level of gonadotropins in a subject such that the levels of gonadotropins are within the normal ranges. In certain embodiments, the gonadotropins levels are selected from the group consisting of luteinizing hormone (LH) level and follicle stimulating hormone (FSH) level.

In certain embodiments, the TBI-associated impairment is a deficit of or poor neurorecovery. In certain embodiments, the deficit to neurorecovery is a post traumatic epilepsy (PTE). In certain embodiments, the deficit to neurorecovery is a cognitive deficit.

In certain embodiments, the cognitive deficit is selected from the group consisting of memory deficit, attention deficit, impaired visual conceptualization, and impaired spatial conceptualization. In certain embodiments, the methods disclosed herein improve cognitive deficits as measured by a cognitive assessment tool. Any cognitive assessment tool known in the art can be used with the subject matter disclosed herein. Non-limiting examples of cognitive assessment tools include Controlled Oral Word Association Test, the Trail Making Test, the Stroop Color-Word Matching Test, the California Verbal Learning Test, the Digit Span Test (from the Wechsler Adult Intelligence Scale-III), the Processing Speed Index.

In certain embodiments, the IL-7 or the IL-7 agonist, and/or TNFα inhibitor are administered to the subject in effective amounts that are sufficient to effect beneficial or desired results, including clinical results. In certain embodiments, the effective amounts have the beneficial or desired results of improving outcome (e.g., reducing long-term disability) of TBI, reducing the risk of developing a TBI-associated impairment, alleviating at least one symptom of a TBI-associated impairment, and/or improving at least one clinical parameters of a TBI-associated impairment. The amount will vary from one individual to another and will depend upon a number of factors, including the overall physical condition of the patient, injury type, injury severity, the underlying cause of TBI or TBI-associated impairments, and biomarker profiles.

In certain embodiments, the methods disclosed herein include administering the IL-7 or IL-7 agonist, and/or the TNFα inhibitor at acute, post-acute, and/or chronic stages of the TBI. In certain embodiments, acute stage of TBI refers to the period within about 24 hours or about one week after occurrence of TBI. In certain embodiments, post-acute stage of TBI refers to the period from about 1 week to up to about 4 weeks after occurrence of TBI. In certain embodiments, early chronic stage of TBI refers to the period from about 4 weeks to about 6 months after occurrence of TBI. In certain embodiments, chronic stage of TBI refers to the period at least about 4 weeks, at least about 6 months, or at least 12 months after occurrence of TBI. In certain embodiments, the IL-7, the IL-7 agonist, and/or the TNFα inhibitor is administered to the subject at a post-acute stage and/or a chronic stage of TBI. In certain non-limiting embodiments, the IL-7, the IL-7 agonist, and/or the TNFα inhibitor is administered to the subject within about 24 hours, within about three days, within about one week, within about two weeks, within about 3 weeks, within about 4 weeks, within about 6 months, within 8 months, or within 12 months from the occurrence of the TBI.

In certain embodiments, the methods disclosed herein include administering an IL-7 to a subject in need thereof. IL-7 is a hematopoietic growth factor secreted by stromal cells in the bone marrow and thymus. IL-7 is important for lymphocyte maturation. In certain embodiments, the IL-7 to be used with the presently disclosed methods is of the same species or a different species of the subject to be treated. In certain embodiments, the IL-7 to be used with the presently disclosed methods is selected from the group consisting of human IL-7, recombinant IL-7, recombinant human IL-7 (rhIL-7), and combinations thereof. In certain embodiments, the IL-7 to be used with the presently disclosed methods is a rhIL-7.

In certain embodiments, the methods disclosed herein include administering an IL-7 agonist to a subject in need thereof. IL-7 agonist refers to a molecule that can activate the IL-7 receptor to produce a biological response that resembles IL-7. In certain embodiments, the IL-7 agonist is an TLR3 agonist disclosed in Jin et al., JCB (2013) 93:413-425, the content of which is incorporated by reference herein in its entirety. In certain embodiments, the IL-7 agonist is a kappa opioid receptor antagonist.

In certain non-limiting embodiments, an effective serum concentration of IL-7 to be achieved by the presently disclosed methods is greater than about 10 pg/ml, greater than about 20 pg/ml, greater than about 25 pg/ml, greater than about 30 pg/ml, greater than about 40 pg/ml, greater than about 50 pg/ml, or greater than about 60 pg/ml. In certain embodiments, the serum concentration of IL-7 is human serum concentration of IL-7.

In certain embodiments, the methods disclosed herein include administering an IL-7 or an IL-7 agonist to a subject in need thereof, wherein the IL-7 or the IL-7 agonist is in an amount of between about 0.1 μg/kg and about 100 μg/kg, or between about 3 μg/kg and about 30 μg/kg. In certain embodiments, the IL-7 or the IL-7 agonist is administered in an amount of about 0.1 μg/kg, about 0.5 μg/kg, about 1 μg/kg, about 2 μg/kg, about 5 μg/kg, about 10 μg/kg, about 15 μg/kg, about 20 μg/kg, about 25 μg/kg, about 30 μg/kg, about 35 μg/kg, about 40 μg/kg, about 45 μg/kg, about 50 μg/kg, about 60 μg/kg, about 70 μg/kg, about 80 μg/kg, about 90 μg/kg, or about 100 μg/kg. In certain embodiments, the IL-7 or the IL-7 agonist is administered in an amount of about 2 μg/kg. In certain embodiments, the IL-7 or the IL-7 agonist is administered in an amount of about 20 μg/kg.

In certain embodiments, the IL-7 or the IL-7 agonist is administered in an amount of between about 10 μg/kg and about 20 μg/kg. In certain embodiments, the IL-7 or the IL-7 agonist is administered in an amount of between about 5 μg and about 5000 μg. In certain embodiments, the IL-7 or the IL-7 agonist is administered in an amount of about 5 pg, about 60 pg, about 120 pg, about 200 pg, about 300 pg, about 400 pg, about 600 pg, about 800 μg, about 1200 μg, about 2000 μg, about 3000 μg, about 4000 μg, or about 5000 pg. In certain embodiments, the IL-7 or the IL-7 agonist is administered in an amount of about 120 μg. In certain embodiments, the IL-7 or the IL-7 agonist is administered in an amount of about 1200 μg.

In certain embodiments, an IL-7 or an IL-7 agonist is administered to the subject daily. In certain embodiments, an IL-7 or an IL-7 agonist is administered to the subject once per day, twice per day, or three times per day. In certain embodiments, an IL-7 or an IL-7 agonist is administered to the subject once per week, every two weeks, every three week, every four weeks, every five weeks, every six weeks, every seven weeks, or every eight weeks. In certain embodiments, an IL-7 or an IL-7 agonist is administered one, two, three, four, five, or six days per week.

In certain embodiments, the methods disclosed herein include administering a TNFα inhibitor to a subject in need thereof. Any suitable TNFα inhibitor known in the art can be used with the presently disclosed methods. In certain embodiments, the TNFα inhibitors is a monoclonal antibody. Non-limiting examples of TNFα inhibitors include adalimumab (Humira®), adalimumab-adbm (Cyltezo®), adalimuab-adaz (Hyrimoz®), adalimumab-atto (Amjevita™), certolizumab pegol (Cimzia®), etanercept (Enbrel®), eanercept-szzs (Ereizil™), golimnumab (Simponi®, Simponi Aria®), infliximab (Remicade®), infliximab-abda (Renflexis®), infliximuab-dyyb (Inflectra®), infliximab-qbtx (Ixifi™), thalidomide (Imimunoprin), lenalidomide (RevIimid®), pomalidomide (Pomalyst®, Imnovid), xanthine derivatives (pentoxifylline), bupropion, hallucinogens (e.g., (R)-DO1, TCB-2, LSD and LA-SS-Az), biosinilars thereof, and combinations thereof.

In certain embodiments, the methods disclosed herein includes administering a TNFα inhibitor to a subject in need thereof, wherein the TNFα inhibitor is administered in an amount of between about 0.5 mg/kg and about 50 mg/kg. In certain embodiments, the TNFα inhibitor is administered in an amount of about 0.5 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 15 mg/kg, about 20 mg/kg, about 25 mg/kg, about 30 mg/kg, about 35 mg/kg, about 40 mg/kg, about 45 mg/kg, or about 50 mg/kg. In certain embodiments, the TNFα inhibitor is administered in an amount of about 2 mg/kg. In certain embodiments, the TNFα inhibitor is administered in an amount of between about 3 mg/kg and about 5 mg/kg. In certain embodiments, the TNFα inhibitor is administered in an amount of between about 5 mg/kg and about 10 mg/kg. In certain embodiments, the TNFα inhibitor is administered as a flat dose in an amount of between about 20 mg to about 500 mg. In certain embodiments, the TNFα inhibitor is administered in an amount of about 20 mg, about 25 mg, about 30 mg, about 35 mg, about 40 mg, about 45 mg, about 50 mg, about 75 mg, about 100 mg, about 150 mg, about 200 mg, about 250 mg, about 300 mg, about 350 mg, about 400 mg, about 450 mg, or about 500 mg. In certain embodiments, the TNFα inhibitor is administered in an amount of about 40 mg or about 50 mg.

In certain embodiments, the TNFα inhibitor is administered to the subject, once per day, twice per week, once per week, every two weeks, every three week, every four weeks, every five weeks, every six weeks, every seven weeks, or every eight weeks. In certain embodiments, the TNFα inhibitor is a monoclonal antibody. In certain embodiments, the TNFα inhibitor is etanercept.

The amounts of IL-7, IL-7 agonist, and TNFα inhibitors administered to the subject disclosed herein can vary depending upon the characteristics of the subject (e.g., age, sex, race, weight, height, BMI, body fat percentage, and/or medical history), frequency of administration, manner of administration, clearance of IL-7, IL-7 agonist, and TNFα inhibitors.

IL-7, IL-7 agonist, and TNFα inhibitors disclosed herein can be administered by any suitable means known in the art, including parenteral, topical, intravenous, subcutaneous, intraperitoneal, intrapulmonary, intranasal, and/or intralesional, intra-arterial, intrathecal, or by local instillation into the central nervous system. Parenteral infusions include intramuscular, intravenous, intraarterial, intraperitoneal, or subcutaneous administration. Intrathecal administration is also contemplated (see, e.g., U.S. Patent Publication No. 2002/0009444 by Grillo-Lopez).

In certain embodiments, the methods disclosed herein include administering an IL-7 or an IL-7 agonist, and a TNFα inhibitor to the subject in need thereof. In certain embodiments, the IL-7 or IL-7 agonist, and the TNFα inhibitor are administered simultaneously or sequentially. In certain embodiments, the methods disclosed herein include first administering an IL-7 or an IL-7 agonist to the subject, then administering a TNFα inhibitor to the subject. In certain embodiments, the methods disclosed herein include first administering a TNFα inhibitor to the subject, then administering an IL-7 or an IL-7 agonist to the subject. In certain embodiments, the subject is a human subject.

5.3 Methods of Predicting and Monitoring Responsiveness to Treatments;

The present disclosure provides methods for predicting a subject who has sustained TBI as likely to develop a TBI-associated impairment, the methods including: determining the level of a biomarker in a sample obtained from the subject, comparing the level of the biomarker to a reference level, identifying the subject as likely to develop the TBI-associated impairment.

The present disclosure also provides methods for identifying a subject who has sustained TBI as likely to respond to a treatment for a TBI-associated impairment, the methods including: determining the level of a biomarker in a sample obtained from the subject, comparing the level of the biomarker to a reference level, identifying the subject as likely to respond to the treatment based on the comparison. In certain embodiments, the methods further includes treating the subject that is identified as likely to respond to the treatment.

In certain embodiments, the reference level is a predetermined level of a biomarker that a level higher than the reference level indicates a subject is likely to be responsive to a treatment of a TBI-associated impairments. In certain embodiments, the reference level is a predetermined level of a biomarker that a level lower than the reference level indicates a subject is likely to be responsive to a treatment of a TBI-associated impairments. In certain embodiments, the reference level is the level of a biomarker from a healthy individual or a population of healthy individuals free of the TBI-associated impairment.

In certain embodiments, the reference level is the level of a biomarker from the same subject collected at an earlier time point.

The present disclosure also provides methods for monitoring a subject's responsiveness to a treatment for a TBI-associated impairment, including determining the level of a biomarker in a sample obtained from the subject before receiving the treatment, determining the level of the biomarker in a sample obtained from the subject during or after receiving the treatment, comparing the levels of the biomarker in the samples, where a change of the level of the biomarker during or after the treatment indicates the responsiveness of the subject to the treatment. In certain embodiments, the methods further include continuing the treatment if the subject is responsive to the treatment, and treating the subject with a different treatment for the TBI-associated impairment if the subject is not responsive to the treatment. In certain embodiments, the method further includes treating the subject with a different dosing regimen for the TBI-associated impairment if the subject is not responsive to the treatment.

In certain embodiments, the level of the biomarker is determined in a blood sample obtained from a subject. In certain embodiments, the blood sample is a plasma sample, a serum sample, or a CNS-derived exosomal fraction of the blood sample. In certain embodiments, the CNS-derived exosomal fraction includes CNS-derived exosomes. In certain embodiments, the sample is obtained from the subject at the post-acute and/or chronic stage of the TBI. In certain embodiments, the sample is obtained from the subject from about 1 week to about 4 weeks after the occurrence of the TBI. In certain embodiments, the sample is obtained from the subject at least about 4 weeks, at least about 6 months, or at least 12 months after occurrence of TBI.

In certain embodiments, the biomarker is IL-7, soluble tumor necrosis factor receptor (sTNFR) (e.g., sTNFRI and sTNFRII), autoantibodies, hormones, white blood cells indices (e.g., Neutrophil-Lymphocyte Ratio (NLR), absolute lymphocyte counts), TNFα, BDNF, soluble receptors, chemokines, or combinations thereof. In certain embodiments, the sTNFR is sTNFRI. In certain embodiments, the autoantibody is APA IgM, APA IgG, AHA IgM, AHA IgG, any IgG or IgM autoantibodies, or any combinations thereof. In certain embodiments, the hormone is selected from gonadotropins testosterone, estrogens, progesterone, thyroid hormones, growth hormones, adrenal hormones, prolactin, vasopressin, oxytocin, and combinations thereof. In certain embodiments, the soluble receptor protein includes sIL-2Ra. In certain embodiments, the chemokine is selected from RANTES, ITAC, and combinations thereof.

Any agents or treatments known in the art for treating TBI-associated impairments, can be used with the methods disclosed herein. In certain embodiments, the treatment for the TBI-associated impairment includes citicoline, a neurostimulator, dopamine agonists, and/or anticonvulsants. In certain embodiments, the treatment includes administering an IL-7 or an IL-7 agonist, and/or a TNFα inhibitor as disclosed in Section 5.2.

In certain embodiments, the methods disclosed herein, further include identifying the subject is likely to respond to a treatment of a TBI-associated impairment or is likely to develop a TBI-associated impairment, if the level of the biomarker is higher than the reference level. In certain embodiments, the biomarker is selected from the group consisting of white blood cells indices (e.g., NLR, absolute lymphocyte counts), sTNFR (e.g., sTNFRI and sTNFRII), TNFα, BDNF, soluble receptors (e.g., sIL2Ra), chemokines (e.g., RANTES, ITAC), and any combinations thereof, and the treatment includes a TNFα inhibitor. In certain embodiments, the biomarker is selected from the group consisting of APA IgM, APA IgG, AHA IgM, AHA IgG, any IgG or IgM autoantibodies, and any combinations thereof, and the treatment includes IL-7 or IL-7 agonist.

In certain embodiments, the reference level of sTNFR is a predetermined level of sTNFR. In certain embodiments, the predetermined level of sTNFR is between about 1000 pg/ml and about 2000 pg/ml. In certain embodiments, the predetermined level of sTNFR is about 1000 pg/ml, about 1100 pg/ml, about 1200 pg/ml, about 1300 pg/ml, about 1400 pg/ml, about 1500 pg/ml, about 1600 pg/ml, about 1700 pg/ml, about 1800 pg/ml, about 1900 pg/ml, or about 2000 pg/ml. In certain embodiments, the predetermined level of sTNFR is about 1500 pg/ml. In certain embodiments, the level of sTNFR is determined in a blood sample obtained from the subject. In certain embodiments, the sTNFR is sTNFRI. In certain embodiments, the methods disclosed herein include identifying the subject is likely to respond to a treatment of a TBI-associated impairment or is likely to develop a TBI-associated impairment, if the level of sTNFRI is higher than about 1500 pg /ml in a blood sample from the subject. In certain embodiments, the treatment includes administering a TNFα inhibitor. In certain embodiments, the treatment includes administering a TNFα inhibitor at the post-acute and/or chronic stage of the TBI.

In certain embodiments, the reference level of NLR is a predetermined level of NLR. In certain embodiments, the predetermined level of NLR is between about 5 and about 50. In certain embodiments, the predetermined level of NLR is about 5, about 10, about 15, about 20, about 30, about 40, or about 50. In certain embodiments, the predetermined level of NLR is about 10. In certain embodiments, the level of NLR is determined in a blood sample obtained from the subject. In certain embodiments, the methods disclosed herein include identifying the subject is likely to respond to a treatment of a TBI-associated impairment or is likely to develop a TBI-associated impairment, if the level of NLR is higher than about 10 in a blood sample from the subject. In certain embodiments, the treatment includes administering a TNFα inhibitor. In certain embodiments, the NLR is measured at the acute and/or post-acute stage and/or chronic stage of the TBI. In certain embodiments, the treatment includes administering a TNFα inhibitor at the post-acute stage and/or chronic stage of the TBI.

In certain embodiments, the methods disclosed herein further include identifying the subject is likely to respond to a treatment of a TBI-associated impairment or is likely to develop a TBI-associated impairment, if the level of the biomarker is lower than the reference level. In certain embodiments, the biomarker is selected from the group consisting of IL-7, hormones (e.g., gonadotropins, testosterones, estrogens, progesterone, thyroid hormones, growth hormones, adrenal hormones, prolactin, vasopressin, oxytocin, and combinations thereof), and any combinations thereof, and the treatment includes IL-7 or IL-7 agonist.

In certain embodiments, the reference level of IL-7 is a predetermined level of IL-7. In certain embodiments, the predetermined level of IL-7 is between about 0 pg/ml and about 100 pg/ml. In certain embodiments, the predetermined level of IL-7 is about 5 pg /ml, about 10 pg/ml, about 15 pg/ml, about 20 pg/ml, about 25 pg/ml, about 30 pg/ml, about 35 pg/ml, about 40 pg/ml, about 50 pg/ml, about 60 pg/ml, about 70 pg/ml, about 80 pg/ml, about 90 pg/ml, or about 100 pg/ml. In certain embodiments, the predetermined level of IL-7 is about 25 pg/ml. In certain embodiments, the level of IL-7 is determined in a blood sample obtained from the subject. In certain embodiments, the methods disclosed herein include identifying the subject is likely to respond to a treatment of a TBI-associated impairment or is likely to develop a TBI-associated impairment, if the level of IL-7 is lower than about 25 pg/ml in a blood sample from the subject. In certain embodiments, the treatment includes administering an IL-7 or an IL-7 agonist.

In certain embodiments, the presently disclosed methods for treating a subject for TBI-associated impairments, include:

determining the level of sTNFR (e.g., sTNFRI, and sTN-FRII) and the level of IL-7 in a sample obtained from the subject;
(i) treating the subject with an IL-7 or an IL-7 agonist if the level of IL-7 is lower than a reference level of IL-7 (e.g., lower than about 25 pg/ml) and the level of sTNFR level is lower than a reference level of sTNFR (e.g., lower than about 1500 pg/ml),
(ii) treating the subject with an IL-7 or an IL-7 agonist and a TNFα inhibitor if the level of IL-7 is lower than a reference level of IL-7 (e.g., lower than about 25 pg/ml) and the level of sTNFR level is higher than a reference level of sTNFR (e.g., higher than about 1500 pg/ml), or
(iii) include treating the subject with a TNFα inhibitor if the level of IL-7 is higher than a reference level of IL-7 (e.g., higher than about 25 pg/ml) and the level of sTNFR level is higher than a reference level of sTNFR (e.g., higher than about 1500 pg/ml).

In certain embodiments, the dose of IL-7 or IL-7 agonist is higher in (ii) than in (i).

In certain embodiments, a decreased level of the biomarker during or after the treatment indicates the responsiveness of the subject to the treatment, wherein the biomarker is selected from the group consisting of white blood cells indices (e.g., Neutrophil-Lymphocyte Ratio (NLR), absolute lymphocyte counts), sTNFR (e.g., sTNFRI and sTNFRII), autoantibodies (e.g., APA IgM, APA IgG, AHA IgM, AHA IgG, or any IgG and IgM autoantibodies), TNFα, BDNF, soluble receptors (e.g., sIL2Ra), chemokines (e.g., RANTES, ITAC), and any combinations thereof. In certain embodiments, an increased level of the biomarker during or after the treatment indicates the responsiveness of the subject to the treatment, wherein the biomarker is selected from the group consisting of IL-7, hormones (e.g., gonadotropins, testosterones, estrogens, progesterone, thyroid hormones, growth hormones, adrenal hormones, prolactin, vasopressin, oxytocin, and combinations thereof) and any combinations thereof.

In certain embodiments, a group-based trajectory analysis (TRAJ) is performed with the presently disclosed methods for identifying a subject who has sustained TBI as likely to respond to a treatment of a TBI-associated impairment including IL-7 or IL-7 agonist, and/or a TNFα inhibitor.

Group-based trajectory modelling (GBTM or TRAJ) is a statistical methodology that can be used to analyze the evolution of a measure over time among groups of individuals, identifying distinct longitudinal groups. GBTM can require determining 1) distribution of the input data, 2) number of distinct groups (or trajectories) that may exist in the data, and 3) the polynomial order of each trajectory. An exemplary group-based trajectory modeling is disclosed in Nagin et al., Ann Nutr Metab. 2014;65(2-3):205-210, the content of which is incorporated by reference herein in its entirety.

The SAS procedure PROC TRAJ and the Stata add-on Traj are able to conduct GTBM. GBTM does not require complete observations for an individual at all time-points.

In certain embodiments, at least two longitudinal data points are collected for a participant's inclusion in biomarker GBTM. GBTM can be applied to continuous, categorical, or dichotomous variables by specifying the distribution as censored normal, zero-inflated Poisson, or Bernoulli distribution respectively. To begin GBTM, a one group model is fit to a quartic polynomial order. Additional groups of the quartic polynomial order are then added. The Bayes factor is used to assess improved performance across two GBTM models, comparing the BIC of each model using the equation $e^{BIC1-BIC2}$. A higher BIC value is preferred, with a Bayes factor >10 is generally considered a meaningful difference between two models. A combination of BIC & Bayes factor model fit diagnostics with clinical/content expertise should be used to identify the number of groups. Group polynomials should then be lowered, until the highest order polynomial for each group is significant (typically $\alpha=0.05$). Once groups have been fit to the appropriate polynomial, average posterior probabilities (APP's) are generated for each group as the APP for group membership, ranging from 0 to 1 with higher values indicating better model fit. Values greater than 0.7 are recommended for each groups APP.

Exemplary applications of GBTM are disclosed in Kumar et al., Brain Behav Immun. 2015; 45:253-262; Munoz et al., Front Mol Neurosci. 2017; 10:44; Santarsieri et al., Brain Behav Immun. 2015; 45:15-27; Wagner et al., J Neurotrauma. 2011; 28(6):871-888; and Niyonkuru et al., J Neurotrauma. 2013; 30(11):938-945, the contents of which are incorporated herein by reference.

In certain embodiments, the presently disclosed methods for identifying a subject who has sustained TBI as likely to respond to a treatment including IL-7 or a IL-7 agonist, include: determining the levels of IL-7 in at least two samples obtained from the subject, assigning a trajectory group membership to the subject based on the level of IL-7, if the subject is assigned a low IL-7 trajectory group membership, the subject is likely to respond to the treatment. In certain embodiments, the methods further include treating the subject that is identified as likely to respond to the treatment with IL-7 or a IL-7 agonist.

In certain embodiments, the presently disclosed methods for identifying a subject who has sustained TBI as likely to respond to a treatment including a TNFα inhibitor, include: determining the levels of sTNFR (e.g., sTNFRI, and sTNFRII) in at least two samples obtained from the subject, assigning a trajectory group membership to the subject based on the levels of sTNFR, if the subject is assigned a high sTNFR trajectory group membership, the subject is likely to respond to the treatment. In certain embodiments, the methods further includes treating the subject that is identified as likely to respond to the treatment with the TNFα inhibitor.

In certain embodiments, the presently disclosed methods for treating a subject for TBI-associated impairments, include:
(a) determining the level of sTNFR (e.g., sTNFRI, and sTNFRII) and the level of IL-7 in at least two samples obtained from the subject;
(b) assigning trajectory group memberships to the subject by assessing the IL-7 and sTNFRI levels of the subject in relation to group-based trajectory analyses derived from a population with TBI,
(c-i) treating the subject with an IL-7 or an IL-7 agonist if the subject is assigned a low IL-7 trajectory group membership and a low sTNFR trajectory group membership,
(c-ii) treating the subject with an IL-7 or an IL-7 agonist and a TNFα inhibitor if the subject is assigned a low IL-7 trajectory group membership and a high sTNFR trajectory group membership, or
(c-iii) treating the subject with a TNFα inhibitor if the subject is assigned a high IL-7 trajectory group membership and a high sTNFR trajectory group membership.

In certain embodiments, the dose of IL-7 or IL-7 agonist is higher in (c-ii) than in (c-i).

In certain embodiments, the TBI-associated impairment is a neuroendocrine dysfunction selected from pituitary deficiencies, gonadotropin deficiencies, adrenocorticotropic hormone deficiencies, thyroid deficiency, and prolactin deficiencies.

In certain embodiments, the neuroendocrine dysfunction is TBI-associated hypogonadotropic hypogonadism. In certain embodiments, the TBI-associated hypogonadotropic hypogonadism is TBI-associated persistent hypogonadotropic hypogonadism (PHH). In certain embodiments, the TBI-associated impairment is a deficit of neurorecovery. In certain embodiments, the deficit to neurorecovery is a post traumatic epilepsy (PTE). In certain embodiments, the deficit to neurorecovery is a cognitive deficit.

In certain embodiments, the cognitive deficit is selected from the group consisting of memory deficit, attention deficit, impaired visual conceptualization, and impaired spatial conceptualization.

In certain embodiments, the subject is a human subject.

5.4 Kits

The present disclosure further provides a kit for identifying a subject who has sustained TBI as likely to respond to a treatment for a TBI-associated impairment. The present disclosure further provides a kit for identifying a subject who has sustained TBI as likely to develop a TBI-associated impairment. The present disclosure further provides a kit for monitoring a subject's responsiveness to a treatment for a TBI-associated impairment.

In certain embodiments, the kit includes a means for detecting a biomarker. In certain embodiments, the biomarker is IL-7, soluble tumor necrosis factor receptor (sTNFR) (e.g., sTNFRI and sTNFRII), autoantibodies, hormones, white blood cells indices (e.g., Neutrophil-Lymphocyte Ratio (NLR), absolute lymphocyte counts), TNFα, BDNF, soluble receptors (e.g., sIL2Ra), chemokines (e.g., RANTES, ITAC), or combinations thereof. In certain embodiments, the sTNFR is sTNFRI. In certain embodiments, the autoantibody is APA IgM, APA IgG, AHA IgM, AHA IgG, any IgG or IgM autoantibodies, or any combinations thereof.

Types of kits include, but are not limited to, packaged biomarker-specific probe and primer sets (e.g., TaqMan probe/primer sets), arrays/microarrays, biomarker-specific antibodies, biomarker-specific beads, which further contain one or more probes, primers, or other reagents for detecting one or more biomarkers of the present disclosure.

In certain non-limiting embodiments, a kit can include at least one antibody for immunodetection of the biomarker(s) to be identified. Antibodies, both polyclonal and monoclonal, specific for a biomarker, can be prepared using conventional immunization techniques, as will be generally known to those of skill in the art. The immunodetection reagents of the kit can include detectable labels that are associated with, or linked to, the given antibody or antigen itself. Such detectable labels include, for example, chemiluminescent or fluorescent molecules (rhodamine, fluorescein, green fluorescent protein, luciferase, Cy3, Cy5, or ROX), radiolabels (3H, 35S, 32P, 14C, 131I) or enzymes (alkaline phosphatase, horseradish peroxidase).

In certain non-limiting embodiments, the biomarker-specific antibody can be provided bound to a solid support, such as a column matrix, an array, or well of a microtiter plate. Alternatively, the support can be provided as a separate element of the kit.

In certain non-limiting embodiments, a kit can include a pair of oligonucleotide primers suitable for polymerase chain reaction (PCR) or nucleic acid sequencing, for detecting one or more biomarker(s) to be identified. A pair of primers can include nucleotide sequences complementary to a biomarker, and be of sufficient length to selectively hybridize with said biomarker. Alternatively, the complementary nucleotides can selectively hybridize to a specific region in close enough proximity 5' and/or 3' to the biomarker position to perform PCR and/or sequencing. Multiple biomarker-specific primers can be included in the kit to simultaneously assay large number of biomarkers. The kit can also include one or more polymerases, reverse transcriptase and nucleotide bases, wherein the nucleotide bases can be further detectably labeled.

In certain non-limiting embodiments, a primer can be at least about 10 nucleotides or at least about 15 nucleotides or at least about 20 nucleotides in length and/or up to about 200 nucleotides or up to about 150 nucleotides or up to about 100 nucleotides or up to about 75 nucleotides or up to about 50 nucleotides in length.

In certain non-limiting embodiments, the oligonucleotide primers can be immobilized on a solid surface or support, for example, on a nucleic acid microarray, wherein the position of each oligonucleotide primer bound to the solid surface or support is known and identifiable.

In certain non-limiting embodiments, a kit can include at least one nucleic acid probe, suitable for in situ hybridization or fluorescent in situ hybridization, for detecting the biomarker(s) to be identified. Such kits will generally include one or more oligonucleotide probes that have specificity for various biomarkers.

In certain non-limiting embodiments, a kit can include one or more primers, probes, microarrays, or antibodies suitable for detecting one or more biomarkers.

In certain non-limiting embodiments, where the measurement techniques in the kit employs an array, the set of biomarkers set forth above can constitute at least 10 percent or at least 20 percent or at least 30 percent or at least 40 percent or at least 50 percent or at least 60 percent or at least 70 percent or at least 80 percent of the species of markers represented on the microarray.

In certain non-limiting embodiments, a biomarker detection kit can include one or more detection reagents and other components (e.g., a buffer, enzymes such as DNA polymerases or ligases, chain extension nucleotides such as deoxynucleotide triphosphates, and in the case of Sanger-type DNA sequencing reactions, chain terminating nucleotides, positive control sequences, negative control sequences, and the like) necessary to carry out an assay or reaction to detect a biomarker. A kit can also include additional components or reagents necessary for the detection of a biomarker, such as secondary antibodies for use in immunohistochemistry.

In certain embodiments, the kit further includes instructions or supporting materials that describe the use of the kit to identify a subject that is likely to respond to a treatment for a TBI-associated impairment and/or reference to a website or publication describing same. In certain embodiments, the kit further includes instructions or supporting materials that describe the use of the kit to identify a subject that is as likely to develop a TBI-associated impairment and/or reference to a website or publication describing same. In certain embodiments, the kit further includes instructions or supporting materials that describe the use of the kit to monitor the responsiveness of a subject to a treatment for a TBI-associated impairment and/or reference to a website or publication describing same. In certain embodiments, the treatment includes an IL-7 or an IL-7 agonist, and/or a TNFα inhibitor as disclosed in Section 5.2.

6. EXAMPLES

The presently disclosed subject matter will be better understood by reference to the following Example, which is provided as exemplary of the presently disclosed subject matter, and not by way of limitation.

Example 1: Examining Longitudinal Adaptive Immune Responses and Relationships Between Il-7 and Anti-Pituitary/Hypothalamic Autoantibodies after Severe-TBI The adaptive autoimmune response plays a highly specific role in neuroprotection after a severe traumatic brain injury (TBI). Autoantibodies (AAbs) to the pituitary (APA) and the hypothalamus (AHA) are present chronically, up to one-year post-injury.

Autoantibodies paired with inflammatory markers provide insights into the adaptive immune response and neuroendocrine recovery post-TBI. Serum interleukin 7 (IL-7) is a key marker associated with adaptive immunity (Riegger et al., Neuroscience. 2009; 158(3):1194-1199). Increased serum IL-7 promotes lympho-proliferation and may enhance neuro-reparative/autoimmune responses after TBI (Lundstrom et al., Semin Immunol. 2012; 24(3):218-224; Nasi et al., Aging Cell. 2006; 5(2):167-175). The primary injury response results immediately after the initial trauma. The secondary injury is a gradually occurring process that is initiated by the injury. Post-injury inflammation is an important component of the secondary injury cascade. Brain inflammation has proved to be a vital target of therapeutic treatments for several brain diseases, including TBI (Jeong et al., Exp Neurobiol. 2013; 22:59-67). Controlled inflammation may be necessary to clear damaged cells after injury.

This study aimed to analyze IL-7 levels to access its association with longitudinal profiles of autoantibodies. It was hypothesized that IL-7 production may promote brain tissue specific AAb production and is neuro-reparative. The secondary hypothesis was that the relationship is moderated by age.

Serum IL-7, IgM/IgG APA and AHA were evaluated from 2 weeks to 12 months post injury for n=129 individuals. Mean levels were produced for each marker from 2wks-3mos, 4-6mos and 7-12mos. Age was dichotomized with the median at 32 years old. Group based trajectory (TRAJ) analyses were for IgM/IgG APA and AHA determined 3 unique longitudinal AAb profiles (high, medium and low TRAJ).

Ordinal Logistic Regression models were run with IL-7 and age as predictors for AAb TRAJ group associations. All main effects were tested for interactions between IL-7 and age. Only significant interaction terms were included in the multivariable model.

Demographic and Clinical Information on Cohort (APA IgM/IgG) were shown in FIGS. 1 and 2. Ordinal logistic regression results of APA IgM/IgG were shown in FIG. 3, and Ordinal logistic regression results of AHA IgM/IgG were shown in FIG. 4. An ordinal logistic regression model (n=89) tested the interaction of dichotomized age and IL-7 effects to show a significant association to APA IgM TRAJ at 4-6mos post-injury (p=0.0423). An ordinal logistic regression model (n=64) tested the interaction of dichotomized age and IL-7 effects to show a trend to APA IgM TRAJ at 7-12mos post-injury (p=0.0836). At 2wks-3mos post-injury, IL-7 was independently associated with APA IgM TRAJ, however there was no significant moderating age effect.

Also, IL-7 was independently associated with APA IgG TRAJ production across the entire sampling period (p<0.04).

In the main effects model, IL-7 did not independently influence AHA IgM production as strongly, with only trends (p=0.08) at 4-12 months post injury. IL-7 was independently associated with AHA IgG production 7-12 months post-injury (p=0.0155).

TBI is associated with long term complications, including persistent hypogonadotropic hypogonadism (PHH). Individuals who develop PHH have poor outcomes, including fatigue and functional deficits (Barton et al., J Head Trauma Rehabil. 2016 Jul-Aug;31(4):277-87). The pilot data also suggests that increased levels of serum APA and AHA IgM are associated with reduced risks for PHH and elevated levels of IgM AAbs may result in protective autoimmunity. PHH may be influenced by autoimmunity in relation to the neuroendocrine system. Cancer studies show that IL-7 therapies can increase T helper cell proliferation, suggesting an enhanced autoimmune response (Capitini et al., Am J Immunol. 2009; 5(3):65-83). While a similar study has not been done in TBI, IL-7 may potentially be an important biological treatment post CNS injury.

This study begins to characterize IL-7 and its relationship to age with autoantibody TRAJ as an outcome among people with severe TBI. The moderating relationship between IL-7 and age showed significant associations to APA IgM at later time points, indicating a delayed autoimmune response in individuals with TBI. AHA IgM did not show a significant moderation between IL-7 and age. However, IL-7 was independently associated with AHA IgG TRAJ from 7-12 months post injury. Together this data implicates IL-7 in generating an autoimmune response to pituitary proteins post-TBI, which may be relevant to neuroendocrine dysfunction.

Example 2: Measuring IL-7 and Autoantibodies in Patients Having Moderate to Severe TBI Moderate to severe traumatic brain injury (TBI) may involve chronic conditions and complications, including neuroendocrine dysfunction, epilepsy, mood disorders, and epilepsy as well as functional/cognitive deficits1. While there is an increased understanding of the acute secondary injury mechanisms post-TBI, far less known about the chronic implications of persistent inflammation on the long-term risk for complication after a moderate-to-severe TBI. Persistent hypogonadotropic hypogonadism (PHH) and post traumatic epilepsy (PTE) are common deficiencies among individuals with moderate-to-severe TBI. The work suggests PHH is affected by autoimmunity as well as age related changes in the neuroendocrine system. Also, the initial data implicated autoimmunity in PTE risk.

In a cohort study of 78 men, 44% of them develop PHH and have associated poor outcomes, including fatigue and functional deficits (Barton et al., J Head Trauma Rehabil. 2016 Jul-Aug;31(4):277-87; Bondanelli et al., J Neurotrauma. 2007; 24(11):1687-1697; Popovic et al., J Endocrinol Invest. 2004; 27(11):1048-1054). Since the specific pathophysiology underlying PHH is not yet fully elucidated, it was investigated the inflammatory pathways associated with autoimmunity after TBI, as characterized by chronic serum autoantibodies (AAbs) to the pituitary (APA) and the hypothalamus (AHA) IgM/IgG, and their potential implications for PHH. Unpublished results suggest that IgM APA profiles over time are highly concordant with PHH status, and that AAb binding for the in house quantitative assay developed for this project is highly specific to pituitary tissue.

Figure 5:
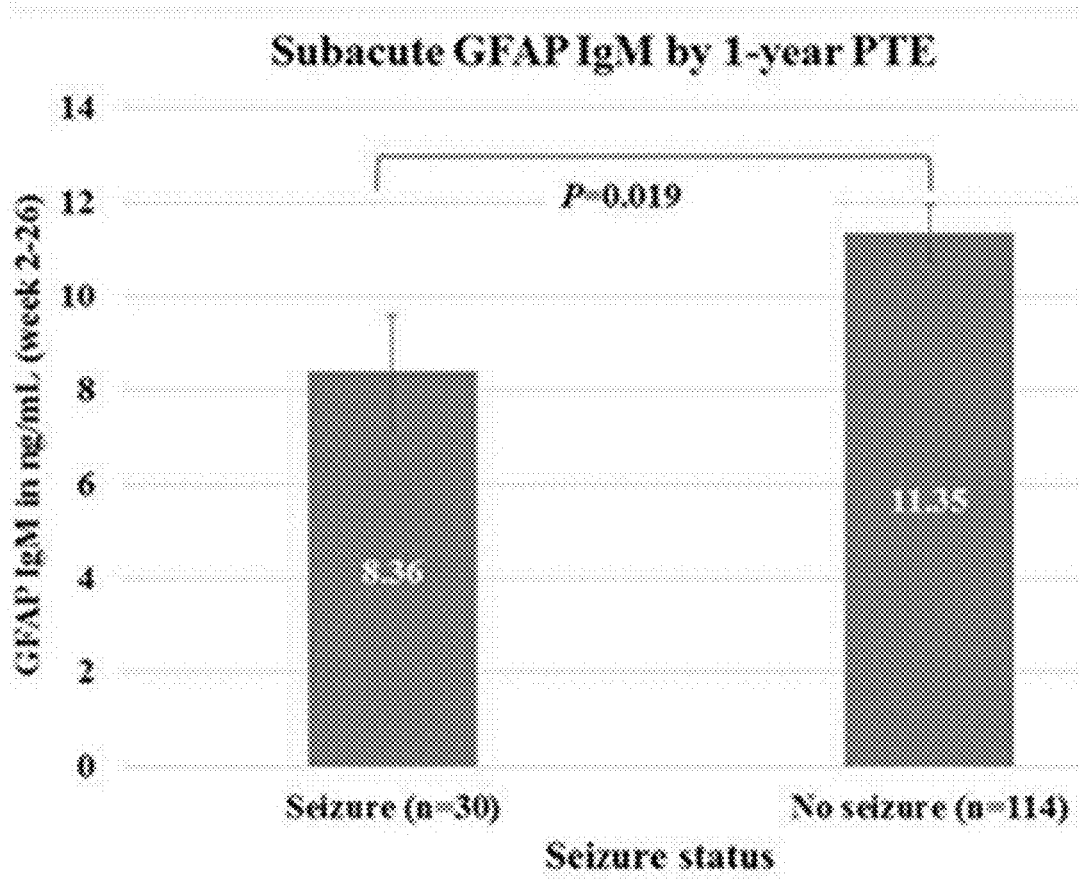

As GFAP is a ubiquitous protein associated with astrogliosis after TBI, and astrogliosis is a prominent pathological characteristic associated with multiple models of epilepsy[4,5]. It was also explored subacute/chronic IgM GFAP levels and their associations with PTE development in 144 subjects with moderate to severe TBI. In this 6 cohort, ~20% of the population developed PTE over the first week post injury. The present example show that mean GFAP AAb levels over the first 6 months post injury are also associated with PTE rates during the first year of recovery (FIG. 5).

The adaptive autoimmune response plays a crucial role in creating an immunological memory to aid in neuroprotection and neurorepair after moderate to severe TBI. The adaptive immune system is critical to protective immunity in terms of functional maintenance and repair, even among healthy individuals (Riegger et al., Neuroscience. 2009; 158(3):1194-1199). Serum interleukin 7 (IL-7) is a key marker associated with adaptive immunity (Riegger et al., Neuroscience. 2009; 158(3):1194-1199). Increased serum IL-7 promotes lymphoproliferation (Lundstrom et al., Semin Immune. 2012; 24(3):218-224; Nasi et al., Aging Cell. 2006; 5(2):167-175), and may enhance the neuro-reparative and autoimmune responses after TBI. IL-7 influences the lymphoproliferation of T cells, which are sensitive to circulating self-antigens in the body after TBI. After CNS injuries, the adaptive immune system response is suppressed, and many individuals experience lymphopenia, potentially due to deficiencies in IL-7 production (Lundstrom et al., Semin Immune. 2012; 24(3):218-224). Lymphopenia is a known reaction to inflammation post CNS injury, therefore, increases in IL-7 may enhance the autoimmune response and promote neurorepair. Those with moderate to severe injuries are highly susceptible to nosocomial infection (Kesinger et al., J Trauma Acute Care Surg 78 (2), 396-402) providing indirect evidence of at least transient state of immunodeficiency occurring after injury that could impact long term outcomes. After injury, IL-7 production eventually increases to induce lymphoproliferation. There is an observed increase in Th-cell production associated with self-antigens, to promote AAb production, aiding in the neuro-reparative process (Schluns et al., Nat Immunol. 2000; 1(5):426-432). This process is characterized as the protective immune response, and suggests that there is an innate mechanism that promotes lymphoproliferation post-CNS injury (Lundstrom et al., Semin Immune. 2012; 24(3):218-224; Schwartz et al., Trends Mol Med. 2001; 7(6):252-258) Increase in IL-7 after injury help restore T-cell homeostasis, and lead to AAb synthesis, which can have protective that lead to decreased frequency of complications such as PTE and PHH. IL-7 profile associations with APA, AHA and GFAP AAbs was evaluated.

Methods

Sample collection through the lab has been done for men and women (n=117) with moderate to severe TBI. Serial serum samples are collected chronically from these patients over 52 weeks after injury. The' samples are stored in −80 degrees Celsius freezers. Autoantibodies, APA and AHA immunoglobulin M (IgM)/immunoglobulin G (IgG) were measured using a custom ELISA generated by the collaborator. IL-7 levels were measured using Luminex technology. The current study analyzes chronic IL-7 levels in association with AAb profiles 2 weeks to 6 months' post-injury. Group based trajectory (TRAJ) analyses were used to identify longitudinal profiles of GFAP AAb (AGA), APA and AHA IgM and IgG over the first-year post TBI. TRAJ were generated separately for individuals with data between 2 weeks and 6 months post-TBI, similar to that generated for the manuscript that is under review. For APA and AHA analyses, Age was dichotomized at the median of 31 years old. An ordinal logistic regression model characterized IL-7 and age as predictors for high, medium and low APA and AHA AAb IgM and IgG trajectories. Simple logistic regression was used to assess IL-7 relationships with high, medium and low AGA trajectories.

Results

IL-7 levels 2 weeks to six months post injury are significantly higher than reported values in healthy controls (2-8 pg/ml).

Figure 6A:
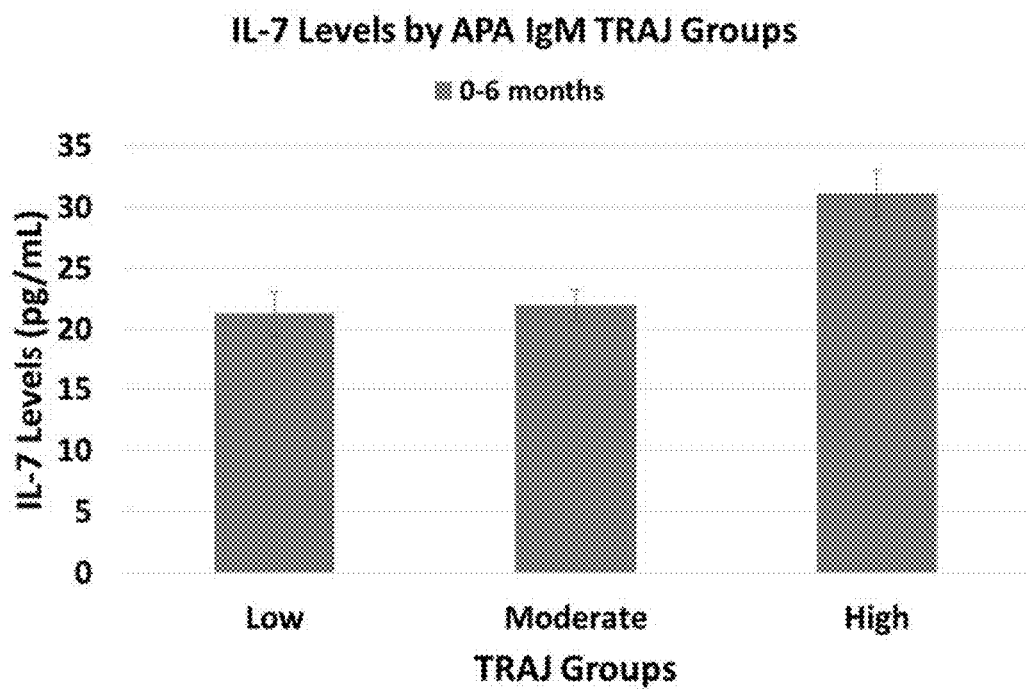
Figure 6B:
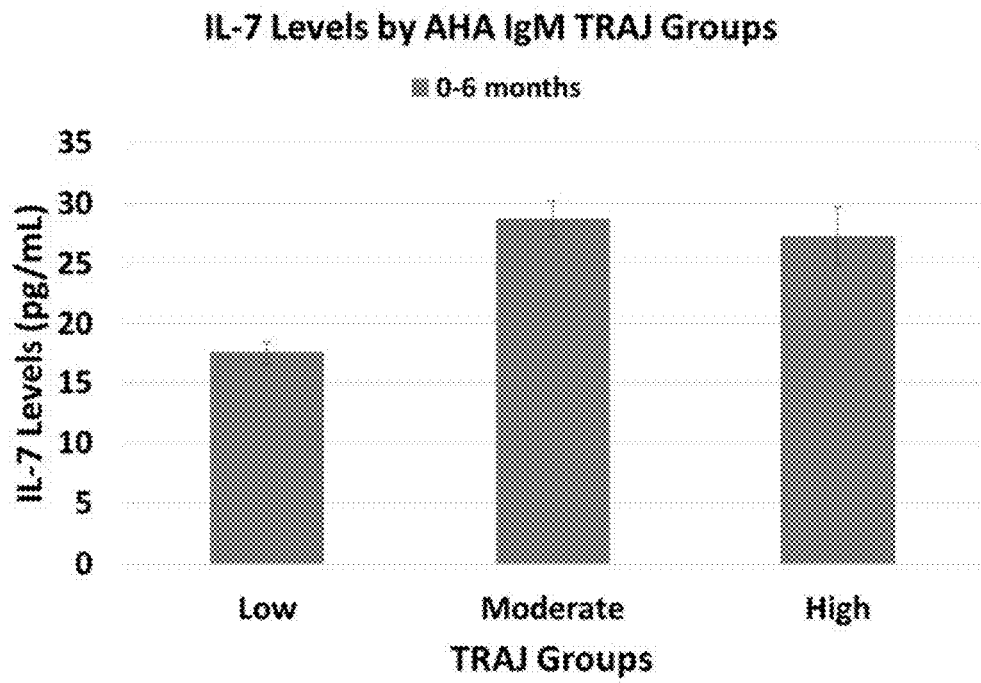
Figure 7:
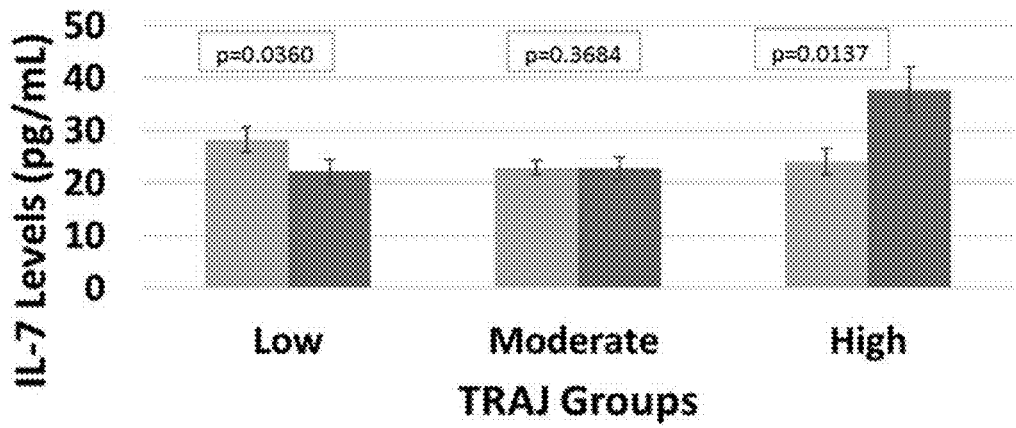

After adjusting for age, the regression results indicate a significant association between IL-7 and IgM APA TRAJ (p=0.0001) and AHA TRAJ (p=0.0003) groups reflecting AAb profiles 2wk to 6-month post-injury. In each case, the data suggest that higher levels of IL-7 are associated with higher IgM AAb profiles (FIGS. 6A-6B). For IgG APA, increases in IL-7 were marginally associated with higher IgG APA TRAJ group membership. Also, there was an IL-7 and age interaction with IgG APA. In the low TRAJ group, younger individuals had higher IL-7, while in the high TRAJ group, older individuals had higher IL-7 (FIG. 7). IL-7 was not significantly associated with IgG AHA TRAJ Group membership.

Figure 8:
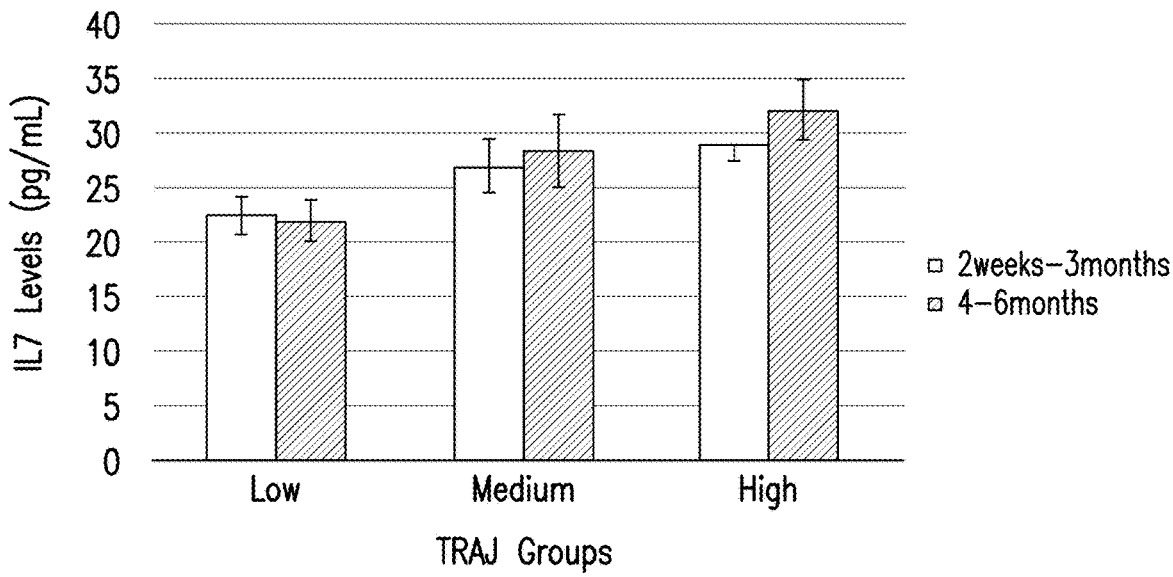

The regression results indicate a significant association between IL-7 and GFAP IgM at 2 weeks-3months (p=0.0508) and 4-6months (p=0.0083) (FIG. 8). There was no significant association between IL-7 and GFAP IgG.

Discussion

The manuscript in review (see other document) has suggested that increased serum APA and AHA IgM are associated with reduced risks for PHH and elevated levels of IgM AAbs may result in protective autoimmunity (Shindo et al., Shock. 2015 April; 43(4):334-43). The pilot PTE data suggest that high IgM AGA is associated with reduced frequency of PTE. The current data in this document demonstrate strong associations with IL-7 and IgM Autoantibody production in the setting of TBI, which appears to be protective. The work also demonstrates the potential for IL-7 in generating an IgG autoimmune response with IgM proteins, particularly for APA post-TBI, which may be relevant to neuro-reparative dysfunction more broadly.

IL-7 may be an important therapeutic target for modifying adaptive (autoimmune) response associated with TBI, which was hypothesized that could support a lymphoproliferative process to increase autoantibody synthesis to circulating CNS antigen. Recombinant IL-7 has been tested in small clinical trials involving immunodeficiency. The administration of recombinant human IL-7, resulted in T-cell production and proliferation, indicating a potential therapeutic significance of IL-7 (MackeII et al., Nat Rev Immunol. 2011; 11(5):330-342). Furthermore, a study using animal models with sepsis and immunosuppression tested the mechanistic actions of recombinant IL-7. The results showed that IL-7 increased splenic and peripheral node T-cell lymphoproliferation. IL-7 also increased the expression of leukocyte adhesion molecules on CD4 and CD8 T cells (Shindo et al., Shock. 2015 April; 43(4):334-43). Further work should replicate findings and explore how aging and immunomodulation might affect adaptive immunity post-TBI, including long-term neuroendocrine dysfunctions. In silico work involving the mathematic characterization of chronic inflammation can be used to simulate potential treatment effects with recombinant IL-7 on AAb profiles.

Example 3 Examining Longitudinal Adaptive Immune Responses and Relationships Between IL-7 and Anti-Pituitary/Hypothalamic Autoantibodies after Severe-TBI There are inflammation responses after TBI Neuroinflammation is a therapeutic target for several brain diseases, including traumatic brain injury (TBI). (Jeong et al., Exp Neurobiol. 2013; 22:59-67) Inflammatory mediators, including cytokines, are elevated with CNS injuries. Secondary injury cascades are gradually evolving processes initiated by pro-inflammatory markers in the CNS and periphery. Post-injury inflammation is important to the secondary injury cascade, however chronic inflammation has not been well characterized post-TBI.

There are autoimmune responses after TBI. Adaptive immunity refers to an antigen-specific immune response used to create an immunological memory that may affect neurorepair after injury.

Blood-brain barrier dysfunction occurs rapidly after TBI, and may allow for systemic exposure to CNS antigens, resulting in successive autoantibody (AAb) production through the adaptive immune response (Chodobski et al., Transl. Stroke Res. 2, 492-516). Persistent hypogonadotropic hypogonadism (PHH) is a common neuroendocrine deficiency that occurs post-TBI (Barton et al., J Head Trauma Rehabil. 2016 Jul-Aug;31(4):277-87). The work suggests PHH risk is affected by autoimmunity as well as age related changes in the neuroendocrine system.

Autoantibodies to the pituitary (APA) and the hypothalamus (AFIA) IgM and IgG are present chronically, up to one-year post-TBI and are associated with hypogonadism. AAbs pose potential neuroendocrine implications to autoimmunity through antigen specific responses.

Cytokine patterns are associated with the adaptive immune response. Increased serum interleukin 7 (IL-7) promotes lymphoproliferation, and IL-7 is associated with autoimmunity after TBI (Riegger et al., Neuroscience. 2009; 158(3):1194-1199.; LundstrOm et al., Semin Immunol. 2012; 24(3):218-224; Nasi et al., Aging Cell. 2006; 5(2): 167-175). Lymphopenia is a common condition after traumatic injury, which may occur following the aseptic acute inflammatory response and may result from deficiencies in IL-7 production (LundstrOm et al., Semin Immunol. 2012; 24(3):218-224). The eventual increase in IL-7 accompanied with lymphoproliferation may lead to CNS autoantibody production (LundstrOm et al., Semin Immunol. 2012; 24(3): 218-224; Schwartz et al., Trends Mol Med. 2001; 7(6):252-258). Aging (older age) diminishes ability for lymphoproliferation and activation of the adaptive immune response (Schwartz et al., Trends Mol Med. 2001; 7(6):252-258). Naïve B cells can alter the function of AAbs through class switching, allowing for the production of IgM and the switched isotype, IgG (Avery et al., The Journal of Immunology. 2008, 181 (3) 1767-1779). The production of different classes of immunoglobulins allows for immune responses to different types of pathogens (Avery et al., The Journal of Immunology. 2008, 181 (3) 1767-1779). Class switching is a critical component of B-cell differentiation, and the formation of an immune response (Avery et al., The Journal of Immunology. 2008, 181 (3) 1767-1779).

The study aimed to analyze chronic IL-7 level associations with longitudinal AAb profiles 2 weeks to 6 months after injury. It was hypothesized that Distinct IL-7 patterns involving the adaptive immune response underlie AAb production to the neuroendocrine system after TBI, and older age moderates IL-7 effects on AAb production after TBI.
Methods The cohort size was n=117. Serum samples were evaluated for AAb levels (APA and AHA) and IL-7 from 2 weeks to 6 months post-TBI. Age was dichotomized at the median of 31 years old. Group based trajectory (TRAJ) analysis was used to identify distinct longitudinal IgG and 1gM AAb profiles (2 weeks to 6 months) for men and women with moderate to severe TBI. Demographic of enrolled subjects are shown in FIG. 9.

Figure 11A:
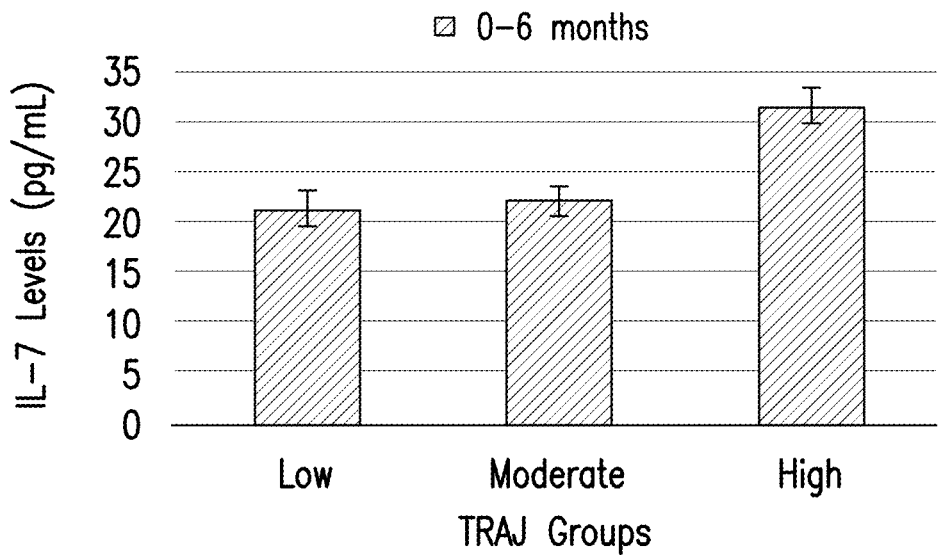
Figure 11B:
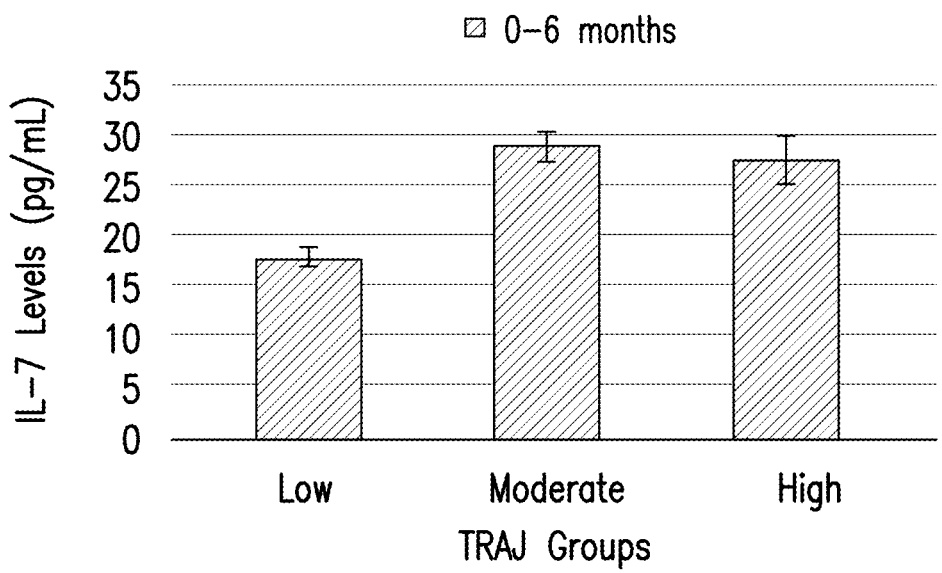
Figure 13:
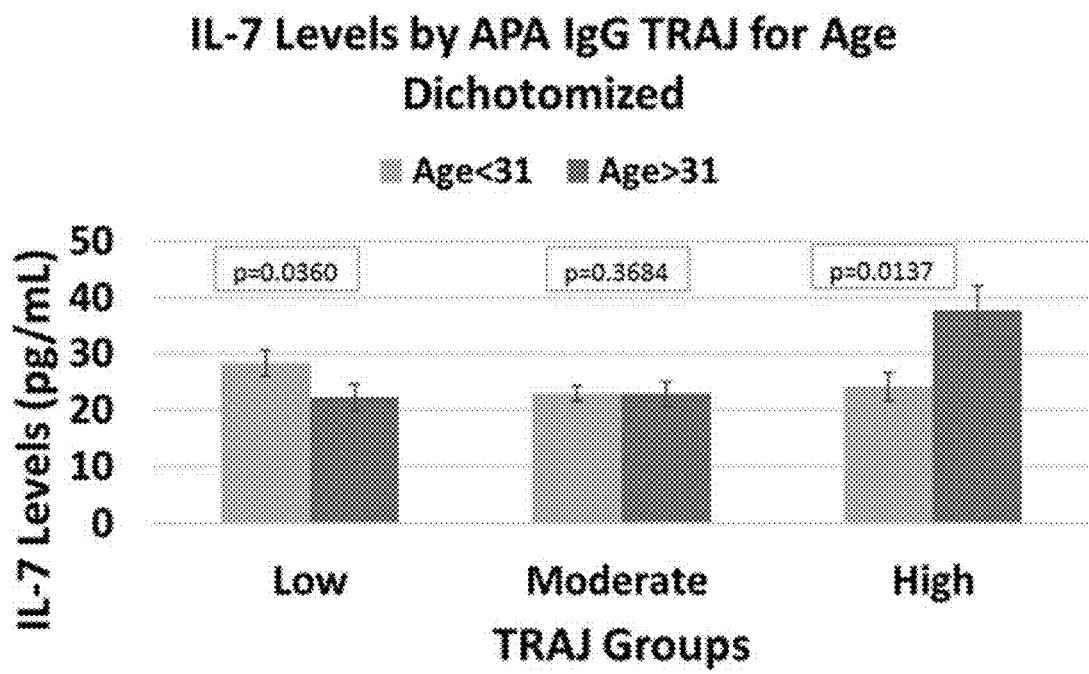
Figures 14A, 14B, 14C, 14D, 14E, 14F, 14G, 14H, 14I, 14J:
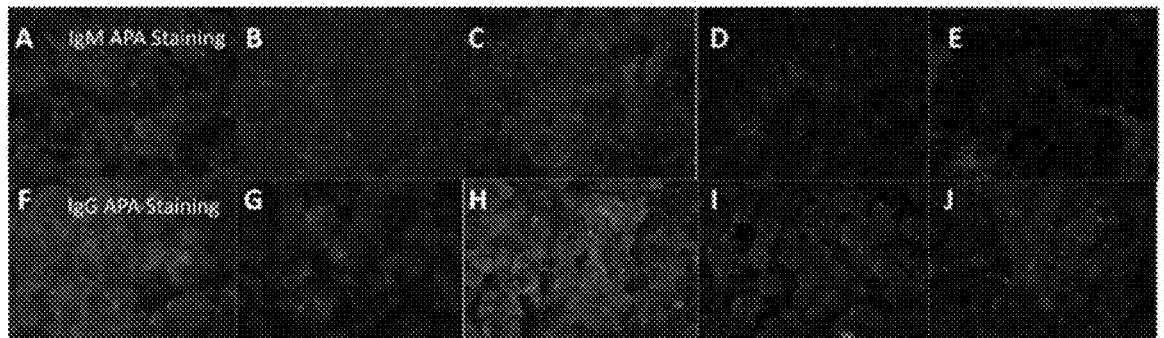
Figures 15A, 15B, 15C, 15D, 15E, 15F, 15G, 15H, 15I, 15J:
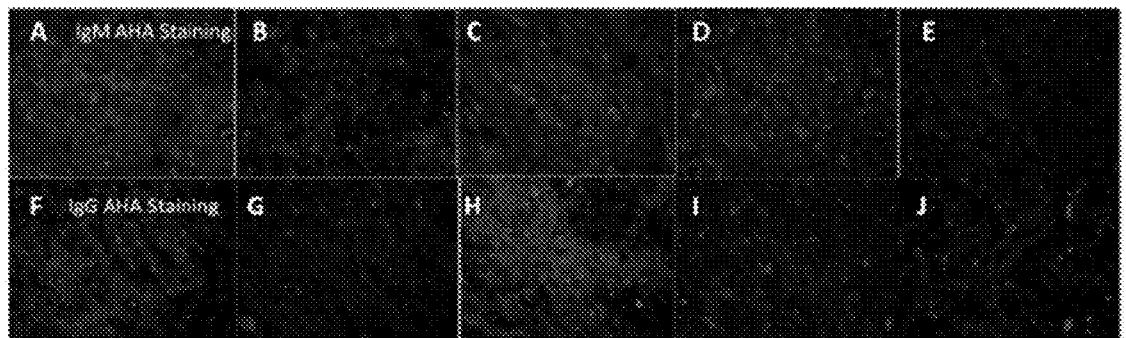
Figures 16A, 16B, 16C, 16D:
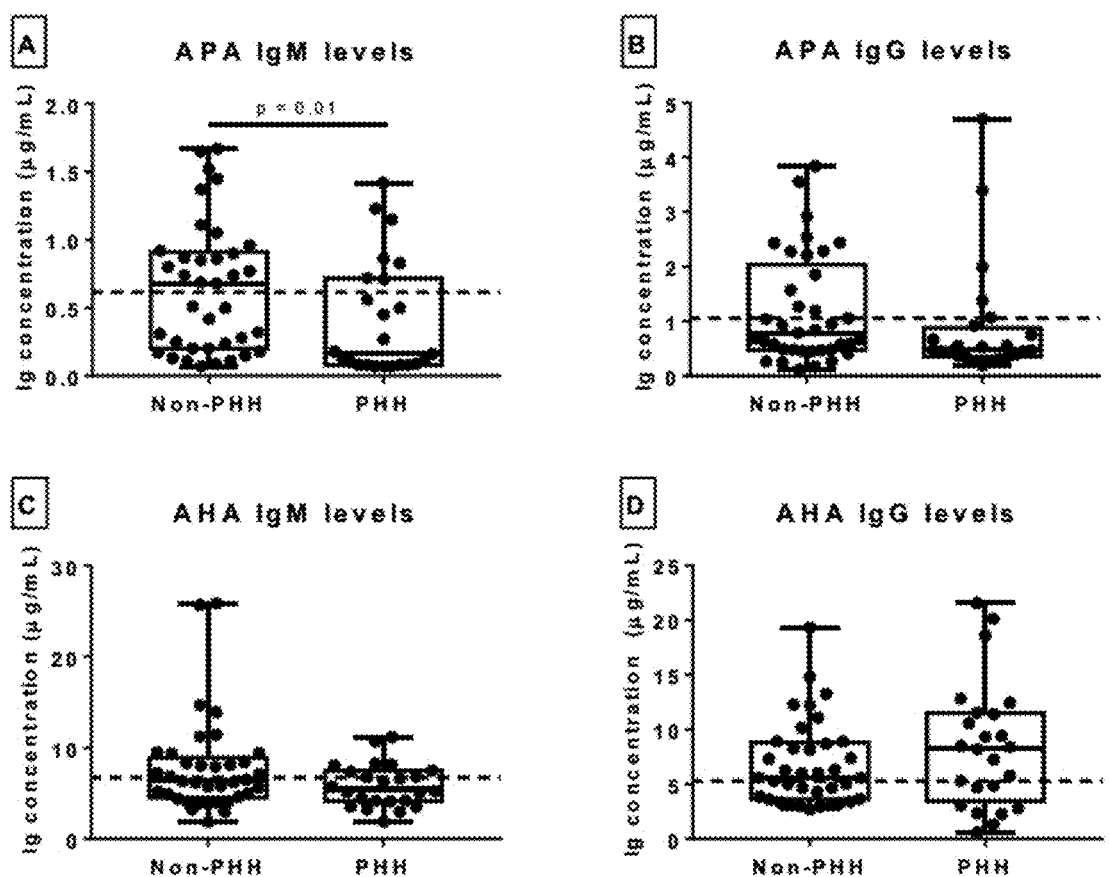
Figure 16E:
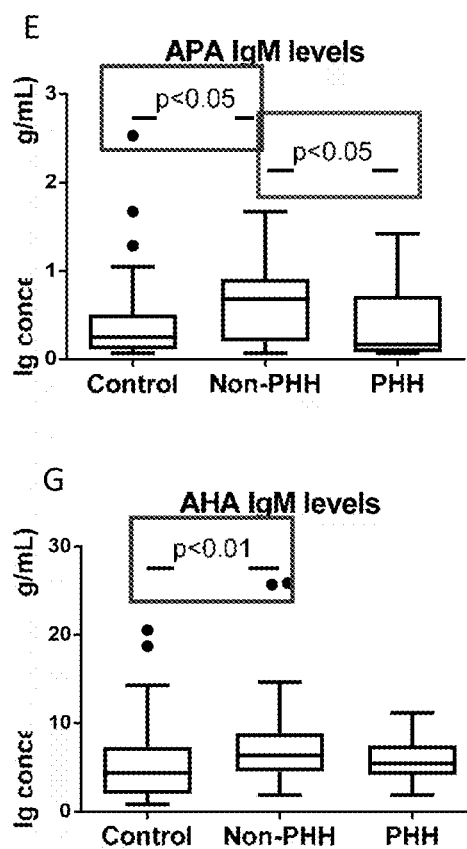
Figure 16F:
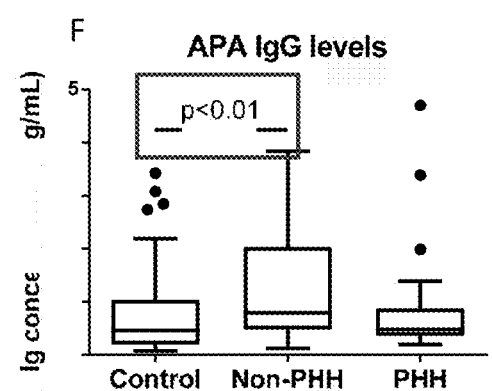
Figure 16G:
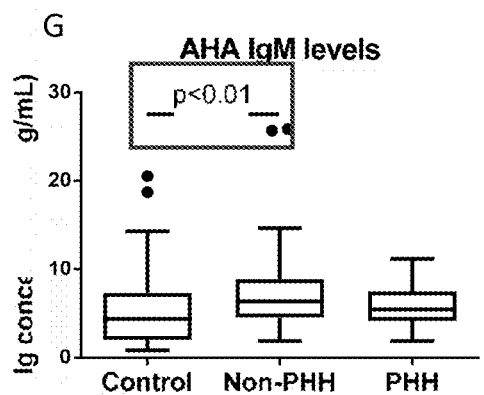
Figure 16H:
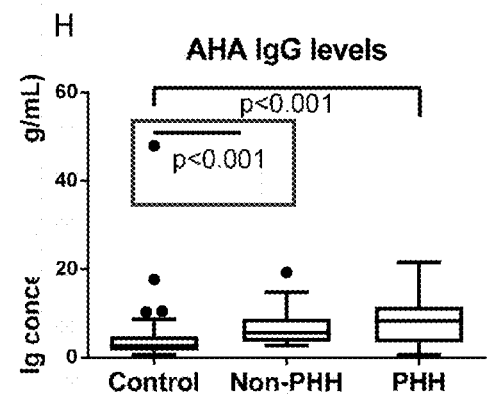

AAb TRAJ group membership was used as outcome measures for IL-7, age, and their potential moderation relationship. Ordinal Logistic Regression models were performed, with 1L-7 and age dichotomized as predictors for AAb TRAJ group associations (FIGS. 10 and 12). IL-7 levels over a 6-month time period increase as IgM autoantibodies to the pituitary and hypothalamus increase from low to high IgM TRAJ group membership (FIGS. 11A-11B). Age and IL-7 were tested for independent associations to AAb TRAJ. Only significant interaction terms were included in reported multivariable models. In the lower IgG TRAJ group, the group of individuals<age 31 had higher levels of IL-7 up to 6-moth post injury compared to the individuals above the median age. In the high TRAJ group, individuals>age 31 years had higher IL-7 levels up to 6mo post injury compared to the individuals<age 31 years (FIG. 13).

Discussion

This study demonstrated an IL-7 and age relationship to neuroendocrine AAb production among individuals with moderate to severe TBI. Relative increases in post-acute/chronic serum APA and AHA IgM are associated with reduced frequency of PHH.

The present data demonstrated that IL-7 levels drive IgM production and that there are age dependent differences in how IL-7 drives IgG AAb production, which may be relevant to both neurological damage and neurorepair. IL-7 likely affects IgM production through T-helper cell lymphoproliferation. The post-acute autoimmune IgM response may be relevant to both neuro-endocrine and neuroreparative function.

IL-7 can influence IgM to IgG class switching (Avery et al., The Journal of Immunology. 2008, 181 (3) 1767-1779; Guimond et al., Nature Immunology. 2009, 10 (2) 149-157; Seo et al., J Virol. 2014 August; 88(16):8998-9009). Excessive IgG production could facilitate neurological damage rather than repair. The age dependent IL-7 effect that influences IgG AAb production may indicate that IL-7 has a greater impact IgM to IgG class switching in older individuals than younger individuals. IL-7 may affect the adaptive immune response after TBI. Circulating IL-7 levels range from 2-8 pg/ml in health adults, but levels can increase to 60 pg/ml during periods of lymphopenia (LundstrOm et al., Semin Immunol. 2012; 24(3):218-224). IL-7 levels in the present TBI cohort were well above reported controls.

Recombinant human IL-7 had been tested in small clinical trials involving immunodeficiency (Mackall et al., Nat Rev Immunol. 2011; 11(5):330-342). Results indicated an increase in T-cell proliferation and production, emphasizing the potential therapeutic implications of IL-7 (Mackall et al., Nat Rev Immunol. 2011; 11(5):330-342). A study used animal sepsis models to induce immunosuppression in order to test the mechanistic actions and recombinant IL-7 (rIL-7). Results indicated rIL-7 administration increased splenic and peripheral node T-cell lymphoproliferation (Shindo et al., Shock. 2015 Apr;43(4):334-43). Using the protein marker, Ki-67 to observe cell proliferation, there was a noticeable increase in splenic CD4 T-cells in mice treated with IL-7 (Shindo et al., Shock. 2015 April; 43(4):334-43). IL-7 also increased leukocyte adhesion molecule expression on CD4 and CD8 T cells (Shindo et al., Shock. 2015 April; 43(4): 334-43).

Cancer studies indicate that rIL-7 therapies can increase T helper cell proliferation in a dose dependent manner, suggesting a possible enhanced autoimmune response with treatment (Capitini et al., Am J Immunol. 2009; 5(3):65-83). Combining rIL-7 administration with other therapies may increase its anti-tumor capabilities, enhanced by its maintenance of lymphocyte homeostasis (Capitini et al., Am J Immunol. 2009; 5(3):65-83). While a similar study has not been done in TBI, rIL-7 can be an important biological treatment post CNS injury.

Example 4: Anti-Pituitary and Anti-Hypothalamus Auto-Antibodies after Traumatic Brain Injury Associated with Hypogonadotropic Hypogonadism in Men Post-traumatic hypopituitarism is a prevalent complication of traumatic brain injury (TBI). Hypogonadotropic hypogonadism is one a common post-traumatic pituitary deficiency, and it is associated with poor outcomes after TBI. The pathogenesis of persistent hypogonadotropic hypogonadism (PHH) remains unclear, although autoimmune and inflammatory mechanisms have been proposed to contribute to this process. In a prospective longitudinal cohort study of men with severe TBI, serum levels of 1gM and IgG autoantibodies against pituitary (APA) and hypothalamus (AHA) were measured via ELISA from two to 26 weeks post-TBI and compared levels among those with and without PHH. Tissue specificity of APA and AHA autoantibodies was confirmed with fluorescence immunohistochemistry. Group-based trajectory analysis (TRAJ) was conducted to identify distinct subgroups having similar longitudinal autoantibody profiles over time. Sixty-one men with severe TBI were recruited from a university hospital level 1 trauma center. Twenty-four (39%) were determined to have PHH based on low longitudinal luteinizing hormone and testosterone profiles. APA 1gM levels were lower in the PHH group compared to the non-PHH group (median 0.17 vs 0.68 ftg/mL, p=0.01). PHH and non-PHH groups had similar mean APA IgG (p=0.06), AHA IgM (p=0.20), and AHA IgG (p=0.38) levels. Three TRAJ groups were identified of APA IgM and of AHA IgM, and APA TRAJ group membership differed based on PHH status ($\times 2$=7.019, p=0.03) and serum testosterone levels at multiple time points (p<0.02). Mediation analyses showed that APA TRAJ group membership accounts for −18% of the variance that age contributes to PHH after TBI. Specifically, individuals in the medium/high APA IgM TRAJ group were at a 51% decreased odds of PHH compared to the low APA IgM TRAJ group (012=0.49, 95%=0.24, 0.99, p=0.018) These findings show a relationship between higher APA IgM levels and reduced frequency of PHH after severe TBI in men, suggesting a role for protective autoimmunity in decreasing risk 7 for PHH development in the first 6 months post-TBI.

The present study found that pituitary and hypothalamic autoantibodies are present after TBI. Unique subgroups of TBI survivors have distinct temporal autoantibody profiles. Serum anti-pituitary IgM is inversely related to secondary hypogonadism after TBI. Anti-pituitary IgM profiles partially mediated age related effects on hypogonadism. Protective autoimmunity may contribute to risk for hypopituitarism after TBI.

Prior work of the inventor reported that 44% of men with severe TBI had persistent hypogonadotropic hypogonadism (PHH) (Barton et al., J Head Trauma Rehabil. 2016 Jul-Aug;31(4):277-87). It was further observed that PHH was associated with worse global outcome scores, more disability, greater fatigue, and reduced functional cognition at 6 and 12 months post-TBI. These results corroborate prior data showing post-traumatic hypogonadism to be a complication associated with worse outcomes (Bondanelli et al., 2007; Carlson et al., 2009; Popovic et al., 2004, J. Endocrinol. Invest. 27, 1048-1054; Wagner et al., 2012, Brain Inj. 26, 1226-1242).

The mechanism for post-traumatic hypopituitarism, including hypogonadism, remains undefined. Traditionally, it has been held that hypopituitarism likely is due to traumatic lesions and vascular injury of the mechanically vulnerable pituitary or hypothalamus, as early post-mortem studies recorded these findings in the majority of autopsies of patients with fatal TBI (Chodobski et al., Transl. Stroke Res. 2, 492-516, 2011; Daniel et al., Lancet Lond. Engl. 2, 927-931, 1959). Among surviving individuals, associations have been observed between post-traumatic hypopituitarism and abnormalities on magnetic resonance imaging of the pituitary gland (Schneider et al., 2007, J. Endocrinol. Invest. 30, RC9-RC12). However, these gross structural changes do not adequately explain many cases of post-traumatic hypopituitarism. Among individuals with mild TBI, where traumatic forces are likely not substantial enough to cause gross pathology, rates of post-traumatic hypopituitarism have been reported up to 45% (Aimaretti et al., 2005). These findings suggest that hypopituitarism is not strictly related to direct trauma of the pituitary or hypothalamus or even injury severity. Other mechanisms for post-traumatic hypopituitarism have been explored, including alterations in the chronic inflammatory process (Kasturi and Stein, 2009, J. Neurotrauma 26, 1315-1324; Tanriverdi et al., 2008, Eur. J. Endocrinol. Eur. Fed. Endocr. Soc. 159, 7-13; Tanriverdi et al., 2010, J. Neurotrauma 27, 301-302).

Some evidence suggests autoimmunity development against the pituitary gland and hypothalamus could be involved in post-traumatic hypopituitarism (Guaraldi et al., 2015, J. Clin. Med. 4, 1025-1035). Blood-brain barrier dysfunction occurs rapidly after TBI (Chodobski et al., Transl. Stroke Res. 2, 492-516; Hay et al., 2015, J. Neuropathol. Exp. Neurol. 74, 1147-1157), which may allow for systemic exposure to otherwise privileged central nervous system (CNS) antigens and subsequent development of autoantibodies. One group has reported that higher serum titers of anti-pituitary and anti-hypothalamus IgG antibodies detected by indirect immunofluorescence are associated with pituitary deficits in 25 individuals with TBI up to 5 years after injury (Tanriverdi et al., Eur. J. Endocrinol. Eur. Fed. Endocr. Soc. 159, 7-13, 2013; Tanriverdi et al., J. Neurotrauma 30, 1426-1433). Their studies have not yet been replicated in independent populations. The data are limited in that they only include patients at three or five years post-TBI and only measure the immunoglobulin G (IgG) class and not immunoglobulin M(IgM) antibodies; thus there remains a paucity of data in this area for which additional research may add a more in-depth understanding of the adaptive immune response post-TBI. These data support autoantibody production as pathogenic in post-traumatic hypopituitarism which aligns with classic autoimmune disease pathophysiology. However, some have hypothesized that under certain conditions, autoimmune activity involving IgM class immunoglobulins may be beneficial to repair and recovery after CNS injury (Schwartz and Raposo, 2014, Neurosci. Rev. J. Bringing Neurobiol. Neurol. Psychiatry 20, 343-358). It was hypothesized that anti-pituitary antibody (APA) and anti-hypothalamus antibody (AHA) levels were detected chronically up to six months in serum after TBI, and that these levels would be associated with PHH status and testosterone levels over time. In a prospective cohort of men with severe TBI and testosterone levels (Barton et al., J Head Trauma Rehabil. 2016 Jul-Aug; 31(4):277-87), longitudinal serum profiles of APA and AHA were characterized and how they related to PHH as a marker of hypopituitarism. Since the antibody response to an antigen classically involves class switching of immunoglobulins over time, both IgM and IgG concentrations were analyzed to characterize the temporal antibody response involving APA and AHA.

Materials and Methods

Study Design and Population

This study was a prospective, longitudinal, observational cohort study. It was consecutively recruited individuals presenting to the university hospital level 1 trauma center with severe TBI, defined by Glasgow Coma Scale (GCS) score <8 at presentation and confirmed computed tomographic findings. This analysis included men aged 16 to 70 years in whom it was able to collect at least 2 subacute (>1 week) blood samples.

Individuals were excluded if they had a history of hypothalamic or pituitary tumors, orchiectomy, luteinizing hormone (LH) therapy, or untreated thyroid disease prior to injury. Demographic and injury information were obtained from patient records, including age, body mass index (BMI), education level, race, GCS score (best in the first 24 hours after injury), injury severity score, length of hospital stay, mechanism of injury, and neuroradiology results from acute admission.

Blood samples were collected during the first week and every two weeks for six months post-injury. Upon collection, samples were centrifuged, aliquoted in polypropylene cryovials, and stored at −80° C. until analysis.

Healthy male volunteers were also recruited to provide blood samples to serve as a reference/control. Individuals were ages 18-70 years and had no history of head injury, neurological disorder, or endocrine disorder. Testosterone levels were measured in 14 male volunteers (median age, 21.5 years; range, 19-58 years), and autoantibody levels were measured in nine male volunteers (median age, 21 years; range, 19-42 years).

Testosterone Assay and PHH Definition

Serum testosterone was measured as described (Barton et al., J Head Trauma Rehabil. 2016 Jul-Aug;31(4):277-87). Briefly, samples were run in duplicate using a radioimmunoassay with the Coat-A-Count® In-vitro Diagnostic Test Kit (Siemens Healthcare Diagnostics). Kits included a solid-phase 125I radioimmunoassay designed for direct, quantitative measurements. Inter-assay and intra-assay percent coefficients of variation (% CV) were <10%. Samples with undetectable levels were assigned the minimum detection limit of the assay.

PHH status was determined as reported in the prior work (Barton et al., J Head Trauma Rehabil. 2016 Jul-Aug;31(4): 277-87). Briefly, individuals with at least two blood samples collected between 1-52 weeks post-injury were dichotomized into PHH or non-PHH groups. Those with at least 50% of samples meeting criteria for hypogonadotropic hypogonadism (testosterone <10 nmol/L with LH<5.6 IU/L)

were categorized as having PHH. Individuals with less than 50% of samples meeting these criteria were categorized in the non-PHH group. These reference values are the medical center pathology lab's minimum normal level and maximum normal level, respectively. These criteria for PHH were determined apriori.

APA/AHA ELISA Protocol 96-well ELISA plates were coated with bovine hypothalamic lysate or bovine pituitary extract (2 µg/well). After plate preparation, 14 of human serum sample was mixed with 994 of Start-Block buffer and then transferred to each well (1:100 dilation) with incubation at 4° C. overnight with shaking. Plates were washed again 4× with Tris-Buffered Saline and Tween® 20 (TBST) wash buffer. Anti-Human Ig/IgM HRP-conjugate (Jackson Immruno Research, as 1:10,000 in TBST Start-block blocking buffer) was added. as a 100p t1 aliquot to each well. Plates were incubated at 25° C., with shaking for 45 mint. After plate washing with 4× TBST, 100 µL, TMB substrate was added to develop color for 15 min. Stop Solution (100 µL) was then added, and plates were read at 450 nm for yellow color of final product. Standard curves were generated using purified human IgG or human IgM (Sigma Co.). Optical density readings were then converted to µg/ml. Intra-assay % XCV was 5-7%, and inter-assay % CV was 15-20%.

Pituitary Tissue Immunohistochemistry

Immunocytochemistry analysis was performed on human pituitary and human hypothalamus paraffin sections (Zyagen, CA, USA). According to the manual, slides were first deparaffinized through Trilogy® solution (Cell Marque, CA, USA) by incubating for 10 min at 95° C. and then blocked for endogenous peroxides with 3% hydrogen peroxide. Then a routine staining was performed after a 1-h blocking step in 10% goat serum. TBI and control patients serum, at a dilution of 1:200, was used and incubated over night at 4° C. Alexa Fluor™ 555 conjugated goat-anti-human IgG or IgM secondary antibody (Invitrogen, CA, USA) was added at a dilution of 1:1.000 and incubated for 1 h at room temperature. The tissues were counterstained with 4,6-diamidine-2-phenylindole for 5 min (Vector Laboratories, Burlingame, CA, USA). Fluorescent images were captured with an X40 objective on the OLYMPUS DP71 fluorescent microscope (Olympus America Inc, Center Valley, PA, USA).

Group-based trajectory analysis. To assess temporal serum autoantibody profiles (over the first 6 months post-injury), it was applied group-based trajectory analysis (TRAJ) (Niyonkuru et al., 2013, J. Neurotrauma 30, 938-945) as reported (Goyal et al., 2013, J. Neurotrauma 30, 946-957; Salonia et al., 2010, J. Neurotrauma 27, 1819-1825; Santarsieri et al., Brain. Behav. Immun. 45, 15-27; Santarsieri et al., J. Neurotrauma 31, 699-712; Wagner et al., 2011, J. Cereb. Blood Flow Metab. Off. J. Int. Soc. Cereb. Blood Flow Metab. 31, 1886-1896; Wagner et al., 2011, J. Neurotrauma 28, 871-888). TRAJ is a method to identify and describe multiple longitudinal patterns of change in time-varying covariates, in order to identify distinct subgroups within the population, by generating trajectory groups comprised of individuals with similar autoantibody profiles over time.

TRAJ groups were generated for both 1gM APA and AHA autoantibodies. It was hypothesized that increased autoantibody production would become apparent beginning in the post-acute phase of injury. As such, TRAJ group formulation was done using data collected 2-26 weeks post-TBI. However, data from all time points are graphed to document auto-antibody time course. TRAJ was conducted after rank transformation of the data (2-26 weeks after injury). Post-hoc autoantibody TRAJ group membership analysis was then done comparing groups on demographic and clinical variables. Temporal testosterone, IgG, and IgM autoantibodies were also graphed as a function of TRAJ group membership.

Statistical Analysis

Statistical analyses were performed with IBM SPSS Statistics Version 23 (Armonk, New York) and with SAS (Statistical Analysis Software) version 9.4 (Cary, North Carolina). Reported variables were assessed for normality using Shapiro-Wilk tests. Median values were reported for non-normally distributed data (interquartile range [IQR]), which included age, autoantibody levels, testosterone levels, BMI, GCS score, and length of hospital stay. Mann-Whitney U tests were used to assess group differences. Autoantibody levels from multiple serum samples over the 2-26 week period were averaged to calculate a single level for each individual. Between-group differences were examined using Mann-Whitney U tests, or Kruskal-Wallis tests with post-hoc comparisons using Dunn's test (Dunn, 01, 1964. Multiple Comparisons Using Rank Sums. Technometrics 6, 241-252) with Bonferroni corrections. Longitudinal between-group differences in testosterone levels were assessed using the Friedman test with post-hoc Wilcoxon signed-rank tests and Bonferroni corrections. Group differences for categorical data, including education level, race, mechanism of injury, radiographic injury type, and autoantibody TRAJ group membership were assessed using Chi-square tests, or Fisher exact tests, where appropriate. All tests of significance were two-sided. P values less than 0.05 were considered significant unless otherwise stated.

Mediation analyses were performed to examine the co-occurring biological relationships between age, autoantibody production, and PHH status. Given the known age effects on adaptive immunity (Pereira and Akbar, 2016, Front. Immunol. 7, 445) and also hypogonadism (Harman et al., 2001, J. Clin. Endocrinol. Metab. 86, 724-731) in the general population, age effects on PHH status would be at least in part due age-related influences on APA IgM TRAJ. To test this hypothesis, mediation analysis was performed using the Baron and Kenny method (Baron and Kenny, 1986). By definition, a full or complete mediation can be established if. 1) age is associated with PHH status (total effect); 2) age is associated with APA IgM TRAJ; 3) APA IgM TRAJ are associated with PHH status after controlling for age; and 4) the association between age and PHH status is attenuated after adjusting for APA IgM TRAJ (indirect effect). Due to a relatively small cohort size, the medium and high groups for APA IgM TRAJ were combined and compared with the low APA IgM TRAJ for the mediation analysis. All three models were adjusted for AHA IgM TRAJ group membership. For all three criteria, a logistic regression model was fitted. As a rule of thumb, a full or complete mediator should have a mediation percentage, defined as the indirect effect divided by total effect, of at least 80% (Baron and Kenny, 1986).

Results

Demographic and Sample Characteristics

Sixty-one men was included from the reported cohort with characterized testosterone levels (Barton et al., J Head Trauma Rehabil. 2016 Jul-Aug;31(4):277-87) and with at least two post-acute blood samples in the first 6 months available for autoantibody analysis. Twenty-four individuals were in the PHH group (39%), and 37 (61%) were in the non-PHH group. Demographic information for this cohort is reported in Table 1. The PHH group median age was 11 years older than that of the non-PHH group (35 vs. 24 years, p=0.02). There were no significant differences between PHH vs. non-PHH groups in body mass index, education level, race, GCS score, injury severity score, length of hospital stays, or mechanism of injury. Acute neuroradiology reports from CT and/or MRI were available for 58 of the 61 individuals. One individual had a subacute hemorrhage in the left thalamus and hypothalamus noted on MRI nine days post-injury, but there were no other reported abnormalities to the hypothalamus or pituitary. Diffuse axonal injury (DAI) on CT imaging was less common in the PHH group than in the non-PHH group (5% vs. 38%, p=0.005) which may be a related to age differences between PHH groups and also age differences in DAI frequencies. The median (IQR) age among those with DAI [23 (18-37) years] tended to be lower than in those without DAI [30 (22-44) years; p=0.086). On medical record review, none of the individuals were pre-scribed testosterone supplementation throughout the follow-up period.

Autoantibody levels and relationship to PHH. A total of 250 individual samples were used for autoantibody measurement, representing a mean of four samples per individual throughout the study period. Autoantibody levels for weeks 2-26 were averaged for each individual. Median (1QR: QI-Q3) levels for all subjects with TBI were: APA IgM, 0.4995 (0.1541-0.8616) pg/mL; APA IgG, 0.6682 (0.4441-1.3016) pg/mL; AHA IgM, 6.3073 (4.1792-8.2095) pg/mL; and AHA IgG, 5.8697 (3.3072-9.3712) pg/mL. Autoantibody levels were graphed by PHH status (FIGS. 12A-12D). Compared to the non-PHH group, the PHH group had lower median (IQR) serum concentrations of APA IgM (p=0.01). PHH and non-PHH groups had similar median levels of APA IgG (p=0.06), AHA IgM (p=0.20), and AHA IgG (p=0.38). In nine healthy male controls, the mean serum concentration was 0.6159 ug/mL for APA 1gM, 1.0611 ug/mL for APA IgG, 6.7498 pg/mL for AHA 1gM, and 5.3060 pg/mL for AHA IgG. There were no significant

TABLE 1

Demographics and patient characteristics

|  | All | Non-PHH | PHH | p-value |
|---|---|---|---|---|
| N (%) | 61 | 37 (61) | 24 (39) | — |
| Age, median (IQR), y | 28 (21-41) | 24 (21-38) | 39 (26-51) | 0.01 |
| BMI, median (IQR), kg/m² | 26 (23-29) | 26 (23-28) | 28 (24-30) | 0.13 |
| Education, n (%) |  |  |  |  |
| <HS | 12 (20) | 6 (16) | 6 (27) | 0.26 |
| HS | 24 (41) | 18 (49) | 6 (27) |  |
| >HS | 23 (39) | 13 (35) | 10 (46) |  |
| Race, n (%) |  |  |  |  |
| Caucasian | 56 (92) | 34 (92) | 22 (92) | >0.99 |
| African American | 3 (5) | 2 (5) | 1 (4) |  |
| Other | 2 (3) | 1 (3) | 2 (4) |  |
| GCS score (best in 24 h), median (IQR) | 7 (6-9) | 7 (6-9) | 8 (6-10) | 0.86 |
| Injury severity score, median (IQR) | 30 (25-38) | 30 (26-38) | 29.5 (25-38) | 0.87 |
| Length of hospital stay, median (IQR), d | 20 (15-27) | 19 (13-25) | 23 (16-30) | 0.12 |
| Mechanism of injury, n (%) |  |  |  |  |
| Motor vehicle accident | 32 (54) | 23 (64) | 9 (39) | 0.15 |
| Motorcycle accident | 16 (27) | 9 (25) | 7 (30) |  |
| Fall/jump | 9 (15) | 3 (8) | 6 (26) |  |
| Bicycle accident | 2 (3) | 1 (3) | 1 (4) |  |
| Radiographic injury type, n (%) |  |  |  |  |
| Subdural hematoma | 36 (61) | 22 (60) | 14 (64) | 0.79 |
| Subarachnoid hemorrhage | 39 (66) | 23 (62) | 16 (73) | 0.57 |
| Diffuse axonal injury | 15 (25) | 14 (38) | 1 (5) | 0.005 |
| Epidural hemorrhage | 8 (14) | 5 (14) | 3 (14) | >0.99 |
| Contusion | 21 (36) | 12 (32) | 9 (41) | 0.58 |
| Intraventricular hemorrhage | 11 (19) | 7 (19) | 4 (18) | >0.99 |
| Intracerebral hemorrhage | 21 (36) | 10 (27) | 11 (50) | 0.10 |
| Other | 3 (5) | 2 (5) | 1 (5) | >0.99 |

Individual Serum Immune Response to Pituitary and Hypothalamic Tissue. Serum from eight unique subjects with severe TBI had a variable immunoreaction with hormone-releasing granule-bearing cells from pituitary tissue and also hypothalamic tissue obtained from human cadaveric controls (see FIGS. 14A-14J and 15A-15J). These results qualitatively demonstrate the specificity of the auto-antibodies measured with ELISA assay to pituitary and hypothalamic tissue. Panels show PHH status and qualitative assessment of 1gM and IgG autoantibody staining from representative subjects within the low and the high TRAJ groups, as well as representative staining from those with low and high IgM/IgG ratios. These results suggest that APA and AHA TRAJ group assignment is highly associated with the staining pattern, as the densest staining was observed in those with high autoantibody TRAJ group membership.

differences between controls and the TBI group in autoantibody levels, although the purpose of the control data was to provide a healthy cohort reference for autoantibody levels. As such, it did not power the study to be able to detect statistical differences between patients with TBI and controls.

Figure 17A:
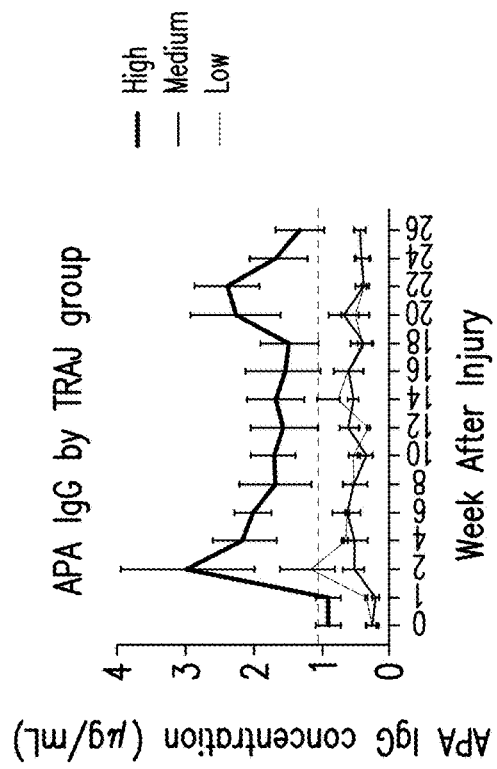
Figure 17B:
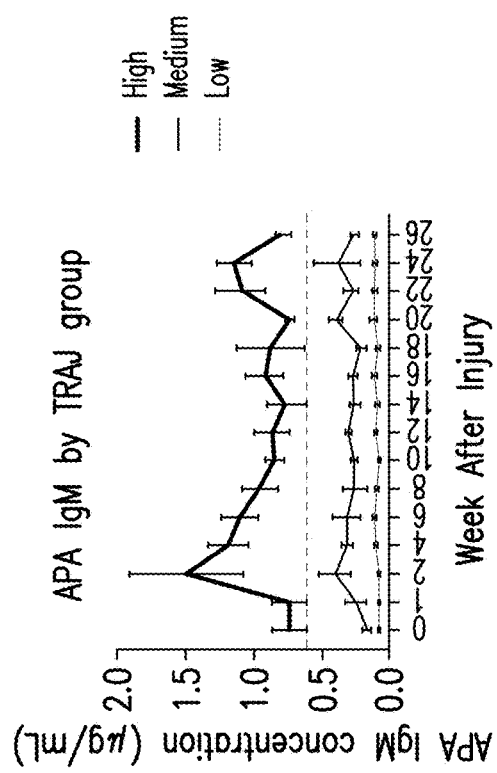
Figure 17C:
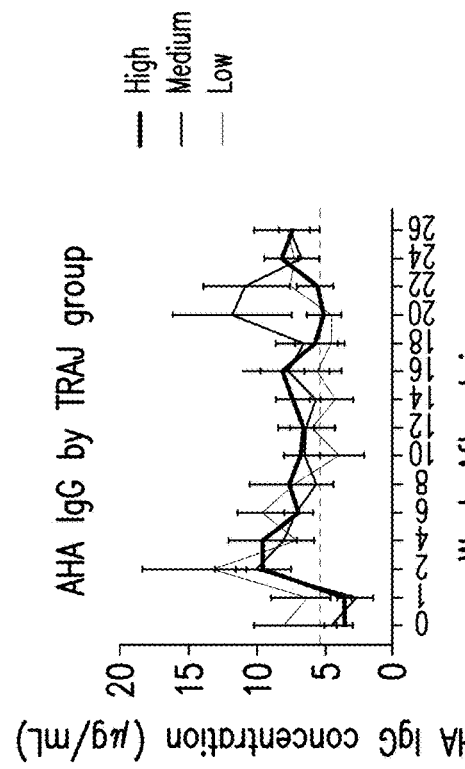
Figure 17D:
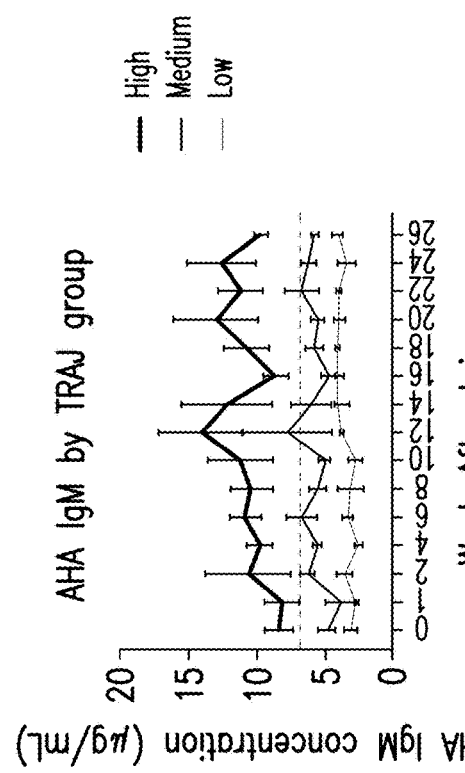
Figure 17E:
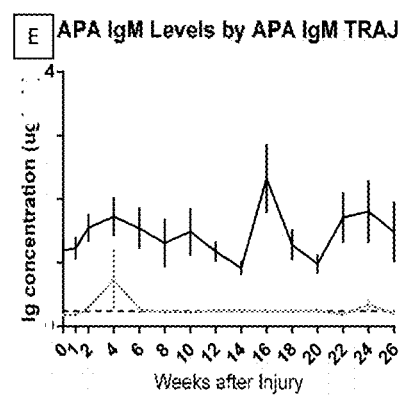
Figure 17F:
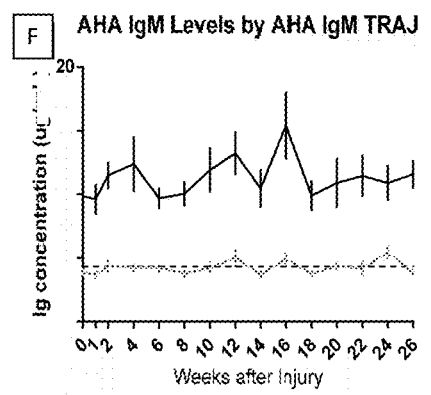
Figure 17G:
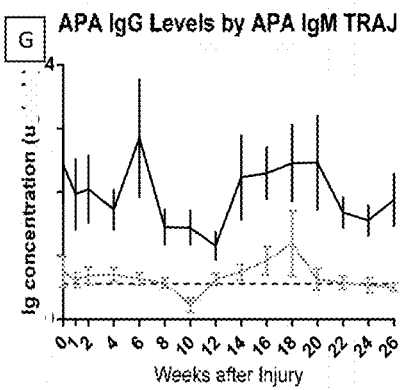
Figure 17H:
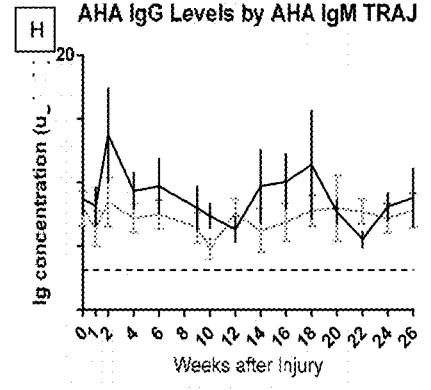

Trajectory group analysis. TRAJ analysis of autoantibody levels over time in this cohort revealed three distinct subgroups of individuals in regard to temporal IgM profiles for both APA and AHA. It was denoted the groups as high, medium, and low, as graphed in FIGS. 16A-16H. For APA TRAJ analysis, there were 28 (46%) individuals in the high group, 16 (26%) in the medium group, and 17 (28%) in the low group. For AHA TRAJ analysis, 23 (38%) individuals were in the high group, 21 (34%) were in the medium group, and 17 (28%) were in the low group. 1gM levels of each TRAJ group 45-c-7 generally were stable over time (FIGS. 17A and 17C). There were significant differences in APA IgM autoantibody levels between APA 1gM TRAJ groups at all time points (p<0.05) by Kruskal-Wallis tests. There were also significant differences in AHA IgM autoantibody between AHA IgM TRAJ groups at all time points (p<0.05). IgG levels were also graphed with respect to IgM TRAJ group membership (FIGS. 17B and 17D). Whereas the low and medium APA 1gM TRAJ groups were similar, the high group had elevated IgG levels, with significant differences observed between the high vs. low/medium TRAJ groups at weeks 0, 1, 4, 6, 8, 10, 22, and 24 (all p-values <0.05).

Additionally, the distribution of individuals with or without PHH was different according to APA IgM TRAJ group. As shown in Table 2, more individuals with PHFI were in the low group, and the majority of individuals without PHH were in the high group.

Figure 18A:
Figure 18B:
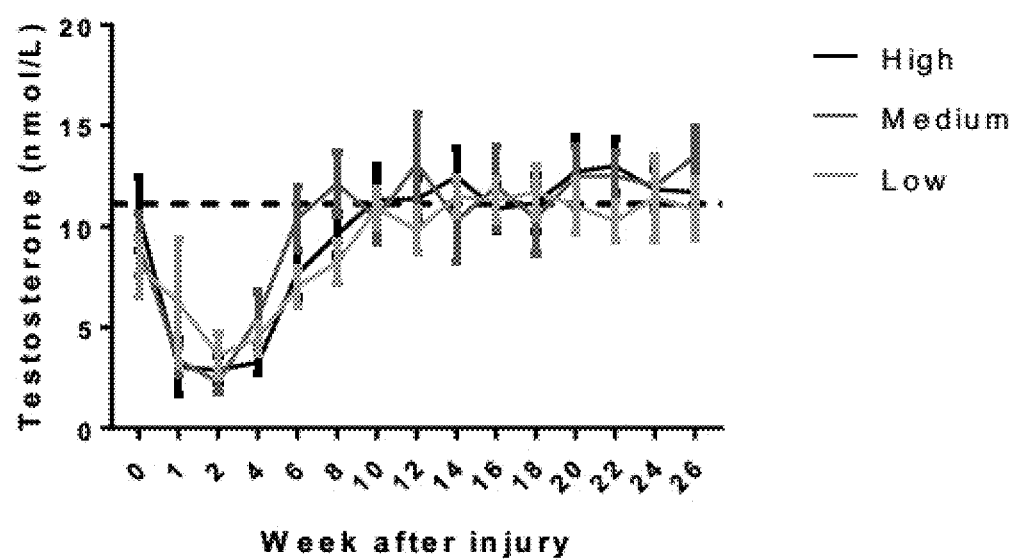

These relationships are also reflected in FIG. 18A where the low group had the lowest mean testosterone levels which were nearly all below the healthy control level. When analyzing longitudinal testosterone levels according to APA IgM TRAJ group (FIG. 18A), there was a significant difference in testosterone levels using the Friedman test (p<0.01). Median (IQR) testosterone levels for the APA IgM low, medium, and high TRAJ groups were 9.3 (7.5-10.1), 11.3 (6.6-12.2), and 11.7 (9.4-12.7), respectively. Post-hoc comparisons using Wilcoxon signed-rank tests and Bonferroni corrections (significance level of 0.017) show the low TRAJ group had lower testosterone levels than the high TRAJ group (p=0.015). No association between AHA TRAJ group and PHH was observed, and as shown in FIG. 18B, there was no difference in longitudinal testosterone levels between AHA IgM TRAJ groups (p=0.28).

TABLE 2

Concordance of APA and AHA IgM trajectory groups by PHH Status

| | APA IgM TRAJ group | | |
|---|---|---|---|
| | Low | Medium | High |
| PHH | 11 (45.8) | 6 (25.0) | 7 (29.2) |
| No PHH | 6 (16.2) | 10 (27.0) | 21 (56.8) |
| | $\chi^2 = 7.019, p = 0.030$ | | |
| PHH | 7 (29.2) | 9 (37.5) | 8 (33.3) |
| No PHH | 10 (27.0) | 12 (32.4) | 15 (40.5) |
| | $\chi^2 = 0.333, p = 0.847$ | | |

Figure 19A:
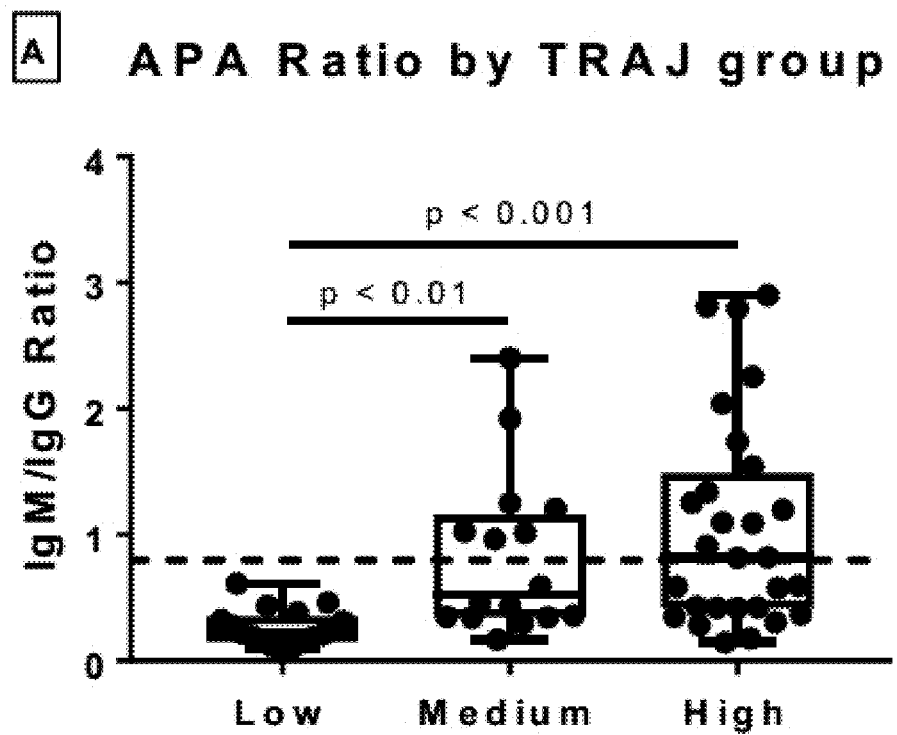
Figure 19B:
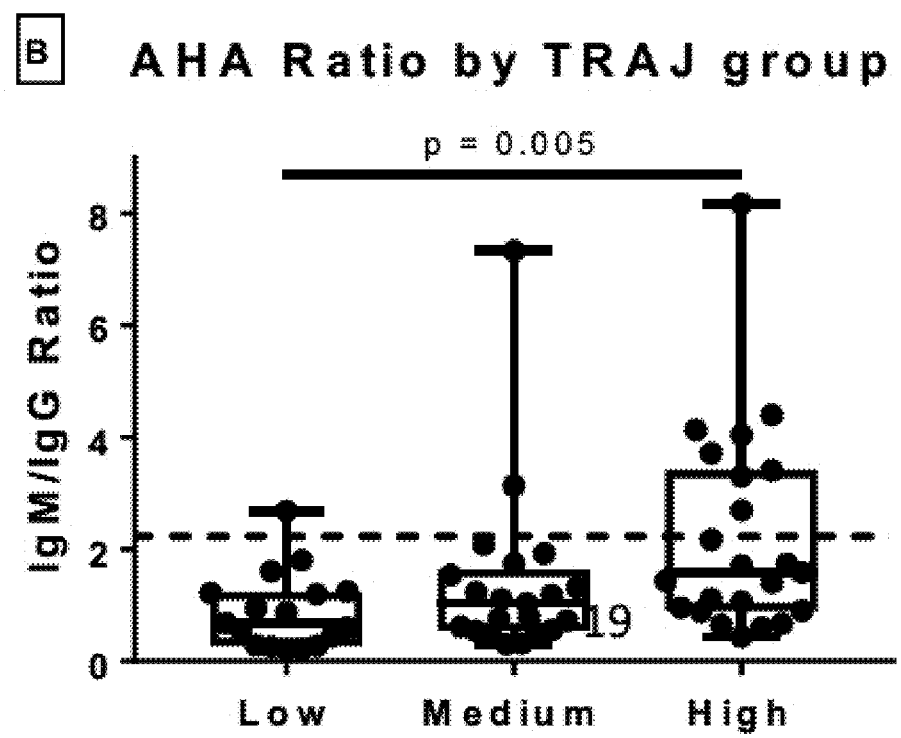

IgM/IgG ratios by TRAJ group membership were explored (FIGS. 19A-19B). Significant differences were noted with IgM/IgG ratio by TRAJ group for both APA (p<0.001) and AHA (p<0.01) autoantibodies by Kruskal-Wallis tests. Post-hoc pairwise comparisons revealed that among APA IgM TRAJ groups, median 1gM/IgG ratios in the low group were significantly lower than both the medium and high groups (FIG. 19A). In the AHA IgM TRAJ group post-hoc analysis, the high TRAJ group had a higher IgM/IgG ratio compared to the low TRAJ group (FIG. 19B). Additionally, this analysis was repeated including the control group to assess for post-hoc pairwise comparisons of the control group IgM/IgG ratio to individual TRAJ groups. The low APA TRAJ group had a lower IgM/IgG ratio than the control group (p 0.001). The low AHA TRAJ group also had a lower IgM/IgG ratio than the control group (p=0.02), but this did not reach statistical significance using Bonferroni corrections (corrected significance level of p=0.008). When comparing controls versus the TBI group as a whole, there were no significant differences in APA ratio (median, 0.69 versus 0.43; p=0.27) or in AHA ratio (median, 1.51 versus 1.11; p=0.16).

Additionally, it was conducted post-hoc comparisons of demographic and clinical characteristics between TRAJ groups. There were no significant differences among APA 1gM TRAJ groups in age, race, education, mechanism of injury, BMJ, GCS, radiographic injury types from admission CT, or length of hospital stay. However, injury severity scores differed between APA IgM TRAJ groups (p=0.04), with a higher median (IQR) severity score in the high group (33.5 [29-42]) than in the medium (29 [17-34]) or low (26 [25-35.5]) groups. Among the ANA IgM TRAJ groups, there were no significant differences in these characteristics.

Multivariate Mediation analysis. The hypothesis that the relationship between age and PHH is partially mediated by age-related effects on APA IgM was formally tested in a multivariate mediation analysis using the Baron and Kenny method. The pathways of the mediation model were all adjusted for the effects of AHA 1gM TRAJ, a potential confounding factor. Results showed that age is significantly associated with PHH status (OR=1.05, 95%=1.01, 1.10, p=0.015). That is, for every year increase in age, there was an associated 5% increase in odds of P1111. Age was also significantly associated with APA IgM TRAJ group (OR=0.96, 95%=0.92, 0.99, p=0.018). Specifically, for each year increase in age there is a corresponding 4% decrease in odds of being in the medium/high APA IgM TRAJ group versus the low APA IgM TRAJ. Further, the mediator, APA IgM TRAJ group, was significantly associated with PHH status, such that individuals in the medium/high APA IgM TRAJ group were at a 510% decreased odd of PHH compared to the low APA 1gM TRAJ group (OR=0.49, 95%=0.24, 0.99, p=0.018). Upon adjusting for the effects of APA 1gM TRAJ, the direct effects of age on PHI-1 status became non-significant (OR=1.04, 95%=1.00, 1.09, p=0.06). Together, these data suggest that APA IgM TRAJ group membership is a partial mediator, accounting for 18.27% of the observed relationship between age and PHI-1 status.

Discussion

Given the growing evidence that post-traumatic hypopituitarism, specifically hypogonadism, is deleterious to long-term outcomes, it is an increasingly important topic of study (Barton et al., J Head Trauma Rehabil. 2016 Jul-Aug;31(4): 277-87; Bondanelli et al., J Neurotrauma. 2007; 24(11): 1687-1697; Carlson et al., 2009 Brain Inj. 23, 336-344; Popovic et al., 2004, J. Endocrinol. Invest. 27, 1048-1054; Wagner et al., 2012, Brain Inj. 26, 1226-1242). Current screening consensus for post-traumatic hypopituitarism (Ghigo et al., 2005, Brain lnj. 19, 711-724) is based on limited and also contradictory evidence on the timeframe in which hypopituitarism develops, and there remains a paucity of evidence on the safety and efficacy of—hormone replacement therapy after TBT.

Despite the clinical relevance of this problem, the pathophysiological mechanisms underlying hypogonadism remain unclear, and the role of aging in contributing to PHH risk after TBI has not been well documented. While the study suggests that those with PHH are older than those without PHH, it was also showed that age and PHH status are independent risk factors for TBI recovery (Barton et al., J Head Trauma Rehabil. 2016 Jul-Aug;31(4):277-87).

In this study, first longitudinal data on APA and AHA levels after TBI was provided, and the relationship between these autoantibodies and PHH in men after moderate to severe TBI was reported. The chief findings show that individuals with PHH have lower APA IgM levels after TBI than individuals without PHH, while IgG levels were similar. TRAJ analysis revealed distinct subgroups of individuals with autoantibody trajectories over the timeframe of 2-26 weeks post-injury. It was also showed that APA IgM TRAJ group membership is a partial mediator of the relationship between age and PHH. These results may provide important biological insight into the role of the immune system in PHH development for men after severe TBI.

APA and AHA levels in relation to post-traumatic hypopituitarism was studied. Tanriverdi et al. evaluated pituitary function and APA levels in 29 individuals at 3 years post-TB1 (Tanriverdi et al., 2008, Eur. J. Endocrinol. Eur. Fed. Endocr. Soc. 159, 7-13). In a follow-up study, pituitary function, APA levels, as well as AHA levels were measured in 25 individuals at 5 years post-TBI (Tanriverdi et al., 2013, J. Neurotrauma 30, 1426-1433). They observed higher IgG autoantibody titers among those with hypopituitarism at both time points. An association between elevated autoantibody titers and hypopituitarism was also found in boxers (Tanriverdi et al., 2010, Eur. J. Endocrinol. Eur. Fed. Endocr. Soc. 162, 861-867). These data led the group to conclude that autoimmunity against the pituitary and hypothalamus plays a pathogenic role in pituitary dysfunction, however the work did not distinguish between IgM and IgG autoantibodies.

Interestingly, when comparing controls versus the TBI group as a whole, there were no significant differences in APA IgM/IgG ratio (median, 0.69 versus 0.43; p=0.27) or in AHA IgM/IgG ratio (median, 1.51 versus 1.11; p=0.16). However, it was also found median APA IgM levels were higher among those with no PHH, compared to those without PHH. In addition to delineating both IgM and IgG autoantibodies, there are other study design differences to consider. Tanriverdi et al. studied a small sample with 14-20% women and which consisted mostly of mild TBI cases and only a few severe TBI cases, whereas the data focus on men with severe TBI (GCS <8). There are substantial differences in secondary injury processes along the injury severity spectrum. Also, it is possible that autoimmunity development and profiles may differ during chronic versus post-acute phases of recovery, wherein the latter is associated with neuroinflammatory processes supporting CNS cell rescue and repair. Differences in TBI pathophysiology between men and women are less well-known. APA and AHA levels in the first six months post-TBI instead of three or five years after injury were measured; yet it is not known how temporal IgG vs. IgM profiles vary over these different time periods.

Additionally, Tanriverdi et al. semi-quantitatively measured APA and AHA using indirect immunofluorescence titers, and as such, reported many individuals with negative titers whereas it was measured autoantibody levels with a quantitative ELISA. Using a higher sensitivity assay, APA and AHA levels in all individuals were detected and were able to compare autoantibody levels among individuals with TBI to healthy controls. These results may indicate that quantitative levels can serve as a more accurate measure and comparison than titers. Other studies have shown measurable levels of autoantibodies to CNS antigens among healthy individuals (Hedegaard et al., 2009, Immunology 128, e451-461). Further, certain work has revealed a better understanding of CNS lymphatic drainage and immune surveillance (Louveau et al., 2015, Nature 523, 337-341). Studies such as these are shifting dogma on CNS immune privilege and demonstrate that even healthy individuals are capable of producing autoimmune responses in the CNS via immune surveillance systems (Engelhardt et al., 2017, Nat. Immunol. 18, 123-131; Louveau et al., 2015, Trends Immunol. 36, 569-577).

Notably, Tanriverdi's work evaluated multiple pituitary axes, including growth hormone, adrenocorticotropic hormone, gonadotropin, and thyroid stimulating hormone deficiency. Given that hypogonadism is arguably thought to be the most common type of pituitary disorder after TBI (Kopczak et al., 2014, J. Neurotrauma 31, 99-107), the current disclosure focused on evaluating PHH as a chronic complication in the population with severe TBI.

The inverse relationship between APA IgM levels and incidence of PHH is an adaptive process. This interpretation of the data supports a growing literature on protective autoimmunity after CNS injury, in which self-antigen recognizing immune cells contribute to injury repair (Schwartz and Raposo, 2014, Neurosci. Rev. J. Bringing Neurobiol. Neurol. Psychiatry 20, 343-358). Interestingly, it was only observed an association between PHH and APA IgM levels, but not IgG levels or IgM/IgG ratios. Naturally-arising IgM autoantibodies to apoptotic cell membranes (Gronwall et al., 2012, Front. Immunol. 3, 66; Vas et al., 2013, Front. Immunol. 4, 4) and leukocytes (Lobo et al., 2010, J. Clin. Immunol. 30 Suppl 1, S31-36) are generated from Bl-cells and are a physiologic (evolutionarily conserved) part of the innate immune system (Gronwall et al., 2012, Front. Immunol. 3, 66; Vas et al., 2013, Front. Immunol. 4, 4); while constitutively expressed (Baumgarth et al., 2005), these autoantibodies are amplified in environments with high concentrations of apoptotic cells (Chen et al., J. Immunol. Baltim. Md 1950 183, 1346-1359; Chen et al., J. Immunol. Baltim. Md 1950 182, 6031-6043) and in pro-inflammatory states (Lobo et al., 2010, J. Clin. Immunol. 30 Suppl 1, S31-36) to increase apoptotic cell phagocytosis (deCathelineau and Henson, 2003, Essays Biochem. 39, 105-117) and activate complement mediated anti-inflammatory pathways (Gray et al., 2007, Proc. Natl. Acad. Sci. U.S.A 104, 14080-14085; Huynh et al., 2002, J. Clin. Invest. 109, 41-50) in an attempt to support immune homeostasis and tissue health. Specifically, IgM antibodies bound to antigens on pathogens or dying cells facilitates lectin pathway activation of the complement system, which in turn, can facilitate phagocytosis, support inflammatory cell recruitment, and modulate the adaptive immune response (Kjaer et al., 2013, Immunol. 56, 413-422). Adaptive immune response signaling molecules like IL-7 can mediate lymphoproliferation of T-cells sensitive to circulating self-antigens and capable of producing IgM autoantibodies (Goldrath and Bevan, 1999, Immunity 11, 183-190; Schluns et al., 2000, Nat. Immunol. 1, 426-432). As such, these processes have led some to characterize these types of reparative responses as contributing to "protective autoimmunity." In the case of blood brain barrier disruption after TBI, autoantibody production to circulating brain antigens, including antigens associated with pituitary and/or hypothalamic tissue, may be useful in clearing dead cells and debris as well as facilitating repair.

Though considered as somewhat controversial, evidence of protective autoimmunity has been reported in multiple CNS conditions such as stroke and spinal cord injury (Graber and Dhib-Jalbut, 2009, Pharmacol. Ther. 121, 147-159; Saltzman et al., 2013, Curr. Phys. Med. Rehabil. Rep. 1; Schwartz and Baruch, 2014, J. Autoimmun. 54, 8-14). High IgM autoantibody levels are thought to protect donor organs (Lobo et al., 2010, J. Clin. Immunol. 30 Suppl 1, 531-36; McAlister et al., 2004, Liver Transplant. Off Publ. Am. Assoc. Study Liver Dis. Int. Liver Transplant. Soc. 10, 315-319), reduce risk for stroke and Alzheimer's disease (Eriksson et al., 2010, J. Alzheimers Dis. JAD 21, 577-584; Fiskesund et al., 2010, Stroke 41, 607-612), and reduce disease burden in auto-immune disorders (Granwall et al., 2012), while low/absent IgM levels enhances pathogenic IgG production associated with autoimmune and other diseases (Vas et al., 2013, Front. Immunol. 4, 4). The concept of protective autoimmunity in TBI may also be supported by other work showing autoantibodies binding to breakdown products of injured neural cells (Stein et al., 2002, J. Neuropathol. Exp. Neurol. 61, 1100-1108). The protective autoimmunity, specifically in the post-acute phases of recovery after TBI, may extend to APA 1gM preserving pituitary function.

Figure 20:
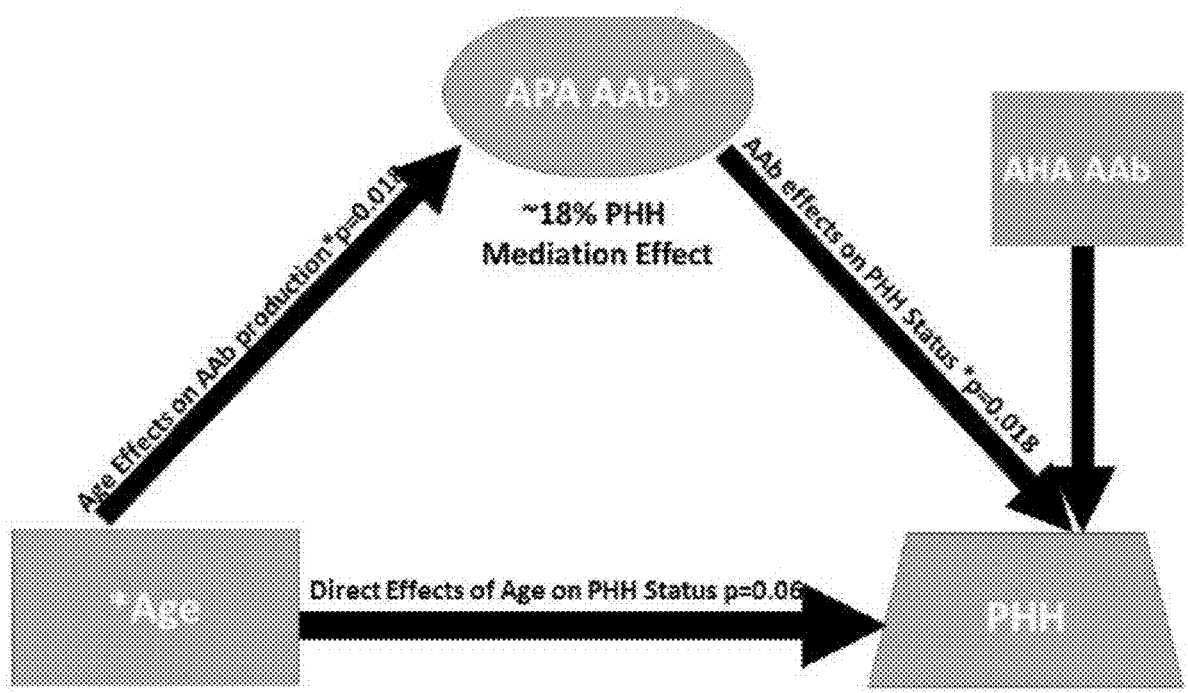

In studying the pathophysiology of post-traumatic hypogonadism it is important to understand the condition in the context of normal aging, because testosterone levels decrease in men in the general population by about 10% per year after the age of 30 (Harman et al., 2001, J. Clin. Endocrinol. Metab. 86, 724-731), and idiopathic hypogonadism can occur as a part of aging (Decaroli, M.C., Rochira, V., 2016. Aging and sex hormones in males. Virulence 1-26). However, there are no clinical guidelines for age-adjustment of normal testosterone levels. Men with PHH were on average older than men without PHH. However, the aging immune system also has decreased capacity to respond to infection and other insults, with limited reactive potential in both T cells and B cells (Aspinall et al., 2014; Frasca et al., 2005, Semin. Immunol. 17, 378-384; Pereira and Akbar, 2016). Thus, it was hypothesized that the age relationship with PHH may be due in part to a decreased capacity to produce 1gM related to aging, which may have deleterious effects on pituitary tissue repair. Mediation analysis was used to address this hypothesis, and it was discovered that APA IgM TRAJ group serves as a partial mediator of the age-PHH relationship (see FIG. 20), capturing nearly 20% of the variance associated with age and PHH status. Specifically, increasing age was associated with a lower likelihood of being in a medium or high compared to low APA 1gM TRAJ group. Additionally, individuals with a medium or high APA IgM TRAJ had a reduced odd of developing PHH. This novel finding gives insight into a potentially protective role of IgM in a causal pathway to the development of PHH. One potential element of these relationships is the cortisol response to injury. Cortisol responses to stressors last longer as humans age (Otte et al., 2005, Psychoneuroendocrinology 30, 80-91), and this prolongation may suppress the immune response, immunoglobulin production and/or result in increased likelihood of developing PHH depending on the individual.

The findings suggest hypopituitarism as a potential area for therapeutic development based on individual risk stratification considering the age and autoantibody levels over time of patients with TBI. This type of personalized, biomarker-based approach to recovery and rehabilitation after TBI fits well within the Rehabilomics framework for rehabilitation-related research aimed at personalizing treatments that improve health and function for those with disabilities. (Wagner, 2010, Eur. J. Phys. Rehabil. Med. 46, 549-556; Wagner and Sowa, 2014, Am. J. Phys. Med. Rehabil. 93, 913-916; Wagner and Zitelli, 2013, Pathophysiology 20, 39-48).

This disclosure should be interpreted within the context of its limitations. The observational findings do suggest that APA 1gM is at least a partial mediator of the aging related causal effects on PHH development. The specific antigens in the pituitary and hypothalamus to which autoantibodies bind in the immunohistochemistry and ELISA assays remain unknown. However, the immunohistochemistry findings support the specificity of these autoantibodies to their target tissues. In this cohort a significant relationship between PHH status and worse multidimensional outcomes were demonstrated (Barton et al., J Head Trauma Rehabil. 2016 Jul-Aug;31(4):277-87).

In conclusion, novel, longitudinal data on APA and AHA levels were reported in the setting of post-traumatic hypopituitarism, specifically PHH. The higher APA IgM levels observed in those without PHH support a protective role of autoantibodies in pituitary dysfunction during the first six months after TBI.

Example 5: Examining Longitudinal Adaptive Immune Response and Relationships Between IL-7 and Anti-Pituitary/Hypothalamic Autoantibodies after Severe-TBI Traumatic brain injury (TBI) is associated with long-term complications, including persistent hypogonadotropic hypogonadism (PHH) in men, for which the studies suggest a link to autoimmunity. Autoantibodies (AAb) to the pituitary and hypothalamus (APA/AHA) following CNS injury are present up to one-year post-injury, and reduced IgM AAb production increases PHH-risk among men with severe TBI. Adaptive immunity, including interleukin 7 (IL-7) production, may promote brain tissue-specific AAb production, which is neuro-reparative and reduces neuroendocrine dysfunction.

Serum IL-7, IgM/IgG APA and AHA levels were evaluated 2-weeks to 12-months post-injury for N=129 individuals (n=580 samples) with severe TBI. Mean IL-7 levels for 2-weeks-3-months (2wk-3mo), 4-6 months (4-6mo), and 7-12 months (7-12mo) were assessed. Age was dichotomized (age=32). Group-based trajectory analyses for APA/AHA IgM and IgG levels identified high, medium, and low trajectory (TRAJ) AAb profiles. Ordinal logistic regression modeled IL-7, dichotomized age, and age*IL-7 interaction effects on AAb TRAJ. At 2wk-3mo, IL-7 was associated with APA IgM TRAJ ($\beta=-0.023$, p=<0.001); though there was not a significant moderating age effect. At 4-6mos, older age moderated the IL-7 relationship to IgM APA levels, such that with constant age, increases in IL-7 were associated with lower APA IgM TRAJ ($\beta=-0.022$, p=0.04). A similar trend was noted at 7-12mo for the IL-7*age interaction ($\beta=-0.026$, p=0.08). IL-7 did not influence IgM AHA production as strongly, with only trends (p<0.08) noted 4-12mo post-injury. IL-7 was associated with IgG APA production across the entire sampling period (p<0.04 all comparisons), while IL-7 was associated with IgG AHA production 7-12 months post-injury (p<0.015). These data implicate IL-7 as relevant to the autoimmune response to pituitary proteins and as relevant to ongoing neuroendocrine dysfunction after TBI.

Example 6: Administration of Recombinant Human IL-7 (rhIL-7) to Mouse Controlled Cortical Impact (CCI) Model This in vivo experiment studied the effect of rhIL-7 in mouse underwent severe CCI that induced traumatic brain injuries. Thirty-three mice underwent severe CCI (n=30) or sham (n=3) received vehicle, low dose, or high dose rhIL-7. The rhIL-7 were given on day 1, day 7 and day 13 (5 µg for the high dose group and 0.5 ug for the low dose group).

The animals were recovered and underwent Novel Object Recognition Testing on day 8, Morris Water Maze Data between day 14 and day 20. Serum cytokine profiles and blood cell flow cytometry were performed. Spleen cell flow cytometry were performed on samples collected on day 2 and day 21.

Figure 21A:
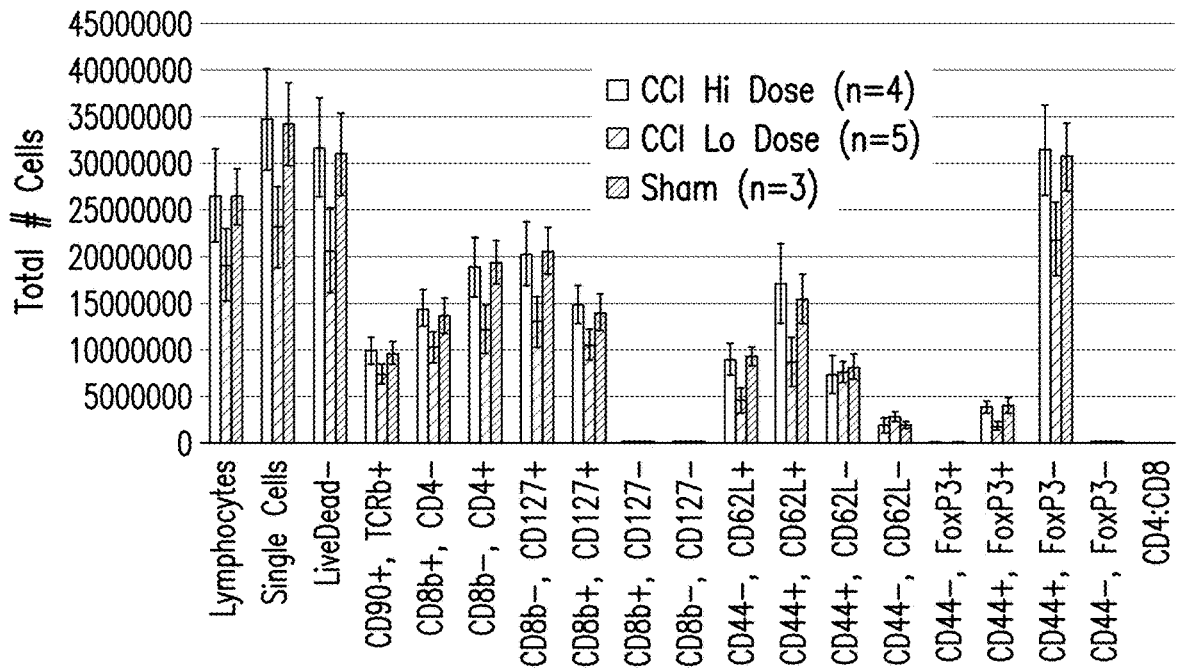
Figure 21B:
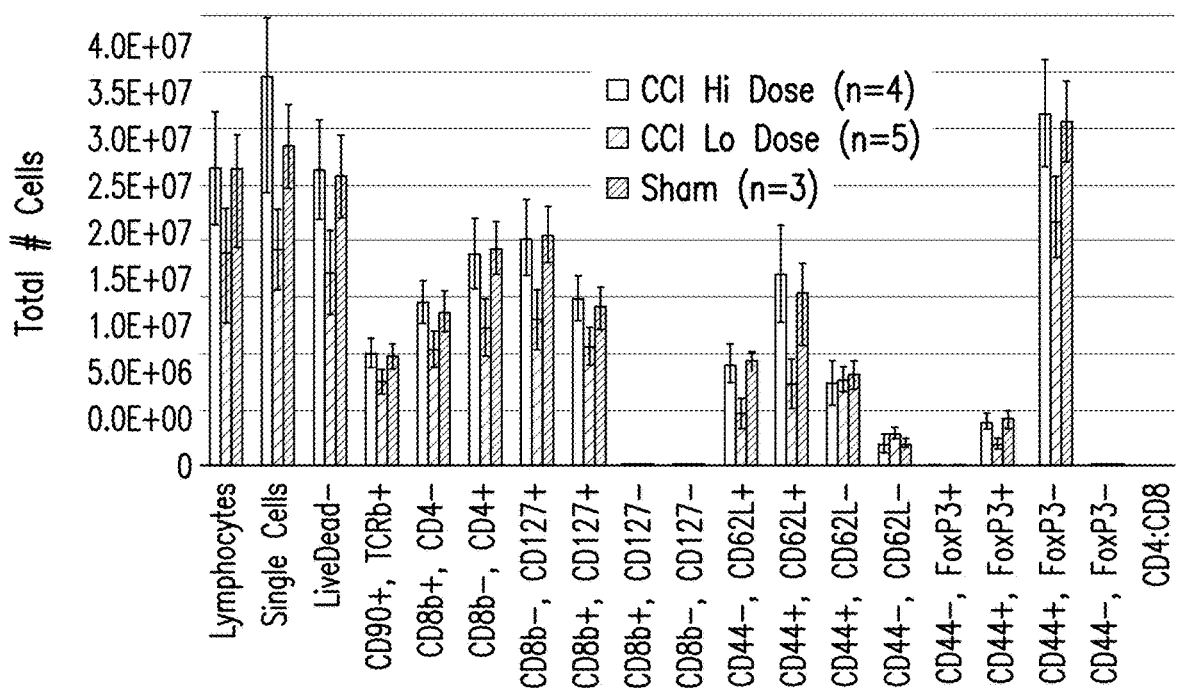

Spleen cell flow cytometry showed that CCI low dose rhIL-7 mice had reduced splenic lymphocyte counts across subtypes by day 21 compared to Sham (FIGS. 21A-21B). High dose rhIL-7 reversed this trend across cell count subtypes (FIGS. 21A-21B). Additionally, Post-injury spleen lymphocyte numbers were reduced in samples collected from day 21 low dose IL-7 group when compared with samples collected from day 2 CCI harvest vehicle. Such reduction was partial rescued by high dose rhIL-7 on day 21 (FIG. 22).

Figure 23A:
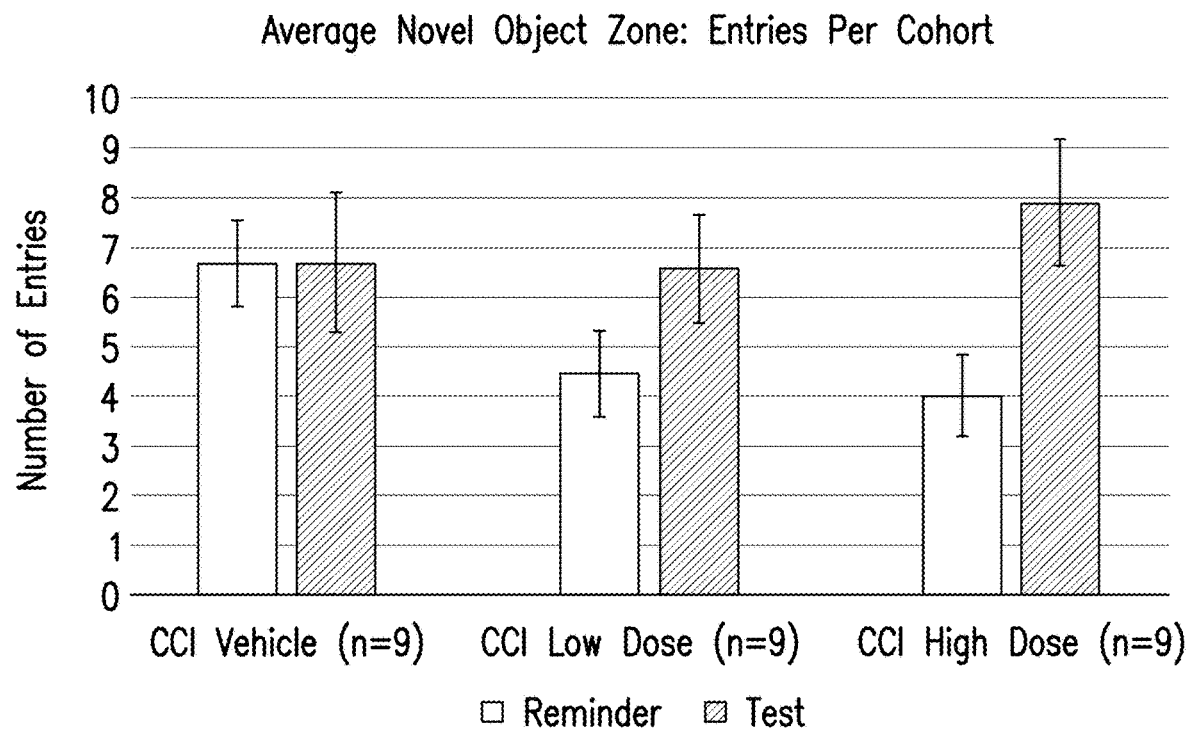
Figure 23B:
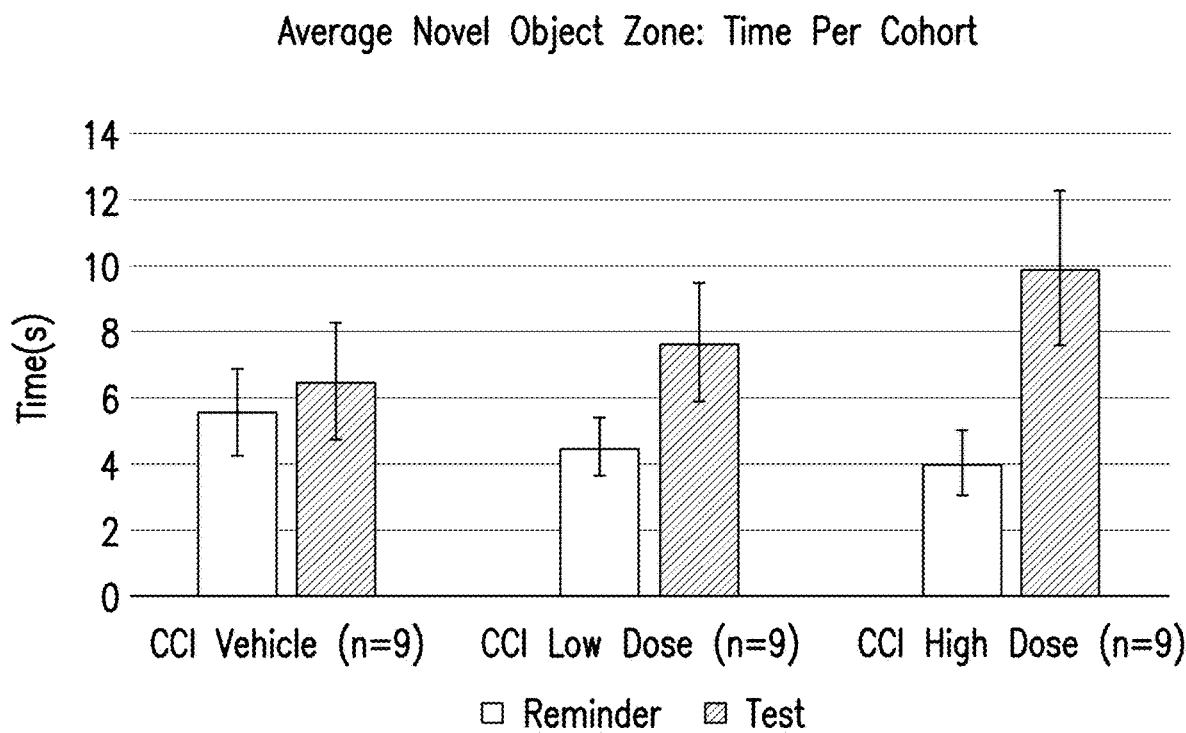
Figure 23C:
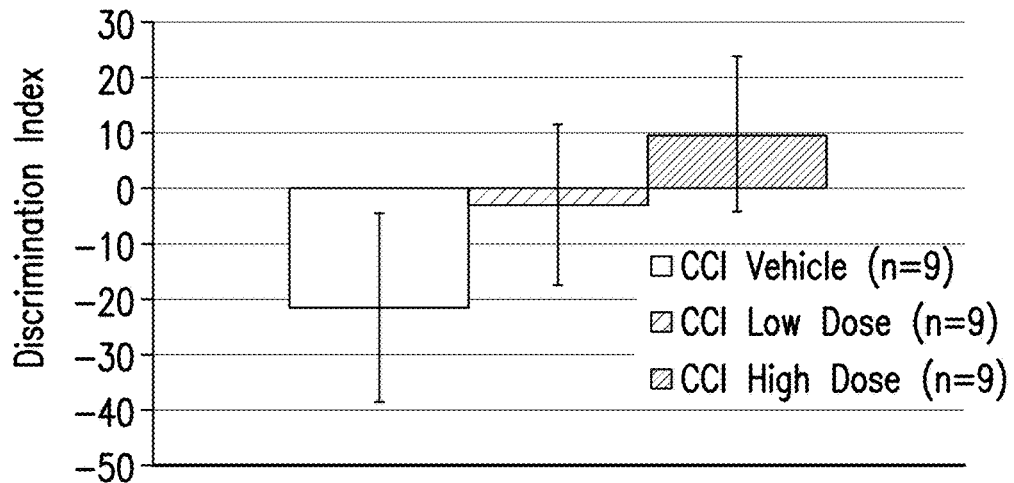
Figure 24:
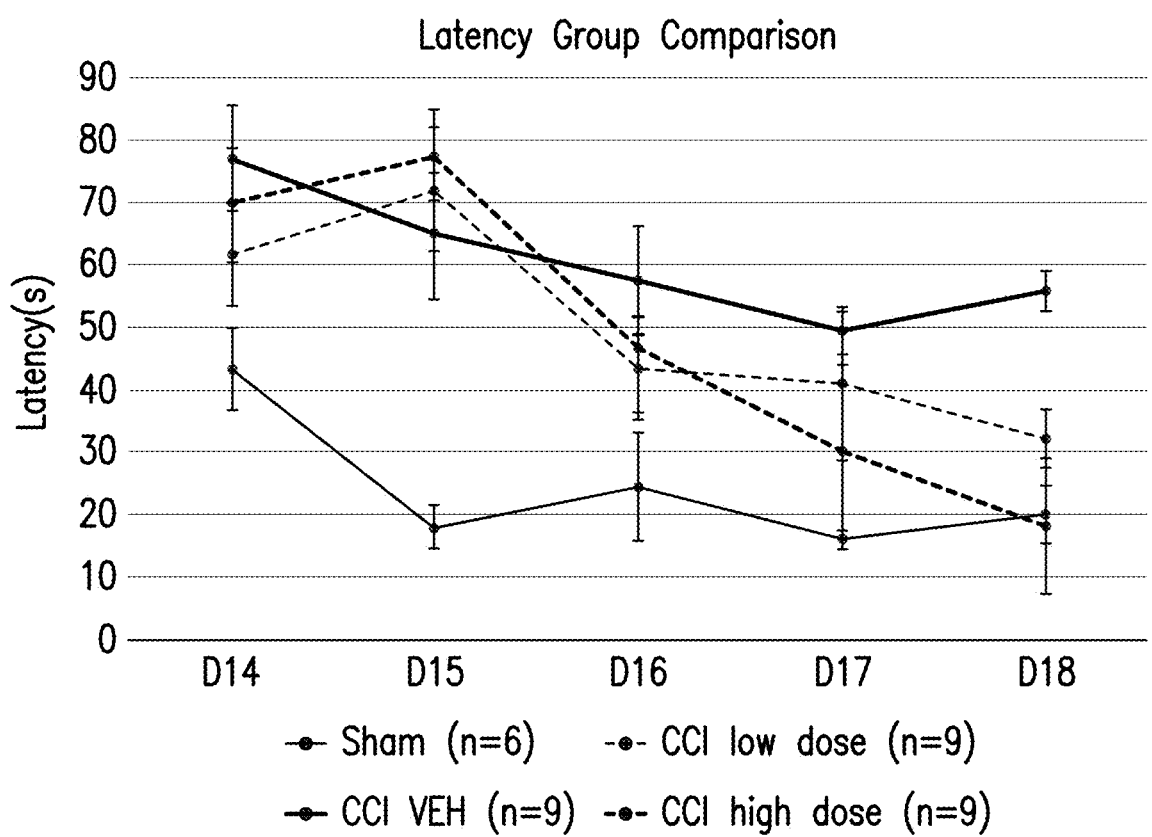
Figure 25A:
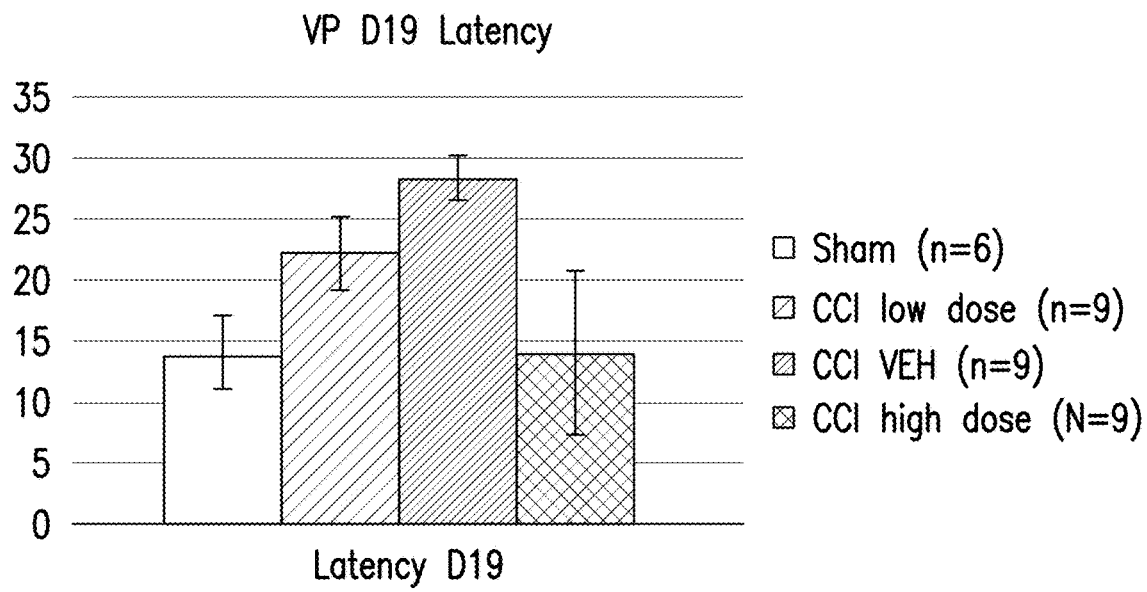
Figure 25B:
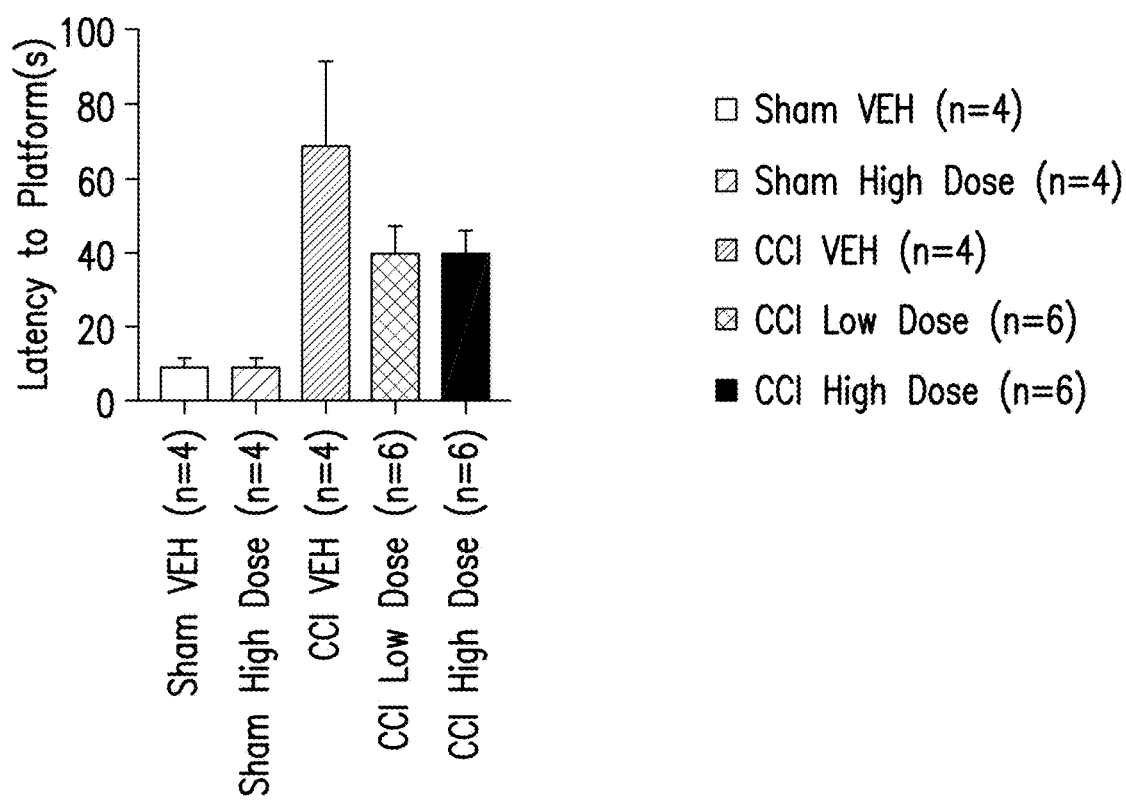
Figure 26A:
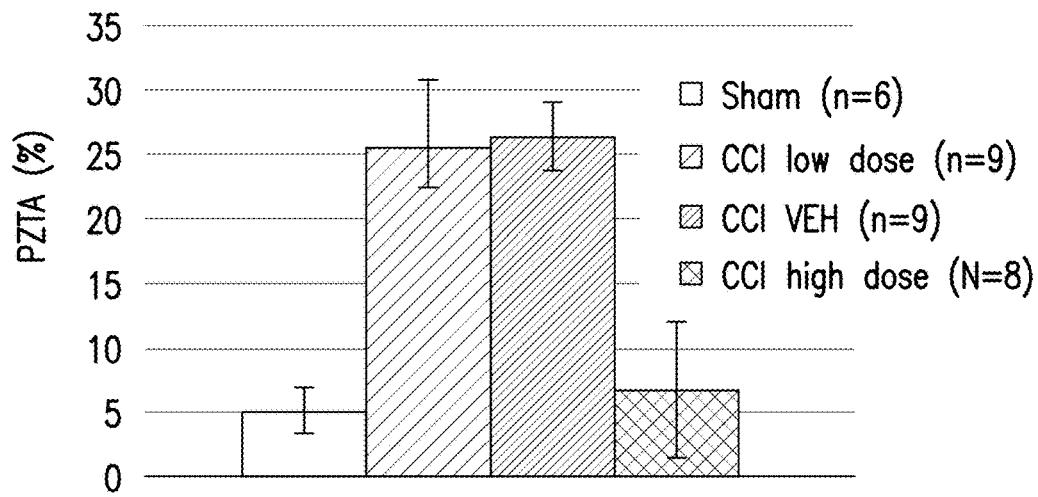

Novel Object Recognition Test was conducted in mice on day 8 post injury. High dose rhIL-7 mice interacted more frequently with novel object than low dose or vehicle mice (FIG. 23A paired t-test results: CCI low dose p=0.14; CCI high dose p=0.019). High dose rhIL-7 mice interacted for longer time with novel object than low dose or vehicle mice (FIG. 23B paired t-test results: CCI low dose p=0.16; CCI high dose p=0.034). Trend of average discrimination index between CCI high and CCI vehicle were also shown (FIG. 23C). Morris Water Maze Acquisition trials were conducted in mice on day 14-day 18 post injury. The latencies were measured (FIG. 24). rmANOVA test showed overall p<0.0001, group effect p=0.0465, day effect p=0.1295, and group*day interaction p=0.0005. Post-hoc pairwise comparisons showed CCI vehicle (VEH) vs. CCI High Dose p=0.0347; CCI VEH vs CCI low dose p=0.0662; CCI VEH vs. Sham p<0.0001. Morris Water Maze Visible Platform (VP) trials were performed on day 19 post injury, latency (FIGS. 25A-25B, 26B) and peripheral zone time allocation (PZTA) (FIGS. 26A, 26D) were measured. Regarding latency, One-way ANOVA showed p=0.0491; post-hoc pairwise comparisons showed p=0.0192 in CCI VEH vs. CCI high dose, p=0.17 in CCI VEH vs. CCI low dose and p=0.0176 in sham vs. CCI high dose. Regarding PZTA, One-way ANOVA showed p=0.0004; post-hoc pairwise comparisons showed p<0.01 in CCI VEH vs. CCI high dose, and p<0.01 in CCI VEH vs. sham. In sum, the results showed that high dose rescued VP trial latencies when compared to vehicle injection.

TBI is associated with Hypogonadism in men over at least the first-year post injury. Hypogonadism is associated with poor global outcomes and functional cognition defects. IgM APA AAb are produced after TBI and appear to be related/responsive to IL-7 levels clinically, even among individuals with PHH. IgM:IgG ratios are boosted by high IL-7

The current study showed that CCI was associated with reduced lymphocytes over time and compared to sham. rhIL-7 at "high" dose restored these counts. High rhIL-7 also improved memory as measured by novel object recognition trials when compared to CCI mice receiving vehicle. High rhIL-7 also significantly improved Morris Water Maze acquisition performance latencies and visible platform trial performance, indicating improvements on other aspects of functional cognition indications.

Example 7 Correlation of IL-7 and Autoantibodies in PHH Patients

Figure 27:
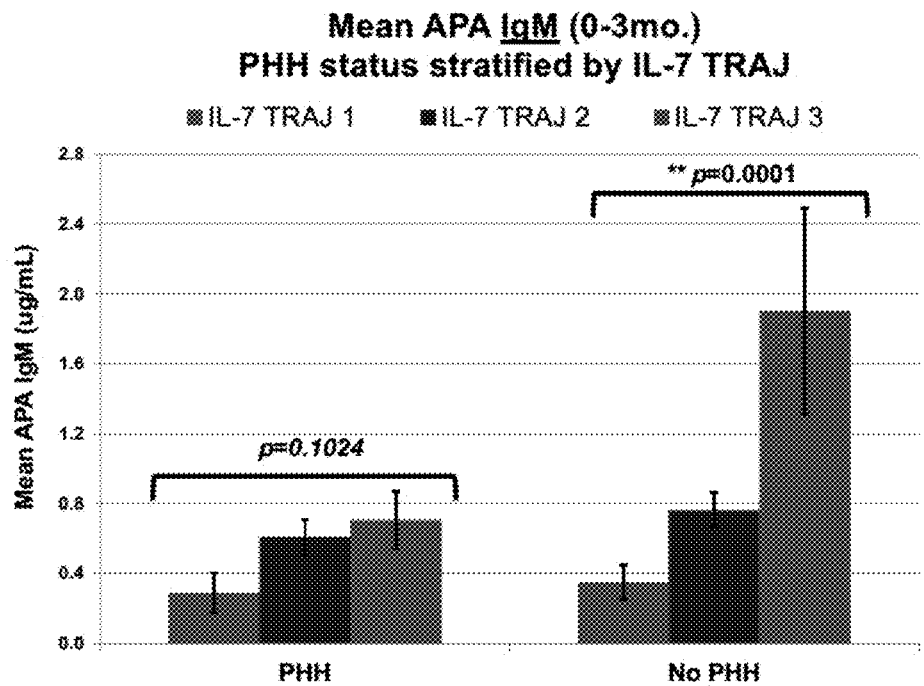
Figure 28:
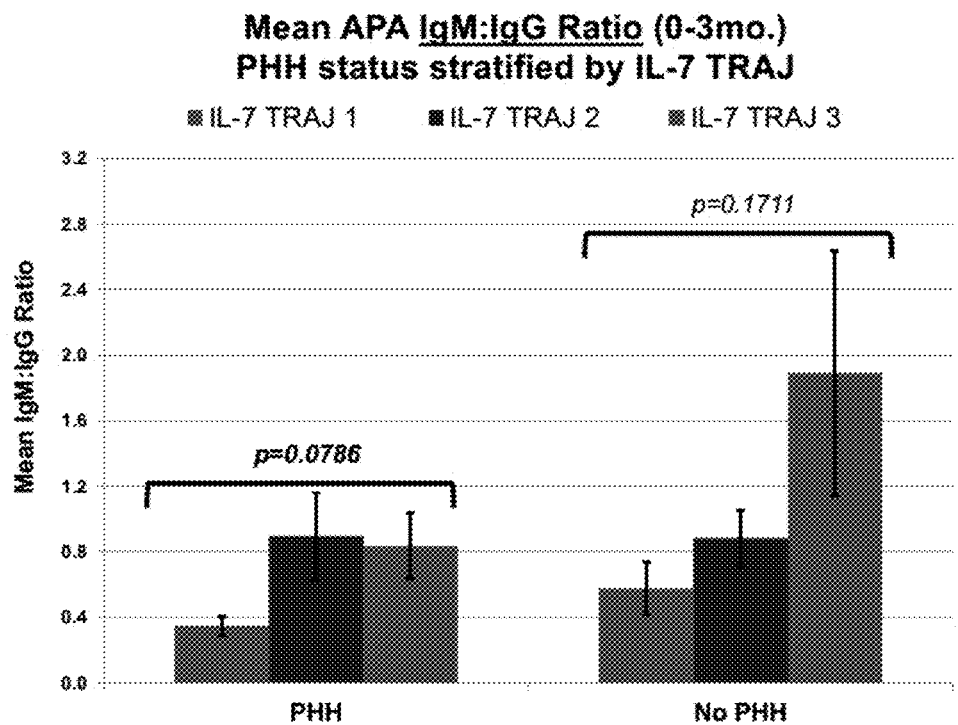

This study investigated the correlation between IL-7 and autoantibodies levels in PHH patients. FIG. 27 showed a trend for APA production with PHH, but large significance with no PHH group, indicating a role for rhIL-7 treatment in augmenting APA IgM for those with PHH. FIG. 28 showed that APA autoantibody ratios (IgM:IgG ratio) mapped to IL-7 production over time, with those in the low and high IL-7 group having lower ratios and PHH, indicating IL-7 may boost autoantibody production. FIG. 29 showed that the effect of IL-7 TRAJ membership on APA IgM:IgG ratios (0-3 mo.) was independent of PHH status, and IL-7 levels were effective in boosting APA autoantibody IgM/IgG ratios, despite having PHH, indicating that rhIL-7 is a good drug candidate—as PHH individuals are as biologically responsive to its effects as those without PHH. FIG. 30 showed that the relationship between 11-7 TRAJ membership and APA IgM TRAJ membership was independent of PHH status. Similar relationships to autoantibody levels noted for IL-7 TRAJ. FIG. 31 showed that the relationship between IL-7 TRAJ membership and APA IgM TRAJ membership was, however, impacted by TCT score (adaptive immunity related biomarker scores, which are derived from biomarkers that reflect the state of the adaptive immune response and are derived from levels of these biomarkers present in blood.). Overall, this study suggested that endogenous IL-7 works to modify adaptive immunity to increase IgM autoantibodies production (and IgM:IgG ratios) for APA, which has a positive impact on PHH status. Also, IL-7 treatment may boost Aab levels and improve outcome.

Example 8: Auto-Antibody (AAb) as Biomarkers for TBI

Figure 67:
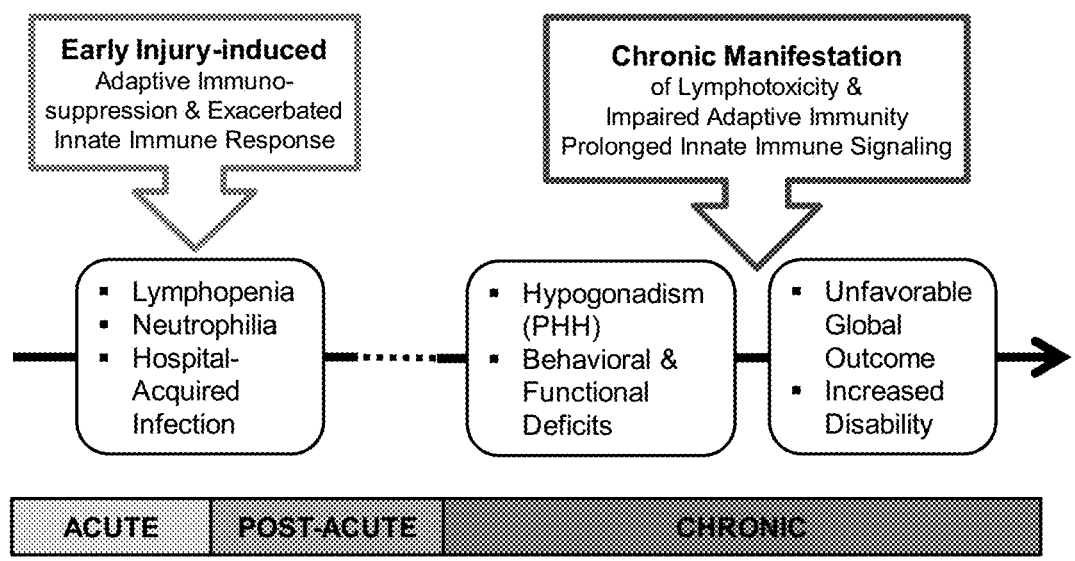
FIG. 67 depicts responses induced at different stages of TBI.

TBI induces different responses at different stages of TBI, which are associated with the recovery and susceptibilities of TBI (FIG. 67). Early injury-induced adaptive immunosuppression and exacerbated innate immune response include lymphopenia, neutrophilia and hospital-acquired infection. Such early injury conditions set the stage for chronic complication onset including a variety of behavioral, functional, physical, deficits and overall poor outcome and increased disability. Particularly, chronic manifestation of lymphotoxicity, impaired adaptive immunity, and prolonged innate immune signaling can lead to hypogonadism, behavioral and functional deficits, and later unfavorable global outcome and increased disability.

The present example examined at immunological targets along the course of recovery that, if altered in the post-acute phase, may mitigate the chronic progression of unfavorable conditions. The present example (1) identified at risk individuals for post-TBI secondary conditions that result from immunosuppression and prolonged over-activation of innate immune pathways; (2) generated clinical data assessments to perform early risk stratification and prevention assessments to guide preclinical study design for post-acute TBI immunomodulation, to identify optimal treatment dosing and effects among a varied TBI population, and to Identify relevant stratification or cut points to inform clinical decision making for management of TBI related secondary conditions and clinical outcome; and (3) assessed role of peripheral immunity in neuro-repair during the post-acute phase of TBI recovery by identifying therapeutic targets that support adaptive immunity while limiting self-perpetuation of innate immunity.

Candidate Biomarkers Examined Included:
Lymphocytes and neutrophils: including ABS concentrations abstracted from EMR, lymphopenia with reduced ABS lymphocytes to a level of less than 1k/uL, neutrophilia with elevated ABS neutrophils to a level of more than 8.0 k/uL, and global phenomenon observed in subjects with moderate to severe TBI, results in increased risk for infection, greater health resource utilization, and worse outcome.

Serum inflammatory marker panel: including about 31 marker Luminex panel purchased from Millipore with a focus on pro- or anti-inflammatory cytokines, chemokines, and soluble receptors.

Anti-pituitary (APA) and anti-hypothalamic (AHA) autoantibodies: measured by custom quantitative ELISA for IgM and IgG measurements (APA and AHA), immunohistochemistry of human serum samples evaluated for AAb specificity to commercially available human pituitary and hypothalamus sections.

Significant differences were found between individuals with TBI versus healthy controls for IgM and IgG AAbs (FIGS. 32A-32D and FIGS. 32U-32Z). These results signified an increase in serum AAb production against brain auto-antigen after TBI.

Figure 32A:
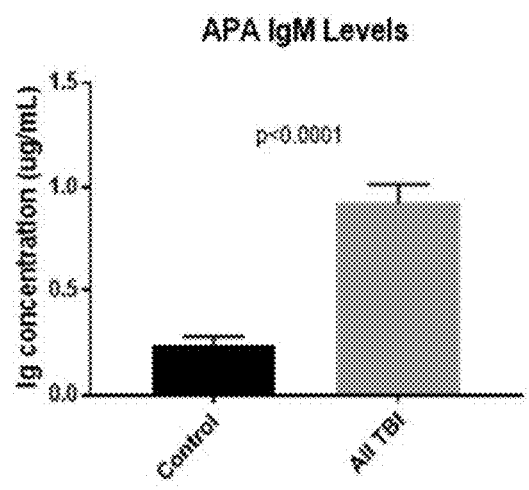
Figure 32B:
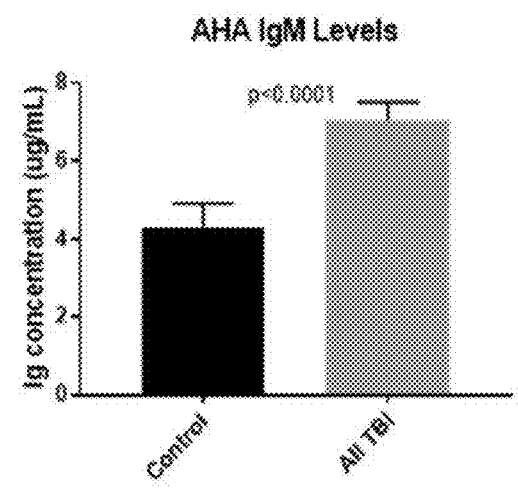
Figure 32C:
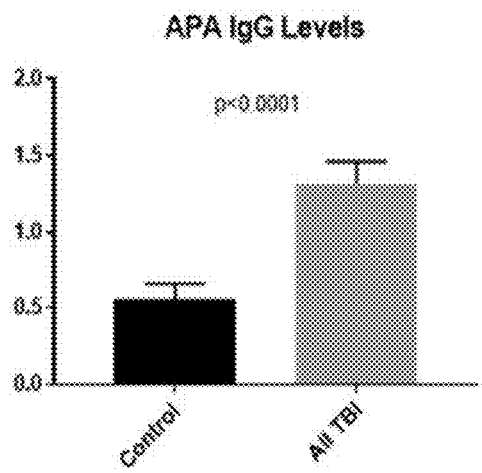
Figure 32D:
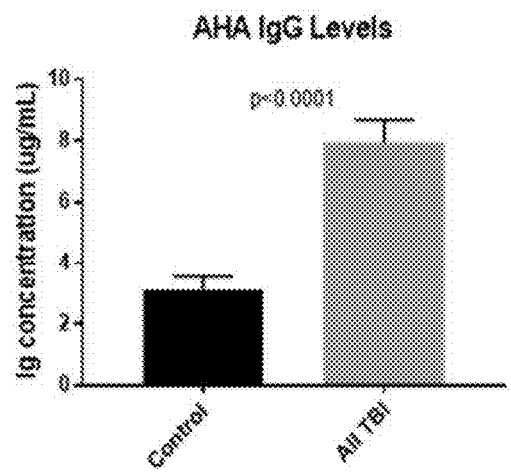
Figures 32E, 32F, 32G, 32H, 32I, 32J, 32K, 32L:
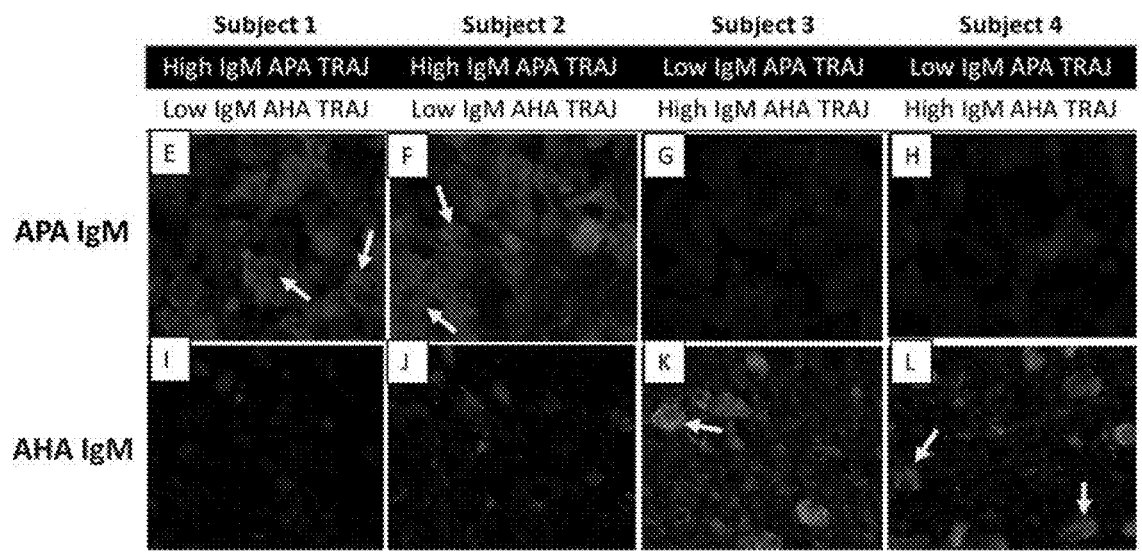
Figures 32M, 32N, 32O, 32P, 32Q, 32R, 32S, 32T:
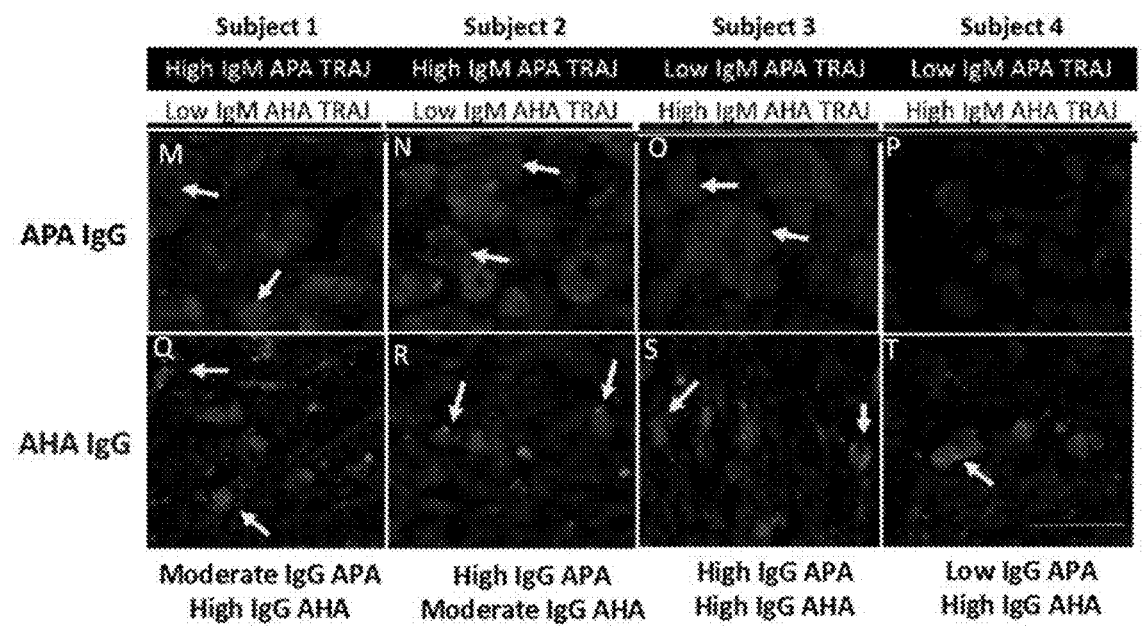
Figure 32U:
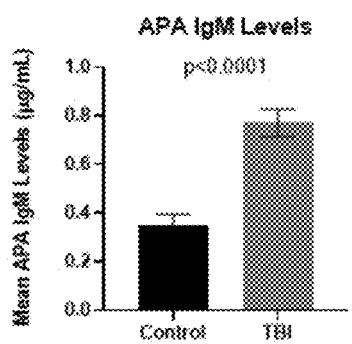
Figure 32V:
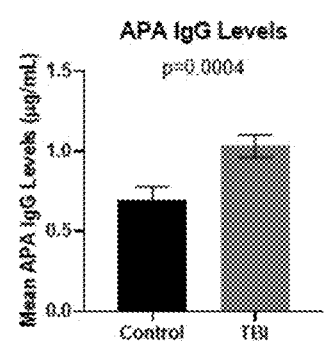
Figure 32W:
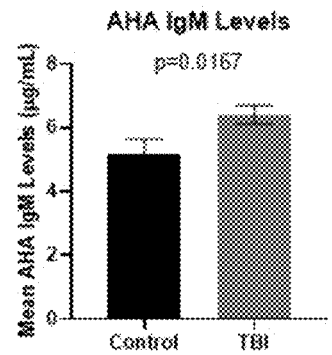
Figure 32X:
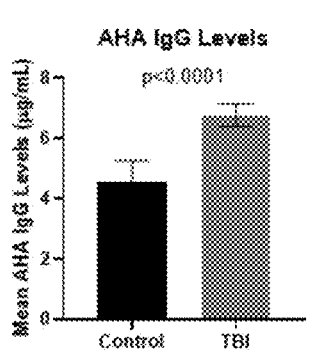
Figure 32Y:
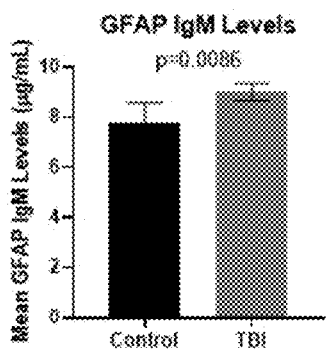
Figure 32Z:
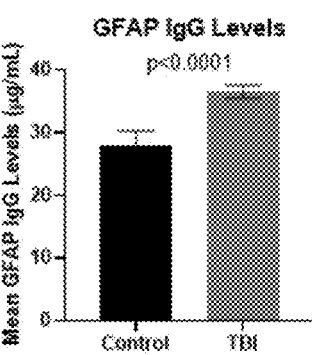

AAb trajectories were examined for 6 months post-TBI (FIGS. 17E-17H). As APA and AHA Autoantibodies are tissue specific and not epitope specific, their values may also map to risk for other neuroendocrine disorders after TBI. Group-based trajectory analysis was performed, which was an algorithmic, data-driven approach to identify unique clusters of individuals with similar biomarker profiles over time. Representative anti-pituitary autoantibody (APA) and anti-hypothalamus autoantibody (AHA) IgM and IgG fluorescence immunohistochemistry staining with selected TBI subacute/chronic serum samples was shown in FIGS. 32E-32T. AAb was roughly stable over time, particularly for IgM AAb. Low TRAJ group was similar to the control group. Significant differences existed in levels by TRAJ groups over time, except the AHA IgG TRAJ group.

Example 9: Group-Based Trajectory (TRAJ) Analysis for IL-7 and sTNFRI

One strength of TRAJ analysis is the early identification of individual's biomarker trajectories over time. The low and high trajectories exhibited distinct spread over time, that is, early identification and distinction is feasible in terms of these biomarkers to project levels at later months based on this accumulated clinical inflammatory data that suggests individuals take a low or high course of biomarker expression course. Great technique for exploring relevant cut points and groupings in the data that may not follow typical comparisons along data distribution metrics like mean/median, etc.

Figure 33A:
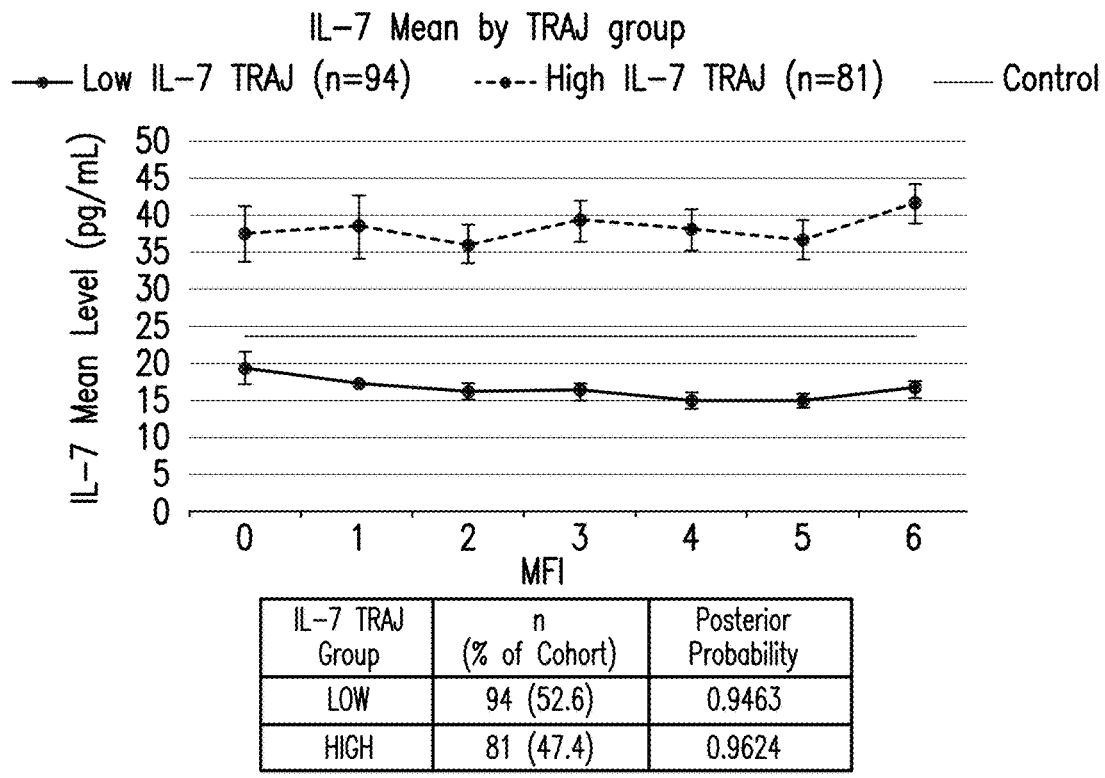
Figure 33B:
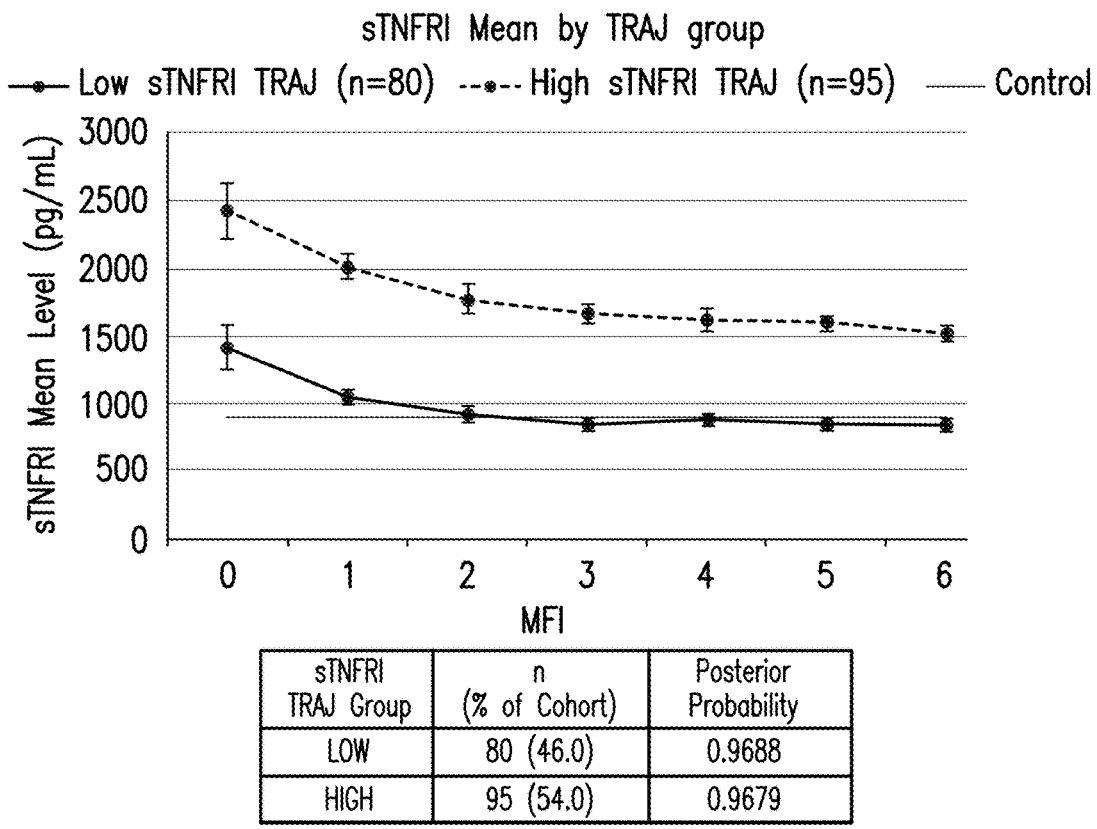
Figure 69:
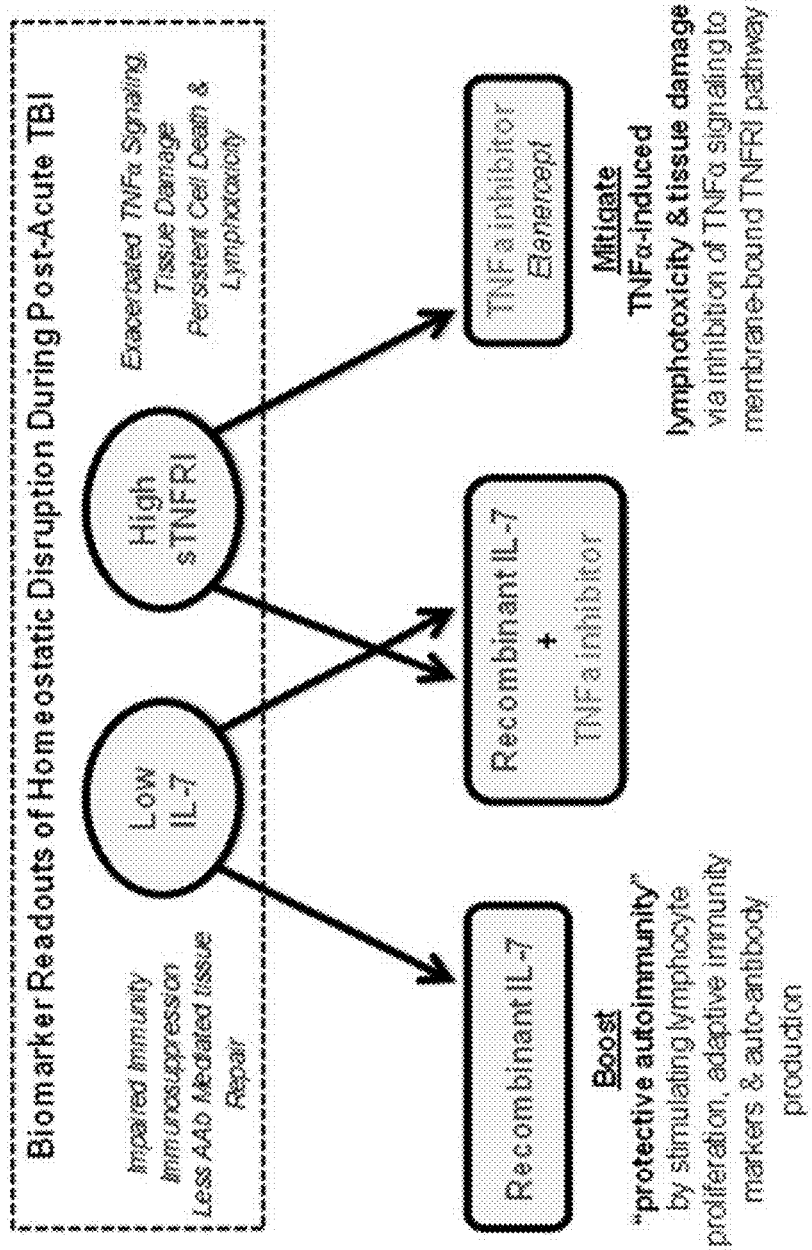
FIG. 69 depicts boosting adaptive immunity may have unintended consequences in terms of boosting other areas of immunity that may perpetuate damage. Constraining unintended inflammatory changes with boosting adaptive immunity may require dual therapy.

Group-based Trajectory (TRAJ) Analysis for IL-7 and sTNFRI delineated subpopulations of individuals with IL-7 and sTNFRI levels that "track together" (exhibit similar levels and fluctuations) over the first 6 months following TBI (FIGS. 33A-33B). Each individual was assigned a membership for both IL-7 and sTNFRI TRAJs, which were later as two points of stratification for treatment considerations. The result showed outstanding classification rate with posterior probabilities. This experiment led to relevant treatment options: as providing Etanercept to support adaptive immunity through its shutdown of reverse TNFα signaling and to reduce innate signaling by neutralizing soluble TNF and/or supplying rIL-7 to support adaptive immunity through AAb production and inflammatory marker stimulation (FIG. 69).

Figure 68:
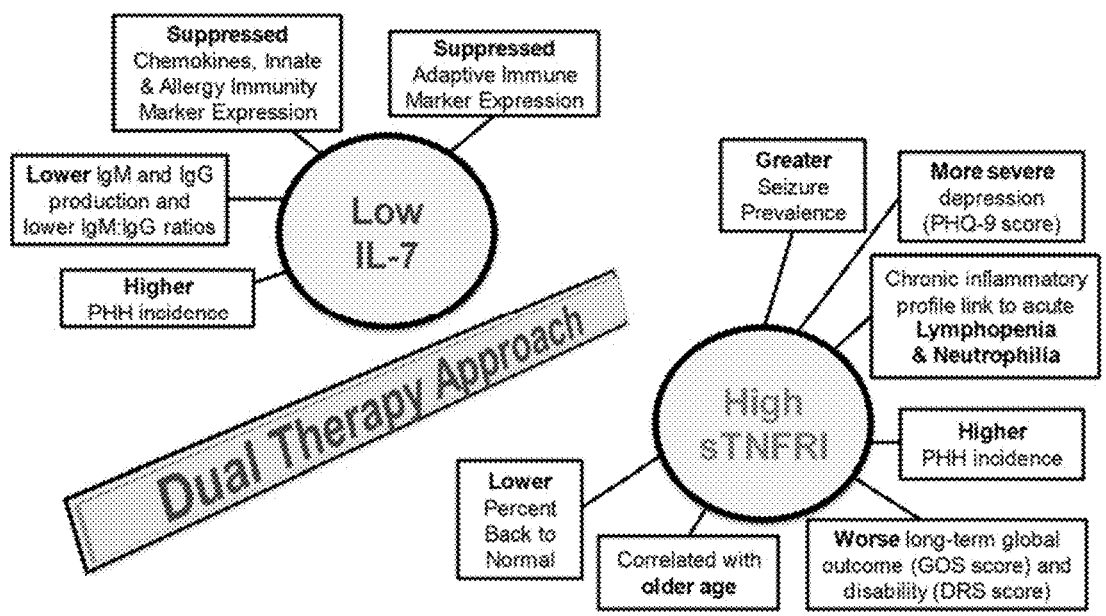
FIG. 68 depicts the benefits of benefits of leveraging a dual approach in that these biomarkers contribute unique prognostic value and immunotherapeutic potential.

IL-7 and sTNFRI can be used as points of stratification because of the biological and clinical implications of non-homeostatic levels in post-TBI response and recovery. The benefits of leveraging a dual approach is that these biomarkers contribute unique prognostic value and immunotherapeutic potential. Age is correlated with sTNFRI, but not IL-7 (FIG. 68). Low IL-7 associates with high PHH incidence, lower IgM and IgG production and lower IgM:IgG ratios, suppressed chemokines, innate and allergy immunity marker expression, and suppressed adaptive immune marker expression. High sTNFRI associates with greater seizure prevalence, more severe depression (PHQ-9 score), chronic inflammatory profile that link to acute lymphopenia and neutrophilia, higher PHH incidence, worse long-term global outcome (GOS score) and disability (DRS score), lower percent back to normal and is correlated with older age. Those correlations indicate a dual therapy approach.

As such, boosting adaptive immunity may have unintended consequences in terms of boosting other areas of immunity that may perpetuate damage. Constraining unintended inflammatory changes with boosting adaptive immunity may require dual therapy. Low IL-7 associates with impaired immunity, immunosuppression and less AAb-mediated tissue repair. High sTNFRI associates with exacerbated TNFα signaling, tissue damage, and persistent cell death and lymphotoxicity, and lymphopenia (FIG. 69).

Recombinant IL-7 is administered to patients with low IL-7 to boost "protective autoimmunity" by stimulating lymphocyte proliferation, adaptive immunity markers and IgM auto-antibody production. TNFα inhibitor, e.g., Etanercept, is administered to patients with high sTNFRI to mitigate TNFα-induced lymphotoxicity and tissue damage via inhibition of TNFα signaling to membrane-bound TNFRI pathway. Recombinant IL-7 and TNFα can be administered to patients with both low IL-7 and high sTNFRI.

The event rates (% of TRAJ) of acute and chronic phenomena/outcomes by IL-7 TRAJ and by sTNFRI TRAJ separately were compared (FIG. 34) This step assessed the capacity to differentiate outcomes through stratifying patient subgroups by one biomarker exclusively. Stratifying by IL-7 levels alone did not elucidate patient subgroups with increased rates of unfavorable outcomes. High IL-7 was associated with reduced hypogonadism and trend for reduced lymphopenia. But stratifying by sTNFR-I levels was considerably stronger as a single biomarker at differentiating outcomes (low sTNFR-I closer to yellow in general, high sTNFR-I more orange and/or red). Time to first infection was not significant both for IL-7(6.02 vs. 5.7) and sTNFRI (5.38 vs. 6.18) groups. As such, sTNFRI had greater capacity than IL-7 alone for chronic outcome differentiation, and chronic sTNFRI profiles can be leveraged as (1) indicator of perpetuating cell death cascades and (2) chronic outcome prognosticator.

Figures 35A, 35B:
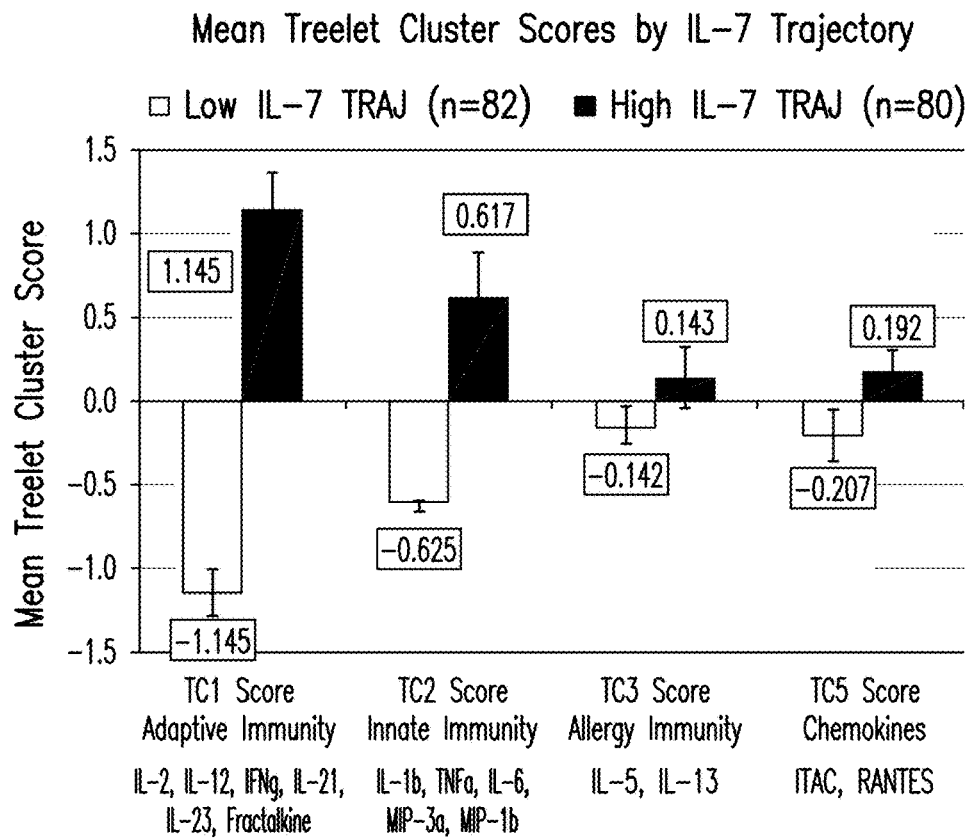

Treelet transformation analysis showed inflammatory and auto-antibody associated with IL-7 (FIGS. 35A-35B). Stratifying individuals by IL-7 TRAJ alone revealed consistent relationships between IL-7 levels and multiple domains of immunity post-injury. Increased inflammatory and auto-antibody productions corresponded with greater IL-7 expression. Treelet Transformation is a form of PCA and cluster analysis where data driven algorithm identifies inter-related clusters of markers carrying the most variance within the cohort. In this analysis, the Treelet derived dendrogram identified unique groups of markers representing elements of immunity. Within each cluster inflammatory load scores were generated for each individual, and these "TC" (treelet cluster) scores were graphed by IL-7 Trajectory Group.

Inflammatory marker levels across multiple arms of immunity, including adaptive, innate, allergy, and chemokine signaling, were all increased in the IL-7 TRAJ group. Thus, chronic IL-7 profiles can be leveraged as an indicator of inflammatory capacity and proxy for state of immune microenvironment. TC4 (soluble receptor cluster) scores did not differ by significantly by IL-7 trajectory. This was considered in the following experiment designs to explore IL-7 expression in the context of microenvironments with different soluble receptors dynamics. Autoimmunity (particularly IgM production) can be boosted by elevated endogenous IL-7 levels. As a form of adaptive immunity, "protective autoimmunity" is mediated through IgM production to self-antigen, by supporting post-injury clean up and repair.

Data shows several utilities of recombinant IL-7 (rIL-7). Endogenous IL-7 elevates innate, adaptive, allergy, and chemotactic immune responsiveness, post-TBI and increases AAb production across all domains. rIL-7 treatment boosts brain-specific IgM AAbs and "protective autoimmunity" enhancing CNS repair, clearance of compromised tissue, and long-term outcome. One explanation is that brain-blood barrier (BBB) damage created a systemic environment for post-injury lymphocyte proliferation where new lymphocytes are sensitized to brain auto-antigen.

TNFα Inhibitor (Etanercept) is a decoy receptor that takes the form of sTNFR-II+Fc domain. It can also prolong the bloodstream half-life, longer-lasting effects than endogenous sTNFRII by using Fc fragment. Etanercept treatment also inhibits binding of soluble TNFα to membrane-bound TNFR-I in order to mitigate TNFα-induced lymphotoxicity and cell death mechanisms characteristic of this pathway. Etanercept's functions include binding and neutralizing soluble TNFα, binding transmembrane TNFα and binding lymphotoxin (TNFα). It is proposed that elevated soluble TNFR-I is a lead indicator of cell-death (by soluble TNFα signaling to membrane-bound TNFRI) because it is released into circulation via proteolytic cleavage from any expressing cell type as a byproduct of this pathway.

TNFR-I as a cognate receptor is expressed on pro-apoptotic, expressed on all cells while TNFR-II also as a cognate receptor is expressed on anti-apoptotic, expressed primarily on immune cells. Pro- and anti-apoptotic roles of TNFα exemplify the need for an orchestrated response in degree and timing of the immune response. Soluble TNFα shows greater affinity for TNFR-I, but Etanercept treatment increases binding competition to neutralize apoptosis of activated T-cells.

Unlike some other anti-TNFα agents, Etanercept inhibits reverse TNFα signaling of lymphocytes to keep these cells activated and functional. Reverse signaling (outside-to-inside) is a regulatory mechanism that drives activated lymphocyte apoptosis and up-regulates anti-inflammatory processes, providing (at least in part) a homeostatic role of soluble TNF receptors outside of the context of TBI..

Figure 36:
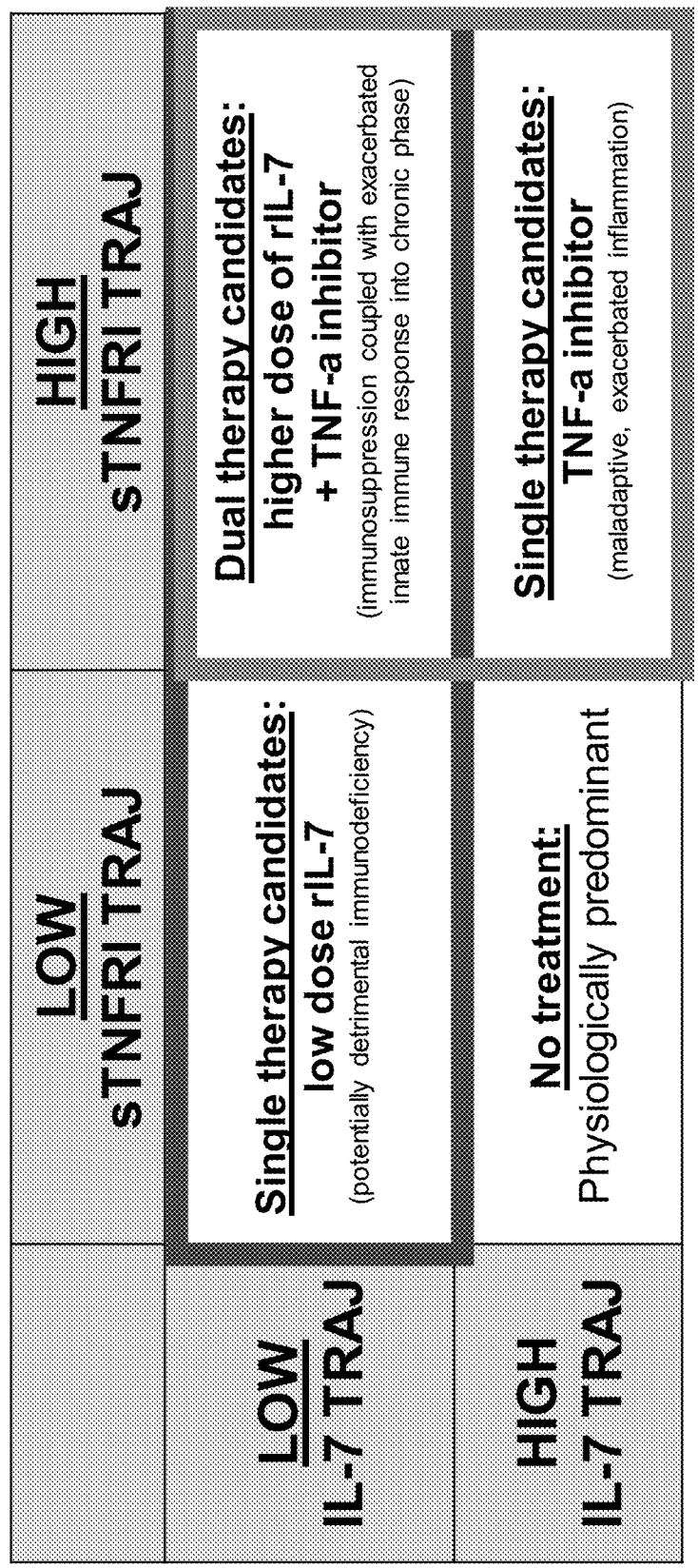

Responsiveness to rhIL-7 therapy and TNFα inhibitor therapy can be effectively assessed by using IL-7 and sTNFRI TRAJ group membership. Identifying some that would respond to either rhIL-7 or TNFα inhibitor (Etanercept, sTNFRII form) alone, while others might require both therapies. It is also proposed that TNFα inhibitor therapy may reduce the upregulation of innate/chemokine, etc. and components of immunity that may be detrimentally raised via rhIL-7 therapy. Individuals were stratified based on IL-7 and sTNFRI TRAJ memberships (low/high) (FIG. 36).

Figure 65:
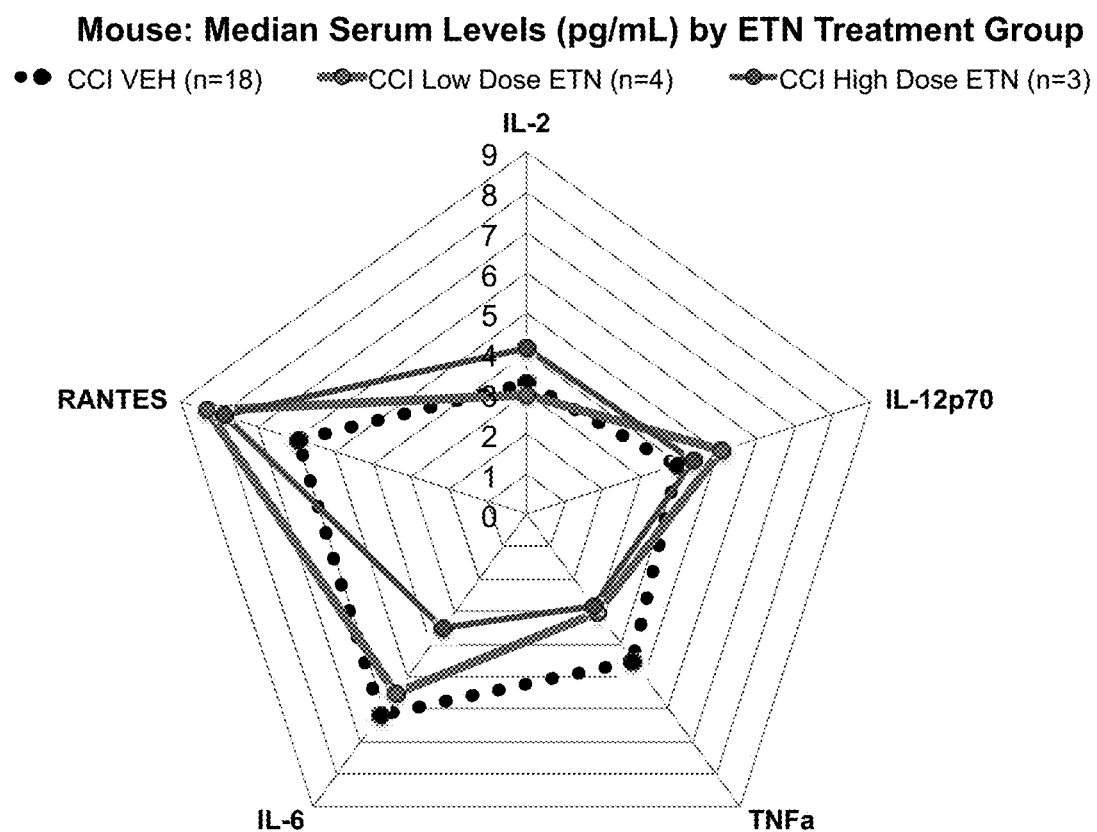

Acute and chronic phenomena event rates (% of stratified group) were analyzed (FIG. 37). Low IL-7 and Low sTNFRI profile group had close to ideal inflammatory profile group in event rates. But still some acute/post-acute phenomena (in particular that could be mitigated with lose dose rIL-7 treatment) may in turn reduce chronic symptoms. High sTNFRI profile groups (column 2 and 3) still drive higher rates of poor acute/chronic undesirable outcomes, suggesting the need to dual approach. Cognitive impairment and headaches were prevalent across the board. As shown in FIG. 65, acute immune cell counts and IL-6 superfamily biology were considered to explain potential related pathophysiology underlying those conditions.

Summary metrics of post-acute treatment candidates revealed interesting resulted in that candidate treatment groups may take on clinical injury phenotypes observed in certain demographic groups (FIG. 38). For example, dual therapy group included older individuals that likely suffer less severe trauma. TNFα inhibitor only treatment group included slightly younger mean age, more severe neurological injury+polytrauma. Statistical comparison of these variables by stratified TRAJ groups (FIG. 39) revealed more detailed data on different parameters, such as age, gender, race, GCS score as best in 24 hours, non-head ISS and time to infection.

Figure 40A:
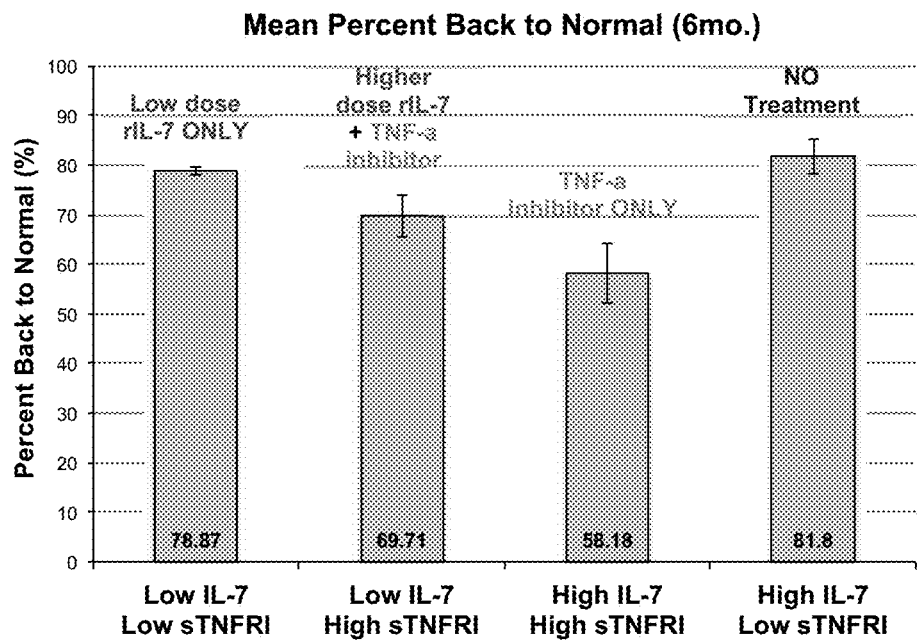
Figure 40B:
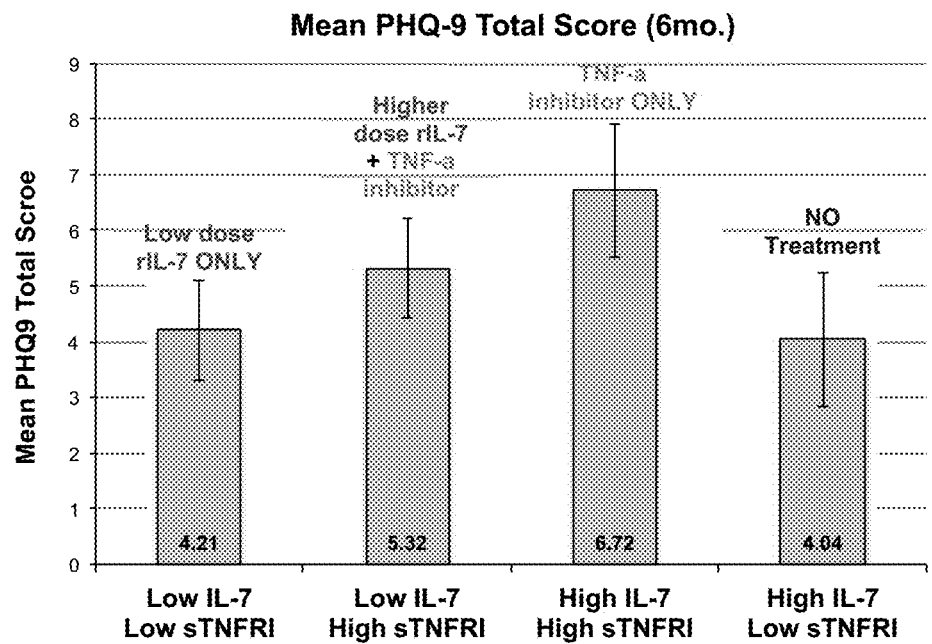

Inflammatory profiles were also associated with psychological assessments and return to life before TBI (FIGS. 40A-40B). Self-perception of "percent back to normal" was greatest in the identified no-treatment group (corresponding with high IL-7 and low sTNFR-I profiles) and low rIL-7 treatment group (corresponding with low IL-7 and low sTNFR-I profiles). As sTNFR-I levels rise, the decline in self-perception of percent back to normal and depression severity are increased. Patient Health Questionnaire-9 (PHQ-9) total score was measured by self-reported assessment of depression severity across various domains. Total depression severity was lowest amongst no-treatment and low rIL-7 treatment groups. The gradual decrease in % back to normal and increase in PHQ-9 Total scores support the differential dosing strategies and single/dual treatment options.

Example 10: NLR as a Proxy Screening Variable for sTNFRI

Figure 41:
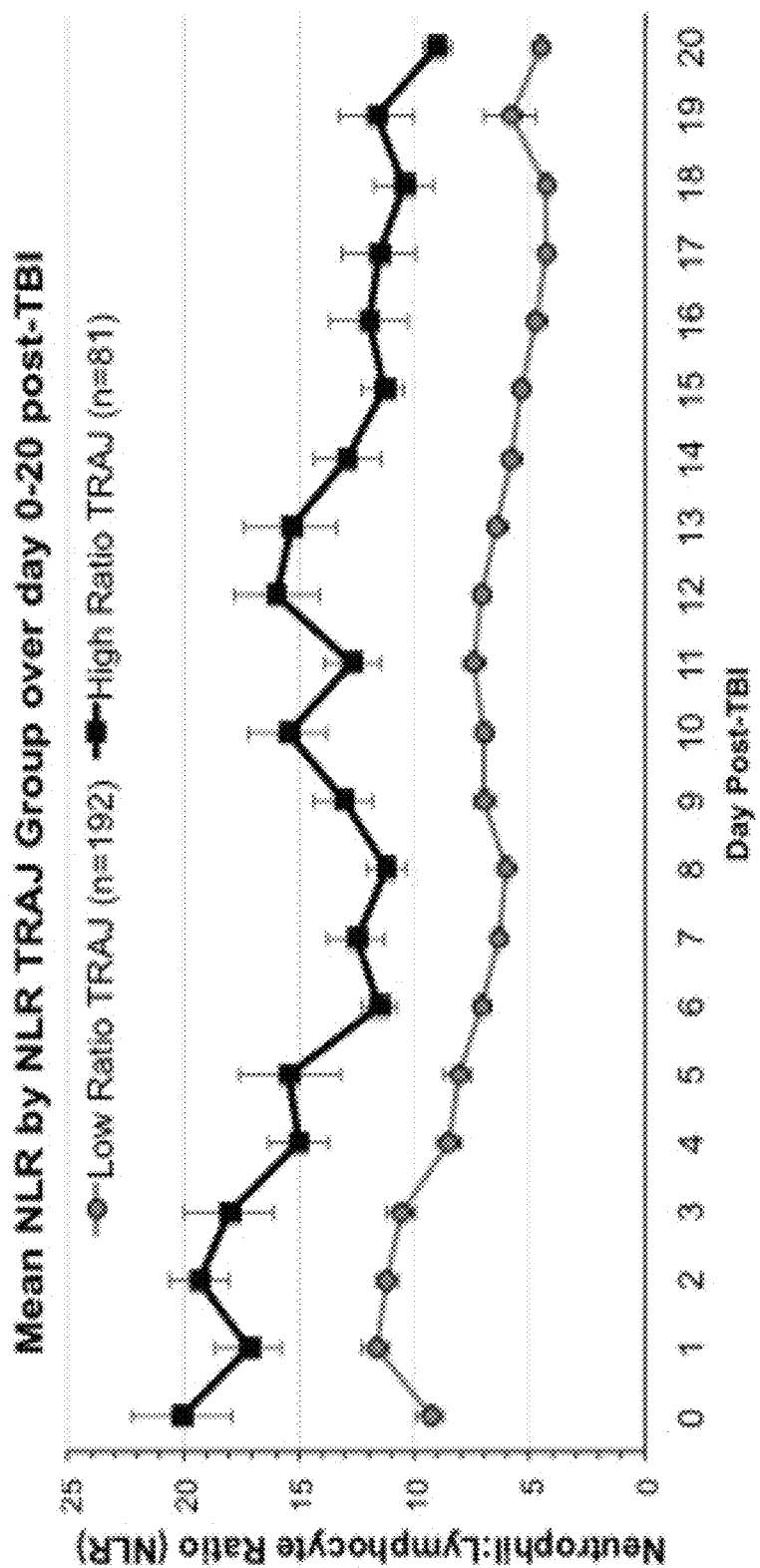

Neutrophil-Lymphocyte Ratio (NLR) trajectories can be used as a proxy for sTNFR levels. High NLR during acute care (3wks) is implicated in exacerbating sTNFRs expression chronically (FIG. 41) Trajectory analysis performed on neutrophil to lymphocyte ratios during the first 3 weeks provided an interesting distinction between patient populations. The higher TRAJ persisted above a ratio of 10 consistently over the first 20 days post-TBI suggesting potential persistent cases of lymphopenia and neutrophilia. This range was grounded in clinical criteria of these conditions.

Figure 42:
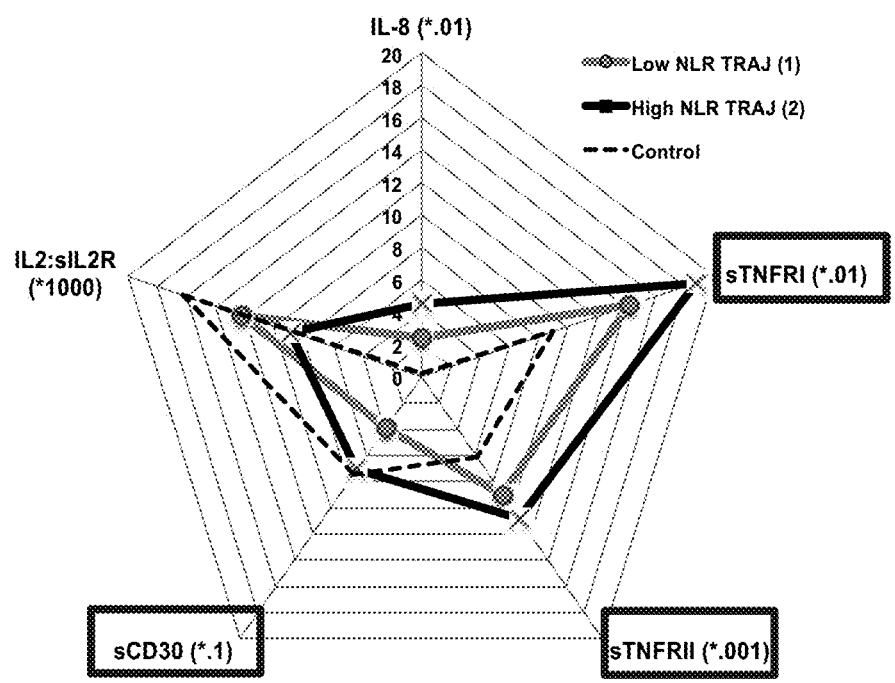

High NLR during acute care (3wks) was implicated in exacerbated sTNFRs expression chronically (FIG. 42). Based on this data, novel acute-care criteria for poor outcome prediction following TBI may be feasible by examining the direct function of sTNFRI effects on both neutrophils and lymphocytes with the onset of innate immune response to TBI and subsequent infection. Simultaneous capture of immune states can be obtained by evaluating lymphopenia (ABS Lymphocyte <1K/uL), neutrophilia (ABS Neutrophils >8K/uL), and low TRAJ with less concurrent lymphopenia vs. neutrophilia.

Figure 43:
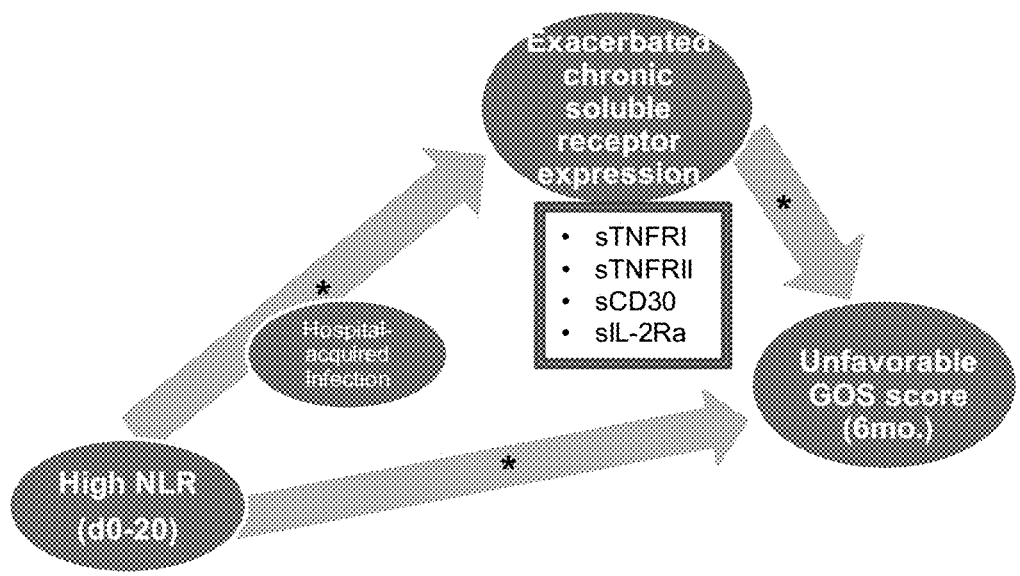

NLR as a proxy screening variable for sTNFRI serves as a basic conceptual model (FIG. 43). High NLR (tracked over the first 3 weeks post-injury) is both a product of and potentiator for exacerbated soluble receptor chronically and negatively impacts recovery. This relationship may partially be mediated by increased infection risk with high NLR profiles.

Acute and chronic phenomena event rates (% of TRAJ) were calculated for low and high NLR groups respectively (FIG. 44). Thus, the present disclosure shows that acute NLRs can be leveraged as outcome prognosticator during acute-care (3 week time period) and early indicator of maladaptive immune states (lymphopenia and neutrophilia) associated with undesirable chronic sequelae.

The peripheral immune cell trajectories of the clinical population were projected on to their endogenous chronic (m0-6) sTNFR-I profiles (FIG. 45). This identified acute states of immunity that have particularly strong concordance to the pathophysiological, exacerbated sTNFR-I state which has been identified as high neutrophil TRAJ (67.09%), low lymphocyte TRAJ (72.22%), and high Neutrophil:Lymphocyte Ratio TRAJ (75.66%). The best capture of this high sTNFR-I state is high NLR, suggesting NLR as a novel pre-screening metric to guide early post-acute administration of Etanercept (TNFα inhibitor).

Example 11: Chronic Inflammation Treelet Analysis

Figure 46A:
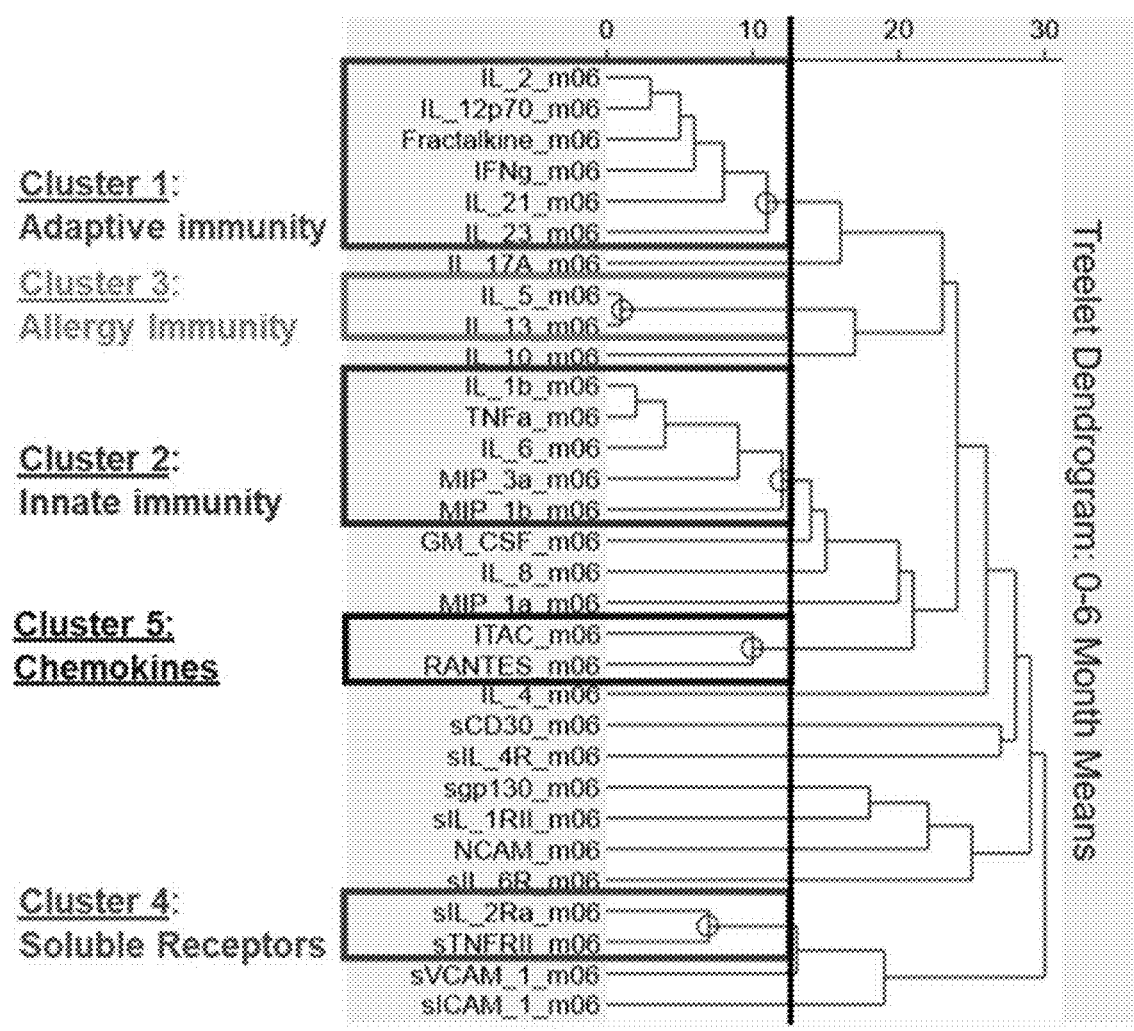
Figure 46B:
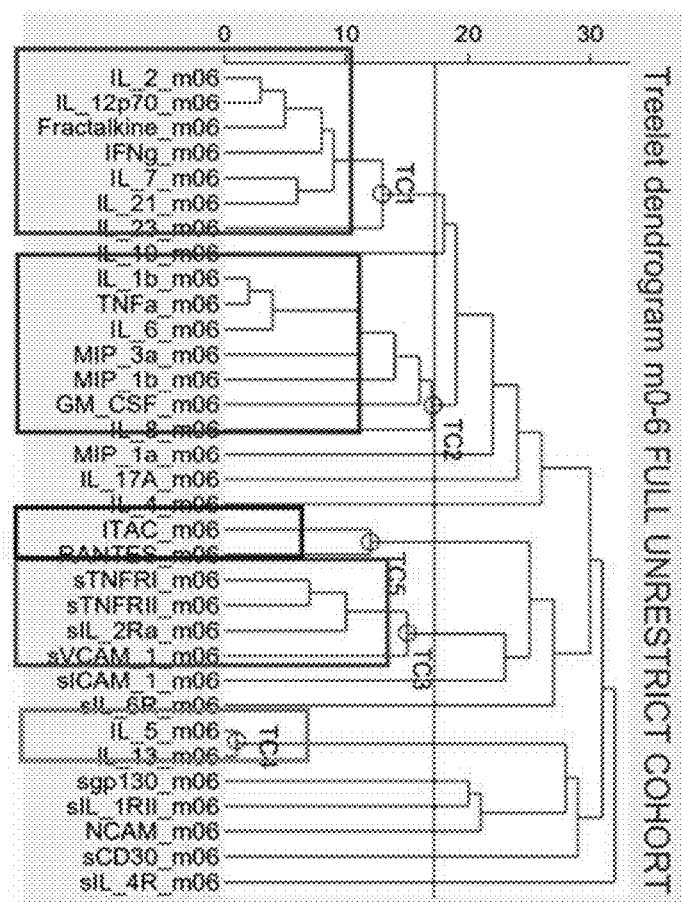

Over the first 6 months following TBI, serum inflammatory marker production clustered into unique expression patterns that map to five main areas of immunity (FIGS. 46A-46B). The specific cohort (n=159) this analysis pertained to have the following data availability: IL-7 and sTNFRI TRAJ memberships; 0-6 months means available for all 31 inflammatory markers in serum. The metrics had 5 clusters optimal with cut-point of 12. This treelet did not include IL-7 or TNFR1 as to eliminate weight contribution to associated treelet cluster scores. When analysis ran with IL-7 and sTNFRI, they fell into the adaptive immunity cluster and soluble receptor cluster, respectively. Individual TC score representing components of immunity and their breakdown by "treatment group" were described. The immunity elements outlined here were used and compared their relative associations with each of the proposed treatment groups in the following slides to better understand the mechanistic underpinnings of the different "inflammatory phenotypes" (derived from IL-7 and sTNFRI group membership) that had been identified earlier (FIG. 35) in the cohort.

Figure 47:
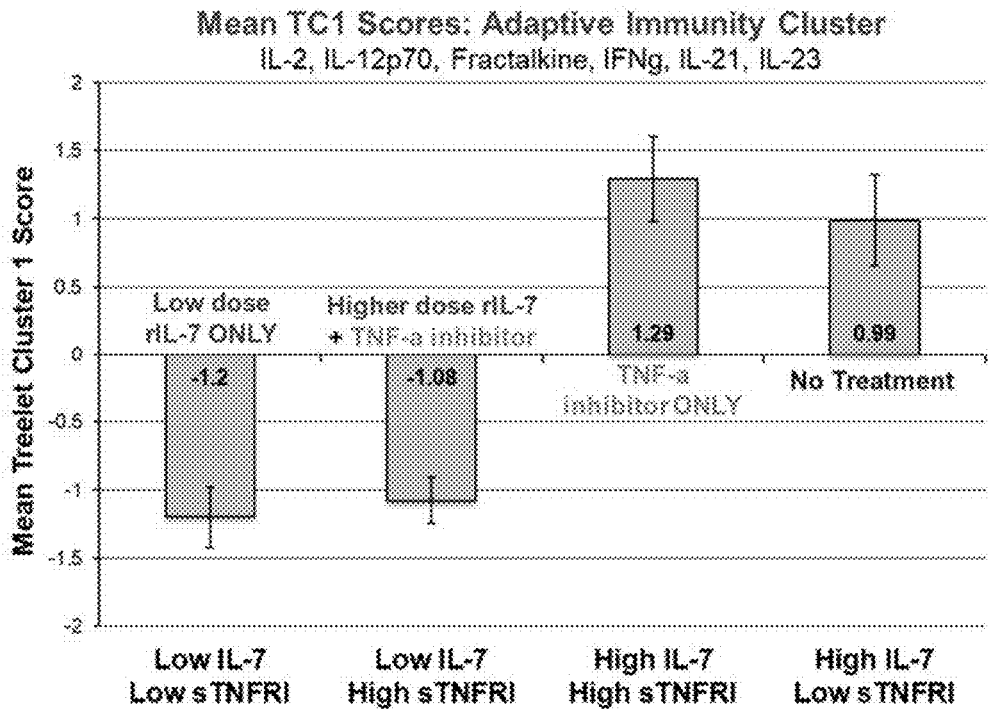
Figure 48:
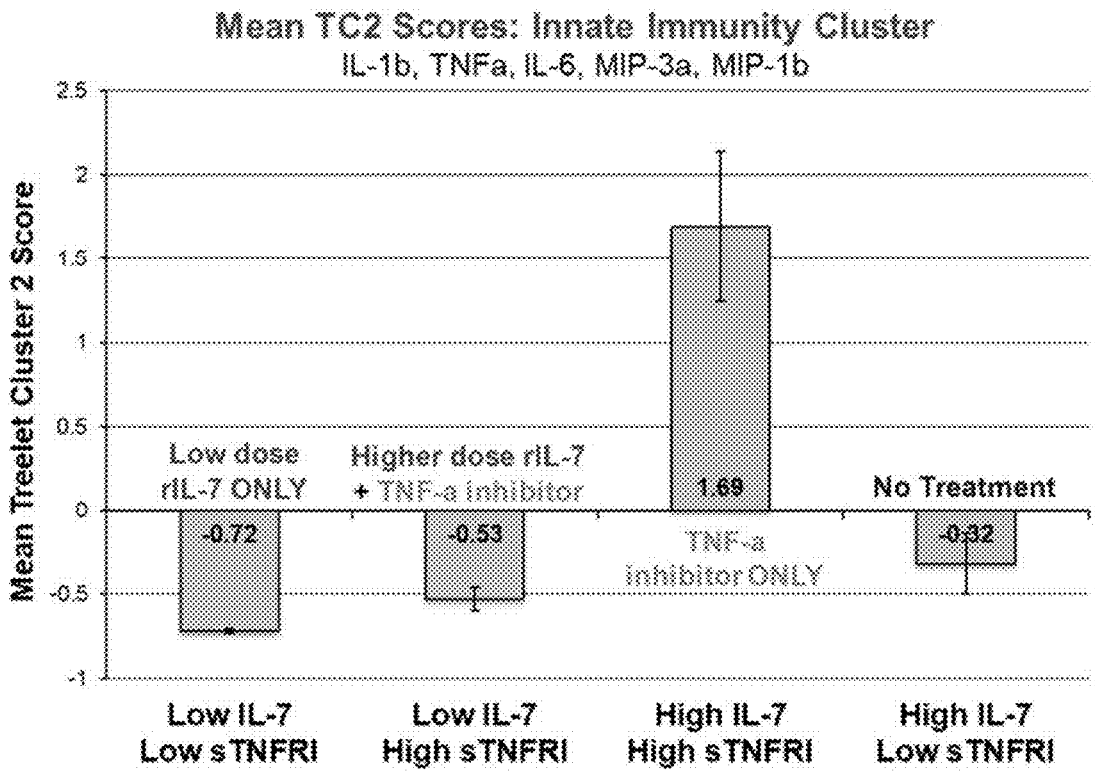
Figure 49:
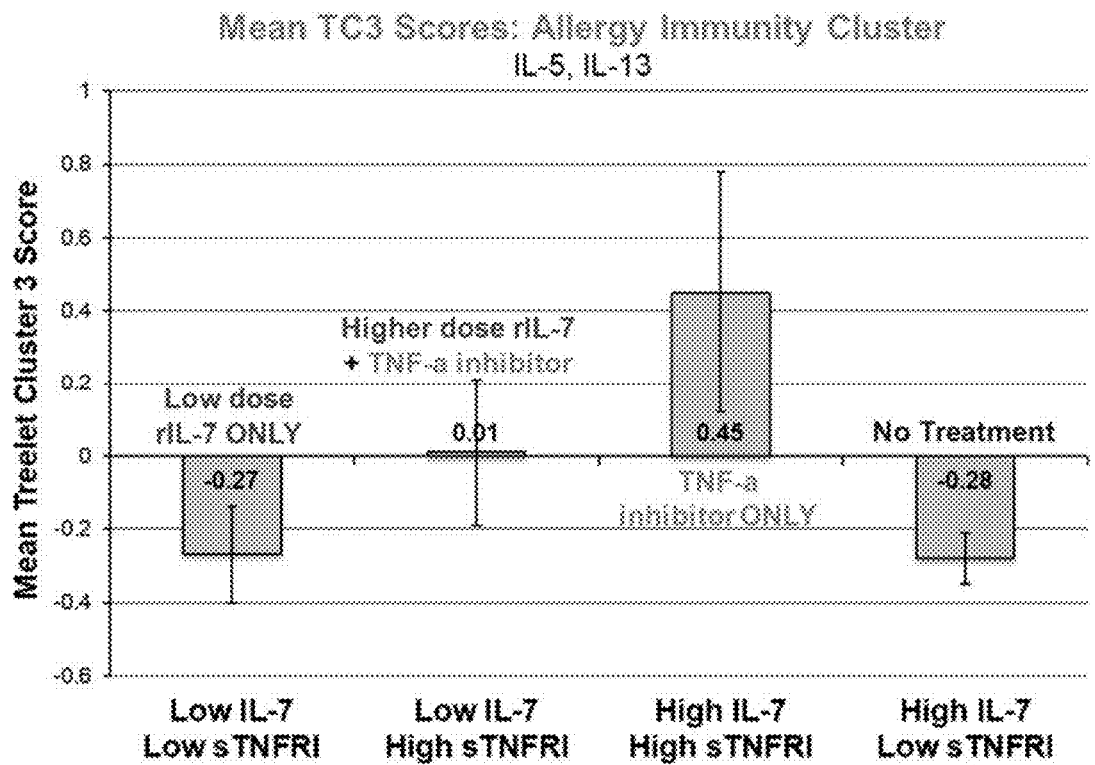
Figure 50:
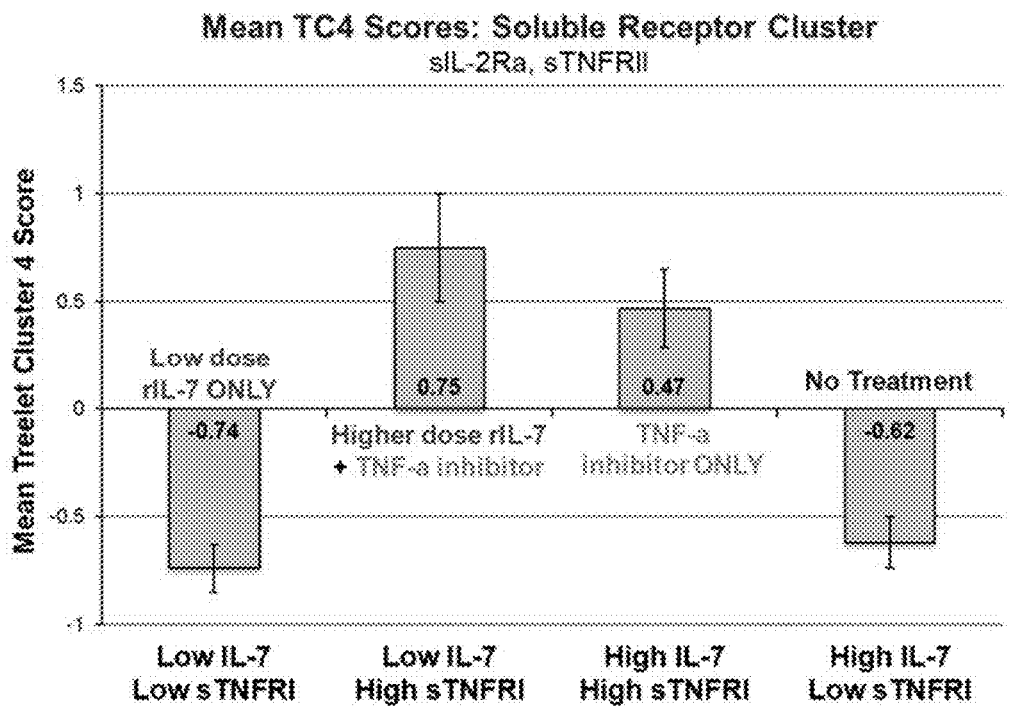
Figure 51:
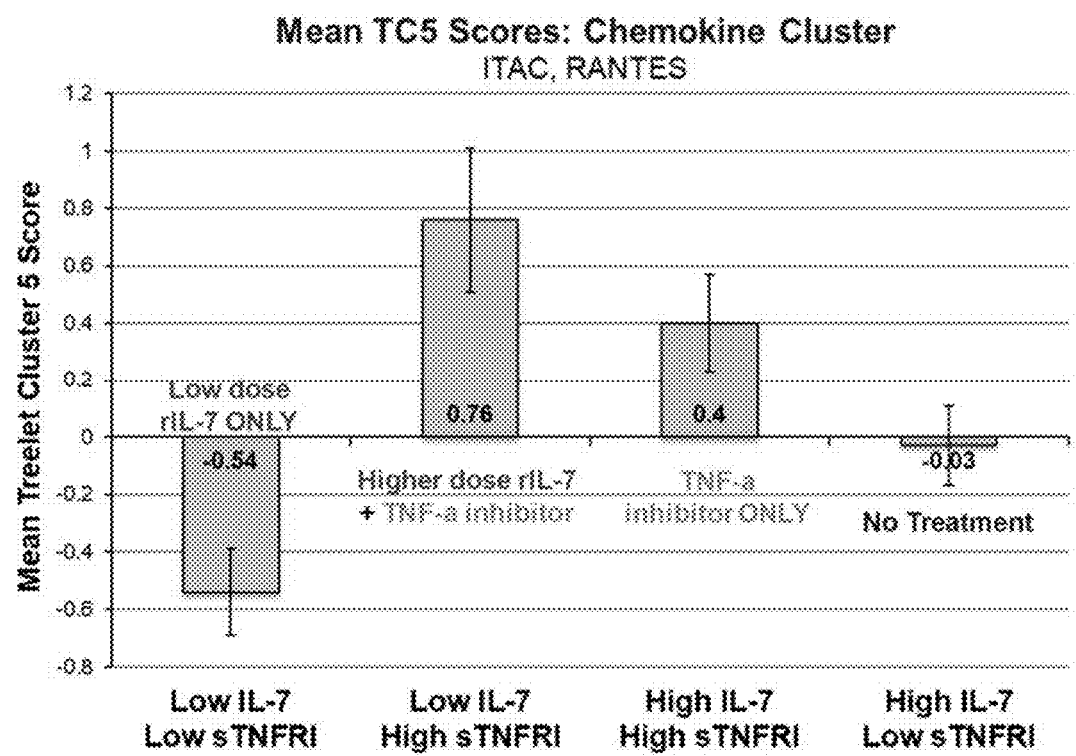

Treelet cluster scores were presented as average weighted scores of the markers denoted for each cluster (FIG. 47). A negative score indicates that on average, individuals have below average levels of the markers in the respective cluster, and positive scores represent above average levels. A score of zero signifies expression levels characteristic of the whole populations' average levels. IL-7 trajectory group membership was strongly associated with adaptive immunity marker expression. IL-7 was strongly associated with amplified innate immunity marker expression in the context of higher sTNFRI (FIG. 48). There was synergistic effect of both high/high on innate immunity. Allergy marker expressions were more variable in the context of sTNFRI. Increases in IL-7 effects on allergy marker expression was amplified in the context of higher sTNFRI expression and indicated in the high/high profile (FIG. 49). This TNF driven phenomenon implicates soluble receptor biology as additional layer of consideration of cytokine dynamics (FIG. 50). Chemokine cluster scores were tracked to both IL-7 and TNFα receptor (FIG. 51). TNF soluble receptor signaling increased chemokines more when IL-7 is low. IL-7 support mitigated this to some degree. This mitigation may be relevant to later cytokine regression models, including interactions between IL-7 and sTNFR1 in predicting PHH.

Example 12: Chronic Auto-antibody Production

Figures 52A, 52B:
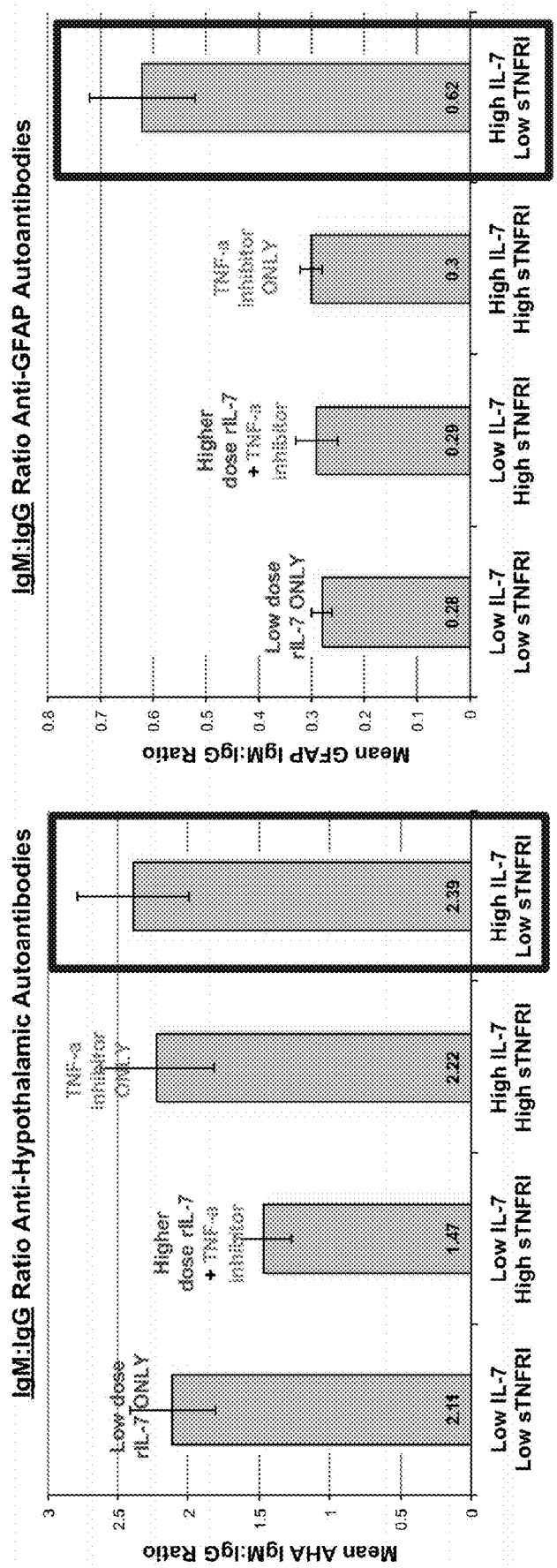
Figure 53A:
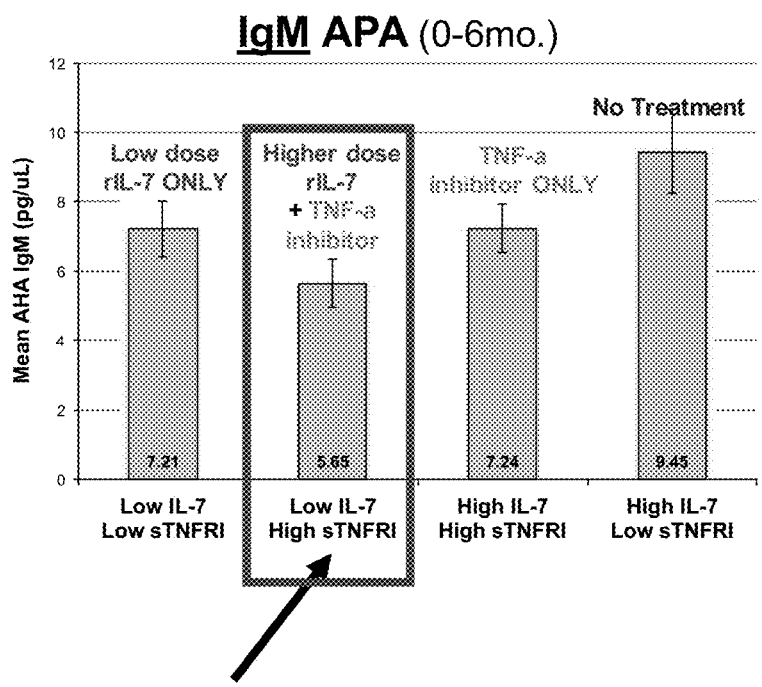
Figure 53B:
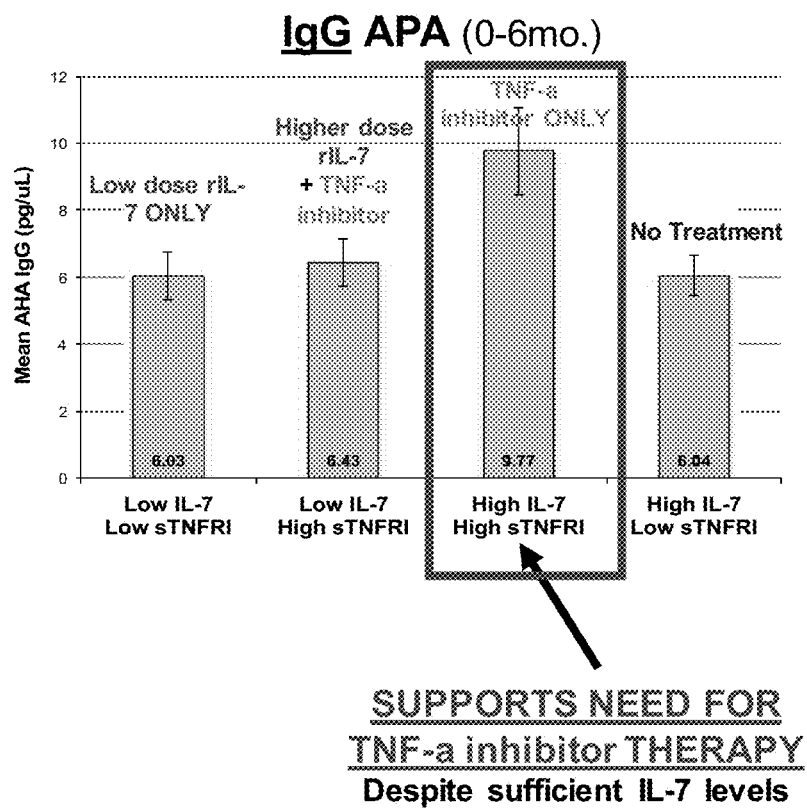
Figure 53C:
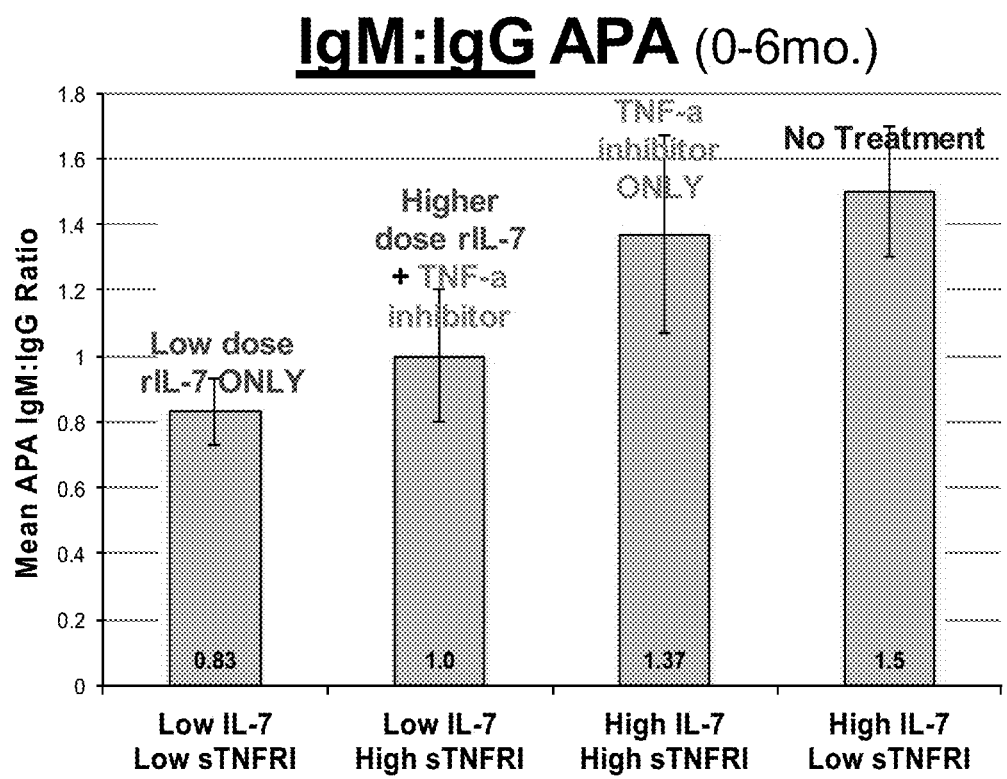

IgM:IgG ratios (0-6 months) by stratified patient grid emphasized that a dual, multifaceted approach may be necessary to mitigate maladaptive auto-antibody production and class-switching processes post-TBI. IgG/IgM class-switching was a function of IL-7 associated IgM production and sTNFRI associated lymphocyte depletion. No treatment group with high IL-7 and low sTNFRI profiles expressed the highest 0-6-month IgM:IgG ratios for AHA (FIG. 52A), APA (FIGS. 53A-53C), and GFAP (FIG. 52B), in the entire TBI cohort. The dual therapy group with low IL-7, high sTNFRI profiles expressed the lowest 0-6-month IgM and IgM:IgG ratios in the entire TBI cohort (FIG. 53A) The result suggests that TNFα and TNFR1 are implicated in immunoglobulin isotype class-switching (IgM >IgG) mechanisms and supports the need for TNFα inhibitor therapy despite sufficient IL-7 levels (FIG. 53B).

Example 13: Persistent Hypogonadotropic Hypogonadism (PHH)

Survivor-based TBI outcome is embodied by neuroendocrine dysfunction, and it is characterized by suppressed adaptive immunity post-TBI. The associated symptoms include fatigue, altered mood, infertility, decreased muscle mass, decreased exercise tolerance, and also serve as an indicator of other co-occurring neuro-endocrinopathies in men with severe TBI. The temporal onset of chronic hypogonadism after TBI, how it impacts outcome, and the mechanism underlying persist (chronic) hypogonadism are important questions to be addressed.

Figure 54A:
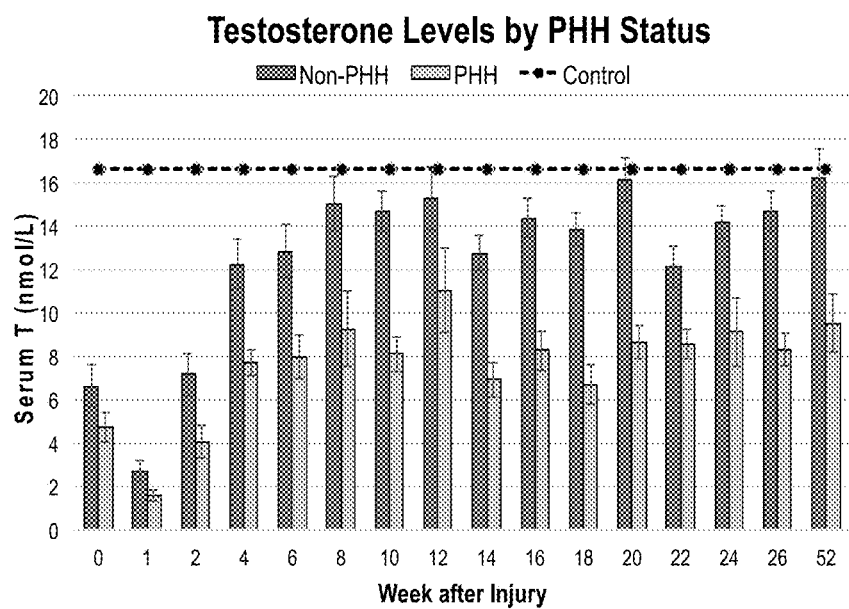
Figure 54B:
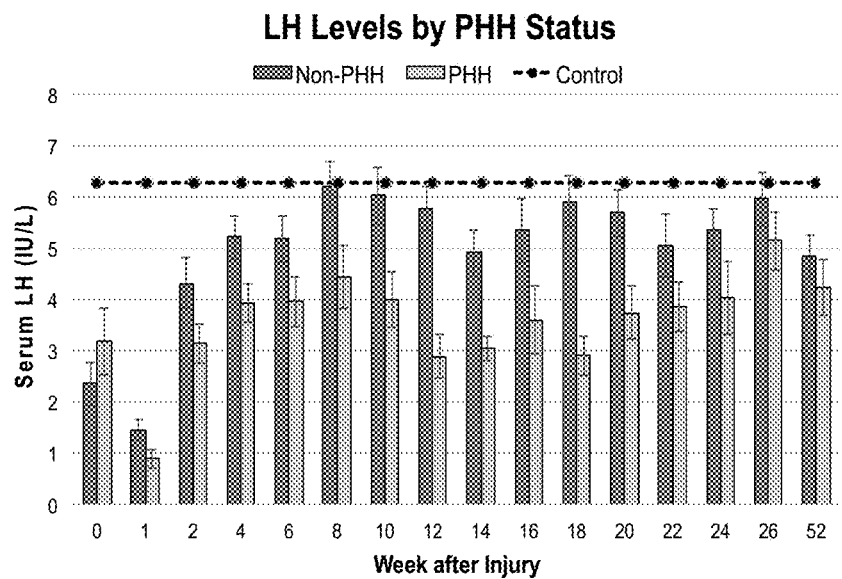

Longitudinal hormone profiles by PHH status were characterized by a low testosterone level with normal or low luteinizing hormone measured via radioimmunoassay and using healthy control cohort as reference group (FIGS. 54A-54B). Seventy-eight men with moderate to severe TBI were tested. Persistent hypogonadism status (PHH) were characterized as having more than 50% time points with hormone levels meeting clinical criteria for hypogonadotropic hypogonadism. Those with PHH also have worse global outcome (GOS) and functional cognition (FIG. 83).

Auto-antibodies against brain antigen were elevated across all types in TBI vs. controls (FIGS. 55A-55D). After TBI, those with PHH reduced production of both IgM and IgG anti-pituitary (APA) and anti-hypothalamus (AHA) auto-antibody types than non-PHH individuals. This data suggested a suppressed adaptive immune response (IgM) in instances of PHH onset.

APA and AHA AAb profiles (IgM and IgG) are associated with PHH status at one year after severe TBI. Potential mechanisms were illustrated for hypogonadism and autoimmunity. Protective autoimmunity potentially is facilitated by CNS auto-antigen presentation after BBB disruption post-TBI and higher levels of IgM, which elicits a more reparative response than IgG. Higher IgM:IgG ratios are indicative of protective autoimmunity in absence of disease. Thus, the presently disclosed subject matter are for restoring adaptive immune response in PHH cases by increasing immune cell (B and T cells) numbers and preventing TNFα-induced lymphotoxicity, indicated by IL-7, RANTES, sTNFRI; and stimulating the inflammatory and auto-antibody production capacity of those cell, indicated by IL-7, RANTES.

Figures 56, 57A:
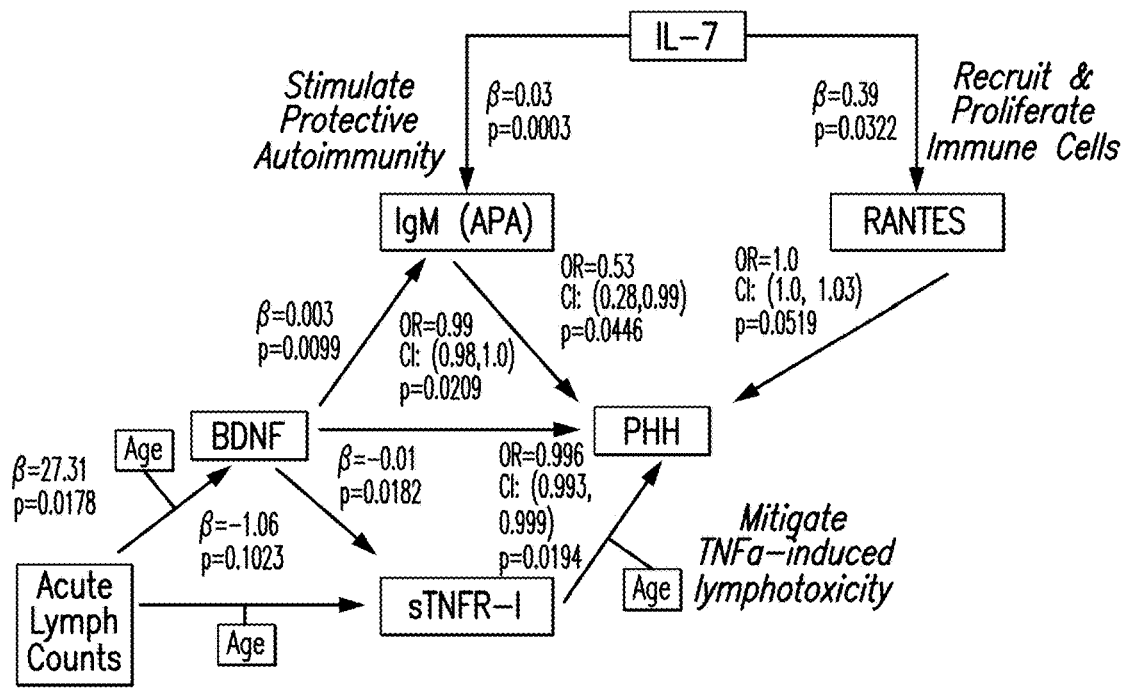

The conceptual model for homeostatic disruptions to immunity post-TBI contributing to PHH is shown in FIG. 56. Individual regression models were adjusted for age and GCS Score (best in 24 hours). And age was shown as moderator in cases where interaction with exposure was significant. These mechanistic pathways contribute to the understanding of PHH. There are two main issues that need addressed (1) immune cell numbers and (2) capacity of those cells to propagate inflammation and auto-antibody production. The first Issue can be addressed via upregulation of chemotactic molecules and inhibition of TNFα cell death. The second issue can be address via IL-7 stimulation of cell activity. The literature shows that lymphocytes can produce brain-derived neurotrophic factor (BDNF) and support hypothalamic BDNF production.

Figure 57B:
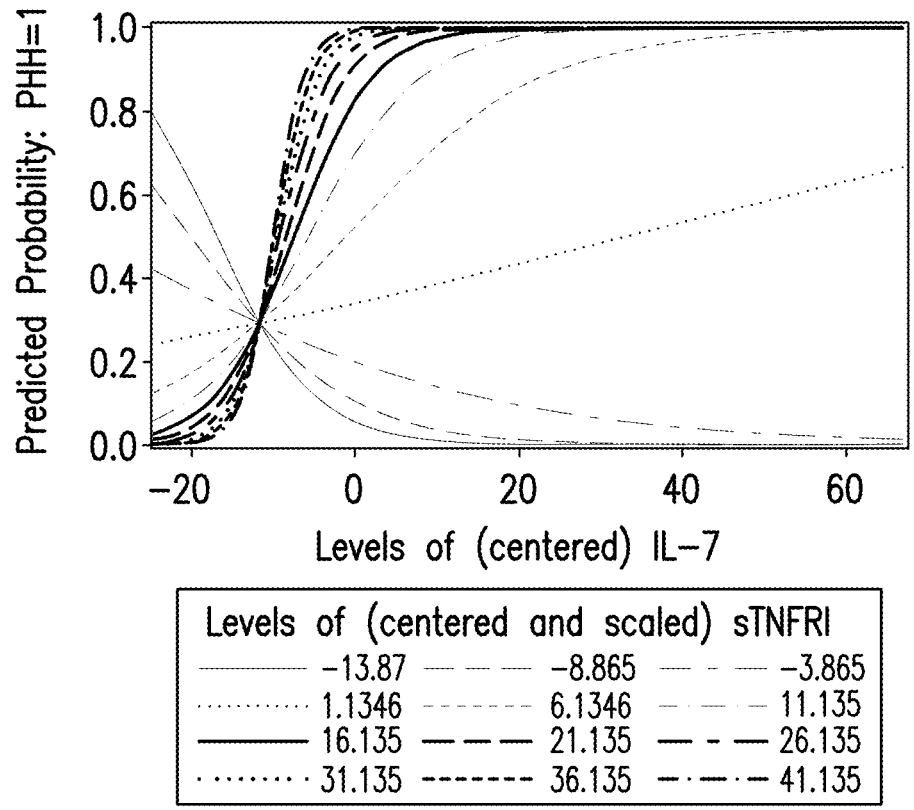

Logistic regression model of PHH outcome on TNFRI and IL-7 Interactions were conducted by testing 125 men with AUC=0.795 (FIGS. 57A-57B). The model integrated mechanistic avenues to PHH onset. Interaction term (FIG. 57B) between IL-7 and sTNRF1 represents dual immune forces at play: IL-7 (lymphoproliferative molecule) vs. sTN-FRI (lymphotoxic cell-death byproduct). Note that interaction graphic refers to month 0-6 mean levels (pg/mL) of IL-7 (not scaled) and sTNFRI (scaled by a factor of 100). The interaction of IL-7 and sTNFRI is key to PHH prediction and relevant to the proposed 4 treatment group rubric developed in the present disclosure.

Figure 57C:
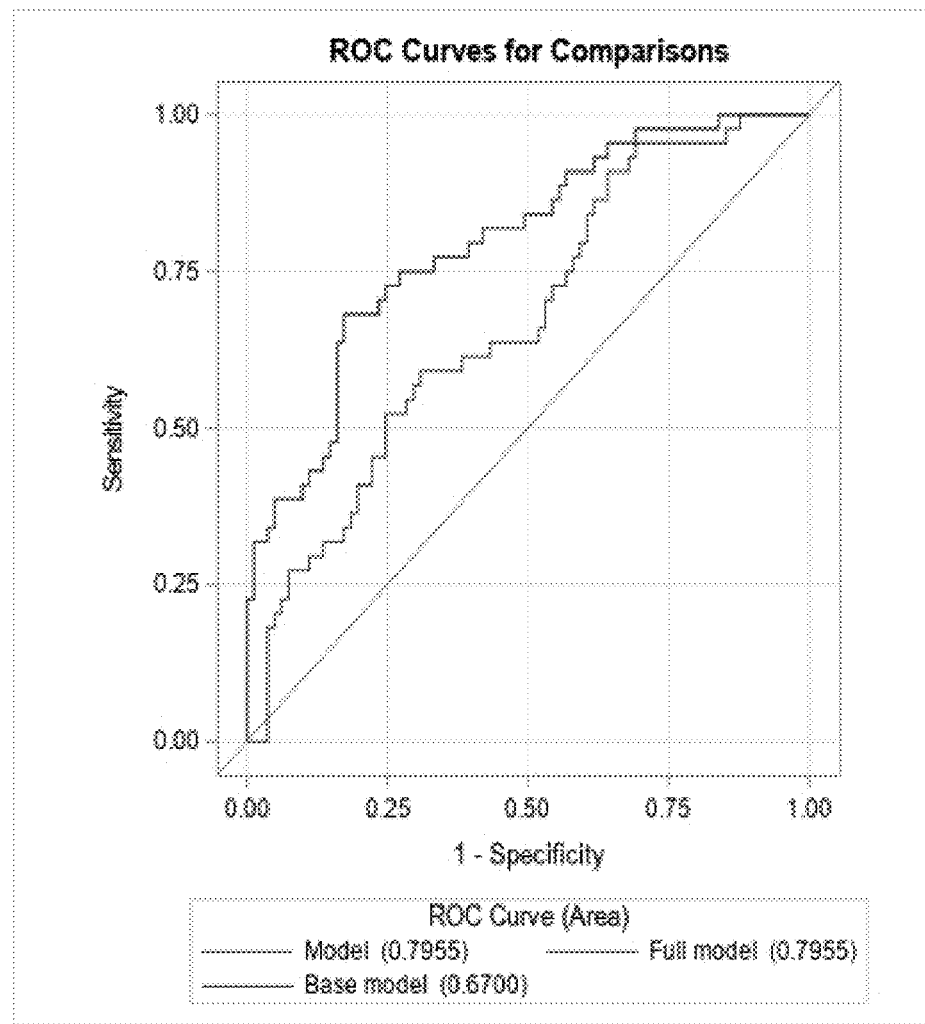

The interaction depicted in FIG. 57B showed probability of PHH on the y-axis and IL-7 on the X-axis. At low sTNFRI percentiles, the risk of PHH went down with increasing IL-7 levels. At sTNFRI level of about 1500pg/mL, the probability of PHH did not change as IL-7 increased. For sTNFRI levels more than 1500 pg/mL, the risk of PHH went up with increasing IL-7. Together this graphic depiction of the data illustrates why boosting IL-7 may require some TNFα inhibition in order to have a therapeutic effect on PHH. The relative level of sTNFRI presented FIG. 57B is contextualized well when referring back to the sTNFRI trajectory groups (FIG. 33). The high trajectory identified expressed sTNFRI levels consistently above the threshold of ~1500 pg/mL, suggesting a group of individuals with increased PHH risk. It is anticipated that similar TNFα thresholds when modeling IL-7 and sTNFRI interactions for other outcomes such as Glasgow Outcome Scale (GOS). The ROC curves in FIG. 57C show that inflammatory markers increase the associated sensitivity of PHH prediction.

Figure 57D:
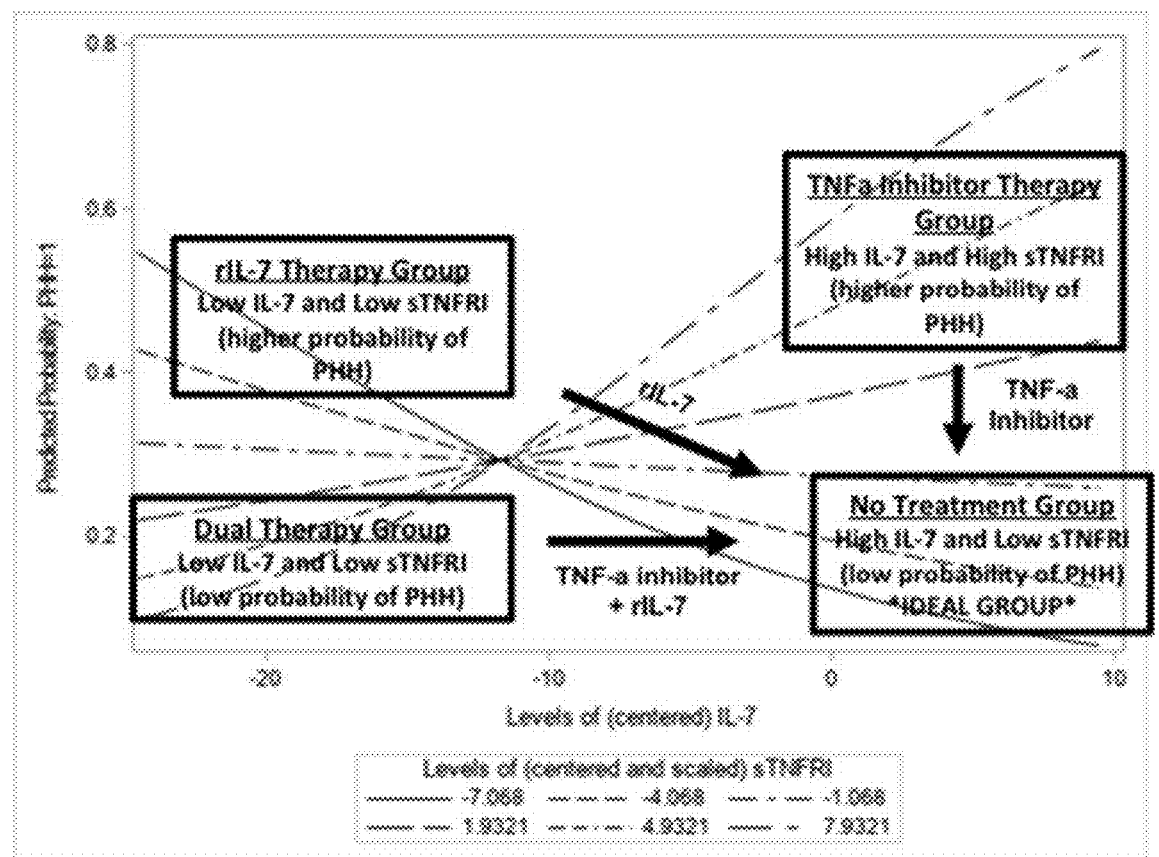

The IL-7× sTNFRI interaction graph illustrated in FIG. 57D shows that the relationship between IL-7 and PHH probability is dependent on the sTNFRI state. If high IL-7/low TNFRI state is the ideal group (right lower quadrant), then individuals in other quadrants can benefit from personalized (precision) immunotherapy treatment for PHH prevention/treatment. The black arrows between each treatment group to the "No Treatment Group" indicates the form of therapy intervention needed to be in the ideal group for PHH prevention.

Figure 57E:
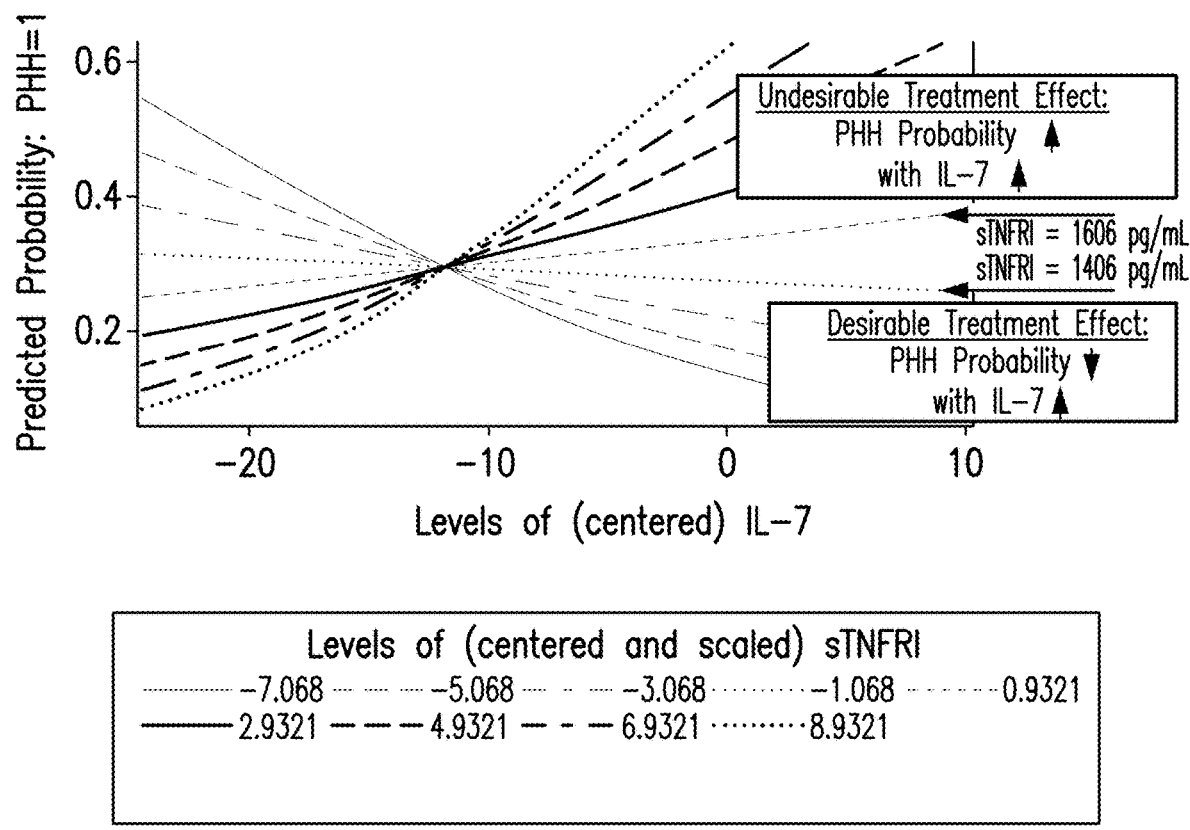

The sTNFRI level in FIG. 57E at which IL-7 treatment effects shift from desirable to undesirable occur at the point at which the slope of the graph (PHH probability by IL-7 level) changes from negative to positive. This suggests that increases of IL-7 in the context of sTNFRI~>1500pg/mL increase probability of PHH. Increased IL-7 decreases the probability of PHH in context of low sTNFRI. When sTN-FRI exceeds ~1500 pg/mL, the protective effect of IL-7 on PHH is lost. Therefore, one must contain sTNFRI levels below this threshold for protective effects of IL-7 treatment to be achieved.

Example 14: Clinical Trial using IL-7 and TNFα inhibitors

Absolute Risk Reduction (ARR) was Calculated Based on the Equation Below:
ARR=Control Event Rate—Experimental Event Rate
Control: Endogenous "Risk" profile
Experimental: Endogenous "Non-Risk or Reduced Risk" Profile. Numbers needed to treat (NNT) was also calculated based on the equation below:
Number of patients who need specific treatment to prevent one additional poor outcome
The ideal NNT value is 1
NNT is the inverse of ARR (NNT=1/ARR)

Figures 58, 59:
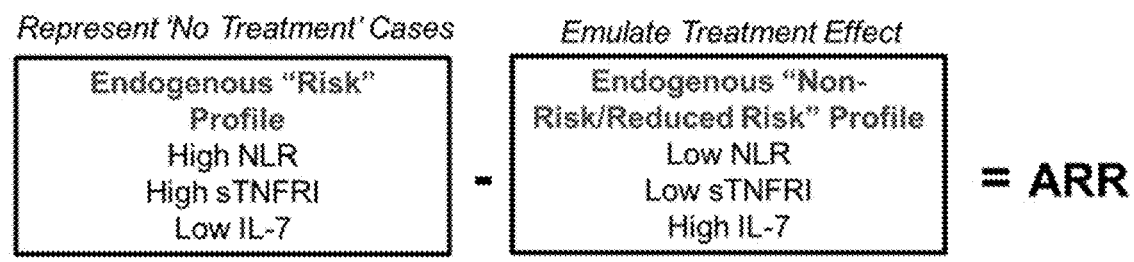

The ARR and NNT concepts were adapted and applied to approximate potential treatment effects with rhIL-7 and Etanercept (ETN). The High Risk TRAJ group was used as the no treatment and the low risk TRAJ group as the treatment group to approximate treatment The no treatment cases bear endogenous "risk" profile with high NLR, high sTNFRI and low IL-7 (FIG. 58). The emulate treatment effect groups are endogenous "non-risk or reduced risk" profile with low NLR, low sTNFRI, and high IL-7 (FIG. 58).

The absolute risk reduction referred to endogenous expression and "no/reduced risk" profile (low NLR, low sTNFRI, high IL-7) versus "risk" profile (high NLR, high sTNFRI, low IL-7). NNT counts ranged from 2-8, suggesting that relatively low numbers of enrollees would be needed to address treatment effects of the dual therapy approach across multiple early screening conditions, outcomes and phenotypes/secondary conditions (FIG. 59)

Figure 60:
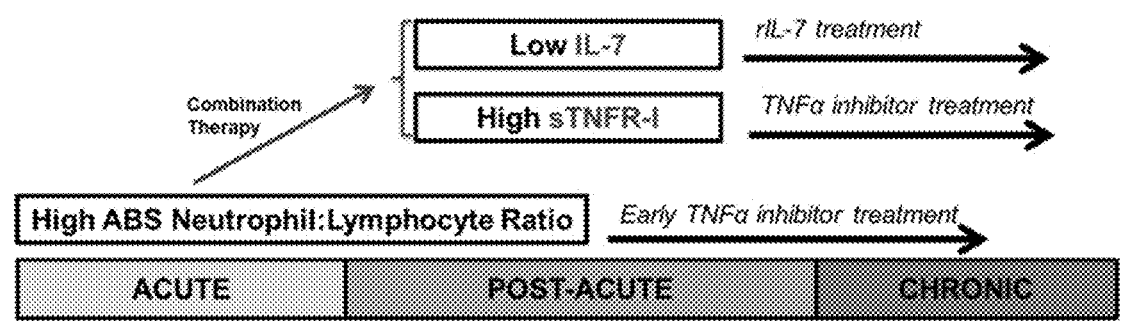

Temporal screening scheme demonstrates a data derived screening and eligibility process for clinical treatment (FIG. 60). NLR may be a useful early screening tool that does not require special assays outside of what is done clinically. Cut offs for each marker are proposed as threshold criteria for "likely responsiveness" to each therapy. This temporal screening scheme leverages the knowledge of inflammatory trajectory courses for the early stratification of individuals and likely responders to the proposed treatments over their injury recovery course, pre-screens and monitors individuals on a high NLR course (ratio >10) during acute/post-acute care (through 3 weeks post-TBI), and screens during the post-acute period for individuals on low IL-7 trajectory with less than 25 pg/mL and high sTNFRI trajectory with more than 1500pg/mL.

Figure 61A:
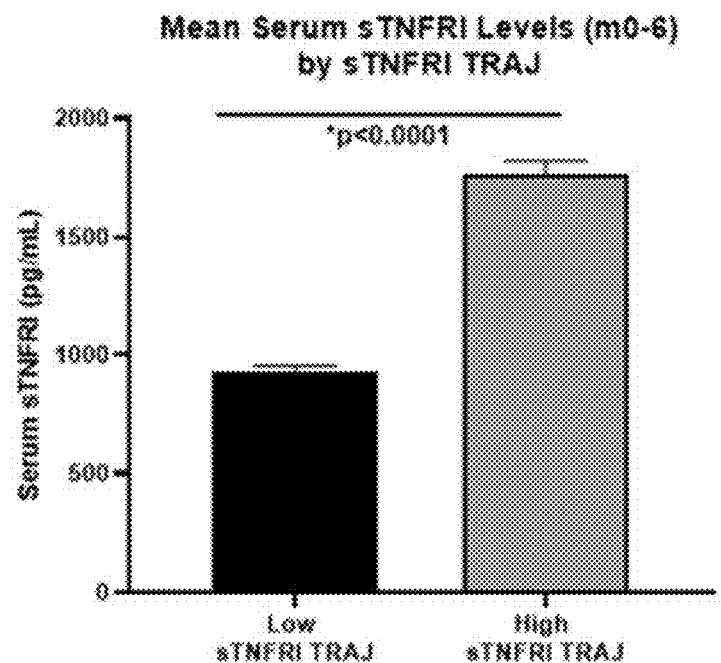
Figure 61B:
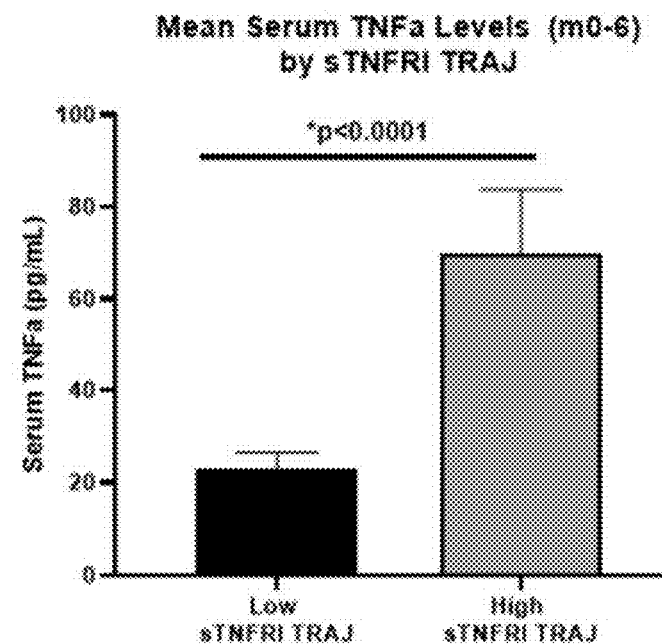

Biomarkers are used in gauging treatment effectiveness. AAb APA Ratios for the high IL-7 TRAJ could be used as a treatment target for IL-7 therapy (FIG. 35B). The effective IL-7 treatment should be initially gauged not only on IL-7 levels observed in the high IL-7 TRAJ, but also in the IgM and IgM: IgG ratios observed in the high TRAJ (FIG. 35B). sTNFRI levels can be used to treat high sTNFRI TRAJ profiles to achieve sTNFRI comparable to low sTNFRI TRAJ (FIG. 61A). An sTNFRI cut point of>1500pg/mL could identify another treatment target group specifically for PHH (FIG. 57). TNFα levels are another indicator (FIG. 61B). The low sTNFRI TRAJ informs ideal serum TNFα to attain with Etanercept treatment administered to high sTN-FRI TRAJ individuals. Low dose Etanercept administration reduces serum TNFα levels by about ⅓. NLR levels in the post-acute phase change with therapy and can be monitored.

Example 15: Animal Studies

The pre-clinical work was to evaluate recombinant human (rh) IL-7 on Controlled Cortical Impact (CCI) mice. Mice underwent severe CCI or sham surgery and then received vehicle, low dose, or high dose rhIL-7 and etanercept. The Dosing regimens for rhIL-7 were: high dose=5 μg and low dose=0.5 μg. Recombinant hIL-7 was administered on day 1, day 7 and day 13. The dosing regimens for Etanercept were: high dose=5 mg/kg and low dose=1 mg/kg. Etanercept was administered on day 1, day 4, day 7, day 10 and day 13. The behavioral testing included Novel Object Recognition Testing (day 8), Morris Water Maze Testing (day 14-day 20) and Open Field Testing (day 8). The spleen lymphocytes (day 2, day 21) were analyzed by Flow Cytometry.

Figure 22A:
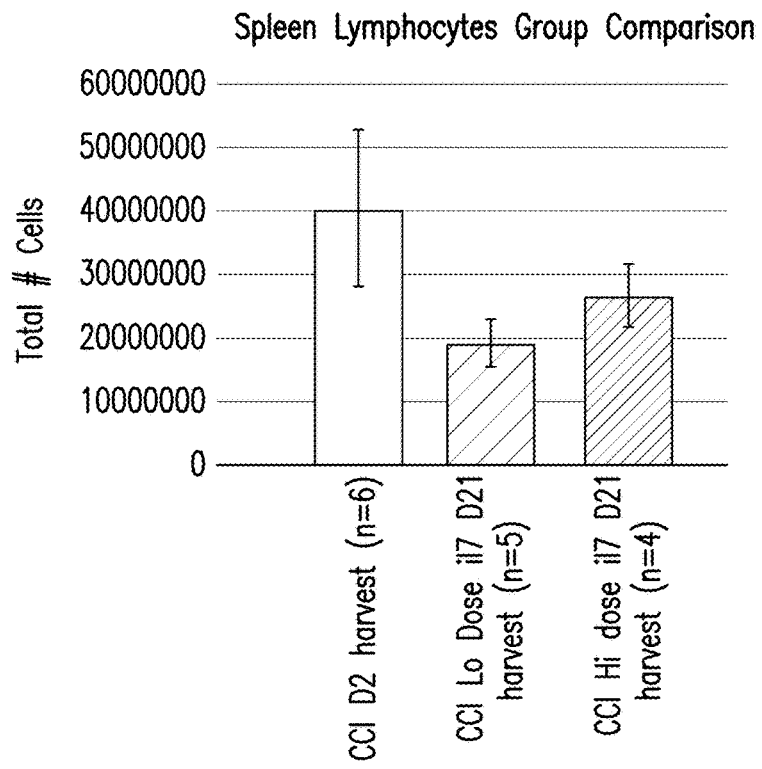
Figure 22B:
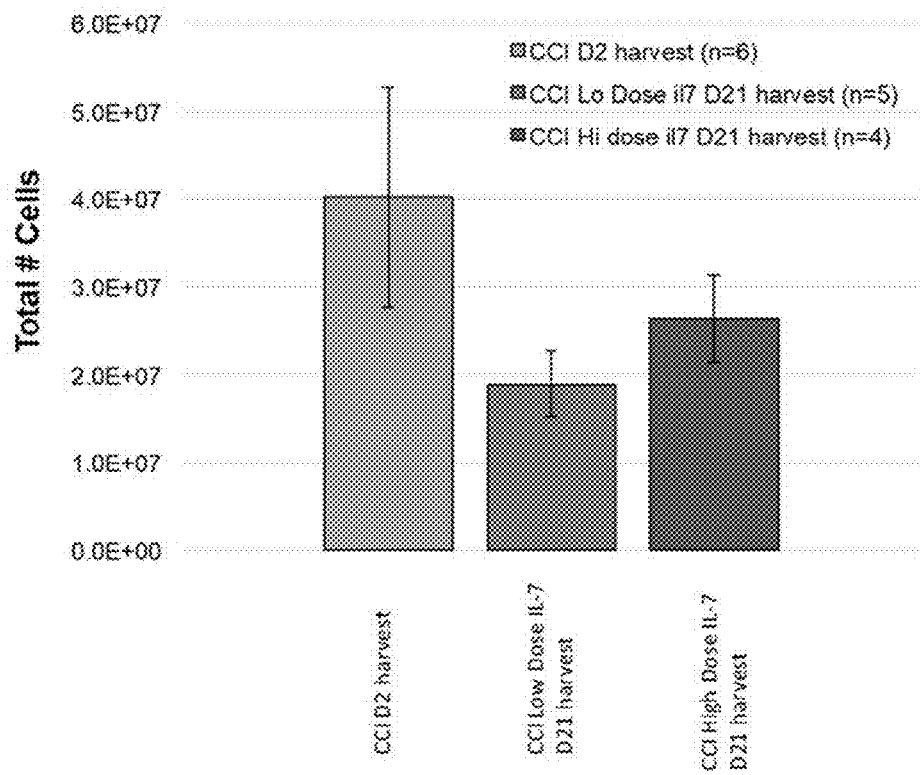
Figure 23D:
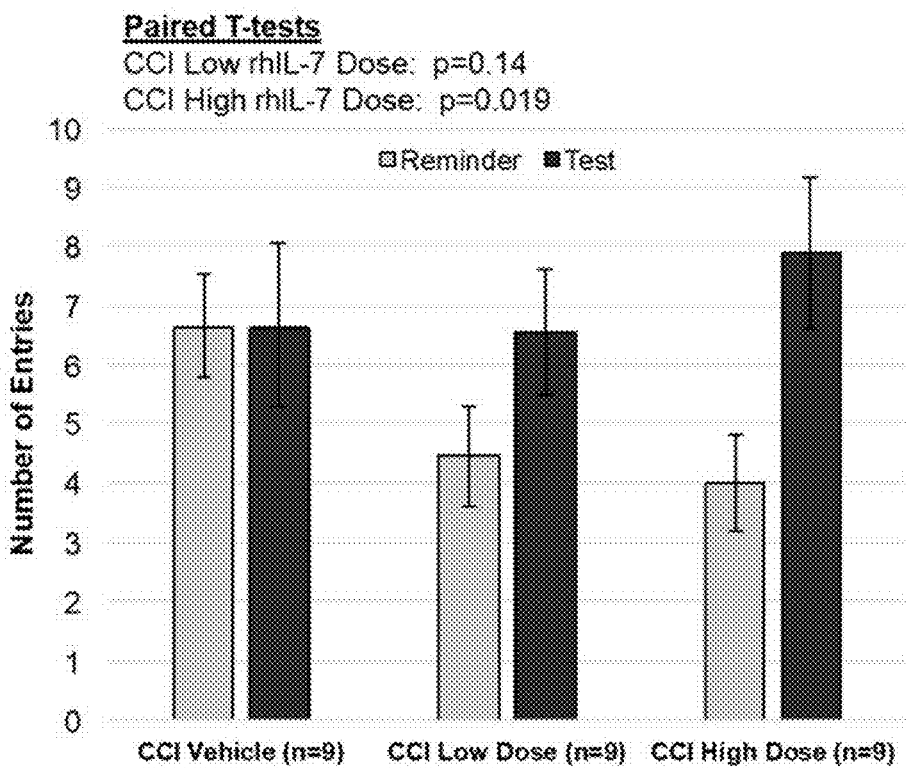
Figure 23E:
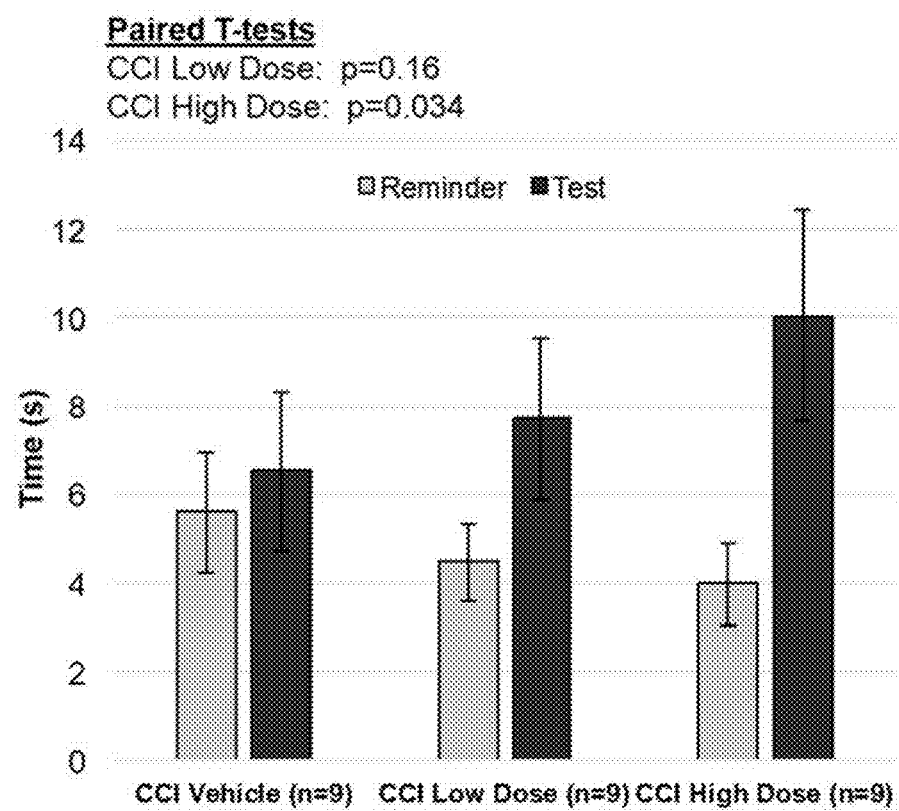
Figure 26B:
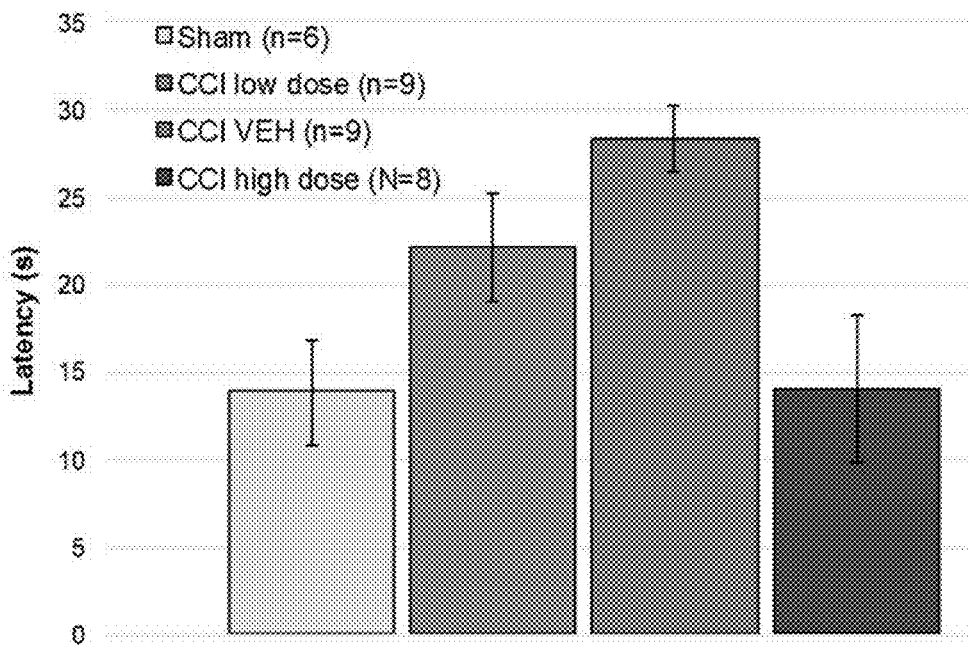
Figure 26C:
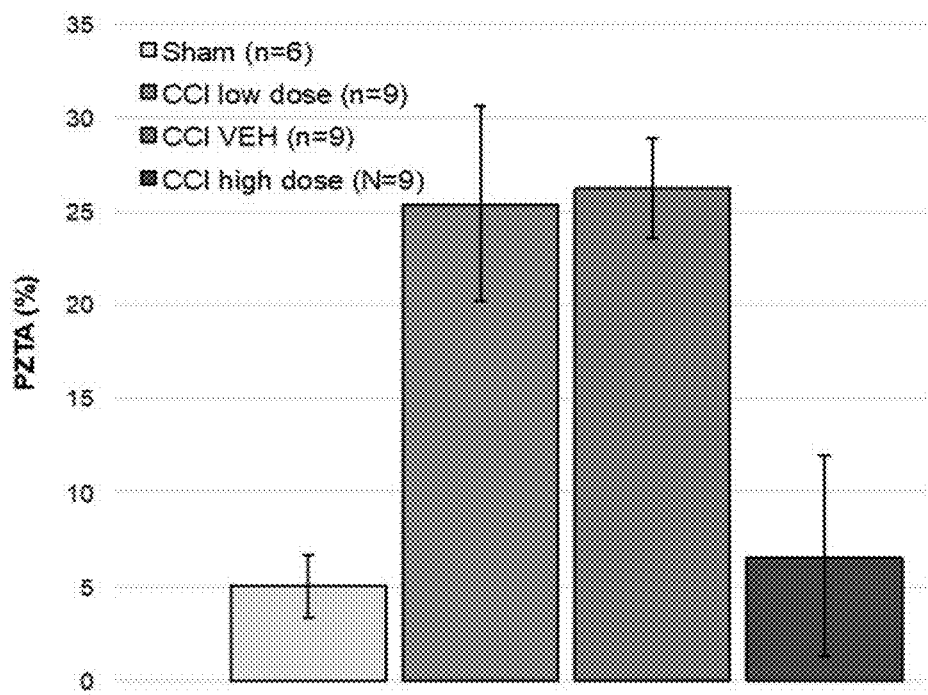
Figure 26D:
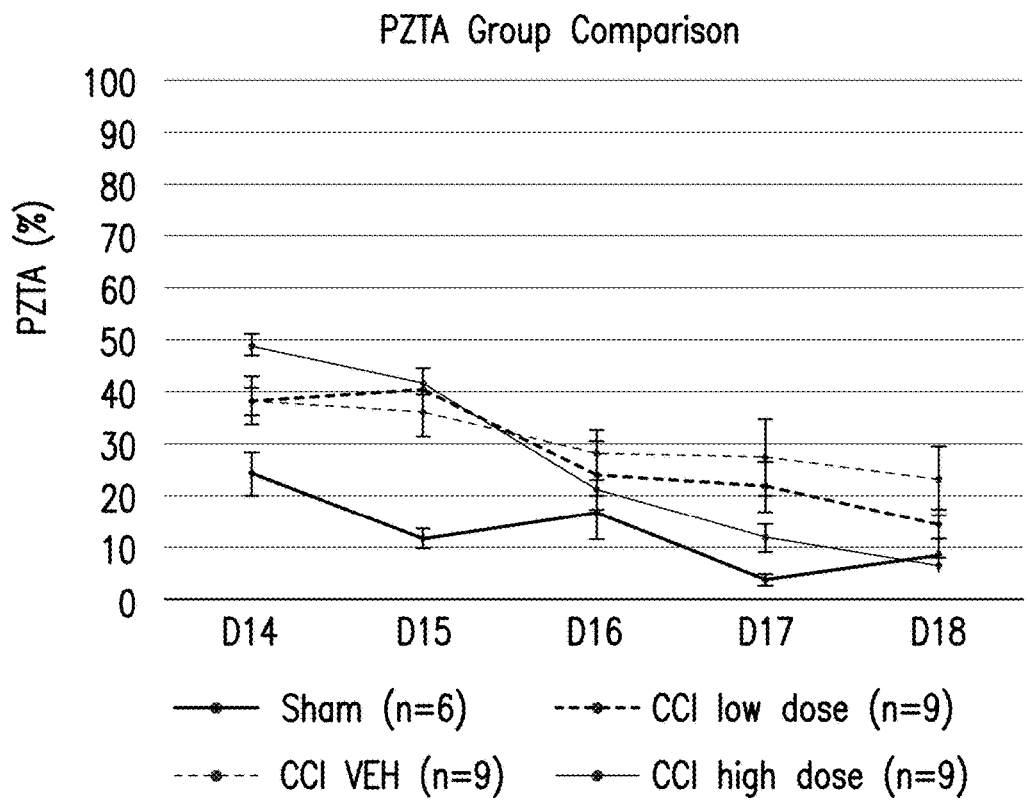

Data suggested that CCI low dose rhIL-7 mice had reduced splenic lymphocyte counts across subtypes by day 21 compared to Sham. High dose rhIL-7 reversed this trend across cell count subtypes (FIG. 21B). Data also showed that compared to day 2 CCI harvest vehicle, lymphocytes were reduced in low dose rhIL-7 at day 21, however were partial rescued with high dose rhIL-7 by day 21. Spleen lymphocyte rescue comparison (day 2 vs. day 21 total) showed that lymphopenia develops over time and persists at points after experimental injury deemed to be in the "early chronic" phase of recovery after TBI (FIGS. 22A-22B). Novel object recognition test (day 8) measured entries and time spent in Zone. High dose rhIL-7 mice interacted more frequently and for longer time with novel object than low rhIL-7 dose and vehicle mice (FIGS. 23D-23E) Morris Water Maze, Visual Platform (day 19) measured latency and anxiety behavior. PZTA reflected anxiety behavior in the water maze where rodents display thigmotaxis. High dose rhIL-7 mice showed reduced latency and reduced anxiety behavior on visual platform test than both low rhIL-7 dose and vehicle mice (FIGS. 26B-26C).

Figure 62:
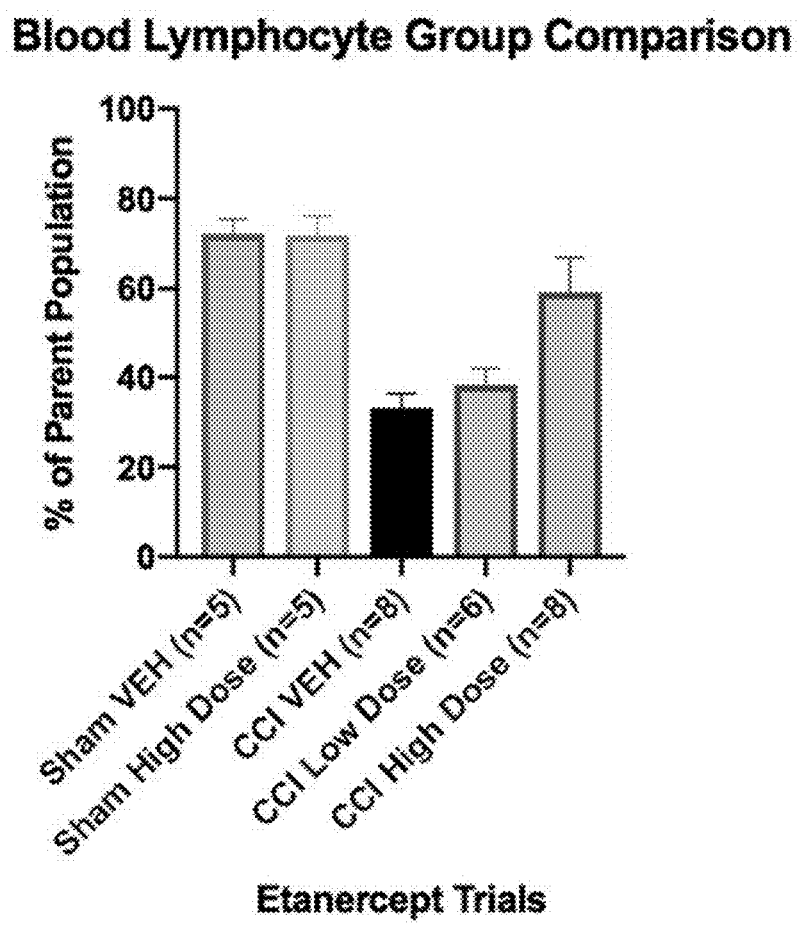

CCI model of TBI causes prolonged and significant lymphopenia. High Dose Etanercept has a robust effect on lymphoproliferation measured on D21 (FIG. 62). The unpaired T-tests for FIG. 62 were calculated: CCI VEH vs. CCI Low Dose: p=0.3314; CCI VEH vs. CCI High Dose: p=0.0079; CCI VEH vs. Sham VEH: p<0.0001; and CCI High Dose vs. Sham VEH: p=0.2325.

Figure 63A:
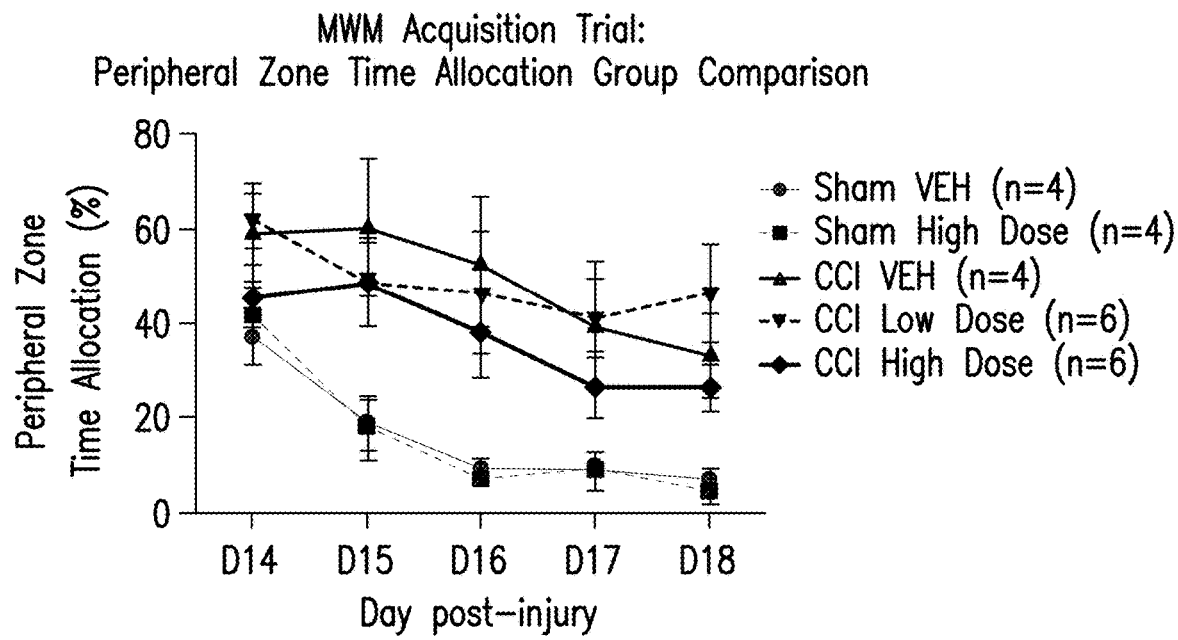
Figure 63B:
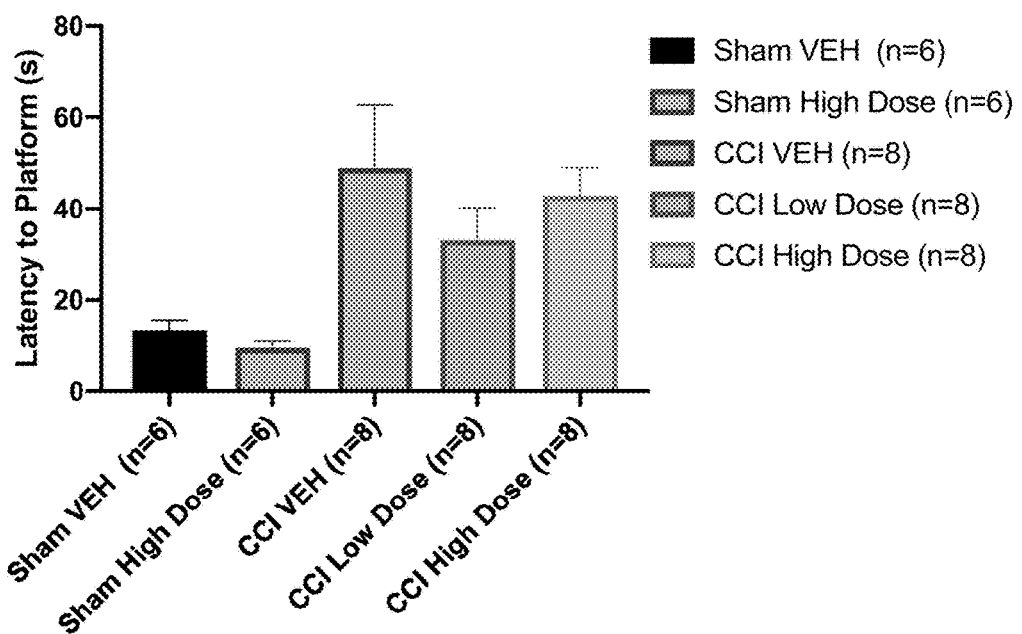

CCI high Etanercept dose treatment significantly lowered PZTA and latency (p<0.05, paired t-test) compared to CCI Vehicle. Both low and high dose treatments improved latency to find a visible platform in the MWM. High doses reduced thigmotaxic behavior in the water maze (FIG. 63A). For a mouse etanercept study on MWM visible platform trial, the following dose range and frequency were used: vehicle, 1 mg/kg or 3 mg/kg on day 1, 4, 7, 10, and 13. The groups included 8 CCI high dose, 8 CC low dose, 8 CCI VEH, 6 sham high dose, and 6 sham VEH. Low dose etanercept had modest effect on visible platform testing (FIG. 63B). The p value of one-way ANOVA was 0.0086. The unpaired t-tests of different groups were calculated: Sham VEH vs Sham High Dose: p=0.2072; Sham VEH vs CCI VEH: p=0.0484; Sham VEH vs CCI Low Dose: p=0.0384; Sham VEH vs CCI High Dose: p=0.0017; Sham High Dose vs CCI VEH: p=0.0312; Sham High Dose vs CCI Low Dose: p=0.0156; Sham High Dose vs CCI High Dose: p=0.0006; CCI VEH vs CCI Low Dose: p=0.3254; CCI VEH vs CCI High Dose: p=0.6967; and CCI Low Dose vs CCI High Dose: p=0.3107.

Figure 64:
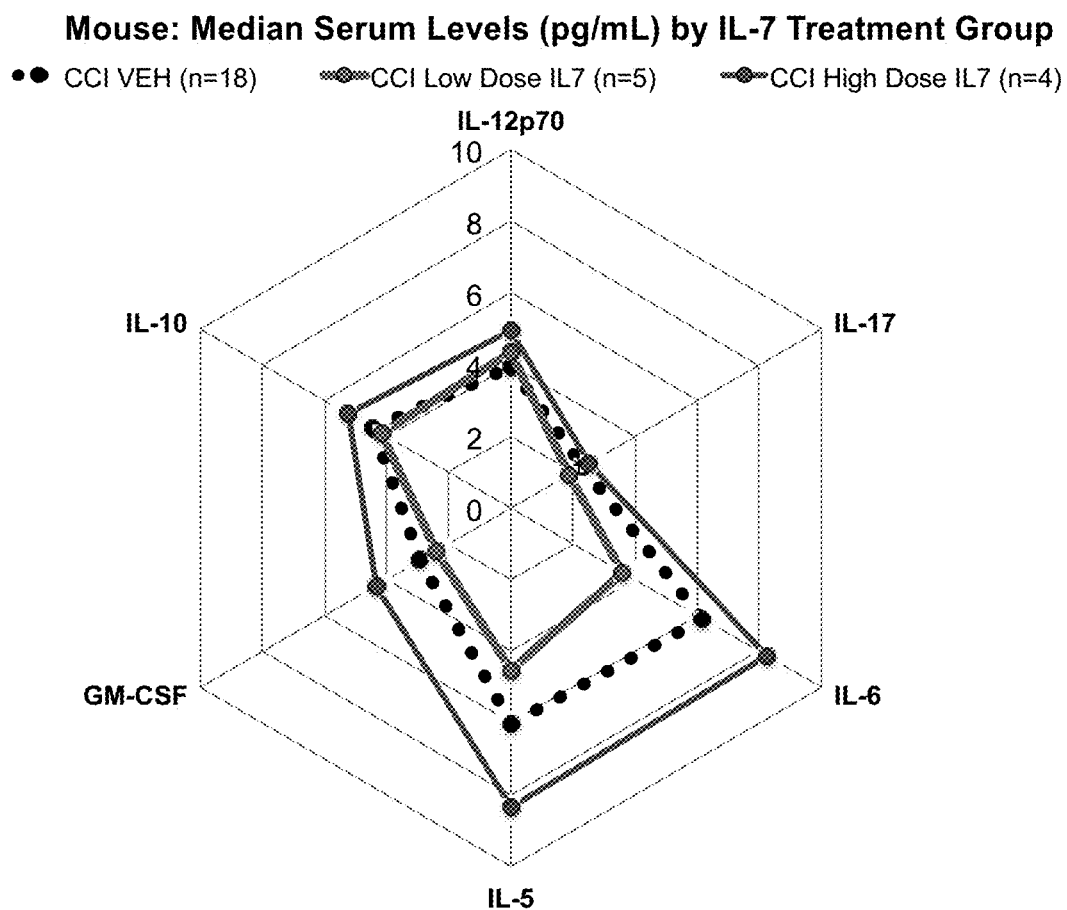

As suggested by endogenous clinical data (treelet), IL-7 had broad effect on boosting all arms of immunity. This study showed that high dose IL-7 had broad effect on increasing markers across multiple arms of immunity compared to other injury groups and that dose-dependent difference observed with low dose IL-7 at or below injured control levels (FIG. 64). Serum profiles after Etanercept treatment (FIG. 65) showed how dual therapy regulates IL-6 boost that accompanies IL-7 treatment, and the strength of leveraging dual therapy approach to manipulate desired arms of immunity.

The present example suggested Etanercept administration to mice facilitated lymphoproliferative mechanisms (via IL-2) and increased cell-trafficking and recruitment (via RANTES). Etanercept (any dose) had rescue effect on RANTES and IL-12, and high dose of Etanercept had rescue effect on IL-2 (FIG. 65). Etanercept also had reduction effect on IL-6 and TNFα proinflammatory propagation molecules, which may play protective role in mediating inflammatory boost when IL-7 is delivered (FIG. 65). Etanercept dosing decreased TNF and IL-6 tamping down innate markers that were (in the case of IL-6) elevated with high IL-7 treatment.

Figure 66:
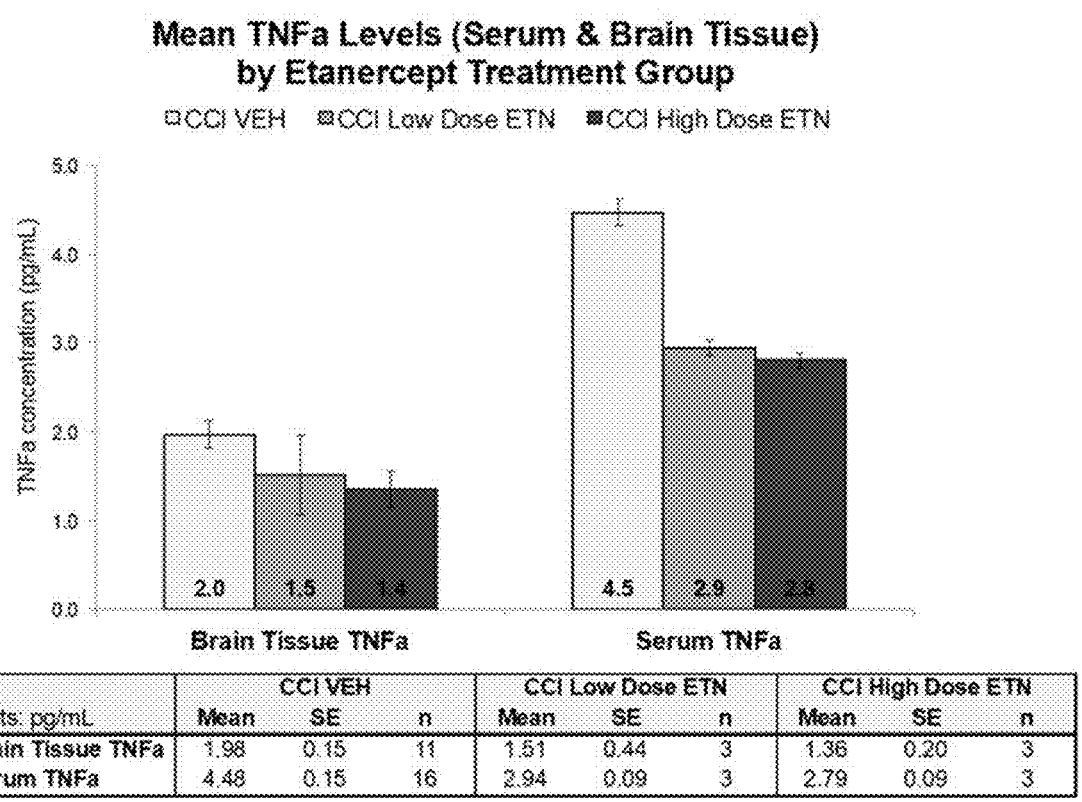

The present example also tested brain and peripheral TNFα expression in Etanercept treated mice. The present data suggested that Etanercept administered peripherally has capacity to moderately reduce TNFα in brain (despite BBB constraints 21 days post-injury) and significantly reduces TNFα in serum (FIG. 66) Overall, the present example showed that CCI associated with reduced splenic lymphocytes over time compared to Sham. The present example also showed that rhIL-7 administered to mice at "high" doses restored splenic lymphocyte counts to sham levels, improved memory-increased novel object recognition compared to VEH and reduced anxiety-like behavior: reduced MWM Visual Platform latency and PTZA. The present example also showed that Etanercept improved some components of MWM, restores lymphocytes, reduces TNFα in tissue and in serum.

PHH exemplar for dual therapy approach showed that TBI is associated with hypogonadism in men over at least the first-year post injury. The PHH exemplar also showed that hypogonadism associations with poor global outcome and disability may be due to an underlying immunodeficiency (reduced IgM and IgM:IgG ratios). The PHH exemplar also showed that IL-7 can be leveraged to boost IgM and IgM:IgG ratios based on the data showing endogenously higher IL-7 post-TBI associated with elevated AAb levels. TNFα inhibitor can be leveraged to reduce lymphotoxicity and restore depleted immune cells and reduce the negative impacts of high IL-7 on other immunity domains.

Example 16 Chronic IL-7 TRAJ Analysis

At high levels of specificity, AAb TRAJ groups increase the associated sensitivity of PHH prediction, better informing true positive cases with PHH (FIG. 70). 84 subjects were enrolled into the cohort, with event rate 37.5%. Base Model was Age plus 2wk-26wk T levels. The AUC base=0.791. APA and AHA from 2 weeks to 6 months were used for TRAJ analysis. AUC base+AHA & APA IgM AAb TRAJ=0.862. ROC Contrast Estimation was chi-sq=2.94, p=0.086.

This model informs the use of these assays as relevant to the pathology and prognosis for PHH in men with moderate to severe TBI. The data suggest that group-based trajectory analysis categorization of individuals with similar IgM APA and IgM AHA levels over time adds nearly 7% additional discrimination capacity in PHH prediction (which is considered excellent), and suggests that AAb profiles over time are important in the development of PHH for men with moderate to severe TBI over the first year after injury. This increase in discrimination capacity trends toward statistical significance. At high levels of specificity, the AAb trajectory group categorization increases the associated sensitivity of PHH prediction, better informing true positive cases with PHH. At low levels of specificity, the AAbs slightly reduce associated sensitivity, potentially informing true negative cases with PHH.

Chronic model of adaptive immunological network shows the roles of IL-7 in adaptive immunity (FIG. 72).

IL-7 group-based TRAJ showed that IL-7 levels post-TBI mapped to adaptive immunity cluster after TBI, and there were unique IL-7 TRAJ groups representing IL-7 profiles over the first 6 months post injury among individuals with moderate to severe TBI. IL-7 TRAJ groups for TBI subjects varied with respect to controls, in which some subjects had levels above mean, at mean, or below mean with respect to control groups. IL-7 levels over time were a leading indicator of the variance observed in this population with regard to adaptive immunity, innate immunity chemotactic cytokines, and allergy immunity markers over time (clusters 1,2,4,5) (FIGS. 73-74). Markers that did not cluster in unrestricted treelet was show in FIG. 75. APA IgM mapped well on to IL-7 TRAJ groupings (FIGS. 76-78).

Lymphopenia is associated with higher infection rates, earlier time to infection, Longer LOS (length of stay), more vent days, more ICU days, and worse one year outcomes. Absolute lymphocyte counts showed that (n=300) chronic IL-7 did not track to early lymphocyte counts. Group based TRAJ analysis on lymphocytes showed prolonged lymphopenia among some individuals with severe Injury. Lymphopenia associated with differences in chronic soluble receptor cluster, which does track to IL-7 TRAJ (FIG. 71 & 79). Demographic/outcomes by IL-7 TRAJ showed that endogenous IL-7 impacts global outcome (FIG. 80). Lymphocyte counts by IL-7 TRAJ showed that there was no significant difference in lymphocyte counts by IL-7 TRAJ, and that endogenous variation in IL-7 is not associated with lymphopenia (FIG. 81). APA IgM by IL-7 TRAJ showed that IL-7 still stimulates IgM AAb production, even within individuals who were lymphopenia over the first 3 weeks after their injury (FIG. 82).

Example 17: Administration of IL-7 to Human Subjects

Individuals with moderate-to-severe traumatic brain injuries (TBI) are at high risk for multiple long-term complications and secondary conditions, including neuroendocrine dysfunction, seizures, cognitive dysfunction, mood disorders, headache, and poor neurorecovery. These conditions have led many to consider TBI as a chronic disease. Lymphopenia and neutrophilia occur and last for at least 20 days post-injury for many individuals with TBI. Despite increasing knowledge about acute secondary injury mechanisms, far less is known about mechanisms underlying the chronic pathology and persistent complications that impact TBI outcome. The present disclosure suggests that early immune system derangements contribute to chronic immune dysfunction and contribute to many of these conditions that occur over the long term after TBI.

After injuries like spinal cord injury (Riegger et al., Neuroscience. 2009; 158(3):1194-1199) and stroke (Brait et al., J Cereb Blood Flow Metab. 2012 April; 32(4): 598-611), the adaptive immune response becomes suppressed, with many individuals having lymphopenia. Lymphopenia is a natural reaction to the aseptic inflammatory response mounted after CNS injury and the pathological stressors that, via communication from the sympathetic nervous system (SNS) (Elenkov et al., Pharmacol Rev. 2000; 52(4):595-638; Kenney MJ, Ganta CK. Autonomic Nervous System and Immune System Interactions. In: Terjung R, ed. Comprehensive Physiology. Hoboken, NJ, USA: John Wiley & Sons, Inc.; 2014:1177-1200), amplify the HPA axis (Prass K, et al., *Journal of Experimental Medicine*. 2003; 198(5):725-736). Also, certain work (Liesz et al., *Exp Neurol*. 2015; 271:46-52) suggests this phenomenon includes a transient immunoglobulin deficiency associated with increased likelihood of infection and moderated by CNS damage markers. After CNS injury, there is eventual lymphoproliferation, including increased Th-cell generation sensitive to circulating self-antigens that generate auto-antibodies that may enhance removal of injured tissue and facilitate neural repair (Schluns et al., *Nat Immunol*. 2000; 1(5):426-432; Ernst et al., *Immunity*. 1999; 11(2):173-181). Some have characterized reparative AAb responses after CNS injury as "protective autoimmunity" (Lii et al., *Brain, Behavior, and Immunity*. 2008; 22(8):1217-1230; Schwartz et al., *Trends Mol Med*. 2001; 7(6):252-258; Schwartz et al., *J Neurol Sci*. 2005;233(1-2):163-166)

It is believed that these protective autoimmune responses may develop via lymphorestorative processes involving adaptive immunity to auto-antigens, which leads to AAbs specific to CNS antigen exposure following the blood brain barrier (BBB) breach that accompanies TBI. IL-7 modulates lymphoproliferative processes to restore T-cell homeostasis. Thus IL-7 may support a reparative neuro-inflammatory environment (Guimond et al., Nature Immunology. 2009; 10(2):149-157) where IL-7 augments reactivity to self-antigens during the lymphoproliferation phase that follows lymphopenia, leading to AAb synthesis (Schluns et al., 2000. Nat. Immunol. 1, 426-432; Ernst et al., Immunity. 1999; 11(2):173-181; Lundstrom et al., P.N.A.S. 2013;110 (19):E1761-E1770; Lundstrom et al., Semin Immunol. 2012; 24(3):218-224). Alternatively, natural AAbs (e.g. neuronal membrane epitopes), constitutively secreted from B1 cells and amplified in response to apoptotic and pro-inflammatory environments could contribute to AAb profiles after TBI, supporting phagocytosis & an anti-inflammatory environment that facilitates tissue repair and homeostasis (Vas et al., 2013. Front. Immunol. 4, 4; Gronwall et al., 2012. Front. Immunol. 3, 66; Lobo et al., Journal of Clinical Immunology. 2010;30(S1):31-36; Baumgarth et al., Springer Semin Immunopathol. 2005; 26(4):347-362).

Although central to adaptive immune function, IL-7 accumulation/consumption can be variable across individuals due to age/stress-related (Lundstrom et al., Semin Immunol. 2012; 24(3):218-224; Lucin, et al., 2009. J. Neurochem. 110, 1409-1421) deterioration of the adaptive immune response, as well as to innate variation in the soluble IL-7receptor (sIL-7R) availability (Lundstrom et al., P.N.A.S. 2013;110 (19):E1761-E1770; Lundstrom et al., Semin Immunol. 2012; 24(3):218-224) and known-genetic variants that impact functional gene expression for sIL-7R (Gregory et al., Nature Genetics. 2007; 39(9):1083-1091; Lundstrom et al., P.N.A.S. 2013;110(19):E1761-E1770). Some suggest IL-7 is a relevant biological target to promote lymphorestoration needed for tissue repair (Lundstrom et al., P.N.A.S. 2013;110(19):E1761-E1770). The present disclosure suggests that IL-7 is a modifiable biological target affecting the adaptive immune response that contributes to neuroendocrine dysfunction, other secondary conditions after TBI, and influences neurorecovery.

The present disclosure suggests that, in TBI, lymphopenia occurs early after injury and extends at least 20 days post injury. The data suggest that this phenomenon of lymphopenia may be due to aberrations in TNF receptor signaling and IL-7 signaling. TBI leads to elevations in chronic serum autoantibody levels, including those specific to the pituitary and to glial fibrillary acid protein (GFAP). IgM AAbs can afford protective immunity after TBI. Further, the present disclosure demonstrates that IL-7 and soluble TNFR signaling are important predictors of secondary conditions and poor outcome. Moreover, the present disclosure demonstrates that, in the setting of low soluble TNFR signaling and low IL-7 levels post-injury, treatment with rhIL-7 may improve recovery when given in the post-acute phase. The present disclosure has accumulated animal data to support rhIL-7 treatment effects in the context of experimental TBI in mice. Below, the present disclosure outline a protocol for a biomarker-based algorithm for implementing a clinical trial to test this hypothesis among likely responders. The present disclosure includes drug description, FDA approval status, and a proposed administration plan for those with moderate to severe TBI who are in the post-acute phase of injury and/or early chronic phase of recovery. The present disclosure supports the use of rhIL-7 as a potential treatment for other forms of acquired neurological injury.

Drug Description:

IL-7, a cytokine derived from bone marrow, thymic stromal, and spleen cells, has been classified as a potent immunomodulator capable of activating, amplifying, and restoring normal immune functioning. That is, IL-7 is critical as a hematopoietic growth factor in maintaining anti-apoptotic processes to enhance immune cell proliferation, differentiation, and survival (Krawczenko et al, Arch Immunol Ther Exp (Warsz). 2005; 53(6):518-525; Fry et al., Blood. 2002;99(11):3892-3904; Francois et al., :CI Insight. 2018;3(5)). Recombinant human IL-7 (rhIL-7), also known as CYT-107, is a glycosylated recombinant protein chemically similar to the endogenous protein measured in humans (NC1.1)rug Dictionary. National Cancer Institute. www.cancerg.ov/publications/dictionaries/cancer-drug. Published Feb. 2, 2011).

CYT-107 acts to increase lymphocytes via two mechanisms: (1) upregulation of T cell cycling and proliferative marker Ki67 (Sheikh et al., Blood. 2016; 127(8):977-988; Sereti et al., Blood. 2009; 113(25):6304-6314), and (2) upregulation of anti-apoptotic and down regulation of pro-apoptotic Bcl-2 family molecules (Khaled et al., Immunol Rev. 2003; 193:48-57).

FDA Approved Uses: Classified as an "investigational drug", rhIL-7 is approved by the FDA for testing in humans for a specified condition, but not approved for commercial marketing and sale. CYT-107 has been experimentally used in a variety of conditions including: sepsis, lymphopenia, oncology, and human immunodeficiency virus (HIV).

The present disclosure generated a biomarker-based treatment protocol for those with moderate to severe TBI, have survived to acute care discharge, and are participating in an inpatient rehabilitation treatment program where appropriate consent and monitoring can be provided (FIG. 84).

Participant Recruitment & Screening for Studies

Study participants are recruited prospectively during their in-patient rehabilitation stay following TBI. Of note, women are not enrolled into initial feasibility study due to risk to fetus if pregnant, and due to potential risks to children being nursed and due to relatively low numbers of women with moderate to severe TBI relative to men. For initial feasibility studies, the goals are to identify a relatively homogenous group of likely responders for treatment; therefore, biological sex and age are restricted. Women are enrolled in safety and efficacy studies and also older/younger adults.

Feasibility Study Inclusion: men, 25 to 50 years old, best GCS score<12 during first 24 hours post admission, positive radiologic findings indicative of TBI, clinically screened as having functional capacity to participate in symptom assessment batteries, informed consent (via subject or appropriate proxy) received within two months of injury or end of rehabilitation stay (whichever occurs first), initial dose received 72 hours before discharge from rehabilitation. Rehabilitation discharge is typically 1-3 months after moderate to severe TBI.

Study inclusion are prioritized to "likely responders", for feasibility studies. That is, patients having had acute care infection illness who are without signs/symptoms of active infection at the time of enrollment. Other individuals who may be likely responders could include those meeting criteria for lymphopenia (ABS lymphocyte counts ≤1 K/uL) and/or with a neutrophil to lymphocyte ratio of 10 for at least 2 time points during acute care. For IL-7 therapy, those with sTNFRI levels below 1500 pg/ml and also IL-7 levels below 25 pg/ml are included.

Safety and Efficacy Study Inclusion: men and women ages 18 to 75 are included if best GCS score<12 during first 24 hours post admission, positive radiologic findings indicative of TBI, clinically screened as having functional capacity to participate in symptom assessment batteries, informed consent (via subject or appropriate proxy) received within two months of injury. For safety and efficacy purposes, studies are conducted that include both women and men in a wider age group. For IL-7 therapy, those with sTNFRI levels below 1500 pg/ml are included. Individuals with IL-7 levels <25 pg/ml may be considered for high dosed rhIL-7 treatments, and those with levels above 25 pg/ml may be considered for low dose rhIL-7 treatment. Dosing structure is based on literature from trials cited above.

Exclusion: clinical/laboratory evidence of active infection, cancer requiring chemotherapy/radiotherapy currently or within last 6 months, hematologic malignancy or lymphoma, autoimmune diseases, HBV or HCV infection, solid organ or bone marrow transplant recipients, lymphocytic leukemia, AIDS-defining illness (category C), splenectomy, hematologic disease associated with hypersplenism, pregnant or lactating women, receiving immunosuppressive drugs (e.g., TNF-alpha inhibitors) or systemic corticosteroids, receiving concurrent immunotherapy or biologic agents, or prior exposure to IL-7 or drugs specifically targeting T cells, history of or active case of aplastic anemia or pancytopenia, thrombocytopenia, leukopenia, neutropenia, melanoma or Merkel cell carcinoma, or discharge to skilled nursing facility (wherein logistic/legal capacity to conducted follow up interviews/examinations is limited).

Dosing Regimen & Administration

CYT-107 is delivered via intra-muscular (IM) injection, or in cases of INR (International Normalized Ratio) >2.5 or platelet count <35,000, CYT-107 is administered subcutaneously.

Two dosing frequency regimens of CYT-107 were investigated in clinical trials related to the Immune Reconstitution of Immunosuppressed Sepsis (IRIS) patients to restore lymphocyte counts (Francois et al., JCIInsight. 2018;3(5)). Patients received either (1) CTY107 at 10 µg/kg twice a week for 4 weeks (high frequency) or (2) CYT107 at 10 µg/kg twice a week for the first week, followed by CYT107 and placebo once a week for the three following weeks. The low dose had a more dramatic effect on CD4+ T cell increases while the high dose effects on CD8+showed specific increases, and both dosing regimens maximized lymphocyte counts to upper normal of most hospital laboratories (3.5 K/µL) (Francois et al., JCIInsight. 2018;3(5)).

Dose escalation (10, 20 and 30 μg/kg) trials of 3 weekly doses have also been conducted in ARV-treated HIV patients with T cell counts between 0.1-0.4 K/μL (Levy et al., Clin Infect Dis. 2012; 55(2):291-300). Doses of CYT-107 up to 20 μg/kg were well tolerated (Levy et al., Clin Infect Dis. 2012; 55(2):291-300). Predominantly naïve and memory (rather than regulatory or activated) T cell increases were observed relatively early at 12 weeks and remained elevated up to one year. In addition to T cell proliferation, thymic output and T cell receptor diversity was increased as well at this dosage. Dose-limiting toxicity has been first observed at 30 μg/kg, accompanied by severe rash, transient grade 3 aminotransferase increase, and no neutralized anti-IL-7 antibody response (Levy et al., Clin Infect Dis. 2012; 55(2): 291-300). Notably the initial mouse data shows that higher dose rhIL-7 elicits an elevated IL-5 level compared to low dose and sham treatment.

Study dosing regimens are to range from 10 to 20 mg/kg and dosing frequency is to range from 1 to 3 times per week. The duration of any dosing regimen ranges from 2-8 weeks. Treatment could begin over a relatively wide window of recovery that spans post-acute to chronic time frames for neurorecovery.

Adverse Events & Symptoms

Participants are monitored closely by study staff for signs and symptoms of adverse reactions to treatment, particularly the development of infection, hematologic abnormalities, autoimmune complications, systemic reactions including flu/fever/fatigue, and joint/limb pain. Drug interactions with CYT-107 are largely unknown. Generally CYT-107 has been well tolerated amongst diverse patient populations across HIV and sepsis clinical trials without evidence of inducing cytokine storm or worsening inflammation or organ dysfunction (Mackall et al., *Nat Rev Immunol.* 2011; 11(5):330-342; Mazzucchelli et al., *Nat Rev Immunol.* 2007; 7(2):144-154; Francois et al., *JCI Insight.* 2018;3(5)). A serious adverse side effect observed has been rash (Francois et al., *JCI Insight.* 2018;3(5); Perales et al., *Blood.* 2012; 120(24): 4882-4891). All other serious adverse events resolved without further complications. Concurrent medications at the time of enrollment and treatment are recorded for evaluative purposes, particularly in the context of adverse side effects/events.

Feasibility Study

At—risk likely responders are enrolled into an RCT defined by those exhibiting lymphopenia (ABS lymphocytes <1K/uL or NLR>10) at a minimum of two time points during the individual's acute care stay and IL-7 levels <25pg/mL and sTNFR1 levels <1500 pg/ml. The present disclosure proposes that these criteria serve as biological proxies for impaired immunity, immunosuppressed states, and less AAb mediated tissue repair. The presently disclosed data suggests strong associations between endogenous IL-7 levels and other arms of immunity including: adaptive, innate, allergy and chemokine, and autoantibody markers. Therefore rhIL-7 (CTY-107) may serve as an immunoadjuvant to restore adaptive immunity, to boost protective autoimmunity in particular, and to mitigate adverse effects of other inflammatory pathways and secondary injury cascades that may contribute to poor outcome. The present disclosure recognizes through the presented data that low endogenous IL-7 levels in combination with high sTNFRI levels may contribute to further damage and risk for poor outcome.

The initial dose (Administration #1) is administered and monitored for 72 hours before inpatient rehabilitation discharge for physician monitoring of allergic reaction, fever, adverse change in mental status, evidence of a Stevens-Johnsons syndrome, or opportunistic infection. Remaining doses are administered at the discharge location. For an initial study, a total of four administrations of rhIL-7 or placebo is delivered over the course of one month at one dose per week. Administration must occur during a 48-hour window allotted for the weekly dose delivery. Windows for more frequent dosing may be used subsequently in other testing.

Thus dosing regimens are administered in conjunction with careful monitoring of IL-7, sTNFR, TNFα, AAb levels and other markers as endo-phenotypes for treatment response. The present disclosure also tracks symptoms, side effects, concurrent medications, and potential therapeutic effects for these studies. The presently disclosed current data suggest that IL-7 can have pleiotropic and lasting effects on immune function. However, soluble TNFR levels are not impacted by variable endogenous levels of IL-7. Nonetheless, the present disclosure assesses these levels and considers refinements in dosing strategy based on data in the context of both therapeutic and adverse treatment response.

Safety and Efficacy Studies:

The present disclosure uses endophenotype and symptoms data from feasibility studies to refine administration parameters for safety and efficacy studies done via RCT. Combination therapy with other immunological targets may be useful in modulating treatment effects to minimize adverse symptoms and side effects as well as shape immune response to optimize therapeutic effects.

The presently disclosed clinical data suggest that individuals with high sTNFRI levels may not respond well to rhIL-7 treatment when given as a monotherapy, and therefore these individuals would not be included in monotherapy trials. Further, the presently disclosed animal data suggests that rhIL-7 dosing can lead to variable changes in pro-inflammatory cytokine (e.g. IL-6) and allergy related cytokine levels (e.g. IL-5).

The initial dose (Administration #1) is administered and monitored for 72 hours before discharge for physician monitoring of allergic reaction, fever, adverse change in mental status, evidence of a Stevens-Johnsons syndrome, or opportunistic infection. Remaining doses are administered at the discharge location. Administration must occur during a 48-hour window allotted for the weekly dose delivery. Higher dose treatment, and increased frequency of treatment up to 3 times per week are studied to establish effective dosing across a range of initial IL-7 and AAb levels as well as identify dosing that optimizes treatment outcome. Windows for more frequent dosing may be used. Treatment can begin over a relatively wide window of recovery that spans post-acute to chronic time frames for neurorecovery.

A significant reduction in rates of persistent hypogonadotropic hypogonadism (PHH) was observed amongst the presently disclosed cohort in the high vs. low endogenous IL-7 trajectories (29.1 vs. 42.5%). Assuming a similar treatment response for those with low IL-7 levels, the present disclosure estimates an absolute risk reduction of 13% and numbers needed to treat (NNT) of 7. The data also show that, in the context of specific chemokine and soluble receptor environments, IL-7 can also have a significant and beneficial effect on global outcome indices like Glasgow outcome Scale (GOS) scores, which is commonly used as a treatment endpoint with acute neuroprotection trials involving the TBI population.

A relatively small-scale clinical trial cohort using rhIL-7 monotherapy may demonstrate efficacy, particularly in relation to a significant reduction in the exemplar condition of PHH with IL-7 mono-therapy. The lasting effect of CYT-107 on absolute lymphocyte counts for up to a year, even at lower dose administrations, may provide the immune reconstitution support to reduce PHH risk and other secondary conditions that negatively impact overall recovery.

Primary/Secondary Outcome Measures:

Blood Draws: Participants undergo a series of blood draws pre- and post-administration of ETN or placebo solution. An initial draw is taken in the rehabilitation facility to assess baseline state before initial dose administration. Subsequent blood draws occur prior to subsequent dose administration and then again for four consecutive weeks post-treatment and up to 6 to 24 months post-injury.

Adverse Events Symptoms Questionnaire: In addition to therapeutic outcomes, participants are monitored closely by a clinical consultant for signs and symptoms of adverse reactions to treatment, particularly the development of infection, hematologic abnormalities, and autoimmune complications Readouts for Intervention Feasibility

- Numbers screened to make enrollment targets
- Clinical and biological tolerance of rhIL-7 (serious adverse events, symptom profiles)
- rhIL-7 and sTNFR1 at enrollment and treatment
- Routine measurements of absolute lymphocyte counts (ALC), absolute neutrophil counts (ANC), NLR.
- Post-enrollment and treatment infection rates
- Hospital resource utilization metrics: hospital readmissions, Emergency Room Visits, relevant doctor appointments
- Global health status (Glasgow outcome Scale) at 6 months post-injury, including mortality Readouts for Clinical Safety

- Clinical and biological tolerance of IL-7 (serious adverse events, symptom profiles)
- IL-7 and sTNFR1 and IgM and IgG Auto antibodies at enrollment and treatment and post-treatment
- inflammatory immune panel at enrollment, treatment, and post-treatment
- Routine measurements of absolute lymphocyte counts (ALC), absolute neutrophil counts (ANC), NLR.
- Routine CBC, full metabolic and electrolyte panel
- Global health status (Glasgow outcome Scale) at 6 and 12 months post-injury, including mortality
- Post-enrollment and treatment infection rates
- Hospital resource utilization metrics: hospital readmissions, Emergency Room Visits, relevant doctor appointments.

Behavioral/Clinical Readouts for Treatment Effectiveness

- Global health status (Glasgow outcome Scale) at 6, 12 and 24 months post-injury, including mortality
- PHH Incidence at 6,12 and 24 months post-injury (for men) based on testosterone and Luteinizing hormone levels.
- Depression and Anxiety: 6, 12 and 24 months post injury. The Patient Health Questionnaire (PHQ)-9, a validated screening tool for major depression, is used to assess presence and severity of depressive symptoms (Donders et al., Arch Phys Med Rehabil. 2017; 98(12): 2514-2519). Component questions include energy levels, concentration, and mood. The Generalized Anxiety Disorder (GAD)-7 is administered to screen for anxiety symptoms (Plummer et al., Gen Hosp Psychiatry. 2016; 39:24-31).
- Fatigue: 6, 12 and 24 months post injury. The Patient Reported Outcomes Measurement Information System (PROMIS) Fatigue scale is utilized at six-months post injury to assess fatigue symptoms affecting daily life activities and participation (Carlozzi et al., Arch Phys Med Rehabil. 2011;92(10 Suppl):552-60). Standardized T-scores are generated for analysis with a mean=50 and SD=10.
- Neuropsychological Assessment: A Brief Test of Adult Cognition by Telephone (BTACT) is administered as a battery to characterize functioning of episodic memory, working memory, reasoning, verbal fluency, and executive function (Lachman et al., Assessment. 2014; 21(4): 404-417). Standardized T-scores are generated for analysis with a mean=50 and SD=10.
- Behavioral Assessment: The Behavioral Assessment Screening Tool (BAST) is administered as a self-report composite measure of behavioral and emotional symptoms using validated individual assessments of cognitive control and emotional state (Juengst et al., Disabil Rehabil. 2019; 41(10):1200-1206).
- Functional Outcome and Disability: Global recovery is assessed using the Glasgow Outcome Scale (GOS) scoring (Jennett et al., Lancet. 1975; 1(7905):480-484). The Disability Rating Scale (DRS) scoring system is used as a more granular assessment of recovery: 1) arousal & awareness, 2) cognitive ability for self-care, 3) physical dependence, 4) psychosocial adaptability for work, housework, or school (Rappaport M, et al., Arch Phys Med Rehabil. 1992; 73(7):628-634). TBI-Quality of Life (TBI-QOL) (Tulsky et al., J Head Trauma Rehabil. 2016; 31(1):40-51) and cognitive/motor scales of the Functional Independence Measure (FIM) (Cook et al., Arch Phys Med Rehabil. 1994; 75(4):390-393) are assessed.

Quantifiable Biological Readouts for Treatment Effectiveness:

- Consider serum as well as CNS derived exosomes for proteomic biomarkers.
- IL-7 and sTNFR1: taken at enrollment and treatment and post treatment.
- IgM and IgG Auto antibodies: taken at enrollment and treatment and post treatment.
- inflammatory immune panel: taken at enrollment, treatment, and post-treatment that includes other soluble receptors, chemokines etc.
- Weekly cellular markers: measurements of absolute lymphocyte counts (ALC), absolute neutrophil counts (ANC), NLR.
- Lymphocyte Cell type specific quantification: T-CD4+, T-CD8+, and T-CD127+(IL-7R) among others
- Quantification of IL-7 receptor: soluble and cellular CD127 expression, genetic expression.
- Quantification of circulating anti-CYT-107 antibodies: during and post treatment
- Quantification of T-Cell molecules: BDNF levels and Ki67 expression.

Example 18: Administration of Etanercept to Human Subjects

Management of care following moderate-to-severe traumatic brain injury (TBI) is a challenge in the neurotrauma field as physicians and caregivers try to address the heterogeneity in recovery profiles that TBI survivors have. The heterogeneity of this patient population is accompanied by variability in the acute secondary injury response. TBI can be particularly incapacitating by the degree to which homeostatic inflammatory mechanisms are disturbed. The primary injury causes cellular tissue damage and dysfunction in brain tissue, as well as dysregulation of immune cell dynamics.

Poor coordination of immune responder cells inflammatory signaling molecules contributes to an ineffective response to injury.

The initial injury disrupts homeostasis in immune functioning. The present disclosure demonstrated the occurrence of acute neutrophilia and lymphopenia in the first 3 weeks post-TBI. These phenomena result as a part of the systemic inflammatory response after hypothalamic-pituitary-adrenal (HPA) activation and the sympathetic surge after injury. Cortisol and catecholamine release lead to the dispersion of neutrophil stores while also increasing their lifespan (Rovlias et al., Surg Neurol. 2001; 55(4):190-196). Neutrophilia has also been reported to coincide with blood brain barrier breakdown and neurodegeneration (McKee et al., FrontImmunol. 2016; 7:556.), exacerbating secondary local and systemic damage through the increased oxidative activity of circulating neutrophils. The sustained elevation of neutrophil levels and contribute to neurodegenerative mechanisms and poor neurorecovery. Prolonged sympathetic activation can also increase lymphocyte apoptosis when prolonged, contributing to lymphopenia and immunosuppression in turn impacting the course of early recovery in acute care (Hazeldine et al., Front Neurol. 2015; 6:235). By integrating these concurrent biological phenomena, the neutrophil-to-lymphocyte ratio (NLR) can serve as a prognostic indicator of outcome in critical illness, additionally confirmed in patients with severe TBI. The coupling of excessive neutrophil levels along with low lymphocytes contribute to high acute NLR, aggravated by HPA axis activation following trauma, associated with unfavorable outcome and mortality 1 year after head trauma (Chen W et al., J Head Trauma Rehabil. 2018;33(1):E53-E59).

Ongoing imbalances in humoral signaling may contribute to chronic peripheral immune dysfunction after TBI. Damaging secondary biochemical cascades result from the biomechanics of TBI (Simon et al., Nat Rev Neurol. 2017; 13(3):171-191), of which post-traumatic inflammation is a significant component to clear cellular debris early after injury. Cytokine and chemokine pathways that are upregulated after trauma can remain elevated for long periods of time after the initial injury in both the CNS and periphery (McKee et al., Front Immunol. 2016;7.:556). Chronically, if not regulated, sustained elevation of certain inflammatory markers can be damaging, contributing to the cytotoxic microenvironment that leads to secondary cell death. This further affects neurological function, cognition, and functional outcome (Lozano et al., Neuro psychiatr Dis Treat. 2015; 11:97-106). Cytokine signaling is conditionally dependent on the state of the immune microenvironment. The shedding of the extracellular domain via proteolytic cleavage of transmembrane receptors generates soluble receptors that can act as either agonists or antagonists for cytokine signaling (Levine et al., J Biol Chem. 2008; 283 (21):14177-14181), often initiating pathogenic pathways such as in the case of tumor necrosis factor-α (TNFα).

The functional multiplicity of TNFα is determined via its interactions with TNFα receptor I (TNFRI) and TNFα receptor II (TNFRII), which exist in both transmembrane and soluble forms. Certain TBI studies using TNFα gene knockout mice show a neuroprotective role for TNFα (Scherbel et al., Proc Natl Acad Sci USA. 1999; 96(15): 8721-8726), which may be mediated by the powerful proinflammatory capacity of TNFα to signal cytokine and chemokine production, as well as cell-surface markers, to aid in tissue repair (Probert et al., Neuroscience. 2015; 302:2-22). Other studies demonstrate that TNFα contributes to brain edema and cell death (Ziebell et al., Neurotherapeutics. 2010; 7(1):22-30). TNFα has the ability to induce apoptosis primarily via its ubiquitous type I transmembrane receptor, which further influences oxidative activity implicated in TNF-induced apoptosis as well (Rath et al., J Clin Immunol. 1999; 19(6):350-364). This may explain why elevated TNFα levels have been associated with unfavorable outcome in TBI studies (Ziebell et al., Neurotherapeutics. 2010; 7(1):22-30; Santarsieri et al., Brain Behav Immun. 2015; 45:15-27). In contrast, membrane-bound TNFRII activation, almost exclusively limited to immune cells, protects cells from apoptosis by stimulating anti-oxidative and cell-survival pathways, promoting tissue regeneration, and suppressing TNFα-induced inflammation (Cope et al., Immunology. 1995; 84(1):21-30; Yang et al., Front Immunol. 2018;9; Szondy et al., Pharmacol Res. 2017;115:124-132) Relative concentrations of cytokines to their respective soluble receptors can also serve as a proxy for the favorable or injurious conditions affecting neurorepair and recovery. The present disclosure demonstrated persistent chronic systemic inflammation for which there are potential therapeutic targets that can be explored, including chronic soluble TNF receptors (sTNFR). The data suggest chronic sTNFRI is associated with the excessive neutrophil levels and low lymphocyte levels (i.e. high NLR) exhibited in the target treatment population, along with secondary nosocomial infection, observed after TBI. The present disclosure shows that sTNFRI is a key biological relationship in mediating long-term global outcome, persistent hypogonadotropic hypogonadism (PHH) and post-traumatic epilepsy (PTE). Chronically-elevated soluble TNF receptors then have the ability to activate transmembrane TNF receptors to induce apoptotic cell death over longer periods of time in a broadened range of cells[9]. Thus, inhibition of the TNFα apoptotic pathways serves as a viable therapeutic target in mitigating the chronic manifestations of acute lymphopenia. The preclinical data suggest functional, behavioral, and immune deficits and chronic inflammation after TBI, for which treatment with Etanercept (ETN) has restorative effects. TNFα/TNFRI can serve as modifiable biological targets affecting innate and adaptive immunity, further influencing recovery after injury.

The present disclosure suggests that acute lymphopenia in the first 3 weeks post-TBI may be at least in part due to perturbations in TNFα signaling. The present disclosure demonstrated a link between high NLR, serving as a novel acute immune marker, and chronic sTNFR signaling. These serve as key prognostic markers predicting long-term functional outcome, identifying subjects likely to respond to TNFα inhibitor therapy, and evidence of treatment effects. The present disclosure uses ETN as a therapeutic agent for treating the effects of TBI in the post-acute and chronic phases of recovery. The potential for beneficial post-acute effects on relevant TBI outcomes is supported, at least indirectly, by some studies showing benefits of treatment on endpoints like cognition and mood (refs from AHA grant below).

Although Etanercept does not readily traverse the blood brain barrier, a body of work has begun to emerge suggesting that systemic treatment with Etanercept can have beneficial effects on CNS function (e.g. cognition, mood) and when given chronically after neurological injuries like stroke and TBI (Thomson et al., Core Evid. 2007; 2(1):51-62; Asadullah et al., Eur J Emerg Med. 1995; 2(4):184-190; Woiciechowsky et al., Nat Med. 1998; 4(7):808-813) and other encephalopathies (Lattanzi et al., Stroke. 2016; 47(6): 1654-1657), and when given in the context of autoimmune and chronic disease (Chrousos et al., N Engl J Med. 1995;

332(20):1351-1362) and in the setting of dementia (Probert et al., *Neuroscience*. 2015; 302:2-22). Rodent studies of retinal degeneration also have shown systemic Etanercept administration can have an impact on CNS function (Probert et al., *Neuroscience*. 2015; 302:2-22; Waage et al., *Leukemia & Lymphoma*. 1994;13(1-2):41-46). The present disclosure recognizes that systemic immunomodulation therapy with the TNFα inhibitor, Etanercept, may be useful to treat TBI related impairments.

Drug Description

ETN is an anti-TNFα agent that functions as an anti-inflammatory soluble decoy receptor to inhibit chronic (Tuttolomondo et al., *Drug Des Devel Ther*. 2014;8:2221-2239) TNFα signaling by binding circulating TNFα and neutralizing its bioactivity (Pandey et al., *Am J Pathol*. 2003; 162(3):933-941; Waetzig et al., *The FASEB Journal*. 2004; 19(1):91-93; Probert et al., *Neuroscience*. 2015; 302:2-22). This TNFα antagonist is a recombinant dimeric fusion protein that takes the form of 2 sTNFRII molecules linked to IgG1 and acts as a TNFα scavenger, inhibiting the propagation of further TNFα-induced inflammatory cascades (Waage et al., *Leukemia & Lymphoma*. 1994;13(1-2): 41-46; Maier et al., *Shock*. 2006; 26(2):122-127). The dimeric structure allows it to bind 2 TNF molecules, thus being more effective than monomeric sTNFRs at neutralizing TNFα activity. The binding of TNFα to ETN blocks interactions with cell surface receptors to prevent TNFα-mediated inflammatory responses (Scott et al., *Drugs*. 2014; 74(12):1379-1410). ETN can be absorbed slowly from subcutaneous tissue, reaching maximum serum concentrations 48 hours after a single dose with similar pharmacokinetic properties between men and women and across ages (Scott et al., *Drugs*. 2014; 74(12):1379-1410). This TNFα antagonist has anti-inflammatory effects to alleviate chronic inflammation (Tuttolomondo et al., *Drug Des Devel Ther*. 2014; 8:2221-2238).

Post-acute administration of ETN mitigates the perpetuating inflammatory cascades into the chronic recovery phase, and, in turn, alleviate inflammatory-based clinical complications. While certain preclinical studies suggest that acute ETN administration, while blood-brain-barrier is compromised, may have some beneficial effects in rodent TBI model (Campbell et al., *J Neurochem*. 2007; 103(6):2245-2255; Chio et al., *J Neurochem*. 2010; 115(4):921-929), no post-acute studies experimental TBI studies have been reported with this drug. Also, no clinical studies exist examining ETN effects at any time point post-injury.

The Federal Drug Administration (FDA) in the United States currently licenses ETN for the following conditions: Rheumatoid Arthritis, Psoriatic Arthritis, Juvenile Idiopathic Arthritis, Ankylosing Spondylitis, and Plaque Psoriasis.

The present disclosure provides a biomarker-based treatment protocol for those with moderate to severe TBI, have survived to acute care discharge, and are participating in an in-patient rehabilitation treatment program where appropriate consent and monitoring can be provided (FIG. 85).

Participant Recruitment & Screening for Studies

Study participants are recruited prospectively during their in-patient rehabilitation stay following TBI. Same as example 17, women are not enrolled into initial feasibility study Feasibility Study Inclusion: men, 25 to 50 years old, best GCS score<12 during first 24 hours post admission, positive radiologic findings indicative of TBI, clinically screened as having functional capacity to participate in symptom assessment batteries, informed consent (via subject or appropriate proxy) received within two months of injury or end of rehabilitation stay (whichever occurs first), initial dose received 72 hours before discharge from rehabilitation, which is typically 1-3 months after moderate to severe TBI.

Study inclusion is prioritized to "likely responders", for feasibility studies. That is, patients having had acute care infection illness who are without signs/symptoms of active infection at the time of enrollment. Other individuals who may be likely responders could include those meeting criteria for lymphopenia (ABS lymphocyte counts ≤1 K/uL) and/or with a neutrophil to lymphocyte ratio of 10 or more for at least 2 time points during acute care. For Etanercept therapy, those with sTNFRI levels above 1200-1500 pg/ml are included in the protocol.

Safety and Efficacy Study Inclusion: men and women ages 18 to 75 are included if best GCS score<12 during first 24 hours post admission, positive radiologic findings indicative of TBI, clinically screened as having functional capacity to participate in symptom assessment batteries, informed consent (via subject or appropriate proxy) received within two months of injury. For safety and efficacy purposes, studies are conducted that include both women and men in a wider age group. For Etanercept therapy, those with sTNFRI levels above 1200-1500 pg/ml are included. Individuals with sTNFRI levels >2000 pg/ml may be considered for higher dosed etanercept treatments. Dosing structure is based on literature from trials cited above.

Exclusion: Clinical/laboratory evidence of active infection, cancer requiring chemotherapy/radiotherapy currently or within last 6 months, hematologic malignancy or lymphoma, autoimmune diseases, HBV or HCV infection, solid organ or bone marrow transplant recipients, lymphocytic leukemia, AIDS-defining illness (category C), splenectomy, hematologic disease associated with hypersplenism, pregnant or lactating women, active receipt of other immunosuppressive drugs (e.g., TNF-α inhibitors) or systemic corticosteroids, receiving concurrent immunotherapy or biologic agents, or prior exposure to IL-7 or drugs specifically targeting T cells, history of or active case of aplastic anemia or pancytopenia, thrombocytopenia, leukopenia, neutropenia, melanoma or Merkel cell carcinoma, or discharge to skilled nursing facility (wherein logistic/legal capacity to conducted follow up interviews/examinations is limited).

Dosing Regimen & Administration

The clinical coordinator injects a subcutaneous (SC) solution of FDA-approved ETN or placebo into the thigh, abdomen, or outer upper arm of the participant. In addition to the exclusions above, patients need to be afebrile (T<37.5° C.) and not on any antibiotics for at least 72 hours prior to dose administration. 25-50 mg is administered per dose at variable frequency.

Feasibility studies: The present disclosure enrolls at-risk likely responders into an RCT defined by those exhibiting lymphopenia (ABS lymphocytes <1K/uL or NLR>10) at a minimum of two time points during the individual's acute care stay and baseline sTNFR1 levels >1500 pg/ml. The present disclosure proposes that these initial criteria serve as biological proxies for impaired immunity, immunosuppressed states, and less AAb mediated tissue repair.

The initial dose (Administration #1) (25 mg) is administered and monitored for 72 hours before discharge for physician monitoring of allergic reaction, fever, adverse change in mental status, evidence of a Stevens-Johnsons syndrome, or opportunistic infection. Remaining doses are administered at the discharge location. As an initial study, a total of four administrations of ETN or placebo is delivered over the course of one month at one dose per week.

Administration must occur during a 48-hour window allotted for the weekly dose delivery. Windows for more frequent dosing may be used subsequently. Treatment could begin over a relatively wide window of recovery that spans post-acute to chronic time frames for neurorecovery.

Thus, dosing regimens are administered in conjunction with careful monitoring of IL-7, sTNFR, TNFα, AAb levels and other markers as endo-phenotypes for treatment response. The present disclosure also tracks symptoms, side effects, concurrent medications, and potential therapeutic effects for these studies. The present disclosure assesses these levels and considers refinements in dosing strategy based on laboratory data in the context of both therapeutic and adverse treatment response.

Safety and Efficacy Studies: As in Example 17, the present disclosure uses endophenotype and symptoms data from feasibility studies to refine administration parameters for safety and efficacy studies done using RCT. Combination therapy with other immunological targets may be useful in modulating treatment effects to minimize adverse symptoms and side effects as well as shape immune response to optimize therapeutic effects.

The initial dose (Administration #1) (25 mg) is administered and monitored for 72 hours before discharge for physician monitoring of allergic reaction, fever, adverse change in mental status, evidence of a Stevens-Johnsons syndrome, or opportunistic infection. Remaining doses are administered at the discharge location. Higher dose treatment (up to 50 mg), and increased frequency of treatment up to 3 times per week is studied to establish effective dosing across a range of initial sTNFR1 and TNFα levels as well as identify dosing that optimizes treatment outcome. Windows for more frequent dosing may be used. Treatment could begin over a relatively wide window of recovery that spans post-acute to chronic time frames for neurorecovery.

A significant reduction in rates of persistent hypogonadotropic hypogonadism (PHH) was observed amongst the cohort in the high vs. low endogenous sTNFR trajectories (24.5 vs. 46.5%). Assuming a similar treatment response for those with high sTNFRI levels, the present disclosure estimates an absolute risk reduction of 22% and numbers needed to treat (NNT) of 5. The presently disclosed data also show that, in the context of specific chemokine and soluble receptor environments, TNFα inhibition can also have a significant and beneficial effect on global outcome indices like Glasgow outcome Scale (GOS) scores, which is commonly used as a treatment endpoint with acute neuroprotection trials involving the TBI population. Based on sTNFR trajectories, absolute risk reduction for poor GOS is 31%, with a NNT=3. Absolute risk reduction for DRS is 17% with NNT=6. Absolute risk reduction is 13% with NNT=8. Based on these data, a relatively small-scale clinical trial cohort using Etanercept monotherapy may demonstrate efficacy, particularly in relation to a significant reduction TBI related impairments such as PHH, PTE, GOS, and DRS.

Adverse Events & Symptoms

Participants are monitored closely by study staff for signs and symptoms of adverse reactions to treatment, particularly the development of infection, hematologic abnormalities, autoimmune complications, systemic reactions including flu/fever/fatigue, and joint/limb pain. Drug interactions with Etanercept include increased infection and neutropenia with Anakinra in rheumatoid arthritis, increased adverse events when administered concurrently with Abatacept, and decreased white blood cell count when given as a combination therapy with sulfasalazine. No interactions of Etanercept administered with glucocorticoids, nonsteroidal anti-inflammatory drugs, methotrexate, or analgesics. Phase III clinical trial of Etanercept have demonstrated no overall age-related differences in adverse events or response to treatment (Scott et al., *Drugs.* 2014; 74(12):1379-1410). Concurrent medications at the time of enrollment and treatment is recorded for evaluative purposes, particularly in the context of adverse side effects/events.

Primary/Secondary Outcome Measures:

Blood Draws: Participants undergo a series of blood draws pre- and post-administration of ETN or placebo solution. An initial draw is taken in the rehabilitation facility to assess baseline state before initial dose administration. Subsequent blood draws occur prior to subsequent dose administration and then again for four consecutive weeks post-treatment and up to 6 to 24 months post-injury.

Adverse Events Symptoms Questionnaire: In addition to therapeutic outcomes, participants are monitored closely by a clinical consultant for signs and symptoms of adverse reactions to treatment, particularly the development of infection, hematologic abnormalities, and autoimmune complications. Multiple drugs interact with ETN including: live vaccines, anakinra, abatacept, cyclophosphamide, and sulfasalazine, and use are tracked as exclusion criteria.

Readouts for Intervention Feasibility
  Numbers screened to make enrollment targets
  Clinical and biological tolerance of etanercept (serious adverse events, symptom profiles)
  IL-7 and sTNFR1 levels at enrollment and treatment
  Routine measurements of absolute lymphocyte counts (ALC), absolute neutrophil counts (ANC), NLR.
  Post-enrollment and treatment infection rates
  Hospital resource utilization metrics: hospital readmissions, Emergency Room Visits, relevant doctor appointments
  Global health status (Glasgow outcome Scale) at 6 months post-injury, including mortality Readouts for Clinical Safety
  Clinical and biological tolerance of IL-7 (serious adverse events, symptom profiles)
  IL-7 and sTNFR1 and IgM and IgG Auto antibodies at enrollment and treatment and post-treatment
  inflammatory immune panel at enrollment, treatment, and post-treatment
  Routine measurements of absolute lymphocyte counts (ALC), absolute neutrophil counts (ANC), NLR.
  Routine CBC, full metabolic and electrolyte panel
  Global health status (Glasgow outcome Scale) at 6 and 12-months post-injury, including mortality
  Post-enrollment and treatment infection rates
  Hospital resource utilization metrics: hospital readmissions, Emergency Room Visits, relevant doctor appointments.

Behavioral/Clinical Readouts for Treatment Effectiveness
  Global health status (Glasgow Outcome Scale) at 6—and 12—and 24-months post-injury, including mortality
  PHH Incidence at 6, 12 and 24-months post-injury (for men) based on testosterone and Luteinizing hormone levels.
  Depression and Anxiety: 6, 12, and 24-months post injury. The Patient Health Questionnaire (PHQ)-9, a validated screening tool for major depression, are used to assess presence and severity of depressive symptoms (Donders et al., *Arch Phys Med Rehabil.* 2017; 98(12): 2514-2519). Component questions include energy levels, concentration, and mood. The Generalized Anxiety Disorder (GAD)-7 are administered to screen for anxiety symptoms (Plummer et al., *Gen Hosp Psychiatry.* 2016; 39:24-31).

Fatigue: 6—and 12—and 24-months post injury. The Patient Reported Outcomes Measurement Information System (PROMIS) Fatigue scale is utilized at six-months post injury to assess fatigue symptoms affecting daily life activities and participation (Carlozzi et al., *Arch Phys Med Rehabil.* 2011;92(10 Suppl):S52-60). Standardized T-scores are generated for analysis with a mean=50 and SD=10.

Neuropsvchological Assessment: A Brief Test of Adult Cognition by Telephone (BTACT) is administered as a battery to characterize functioning of episodic memory, working memory, reasoning, verbal fluency, and executive function (Lachman et al., *Assessment.* 2014; 21(4): 404-417). Standardized T-scores are generated for analysis with a mean=50 and SD=10.

Behavioral Assessment: The Behavioral Assessment Screening Tool (BAST) is administered as a self-report composite measure of behavioral and emotional symptoms using validated individual assessments of cognitive control and emotional state (Juengst et al., *Disabil Rehabil.* 2019; 41(10):1200-1206).

Functional Outcome and Disability: Global recovery is assessed using the Glasgow Outcome Scale (GOS) scoring (Jennett et al., *Lancet.* 1975; 1(7905):480-484). The Disability Rating Scale (DRS) scoring system is also used in the same way as Example 17.

Quantifiable Biological Readouts for Treatment Effectiveness:

Consider serum as well as CNS derived exosomes for proteomic biomarkers.

IL-7 and sTNFR1: taken at enrollment and treatment and post treatment.

IgM and IgG Auto antibodies: taken at enrollment and treatment and post treatment.

inflammatory immune panel: taken at enrollment, treatment, and post-treatment that includes other soluble receptors, chemokines etc.

Weekly cellular markers: measurements of absolute lymphocyte counts (ALC), absolute neutrophil counts (ANC), NLR.

Lymphocyte Cell type specific quantification: T-CD4+, T-CD8+, and T-CD127+(IL-7R) among others Quantification of other inflammatory markers: chemokines (RANTES, ITAC), soluble receptors (sIL-2ra, sTNFRII) genetic expression.

Quantification of circulating anti-etanercept antibodies: during and post treatment Quantification of T-Cell molecules: BDNF levels and Ki67 expression.

Example 19: Dual Immunotherapy

The presently disclosed animal data supports treatment effects in the context of TBI. It suggests that Etanercept (ETN) has restorative effects on functional, behavioral and immune deficits and inflammation after TBI, including reductions in brain tissue levels of TNFα. The presently disclosed data on rhIL-7 treatment in mice also shows behavioral improvements and evidence of lymphoproliferation after TBI. Dose response data with low and high dose rhIL-7 shows that while high doses result in higher levels of proinflammatory markers like IL-6 while low dose rhIL-7 shows reduced levels of IL-6 compared to uninjured controls. These data suggest the need for dual therapy as the present disclosure shows that etanercept administration reduces serum IL-6 levels; that is Etanercept treatment may curb rises in innate and other elements of immunity observed with higher rhIL-7 dosing. Clinically, the present disclosure found that low endogenous levels of IL-7 in combination with high sTNFRI levels may contribute to further damage and risk for poor outcome. Furthermore, these individuals may experience chronically elevated immune-mediated inflammation coupled with aggravated immunosuppression. TBI patients with higher sTNFRI levels and lower IL-7 levels will benefit from a dual therapy of rIL-7 and ETN to mitigate the adverse chronic inflammation while also working to boost immune response, overall leading to better long-term outcomes and sustained neuro-recovery.

The present disclosure provides a biomarker-based algorithm for implementing a clinical trial to test this hypothesis among likely responders. The present disclosure provides treating subjects with moderate to severe TBI who are in the post-acute phase of injury and/or early chronic phase of recovery for implementing a dual therapy approach of rIL-7 and ETN.

The present disclosure provides a biomarker-based treatment protocol for those with moderate to severe TBI, have survived to acute care discharge, and are participating in an in-patient rehabilitation treatment program where appropriate consent and monitoring can be provided. The present disclosure additionally identifies groups of individuals who will benefit from monotherapy of CYT-107 or Etanercept, as well as a subgroup of individuals who will require dual therapy of both interventions.

Participant Recruitment & Screening for Studies

Study participants are recruited prospectively during their in-patient rehabilitation stay following TBI. Same as Example 17, women are not enrolled into initial feasibility study.

Feasibility Study Inclusion: men, 25 to 50 years old, best GCS score<12 during first 24 hours post admission, positive radiologic findings indicative of TBI, clinically screened as having functional capacity to participate in symptom assessment batteries, informed consent (via subject or appropriate proxy) received within two months of injury or end of rehabilitation stay (whichever occurs first), initial dose received 72 hours before discharge from rehabilitation.

Study inclusion is prioritized to "likely responders", for feasibility studies. CYT-107 likely responders include patients having had acute care infection illness who are without signs/symptoms of active infection at the time of enrollment as well as individuals who may be likely responders could include those meeting criteria for lymphopenia (ABS lymphocyte counts ≤1 K/uL) and/or with a neutrophil to lymphocyte ratio of 10 for at least 2 time points during acute care. All IL-7 likely responders additionally have sTNFRI levels below 1200-1500 pg/ml. Etanercept likely responders include individuals with sTNFRI levels above 1200-1500 pg/ml. For dual CYT-107 and Etanercept therapy, those with sTNFRI levels above 1200-1500 pg/ml and also IL-7 levels below 25 pg/ml are included.

Safety and Efficacy Study Inclusion: men and women ages 18 to 75 are included if best GCS score<12 during first 24 hours post admission, positive radiologic findings indicative of TBI, clinically screened as having functional capacity to participate in symptom assessment batteries, informed consent (via subject or appropriate proxy) received within two months of injury. For safety and efficacy purposes, studies are conducted that include both women and men in a wider age group. For dual CYT-107 and Etanercept therapy, those with sTNFRI levels above 1200-1500 pg/ml and also IL-7 levels below 25 pg/ml are included. Individuals with IL-7 levels at or below 25 pg/ml may be considered for high dosed rhIL-7 treatments, and those with levels above 25 pg/ml may be considered for low dose rhIL-7 treatment. Dosing structure is based on literature from trials cited above.

Exclusion: clinical/laboratory evidence of active infection, cancer requiring chemotherapy/radiotherapy currently or within last 6 months, hematologic malignancy or lymphoma, autoimmune diseases, HBV or HCV infection, solid organ or bone marrow transplant recipients, lymphocytic leukemia, AIDS-defining illness (category C), splenectomy, hematologic disease associated with hypersplenism, pregnant or lactating women, receiving of other immunosuppressive drugs or systemic corticosteroids, receiving concurrent immunotherapy or biologic agents, or prior exposure to IL-7 or drugs specifically targeting T cells, history of or active case of aplastic anemia or pancytopenia, thrombocytopenia, leukopenia, neutropenia, melanoma or Merkel cell carcinoma, or discharge to skilled nursing facility (wherein logistic/legal capacity to conducted follow up interviews/examinations is limited).

Dosing Regimen & Administration

CYT-107 is delivered via intra-muscular (IM) injection, or in cases of INR (International Normalized Ratio) >2.5 or platelet count <35,000, CYT-107 are administered subcutaneously. The present disclosure provides dosing regimens to range from 10 to 20 mg/kg and dosing frequency to range from 1 to 3 times per week. The duration of any dosing regimen ranges from 2-8 weeks.

A subcutaneous (SC) solution of FDA-approved Etanercept or placebo is injected into the into the thigh, abdomen, or outer upper arm of the participant. In addition to the exclusions above, patients need to be afebrile (T<37.5° C.) and not on any antibiotics for at least 72 hours prior to Etanercept administration. 25-50 mg of Etanercept is administered per dose at variable frequency, likely 1 to 2 times per week for 4 to 8 weeks.

Adverse Events & Symptoms

Participants are monitored closely by study staff for signs and symptoms of adverse reactions to treatment, particularly the development of infection, hematologic abnormalities, autoimmune complications, systemic reactions including flu/fever/fatigue, and joint/limb pain. Drug interactions with CYT-107 are largely unknown. Generally, CYT-107 has been well tolerated amongst diverse patient populations across HIV and sepsis clinical trials without evidence of inducing cytokine storm or worsening inflammation or organ dysfunction (Yang et al., *FrontImmunol.* 2018;9; Tuttolomondo et al., *Drug Des Devel Ther.* 2014; 8:2221-2238; Campbell et al., *J Neurochem.* 2007; 103(6):2245-2255). The only serious adverse side effect observed has been rash (Yang et al., *Front Immunol.* 2018;9; Pandey et al., *Am J Pathol.* 2003; 162(3):933-941). All other serious adverse events resolved without further complications. Drug interactions with Etanercept include increased infection and neutropenia with Anakinra in rheumatoid arthritis, increased adverse events when administered concurrently with Abatacept, and decreased white blood cell count when given as a combination therapy with sulfasalazine. Concurrent medications at the time of enrollment and treatment are recorded for evaluative purposes, particularly in the context of adverse side effects/events.

Feasibility Studies

The present disclosure provides enrolls at-risk likely responders into an RCT defined by those exhibiting lymphopenia (ABS lymphocytes <1K/uL or NLR>10) at a minimum of two time points during the individual's acute care stay and baseline IL-7 levels <25pg/mL and sTNFR1 levels greater than 1200-1500 pg/ml. The present disclosure provides proposes that these initial criteria serve as biological proxies for impaired immunity, immunosuppressed states, elevated TNF-α, signaling, and less AAb mediated tissue repair. The presently disclosed data suggests strong associations between endogenous IL-7 levels and other arms of immunity including: adaptive, innate, allergy and chemokine, and autoantibody markers. Therefore, rhIL-7 (CTY-107) may serve as an immuno-adjuvant to restore adaptive immunity, boost protective autoimmunity in particular, and to mitigate adverse effects of other inflammatory pathways and secondary injury cascades that may contribute to poor outcome.

The present disclosure provides recognizes that low endogenous IL-7 levels in combination with high sTNFRI levels may contribute to further damage and risk for poor outcome. The data additionally shows that individuals with elevated sTNFRI levels but lowered endogenous IL-7 levels may experience poor outcome due to chronic elevated immune-mediated inflammation in addition to exacerbated immunosuppression. These individuals uniquely benefit from a dual therapy of Etanercept to mitigate adverse inflammatory effects while rhIL-7 (CTY-107) boost immune response and alleviate possible immunodeficiency.

The initial dose (Administration #1) of Etanercept and/or CTY-107 is administered and monitored for 72 hours before discharge for physician monitoring of allergic reaction, fever, adverse change in mental status, evidence of a Stevens-Johnsons syndrome, or opportunistic infection. Remaining doses are administered at the discharge location. For an initial study, a total of four administrations of rhIL-7 and/or Etanercept or placebos is delivered over the course of one month at one dose per week. Administration must occur during a 48-hour window allotted for the weekly dose delivery. Windows for more frequent dosing may be used subsequently.

Thus, dosing regimens are administered in conjunction with careful monitoring of IL-7, sTNFR, TNFα, AAb levels and other markers as endo-phenotypes for treatment response. The present disclosure provides also track symptoms, side effects, concurrent medications, and potential therapeutic effects for these studies. the current data suggest that IL-7 can have pleiotropic and lasting effects on immune function. The present disclosure provides additionally assesses sTNFRI levels and also consider refinements in dosing strategy based on laboratory data in the context of both therapeutic and adverse treatment response.

Safety and Efficacy Studies:

The present disclosure provides uses endophenotype and symptoms data from feasibility studies to refine administration parameters for safety and efficacy studies done via RCT. Combination therapy with other immunological targets may be useful in modulating treatment effects to minimize adverse symptoms and side effects as well as shape immune response to optimize therapeutic effects. Further, the animal data suggests that rhIL-7 dosing could lead to variable changes in pro-inflammatory cytokine (e.g. IL-6) and allergy related cytokine levels (e.g. IL-5).

The initial dose (Administration #1) is administered and monitored for 72 hours before discharge for physician monitoring of allergic reaction, fever, adverse change in mental status, evidence of a Stevens-Johnsons syndrome, or opportunistic infection. Remaining doses are administered at the discharge location. Administration should occur during a 48-hour window allotted for the weekly dose delivery. Higher dose treatment, and increased frequency of treatment up to 3 times per week are studied to establish effective dosing across a range of initial IL-7, sTNFRI, and AAb levels as well as identify dosing that optimizes treatment outcome. Windows for more frequent dosing may be used.

A significant reduction in rates of persistent hypogonadotropic hypogonadism (PHH) was observed amongst the presently disclosed cohort in dual-therapy treatment (High sTNFRI, Low IL-7 TRAJ's) vs no-treatment or endogenously ideal group (Low sTNFRI, High IL-7 TRAJ's) (51.4 vs. 14.3%). Assuming a similar treatment response for those with low IL-7 levels, the present disclosure provides estimates an absolute risk reduction of 37.1% and numbers needed to treat (NNT) of 3. The presently disclosed data also show that, in the context of specific chemokine and soluble receptor environments, elevated IL-7 and lowered sTNFRI can also have a significant and beneficial effect on global outcome indices like Glasgow outcome Scale (GOS) scores, which is commonly used as a treatment endpoint with acute neuroprotection trials involving the TBI population.

A relatively small-scale clinical trial cohort using rhIL-7 and TNFα inhibitor dual-therapy may demonstrate efficacy, particularly in relation to a significant reduction in the exemplar condition of PHH and in improving global outcome. By reducing the soluble receptor signaling of TNFα following TBI, Etanercept may mitigate chronic damage of elevated inflammation following moderate-to-severe TBI, while the lasting effect of CYT-107 on absolute lymphocyte counts for up to a year, even at lower dose administrations, may provide the immune reconstitution support to reduce PHH risk and other secondary conditions that negatively impact overall recovery=.

Primary/Secondary Outcome Measures:
  Blood Draws: Participants undergo a series of blood draws pre- and post-administration of ETN or placebo solution. An initial draw is taken in the rehabilitation facility to assess baseline state before initial dose administration. Subsequent blood draws occur prior to subsequent dose administration and then again for four consecutive weeks post-treatment and up to 6 to 24 months post-injury.
  Adverse Events Symptoms Questionnaire: In addition to therapeutic outcomes, participants are monitored closely by a clinical consultant for signs and symptoms of adverse reactions to treatment, particularly the development of infection, hematologic abnormalities, and autoimmune complications Readouts for Intervention Feasibility
    Numbers screened to make enrollment targets
    Clinical and biological tolerance of rhIL-7 (serious adverse events, symptom profiles)
    rhIL-7 and sTNFR1 at enrollment and treatment
    Routine measurements of absolute lymphocyte counts (ALC), absolute neutrophil counts (ANC), NLR.
    Post-enrollment and treatment infection rates
    Hospital resource utilization metrics: hospital readmissions, Emergency Room Visits, relevant doctor appointments
    Global health status (Glasgow outcome Scale) at 6 months post-injury, including mortality Readouts for Clinical Safety
    Clinical and biological tolerance of IL-7 (serious adverse events, symptom profiles)
    IL-7 and sTNFR1 and IgM and IgG Auto antibodies at enrollment and treatment and post-treatment
    inflammatory immune panel at enrollment, treatment, and post-treatment
    Routine measurements of absolute lymphocyte counts (ALC), absolute neutrophil counts (ANC), NLR.
    Routine CBC, full metabolic and electrolyte panel
    Global health status (Glasgow outcome Scale) at 6 and 12 months post-injury, including mortality
    Post-enrollment and treatment infection rates
    Hospital resource utilization metrics: hospital readmissions, Emergency Room Visits, relevant doctor appointments.
Behavioral/Clinical Readouts for Treatment Effectiveness
    Global health status (Glasgow outcome Scale) at 6, and 24 months post-injury, including mortality
    PHH Incidence at 6, 12 and 24 months post-injury (for men) based on testosterone and Luteinizing hormone levels.
    Depression and Anxiety: 6, 12 and 24 months post injury. The Patient Health Questionnaire (PHQ)-9, a validated screening tool for major depression, is used to assess presence and severity of depressive symptoms (Donders et al., *Arch Phys Med Rehabil.* 2017; 98(12): 2514-2519). Component questions include energy levels, concentration, and mood. The Generalized Anxiety Disorder (GAD)-7 is administered to screen for anxiety symptoms (Plummer et al., *Gen Hosp Psychiatry.* 2016; 39:24-31).
    Fatigue: 6, 12 and 24 months post injury. The Patient Reported Outcomes Measurement Information System (PROMIS) Fatigue scale is utilized at six-months post injury to assess fatigue symptoms affecting daily life activities and participation (Carlozzi et al., *Arch Phys Med Rehabil.* 2011;92(10 Suppl):552-60). Standardized T-scores are generated for analysis with a mean=50 and SD=10.
    Neuropsychological Assessment: A Brief Test of Adult Cognition by Telephone (BTACT) is administered as a battery to characterize functioning of episodic memory, working memory, reasoning, verbal fluency, and executive function (Lachman et al., *Assessment.* 2014; 21(4): 404-417). Standardized T-scores are generated for analysis with a mean=50 and SD=10.
    Behavioral Assessment: The Behavioral Assessment Screening Tool (BAST) is administered as a self-report composite measure of behavioral and emotional symptoms using validated individual assessments of cognitive control and emotional state (Juengst et al., *Disabil Rehabil.* 2019; 41(10):1200-1206).
    Global recovery is assessed using the Glasgow Outcome Scale (GOS) scoring (Jennett et al., *Lancet.* 1975; 1(7905):480-484). The Disability Rating Scale (DRS) scoring system is used the same way as Example 17.
Quantifiable Biological Readouts for Treatment Effectiveness:
    Consider serum as well as CNS derived exosomes for proteomic biomarkers.
    IL-7 and sTNFR1: taken at enrollment and treatment and post treatment.
    IgM and IgG Auto antibodies: taken at enrollment and treatment and post treatment.
    immune panel: taken at enrollment, treatment, and post-treatment that includes other soluble receptors, chemokines etc.
    Weekly cellular markers: measurements of absolute lymphocyte counts (ALC), absolute neutrophil counts (ANC), NLR.
    Lymphocyte Cell type specific quantification: T-CD4+, T-CD8+, and T-CD127+(IL-7R) among others Quantification of IL-7 receptor: soluble and cellular CD127 expression, genetic expression.

Quantification of circulating anti-CYT-107 antibodies: during and post treatment Quantification of T-Cell molecules: BDNF levels and Ki67 expression.

Example 20: Treelet Methods Used herein

Treelet transform (TT) is a statistical tool of dimension reduction (Gorst-Rasmussen et al., Stata Journal. 2012; 12(1):130-146; Gorst-Rasmussen et al., Am J Epidemiol. 2011; 173(10):1097-1104; Lee AB, Nadler B. Treelets—A Tool for Dimensionality Reduction and Multi-Scale Analysis of Unstructured Data). TT is best applied to structure high-dimensional data (i.e. data with a high number of variables) with variable redundancy (i.e. where a large number of variables can be represented by a smaller subset). By conducting principal components analysis (PCA) in a hierarchical clustering framework, TT produces clusters of variables, which can be summarized using a treelet cluster score to represent cluster membership. In the TT tree, the two most strongly correlated variables join, and a local PCA is conducted to derive a sum score for these two variables. This process is repeated until all components have joined into a single "branch". A cut-level is then determined using cross-validation to determine meaningful clusters. Treelet is said to produce clusters that reflect the underlying structure of the data as a whole.

TT can be performed using STATA and R statistical software. Inclusion in TT analysis requires complete data for all variables (or components) and that data be stored. TT requires the specification of 1) the number of clusters and 2) a cut-level at which components significantly cluster. Deriving the number of clusters is a data-driven process, dependent both upon the number of components contained in a cluster (preferred >2 components in a cluster) and the sparsity of data desired. For a given number of clusters, a K-fold cross-validation process identifies the optimal cut-point that maximizes the variance explained by the TT clusters while reducing variables into a meaningfully sparse number of components. TT generates a dendrogram as a visual representation of the hierarchical joining of the input variables.

TT was performed in a group of 159 individuals with moderate-to-severe-TBI to identify five clinically/biologically meaningful clusters of inflammatory markers (n=31). The present disclosure identified that inflammation markers generally cluster in unique patterns that likely represent five arms of immunity. Treelet cluster scores represent levels of inflammatory markers for a given cluster, acting as a general quantitative measurement of unique immune function within each cluster. These clusters represent the overall state of inflammatory arms of adaptive immunity, innate immunity, allergy immunity, soluble receptors, and chemokines. Further, they represent a novel approach to identifying inflammatory markers that vary as a function of sTNFR1 TRAJ group membership and IL-7 TRAJ group membership.

This methodology was applied in the context of grouping international classification of disease codes for purposes of outcome assessment in a TBI population (Kumar et al., J Head Trauma Rehabil. 2018; 33(1):15-24, the content of which is incorporated by reference in its entirety).

Example 21: Group Based Trajectory Methods Used Herein

GBTM has been applied to longitudinal biomarker data (Kumar et al., Brain Behav Immun. 2015; 45:253-262; Munoz et al., Front Mol Neurosci. 2017; 10:44; Santarsieri et al., Brain Behav Immun. 2015; 45:15-27; Wagner et al., J Neurotrauma. 2011; 28(6):871-888), including a methodology paper for biomarker applications (Niyonkuru et al., J Neurotrauma. 2013; 30(11):938-945). The presently disclosed subject matter with IL-7 and sTNFR1, GBTM identified unique pairs of trajectories of both IL-7 and sTNFR1 respectively. Both IL-7 trajectories displayed a linear (zero-order) trend, with one group maintaining high average IL-7 levels from 0 to 6-months post-TBI and the second group maintaining a trajectory of IL-7 levels compared to uninjured. The sTNFR1 trajectories indicated two decliner groups: one group with levels consistently above and another with initially elevated levels of sTNFR1 before declining to at or below sTNFR1 levels of uninjured controls. Groups were used for patient stratification, evaluation of risk reduction, estimation of potential treatment effects, cut points for the initiation of co-treatment for some individuals and potential therapeutic readouts for this application.

The present disclosure uniquely applied TRAJ group analyses for IL-7 and sTNFR1 as novel method of stratifying patients for potential treatment, assessing risk for TBI related impairments, and as a group selection strategy for graphing other inflammatory markers (e.g. chemokines, soluble receptors etc.) that vary as a function of treatment.

Example 22: Anti-Pituitary and Anti-Hypothalamus Autoantibodies after Moderate-to-Severe Traumatic Brain Injury: Associations with Inflammation and Hypogonadotropic Hypogonadism in Men Post-traumatic hypopituitarism is a prevalent complication of traumatic brain injury (TBI). Hypogonadotropic hypogonadism is one of the most common deficiencies that result from post-traumatic hypopituitarism, and it is associated with poor outcomes after TBI. The pathogenesis of persistent hypogonadotropic hypogonadism (PHH) remains unclear. In a prospective longitudinal cohort study, men with moderate-to-severe TBI (n=143) were recruited from a university hospital, and 39 healthy men provided blood samples as controls. Samples were collected from participants 1-12 months post-TBI. TBI cohort (N=1226) and control (N=39) samples were assayed for testosterone (T) and luteinizing hormone (LH), and these data were used to adjudicate PHH status for TBI participants. TBI and control samples also were measured for IgM and IgG autoantibodies against pituitary (APA) and hypothalamus (AHA) via ELISA 1-6 months post-injury, and levels were compared among those with and without PHH.

A panel of inflammatory molecules was assayed to characterize inflammatory responses in the context of autoimmune profiles. Tissue antigen specificity for APA and AHA was confirmed with ICH with cadaveric human pituitary and hypothalamus sections, respectively. Compared to healthy controls, men with TBI had higher APA IgM levels (mean 0.94 vs 0.24 µg/mL, p<0.0001), APA IgG (mean 1.34 vs 0.56 µg/mL, p<0.0001), AHA IgM (mean 7.04 vs 4.32 µg/mL, p<0.0001), and AHA IgG (mean 7.93 vs 3.13 µg/mL, p<0.001). Fifty-one men with TBI (36%) were determined to have PHH. APA IgM and AHA IgM levels were lower in the PHH group compared to those without PHH (mean 0.62 vs 1.11 µg/mL, p=0.06 and 5.38 vs 7.94 µg/mL, p=0.02 respectively). PHH and non-PHH groups had similar mean levels of APA IgG (p=0.29) and AHA IgG (p=0.86). Mean IL-7 and Fractalkine levels correlated with APA and AHA IgM levels. The PHH group had higher mean sTNFRI, sTNFRII, RANTES and sIL-2Ru levels than the non-PHH group. Higher IgM levels in the absence of PHH may suggest a role for protective autoimmunity against PHH development post-TBI.

One likely significant contributor to post-injury disability is post-traumatic hypopituitarism, which is a well-documented chronic complication of TBI (Masel et al., 2014. *J. Neurotrauma* 32, 1902-1910; Schneider et al., 2007. *JAMA* 298, 1429-1438). In the largest prospective cohort screening study to date, 340 individuals with TBI admitted to inpatient rehabilitation were screened for pituitary hormone deficiencies (Kopczak et al., *J. Neurotrauma* 31, 99-107). Thirty-seven percent were noted to have lab values consistent with hypopituitarism, and the most common deficiency was hypogonadism, where 40% of men were deficient in testosterone (estrogen was not reported in women). Other work suggests growth hormone may be the most common post-traumatic pituitary deficiency, with gonadotropin, adrenocorticotropic, and thyroid stimulating hormones having lower incidence (Tanriverdi et al., 2015. *Endocr. Rev.* 36, 305-342). Despite these differences with incidence, recent work suggests that symptoms specific to hypogonadism are often predictive of other co-occurring neuroendocrinopathies; therefore, hypogonadism symptoms may be a useful screening tool for identifying patients that need comprehensive testing for hypopituitarism (Cuesta et al., 2016b. *Clin. Endocrinol.* (Oxf.) 84, 92-98). It was reported that 44% of men with severe TBI had persistent hypogonadotropic hypogonadism (PHH) (Barton et al., *J Head Trauma Rehabil.* 2016 Jul-Aug;31(4):277-87). It was further observed that PHH was associated with worse global outcome scores, more disability, greater fatigue, and reduced functional cognition at 6 and 12 months post-TBI. These results corroborate prior data showing post-traumatic hypogonadism to be a complication associated with worse outcomes (Bondanelli et al., 2007 *J. Neurotrauma* 24, 1687-1697; Carlson et al., 2009 *Brain Inj.* 23, 336-344; Popovic et al., 2004, *J. Endocrinol. Invest.* 27, 1048-1054; Wagner et al., 2012, *Brain Inj.* 26, 1226-1242).

The mechanism for post-traumatic hypopituitarism, including hypogonadism, remains undefined. Traditionally, it has been held that hypopituitarism likely is due to traumatic lesions and vascular injury of the mechanically vulnerable pituitary or hypothalamus, as early post-mortem studies recorded these findings in the majority of autopsies of patients with fatal TBI (Crompton, M. R., 1971. *Brain J. Neurol.* 94, 165-172; Daniel et al., 1959. *Lancet Lond. Engl.* 2, 927-931). Among TBI survivors, associations have been reported between post-traumatic hypopituitarism and abnormalities on magnetic resonance imaging of the pituitary gland (Schneider et al., 2007. *J. Endocrinol. Invest.* 30, RC9-RC12). However, gross structural changes do not entirely explain all cases of post-traumatic hypopituitarism. Among individuals with mild TBI, where traumatic forces do not cause visible structural abnormalities on imaging studies, rates of post-traumatic hypopituitarism have been reported up to 45% (Aimaretti et al., *J. Clin. Endocrinol. Metab.* 90, 6085-6092, 2005; O'Neil et al., 2013. Complications of Mild Traumatic Brain Injury in Veterans and Military Personnel: A Systematic Review, VA Evidence-based Synthesis Program Reports). These findings suggest that hypopituitarism is not strictly related to direct trauma of the pituitary or hypothalamus or even injury severity. Other mechanisms for post-traumatic hypopituitarism have been explored, including alterations in the chronic inflammatory and autoimmune responses (Kasturi, et al., 2009. *J. Neurotrauma* 26, 1315-1324; Tanriverdi et al., 2008. *Eur. J. Endocrinol. Eur. Fed. Endocr. Soc.* 159, 7-13; Tanriverdi et al., 2010b. *J. Neurotrauma* 27, 301-302).

Increasing collective evidence suggests that blood samples collected after TBI contain autoantibodies to multiple brain proteins including glial fibrillary acidic protein (GFAP), S100 calcium-binding protein B (S100B), myelin basic protein (MBP) and glutamate receptors (Wang et al., 2018. *Expert Rev. Mol. Diagn.* 18, 165-180; Yang et al., 2017 *Curr. Phys. Med. Rehabil. Rep.* 5, 22-29). Some evidence also suggests autoimmunity development against the pituitary gland and hypothalamus could be involved in post-traumatic hypopituitarism (Guaraldi et al., 2015. *J. Clin. Med.* 4, 1025-1035). Blood-brain barrier dysfunction occurs rapidly after TBI (Chodobski et al., *Transl.* Stroke Res. 2, 492-516; Hay et al., 2015, *J. Neuropathol. Exp. Neurol.* 74, 1147-1157), which may allow for systemic exposure to otherwise privileged central nervous system (CNS) antigens and subsequent development of autoantibodies ((Yang et al., 2017 *Curr. Phys. Med. Rehabil. Rep.* 5, 22-29). One group has reported that higher serum titers of anti-pituitary and anti-hypothalamus IgG antibodies detected by indirect immunofluorescence are associated with pituitary deficits in 25 individuals with TBI up to 5 years after injury (Tanriverdi et al., 2013. *J. Neurotrauma* 30, 1426-1433; Tanriverdi et al., 2008. *Eur. J. Endocrinol. Eur. Fed. Endocr. Soc.* 159, 7-13). Their studies have not yet been replicated in independent populations. The data only include patient assessments at three or five years post-TBI and only measure the immunoglobulin G (IgG) class antibodies. These data support autoantibody production as pathogenic in post-traumatic hypopituitarism, which aligns with classic autoimmune disease pathophysiology.

IgM antibodies are the earliest isotype expressed during immune development and can promote B and T cell secretion to restrain the development of inflammation (Notley et al., 2011. *J. Immunol. Baltim. Md* 1950 186, 4967-4972). In some cases, IgM antibodies have been linked to directly neutralizing pathogens, while initiating adaptive immune responses from follicular B-cells (Boes et al., 1998 *J. Exp. Med.* 188, 2381-2386; Haas et al., 2005. *Immunity* 23, 7-18). Further, some have hypothesized that under certain conditions, autoimmune activity involving IgM class immunoglobulins may be beneficial to repair and recovery after CNS injury (Schwartz et al., Neuroscientist. 2014 Aug;20(4):343-358). The characterization of autoantibody production after CNS injury may help improve the understanding of TBI pathobiology.

In addition to autoantibody production, there are other inflammatory factors downstream that occur as a part of the adaptive immune response. Certain prior data suggest that autoantibody production after brain injury may promote tissue repair and facilitate neuroinflammation (Kobeissy et al., 2013. *Front. Neurol.* 4, 186; Zhang et al., *PLoS One.* 2014 Mar. 25; 9(3):e92698.). There is also evidence of an influx of peripheral inflammatory cells into the brain following BBB breach (Holmin et al., 1998. *Neurosurgery* 42, 291-298). The time frame for cellular immunity suggests a potentially prolonged period for therapeutic intervention that moderates both pro- and anti-inflammatory responses. The harmful or beneficial impacts of systemic immune responses depend largely on timing post-injury (Chodobski et al., 2011. *Transl. Stroke Res.* 2, 492-516). Certain work has been done in a clinical population with moderate to severe TBI in characterizing chronic elevations of serum inflammatory markers and their associations with long-term global outcome (Kumar et al., *Brain Behav Immun.* 2015; 45:253-262). However, additional characterization of chronic inflammatory biomarker patterns, including autoantibody production, could inform the recovery mechanisms needed to restore homeostatic balance and mitigate the occurrence and secondary conditions, including PHH.

Anti-pituitary antibody (APA) and anti-hypothalamus antibody (AHA) could be detected in serum via immunological assays up to six months after TBI, and that these levels would be associated with PHH status and testosterone (T) levels over time. It was further hypothesized that characterizing key inflammatory markers associated with adaptive immunity (including autoimmunity) would help us identify individuals at risk for PHH based on their role in peripheral cell signaling and trafficking. In a prospective cohort of men with moderate and severe TBI, PHH status, the present disclosure characterized longitudinal serum APA and AHA profiles, and how these profiles relate to PHH as a marker of hypopituitarism. The present disclosure also characterized multiple inflammatory markers over this same time period to evaluate associations with PHH and autoantibody production.

Materials and Methods
Study Design and Population

The University of Pittsburgh Institutional Review Board approved this research. Informed consent was provided by next-of-kin for participants with TBI. Participants with TBI whose cognitive status improved sufficiently over the time frame of the study procedures was given the opportunity to self-consent. Healthy volunteers self-consented to provide blood samples.

This study was a prospective, longitudinal, observational cohort study. The present disclosure prospectively recruited individuals from two cohorts. The first cohort included individuals presenting to the university hospital level 1 trauma center with severe TBI, defined by Glasgow Coma Scale (GCS) score <8 at presentation and confirmed computed tomographic findings, who survived to acute care discharge. The second cohort included individuals with moderate or severe TBI (GCS<13) presenting to acute inpatient rehabilitation after acute hospital discharge. This analysis included men aged 17 to 78 years in whom the present study was able to collect at least 2 blood samples beginning at least 2 weeks after injury. Individuals were excluded if they had a history of hypothalamic or pituitary tumors, orchiectomy, luteinizing hormone (LH) therapy, untreated thyroid disease prior to injury, or hormone levels consistent with primary hypogonadism. Individuals were excluded in cases of primary hypogonadism, wherein hormone values for T were lower than the medical center pathology lab's minimum normal T level and where LH values were higher than the maximum cut-off across multiple sample points per subject.

Demographic and injury information were obtained from patient records, including age, body mass index (BMI), education level, race, GCS score (best in 24 hours), injury severity score, length of hospital stay, mechanism of injury, and neuroradiology results from acute admission.

Derivation of the Cohorts Used for Analysis

FIG. 86 shows how the cohort was derived based on the data available for analysis. 143 men (n=1225 samples) had T and LH data generated that were clinically adjudicated for PHH status over the course of one-year post-injury. Out of the 143 men adjudicated for PHH, 137 had autoantibody data and 138 had inflammation data. 132 participants had both autoantibody and inflammation data. Out of the 137 with autoantibody data, 124 individuals received trajectory group assignments. Of these men, 137 had autoantibody data (n=592 samples), and 138 (n=930 samples) had inflammation data measured up to 6 months post-TBI. Furthermore, 132 men out of this cohort had both autoantibody and inflammatory data for analysis. Of the 137 men with autoantibody data, 124 had at least 2 samples at time points over the course of the first 6 months post-TBI for group-based trajectory analysis outlined in section 2.7.

Upon collection, samples were centrifuged, aliquoted in polypropylene cryovials, and stored at −80° C. until analysis. Healthy male volunteers provided blood samples to serve as a reference/control. Controls were ages 18-68 years and had no history of head injury, neurological disorder, or endocrine disorder. Autoantibody levels were measured in these 39 male volunteers (median age, 31 years). Testosterone and LH levels were measured in a subset of 11 male volunteers (median age, 21 years; range, 19-57 years).

Testosterone and Luteinizing Hormone Assays and PHH Definition

Of the 1225 samples utilized for this analysis, a portion of these serum samples (N=786 samples) were assayed for testosterone and LH levels (Barton et al., *J Head Trauma Rehabil.* 2016 Jul-Aug;31(4):277-87) using a radioimmunoassay with the Coat-A-Count® In-vitro Diagnostic Test Kit (Siemens Healthcare Diagnostics). Kits included a solid-phase $^{125}$I radioimmunoassay (RIA) designed for direct, quantitative measurements. Testosterone and LH inter-assay and intra-assays percent coefficients of variation (% CV) were all <10%. Samples with undetectable levels were assigned the minimum detection limit of the assay. The remaining samples (N=439 samples) were assayed for T (Monobind Inc.) and LH (BioVendor) levels using enzyme-linked immunosorbent assays (ELISAs). The inter-assay and intra-assay % CV for both ELISAs were <10%, and any samples that fell below the detection limit were assigned the value of the detection limit for the respective assay. The present disclosure measured T and LH for a subset of samples (N=47 for T and N=44 for LH) in order to determine a correlation between the two assay methodologies. Linear regression equations were generated for both T and LH data to fit the correlation between hormone measurements by RIA and ELISA. ([RIA T=1.0023*[ELISA T]+0.2451]) and ([RIA LH=1.3248*[ELISA LH]—0.2183]). ELISA sample values were converted using these linear regression equations and the measurements for the two assay types were pooled into one dataset.

PHH status was determined as reported in prior work (Barton et al., *J Head Trauma Rehabil.* 2016 Jul-Aug;31(4): 277-87). Briefly, individuals with at least two blood samples collected between 1-12 months post-injury were dichotomized into PHH or non-PHH groups. The average number of testosterone and LH samples used per participant to adjudicate the cohort for PHH was n=8.57 samples. Those with at least 50% of samples meeting criteria for hypogonadotropic hypogonadism (testosterone<10nmol/L with LH<5.61U/L) were categorized as having PHH. Individuals with less than 50% of samples meeting these criteria were categorized in the non-PHH group ((Barton et al., *J Head Trauma Rehabil.* 2016 Jul-Aug;31(4):277-87).

APA AHA Autoantibody ELISA Protocol

Autoantibody levels were measured in serum (n=m592 samples) using custom ELISA plates. Custom 96-well ELISA plates were coated with bovine hypothalamic lysate or bovine pituitary extract (2 µg/well), After plate preparation, 1 µL of human serum sample was mixed with 99 µp of Start-Block buffer and transferred to each well (1:100 dilution) with incubation at 4° C. overnight with shaking. Plates were washed again 4× with Tris-Buffered Saline and Tween® 20 (TBST) wash buffer. Anti-Human 1gG/IgM HRP-conjugate (Jackson ImmunoResearch, as 1:10,000 in TBST Start-block blocking buffer) was added as a 100 μL aliquot to each well. Plates were incubated at 25'C, with shaking for 45 min. After plate washing with 4× TBST, 100 μL TMB substrate was added to develop color for 15 min. Stop Solution (100 μL) was then added, and plates were read at 450 nm for yellow color of final product.

As a part of assay development, two standard curves were constructed-one for human IgG, and one for human IgM using their respective antibody specific to them. It is important to note that these standard curves are not APA or AHA specific, but rather, IgM or IgG specific. They are used on the same plate when assaying both APA and AHA levels for the serum samples. Standard curves were introduced by adding 0, 17, 26, 39, 58.5, 88, 131.5, 198, 296, 444, 666 and 1,000 ng/mL (50 uL) of either purified human IgG or human IgM (Sigma Co.) to the first rows of the ELISA-plate (see FIGS. 87A-87B ). Upon blocking and washing as above, Anti-Human IgG or IgM HRP-conjugate (1:10,000 in TBST Startblock blocking buffer) was added to these wells and then proceeded with TMB substrate addition. Thus, optical density readings reflect the presence of human APA or AHA IgG or IgM, and these readings were converted to IgG or IgM concentration in μg/mL. 50 μL of standards were used, while 1 μL of human serum per sample was loaded per assay—thus a dilution factor of 50 was applied to determine the actual human subject APA and AHA serum concentrations. Intra-assay % CV was 5-7%, and inter-assay % CV was 15-20%.

Pituitary and Hypothalamic Tissue Immunohistochemical Staining with APA and AHA in Human TBI Serum Immunocytochemistry (ICH) analysis was performed on human pituitary and human hypothalamus paraffin sections per vendor instructions (Zyagen, CA, USA). Slides were first deparaffinized through Trilogy® solution (Cell Marque, CA, USA) by incubating for 10 min at 95° C. and then blocked for endogenous peroxides with 3% hydrogen peroxide. Then routine staining was performed after a 1-h blocking step in 10% goat serum. TBI and control participants' serum, at a dilution of 1:200, was used and incubated over night at 4° C. Alexa Fluor™ 555-conjugated goat-anti-human IgM or IgM secondary antibody (Invitrogen, CA, USA) was added at a dilution of 1:1,000 and incubated for 1 h at room temperature. The tissues were counterstained with 4,6-diamidine-2-phenylindole (DAPI) for 5 min (Vector Laboratories, Burlingame, CA, USA). Fluorescent images were captured with an X40 objective on the OLYMPUS DP7 I fluorescent microscope (Olympus America Inc., Center Valley, PA, USA).

Inflammatory Marker Luminex Bead Assay

Cytokine levels were measured in serum (n=930 samples) using a Luminex™ bead array assay (Millipore, Billerica, Massachusetts). These multiplex assays used microsphere technology where assay beads were tagged with various fluorescent-labeled markers. The binding for each protein onto the multiplex bead was analyzed with a fluorescence detection laser optic system. The Human High Sensitivity T cell Magnetic Bead Panel included interleukin (IL)-10, IL-12(p70), IL-13, IL-10, IL-2, IL-21, IL-4, IL-23, IL-5, IL-6, IL-7, IL-8, Macrophage Inflammatory Protein (MIP)-1a, MIP-10, Tumor Necrosis Factor (TNF)-a, Fractalkine, Granulocyte Macrophage Colony Stimulating Factor (GM-CSF), Interferon-inducible T-cell alpha chemoattractant (ITAC) and Interferon (IFN)-y. The intra-assay % CV was <5%. The inter-assay % CV was <20%. The Human Neurodegenerative Disease Magnetic Bead included soluble Intracellular Adhesion Molecule (sICAM)-1, Regulated upon Activation, Normal T-cell Expressed and Secreted (RANTES), Neural Cell Adhesion Molecule (NCAM) and soluble Vascular Adhesion Molecule (sVCAM)-1. The intra-assay % CV was <6%. The inter-assay % CV was <13%. The Human Soluble Cytokine Receptor Magnetic Bead Panel included soluble (s) CD30, soluble glycoprotein (sgp) 130, soluble IL-1 receptor (sIL-1R)-I, sIL-1RII, sIL-2a, sIL-4R, sIL-6R, sTNFRI, and sTNFRII. The intra-assay % CV was <10% while inter-assay % CV was <15%.

Group-Based Trajectory Analysis

To assess temporal serum autoantibody profiles (over the first 6 months post-injury), the present disclosure applied group-based trajectory (TRAJ) analysis (Niyonkuru et al., *J Neurotrauma*. 2013; 30(11):938-945) (Goyal et al., 2013, *J. Neurotrauma* 30, 946-957; Salonia et al., 2010, *J. Neurotrauma* 27, 1819-1825; Santarsieri et al., *Brain. Behav. Immun.* 45, 15-27; Santarsieri et al., *J. Neurotrauma* 31, 699-712; Wagner et al., 2011, J. Cereb. Blood Flow Metab. Off. J. Int. Soc. Cereb. Blood Flow Metab. 31, 1886-1896; Wagner et al., 2011, *J. Neurotrauma* 28, 871-888). TRAJ analysis is a data-driven technique that leverages longitudinal patterns of a time-varying dependent variable in order to identify distinct subgroups within the population expressing similar temporal levels over time. TRAJ analysis was conducted after rank transformation of the autoantibody data collected 1-6 months after injury and yielded two TRAJ groups (high and low) for both IgM and IgG APA and AHA autoantibodies. The two-group model output for each autoantibody marker had an optimal Bayesian Information Criterion (BIC), and posterior probabilities were >90% for all TRAJ group assignments. The present disclosure used TRAJ group membership to classify individuals and identify specific individuals with discordant APA vs. AHA autoantibody profiles over time for which to conduct the fluorescent immune-histochemical staining analysis.

Statistical Analysis

Statistical analyses were performed with SAS (Statistical Analysis Software) version 9.4 (Cary, North Carolina). Reported variables were assessed for normality using Shapiro-Wilk tests. Age, autoantibody levels, testosterone levels, BMI, GCS score, and length of hospital stay were reported as a median with interquartile range (IQR). Mann-Whitney U tests were used to assess group differences for PHH and non-PHH groups. Group differences for categorical data, including education level, race, mechanism of injury, radiographic injury type, were assessed using Chi-square tests, or Fisher's exact tests, where appropriate.

Autoantibody and inflammatory marker levels from multiple serum samples over the 1-6-month period were averaged for each individual. Between-group differences with autoantibodies and inflammatory markers and PHH were examined using Mann-Whitney U tests or Kruskal-Wallis tests. Spearman correlations were used to assess autoantibody levels and inflammatory marker levels. Binary logistic regression models were used to assess associations between independent variables and a dichotomous dependent variable such as PHH status or autoantibody TRAJ group membership. Multi-variable regression was used to test associations of APA and AHA IgM and PHH while adjusting for other covariates. P-values less than 0.05 were considered significant.

Results

Demographic and Clinical Characteristics

The present disclosure recruited 143 men having at least two post-acute blood samples drawn in the first 12 months available for hormone analysis. Fifty-one individuals (36%) had persistently low Testosterone and LH levels and were designated as the PHH group. Demographic information for this cohort is reported in Table 3. There were no significant differences between PHH vs. non-PHH groups in age, body mass index, education level, race, GCS score, injury severity score, length of hospital stay, or mechanism of injury. Acute care neuroradiology reports from CT and/or MRI were available for 128 of the 143 individuals. Subarachnoid hemorrhage (SAH) on CT imaging was less common in the PHH group than in the non-PHH group (27% vs. 39%, p=0.05). Diffuse axonal injury (DAI) on CT imaging tended to be less common in the PHH group than in the non-PHH group (28% vs. 42%, p=0.07).

used for autoantibody measurement. Mean control and TBI autoantibody levels (averaged over 1 to 6 months) are shown in FIGS. 32A-32D. Concentrations of all Ig types measured were significantly higher in TBI participants compared to healthy controls for all autoantibodies. Healthy male controls (n=39) had lower levels of all autoantibodies compared to men with TBI. APA IgM (mean 0.24 vs 0.94 µg/mL, p<0.0001), APA IgG (mean 0.56 vs 1.34 µg/mL, p<0.0001), AHA IgM (mean 4.32 vs 7.04 µg/mL, p<0.0001), and AHA IgG (mean 3.13 vs 7.93 µg/mL, p<0.0001) (FIGS. 32A-32D).

TABLE 3

Standard curves and IgM/IgG anti-pituitary (APA) and anti-hypothalamus (AHA) autoantibody levels in TBI subject serum and non-TBI control serum samples TBI patient demographics and characteristics

|  | All | Non-PHH | PHH | p-value |
|---|---|---|---|---|
| N (%) | 143 | 92 (64.34) | 51 (35.66) | — |
| Age, median (IQR), y | 31 (26) | 28.5 (22.5) | 35 (27) | 0.08 |
| BMI, median (IQR), kg/m$^2$ | 25.87 (5.26) | 25.84 (4.26) | 26.50 (6.51) | 0.34 |
| Education, n (%) |  |  |  | 0.16 |
| <HS | 42 (29.37) | 22 (15.38) | 20 (13.99) |  |
| HS | 56 (39.16) | 39 (27.27) | 17 (11.89) |  |
| >HS | 45 (31.47) | 31 (21.68) | 14 (9.79) |  |
| Race, n (%) |  |  |  | 0.75 |
| Caucasian | 122 (92.42) | 78 (59.09) | 44 (33.33) |  |
| African American | 8 (6.06) | 6 (4.55) | 2 (1.52) |  |
| Other | 2 (1.52) | 1 (0.76) | 1 (0.76) |  |
| GCS score (best in 24 h), median (IQR) | 8 (4) | 8 (4) | 7.5 (4) | 0.62 |
| Non-head injury severity score, median (IQR) | 26 (15) | 26 (17) | 29 (16) | 0.37 |
| Length of hospital stay, median (IQR), d | 12 (9) | 19 (14) | 20.5 (18) | 0.1 |
| Mechanism of injury, n (%) |  |  |  | 0.31 |
| Motor vehicle accident | 48 (36.09) | 35 (26.32) | 13 (9.77) |  |
| Motorcycle accident | 30 (22.56) | 16 (12.03) | 14 (10.53) |  |
| Fall/jump | 35 (26.32) | 24 (18.05) | 11 (8.27) |  |
| Off-road vehicle | 10 (7.52) | 5 (3.76) | 5 (3.76) |  |
| Bicycle | 4 (3.01) | 3 (2.26) | 1 (0.75) |  |
| Other | 6 (4.51) | 2 (1.50) | 4 (3.01) |  |
| Radiographic injury type, n (%) |  |  |  |  |
| Subdural hematoma | 88 (69.29) | 53 (41.73) | 35 (27.56) | 0.07 |
| Subarachnoid hemorrhage | 83 (65.87) | 49 (38.89) | 34 (26.98) | 0.05 |
| Diffuse axonal injury | 13 (10.32) | 11 (8.73) | 2 (1.59) | 0.14 |
| Epidural hemorrhage | 27 (21.43) | 19 (15.08) | 8 (6.35) | 0.65 |
| Contusion | 73 (57.94) | 47 (37.30) | 26 (20.63) | 1.0 |
| Intraventricular hemorrhage | 40 (31.75) | 27 (21.43) | 13 (10.32) | 0.84 |
| Intraparenchymal hemorrhage | 63 (50.00) | 43 (34.13) | 20 (15.87) | 0.58 |
| Midline Shift | 42 (36.84) | 27 (23.68) | 15 (13.16) | 0.68 |

To quantitatively assess serum IgM and IgG APA and AHA autoantibody levels in TBI participants and non-TBI control serum samples, the present disclosure developed direct ELISAs for both APA and AHA and each immunoglobulin type (IgM and IgG). The present disclosure also generated IgM and IgG class autoantibody standard curves with each assay run to calculate the actual APA or AHA IgM and IgG autoantibody concentrations (titers) in human subject serum. FIG. 87A-87B shows the standard curves for IgM (A) and IgG (B) by plotting the added IgG, IgM concentrations (x-axis) versus calculated IgG or IgM concentrations (recovery) based on absorbance (optical density) values (mean +/−SD from four independent runs). Linear regression was performed with regression coefficient $R^2 > 0.99$ (FIG. 87A-87B). From these standard curve plots, the present disclosure found reliable predictability of IgM and IgG concentrations (based on IgM, IgG recovery) as well as optimal assay robustness (based on the low SD values across the full range of the standard curve).

Figure 55A:
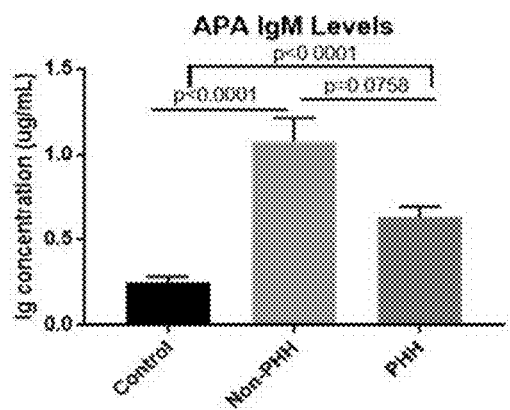
Figure 55B:
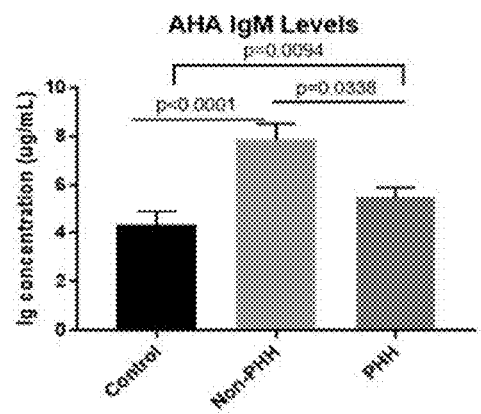
Figure 55C:
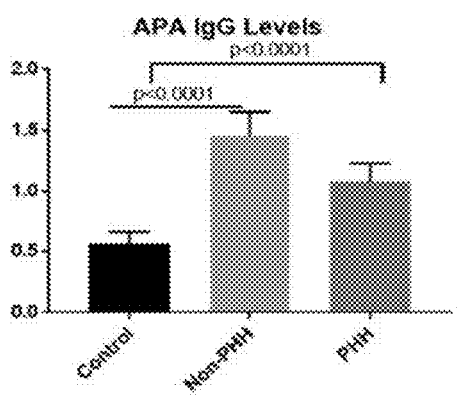
Figure 55D:
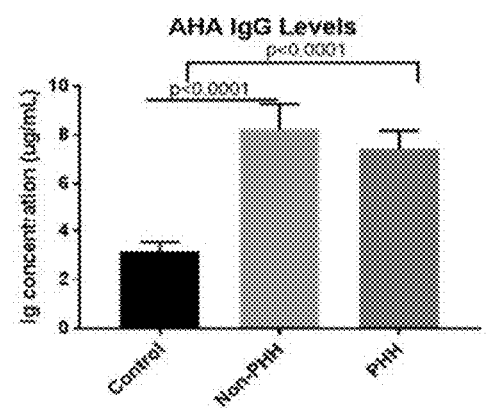

For serum testing, a total of 592 individual samples from 137 participants with TBI throughout the study period were Autoantibody Relationships to PHH Mean 1-6-month autoantibody levels were graphed by PHH status along with healthy control levels (FIGS. 55A-55D). Compared to the non-PHH group, the PHH group tended to have lower serum concentrations of APA IgM (mean 0.62 vs. 1.11 µg/mL, p=0.06) and AHA IgM (mean 5.38 vs. 7.94 µg/mL, p=0.02) (FIGS. 55A-55B). There were no significant differences in APA or AHA IgG levels between the non-PHH and PHH group (FIGS. 55C-55D).

Autoantibody Group-Based Trajectory Analysis

TRAJ analysis of autoantibody levels over time in this cohort revealed two distinct subgroups of individuals regarding temporal IgM profiles for both APA and AHA. The present disclosure denotes the groups as high and low, as graphed in FIGS. 88A-88B. For APA IgM TRAJ analysis, there were 72 (58%) individuals in the high group, and 52 (42%) in the low group. For AHA IgM TRAJ analysis, 59 (48%) individuals were in the high group, and 65 (52%) were in the low group. IgM levels of each TRAJ group generally were stable over time (FIGS. 88A-88B) consistent with a zero-order polynomial fit to the data generated in TRAJ analysis. There were significant differences in autoantibody levels by TRAJ groups for all autoantibodies. There were significant differences in APA IgM autoantibody levels by APA IgM TRAJ group membership at all monthly time points (p<0.05 all comparisons). For both APA and AHA IgM analyses, low TRAJ group membership autoantibody levels were quite similar to controls, while high TRAJ group membership levels were substantially above the reference control group (p<0.05).

Individual TBI Serum IgM and IgG Autoantibody Reactivity to Human Pituitary and Hypothalamic Tissue Sections To confirm that serum from participants with high ELISA signals for APA and AHA in fact label their respective brain tissue targets (pituitary and hypothalamus, respectively), the present disclosure obtained pituitary and hypothalamic paraffin sections from human cadaveric controls for fluorescent immune-histochemical staining analysis. For this assessment, the present disclosure presents 8 representative immunohistochemistry (IHC) slide preparations using cadaveric specimens of hypothalamic and pituitary tissue to measure IgM APA and AHA staining from 4 participants classified as within specific low and the high APA and AHA IgM TRAJ groups. FIGS. 32F-32L shows representative results of immunofluorescent autoantibody staining using serum samples from TBI participants. Here the present disclosure notes that serum samples with high APA IgM show robust immunoreactivity with hormone-releasing granule-bearing cells from pituitary tissue, while serum samples with high AHA IgM show robust neuron staining in hypothalamic tissue sections (FIGS. 32F-32L). Cell labeling was confirmed by counterstaining with DAPI to show nuclei.

Participants 1 and 2 were in the high APA IgM TRAJ group and low AHA IgM TRAJ group, and they showed strong APA IgM pituitary tissue staining (see yellow arrows) and weaker AHA IgM pituitary staining (FIGS. 32F-32L). Participants 3 and 4, were in the high AHA IgM TRAJ group, but low APA IgM TRAJ group and showed strong hypothalamic tissue staining for IgM (see yellow arrows) but weak pituitary APA IgM staining. These results support the quantification and tissue specificity of the APA and AHA autoantibodies measured with ELISA.

Utility of APA and AHA IgM in PHH Categorization

Since IgG autoantibodies were not significantly different by PHH status, the present disclosure modeled the utility of IgM autoantibodies and the associations to PHH. A binomial logistic regression model (Table 4) was run to test the relationship between APA IgM mean levels and PHH, while adjusting for age and GCS score (best in 24 h). Table 4 shows that every unit increase of APA IgM protects against PHH by 48.6% (p=0.03). A logistic regression model was also run to observe the predictive capabilities of AHA IgM levels for PHH (Table 5). AHA IgM was significantly associated with PHH (p=0.03), wherein for every unit increase in AHA IgM there was 110% lower odds of PHH.

TABLE 4

Multivariable Logistic Regression with APA IgM predicting PHH
Logistic Regression for Outcome of PHH (N = 126)

| Variable | Odds Ratio (95% CI) | p-value |
|---|---|---|
| Age | 1.025 (1.000, 1.049) | p = 0.05 |
| GCS | 0.881 (0.768, 1.010) | p = 0.07 |
| APA IgM levels | 0.486 (0.253, 0.933) | p = 0.03 |

TABLE 5

Multivariable Logistic Regression with AHA IgM predicting PHH
Logistic Regression for Outcome of PHH (N = 126)

| Variable | Odds Ratio (95% CI) | p-value |
|---|---|---|
| Age | 1.017 (0.993, 1.043) | p = 0.17 |
| GCS | 0.903 (0.791, 1.033) | p = 0.14 |
| AHA IgM levels | 0.890 (0.800, 0.991) | p = 0.03 |

Inflammatory Associations with APA AHA IgM

Motivated by IgM-specific autoantibody differences by PHH status, the present disclosure investigated potential inflammatory associations related to the differential expression of APA and AHA IgM. Table 6 indicates markers that were both significantly correlated and had at least a moderate relationship (r>0.3). IL-7 and Fractalkine were both significantly and positively correlated with APA IgM, while Fractalkine was significant and positively correlated with AHA IgM levels. IL-2, IL-8, IL-10 and IL-21 were all also significantly correlated with APA IgM (p<0.05), as they had relatively weaker correlation coefficients (r<0.3). Similarly, IL-2, IL-4, IL-12p70, sTNFRI and sIL-2Ra all had small correlation coefficients but were significantly associated with AHA IgM.

TABLE 6

Spearman Correlations between inflammatory markers and IgM autoantibodies

| Variable | APA IgM | AHA IgM |
|---|---|---|
| IL-7 | r = 0.35<br>p = <0.0001<br>N = 132 | — |
| Fractalkine | r = 0.30<br>p = 0.0007<br>N = 131 | r = 0.30<br>p = 0.0005<br>N = 131 |

Inflammatory Associations to PHH

The present disclosure then tested the entire inflammatory 33 biomarker panel for associations to PHH. FIG. 89 depicts 1-6 month mean levels (pg/mL) by PHH status for the significant associations (p<0.05) in the panel. Mean levels of each marker were scaled by a multiple of $10^8$ accordingly to fit a 0-20 µg/mL range. sTNFRI, sTNFRII, RANTES and sIL-2Ra all were higher in the PHH group than in the non-PHH group. Conversely, GM-CSF levels were higher in the non-PHH group than in the PHH group. Only GM-CSF levels were higher in non-PHH individuals while sTNFRI, sTNFRII, RANTES and sIL-2Ru levels were significantly higher in PHH, Discussion Given the growing evidence that post-traumatic hypopituitarism, specifically hypogonadism, is deleterious to long-term outcomes, it is an increasingly important topic of study (Bondanelli et al., 2007 *J. Neurotrauma* 24, 1687-1697; Carlson et al., 2009 Brain Inj. 23, 336-344; Popovic et al., 2004, *J. Endocrinol. Invest.* 27, 1048-1054; Wagner et al., 2012, *Brain Inj.* 26, 1226-1242). Guidelines on screening for post-traumatic hypopituitarism (Tanriverdi et al., 2015. *Endocr. Rev.* 36, 305-342; Ghigo et al., 2005. Brain Inj. 19, 711-724) are based on limited evidence on the timeframe in which hypopituitarism develops, and there remains a paucity of evidence on the safety and efficacy of hormone replacement therapy after TBI. Despite the clinical relevance of this problem, the pathophysiological mechanisms underlying post-traumatic hypogonadism are unclear, and the role of aging in contributing to PHH risk after TBI is not well documented. Those with PHH are older than those without PHH, yet age and PHH status are independent risk factors for TBI recovery (Barton et al., *J Head Trauma Rehabil.* 2016 Jul-Aug;31(4):277-87).

Here the present disclosure provides the first longitudinal quantitative data on APA and AHA levels after TBI, and discloses relationships between these autoantibodies and PHH in men after moderate to severe injury. Men with TBI have elevated APA and AHA levels compared to healthy volunteers (FIGS. 32A-32D), and individuals without PHH had elevated IgM autoantibody levels compared to both healthy controls and PHH individuals (FIGS. 55A-55D). The present disclosure also showed reduced PHH prevalence among those with increased APA and AHA 1gM levels while adjusting for age and GCS (Tables 4 and 5). Further, several markers representing adaptive immunity, chemokine signaling, and microglial activation are associated with autoantibody production and PHH (Table 6 and FIG. 89). These results provide important biological insight into the immune system and PHH development.

APA and AHA associations with post-traumatic hypopituitarism have been studied in mixed groups of men and women 3-5 years after mild to severe TBI (Tanriverdi et al., 2013. *J. Neurotrauma* 30, 1426-1433; Tanriverdi et al., 2008. *Eur. J. Endocrinol. Eur. Fed. Endocr.* Soc. 159, 7-13). They each showed higher IgG autoantibody titers associated with hypopituitarism. Elevated autoantibody titers and hypopituitarism has also been shown in boxers (Tanriverdi et al., 2010a. *Eur. J. Endocrinol. Eur. Fed. Endocr. Soc.* 162, 861-867). Together, these data suggest a pathogenic role for autoantibodies in pituitary function, however the work did not distinguish between IgM and IgG autoantibodies.

In contrast, the present disclosure found mean APA and AHA IgM levels were higher among those without PHH, compared to those with PHH after TBI (FIGS. 55A-55D). IgG levels were modestly lower in PHH at this time point which is in contrast to previous literature showing high levels related to disease. However, these levels are measured much sooner than previous studies, which may contribute the differences. Ig class specificity may be a temporal function of autoantibody production in response to brain specific antigens associated with blood brain barrier breach post-injury. The temporal onset of autoimmunity development against pituitary and hypothalamic tissue may differ (years versus months) post-injury; the latter may be associated with neuroinflammatory processes supporting CNS cell rescue and repair. Also, the data focus on men with moderate-to-severe TBI (GCS<13). While differences in TBI pathophysiology between men and women are less well-known, sex differences in secondary injury processes exist along the injury severity spectrum (Wagner et al., 2000. *J. Trauma* 49, 404-410).

Tanriverdi et al. reported many individuals with negative titers using a semi quantitative assay (Tanriverdi et al., 2010. *Eur. J. Endocrinol. Eur. Fed. Endocr. Soc.* 162, 861-867), however, the present disclosure used quantitative ELISA to measure APA and AHA levels in all individuals and were able to quantitatively compare autoantibody levels between individuals with TBI (with and without PHH) to healthy controls. Other studies have shown measurable levels of autoantibodies to CNS antigens in healthy individuals (Hedegaard et al., 2009, Immunology 128, e451-461; Nielsen et al., 2001. *Eur. J. Immunol.* 31, 2660-2668; O'Connor et al., 2003. *J. Neuroimmunol.* 136, 140-148), suggesting arole for "protective autoimmunity" via brain-specific autoantibody production post-TBI. Further, work on CNS lymphatic drainage and immune surveillance (Louveau et al., 2015b. *Nature* 523, 337-341) suggests brain-periphery crosstalk and a role for systemic immunity in the injury response. Studies such as these are shifting dogma on CNS immune privilege and demonstrate that even healthy individuals are capable of producing autoimmune responses to CNS antigens via immune surveillance systems (Engelhardt et al., 2017, *Nat. Immunol.* 18, 123-131; Louveau et al., 2015, *Trends Immunol.* 36, 569-577).

The present disclosure also confirmed that serum from TBI participants with high APA or AHA IgM levels can in fact be used as a specific immunofluorescent label pituitary and hypothalamus tissue sections (FIGS. 32F-32L).

Multiple pituitary axes have been characterized, including growth hormone, adrenocorticotropic hormone, gonadotropin, and thyroid stimulating hormone deficiency (Tanriverdi et al., 2015. *Endocr. Rev.* 36, 305-342; Tanriverdi et al., 2017. *Best Pract. Res. Clin. Endocrinol. Metab.* 31, 3-11). Given that hypogonadism, characterized by testosterone deficiency, is arguably the most common type of pituitary disorder after TBI (Kopczak et al., 2014, *J. Neurotrauma* 31, 99-10), and symptomatic hypogonadism indicative of other co-occurring neuroendocrinopathies (Cuesta et al., 2016b. *Clin. Endocrinol.* (Oxf) 84, 92-98), the present disclosure focused on evaluating PHH as a secondary condition after moderate to severe TBI.

Based on these results, the present disclosure hypothesizes that the inverse relationship between both APA and AHA IgM levels and PHH represent an adaptive immune process. This hypothesis is supported by a growing literature on protective autoimmunity after CNS injury, in which self-antigen recognizing immune cells contribute to injury repair (Schwartz et al., *Neuroscientist.* 2014 August; 20(4): 343-358). Interestingly, significant autoantibody associations to PHH were IgM specific and not IgG. Naturally-arising IgM autoantibodies to apoptotic cell membranes (Gronwall et al., 2012. *Front. Immunol.* 3, 66; Vas et al., 2013. *Front. Immunol.* 4, 4) and leukocytes (Lobo et al., 2010, *J. Clin. Immunol.* 30 Suppl 1, 531-36) are generated from B1-cells and are a physiologic (evolutionarily conserved) part of the innate immune system (Gronwall et al., 2012. *Front. Immunol.* 3, 66; Vas et al., 2013. *Front. Immunol.* 4, 4); while constitutively expressed (Baumgarth et al., 2005 *Springer Semin. Immunopathol.* 26, 347-362), these autoantibodies are amplified in environments with high concentrations of apoptotic cells (Chen et al., 2009a. *J. Immunol. Baltim. Md* 1950 183, 1346-1359; Chen et al., 2009b. J. *Immunol.* Baltim. Md 1950 182, 6031-6043) and in pro-inflammatory states (Lobo et al., 2010, *J. Clin. Immunol.* 30 Suppl 1, S31-36) to increase apoptotic cell phagocytosis (deCathelineau et al., 2003. *Essays Biochem.* 39, 105-117) and activate complement mediated anti-inflammatory pathways (Gray et al., 2007, *Proc. Natl. Acad. Sci. U. S.* A. 104, 14080-14085; Huynh et al., 2002, *J. Clin. Invest.* 109, 41-50) in an attempt to support immune homeostasis and tissue health. Specifically, IgM antibodies bound to antigens on pathogens or dying cells facilitate lectin pathway activation of the complement system, which in turn, can facilitate phagocytosis and inflammatory cell recruitment, as well as modulate the adaptive immune response (Kjaer et al., 2013. *Mol. Immunol.* 56, 413-422). Adaptive immunity signaling molecules like IL-7 support T-cell lymphoproliferation capable of producing IgM autoantibodies sensitive to circulating self-antigens (Goldrath and Bevan, 1999, *Immunity* 11, 183-190; Schluns et al., 2000, Nat. *Immunol.* 1, 426-432). These processes have led some to characterize these types of reparative responses as contributing to "protective autoimmunity." With blood brain barrier disruption and systemic exposure to CNS inflammation via lymphatic drainage mechanisms after TBI (Louveau et al., 2015b. *Nature* 523, 337-341), autoantibody production to circulating brain antigens, including antigens associated with pituitary and/or hypothalamic tissue, may help clear dead cells and debris as well as facilitate repair.

Evidence of protective autoimmunity has been reported in other CNS conditions such as stroke and spinal cord injury (Brait et al., 2012, *J Cereb Blood Flow Metab.* 2012 Apr; 32(4): 598-611; Graber et al., 2009. *Pharmacol. Ther.* 121, 147-159; Saltzman et al., 2013. Curr. Phys. Med. Rehabil. Rep. 1; Schwartz et al., 2014. *J. Autoimmun.* 54, 8-14). High IgM autoantibody levels are thought to protect donor organs (Lobo et al., 2010. J. *Clin. Immunol.* 30 Suppl 1, S31-36; McAlister et al., *Liver Transpl.* 2004 February;10(2):315-9), reduce risk for stroke and Alzheimer's disease (Eriksson et al., 2010, *J. Alzheimers Dis. JAD* 21, 577-584; Fiskesund et al., 2010, *Stroke* 41, 607-612) and reduce disease burden in autoimmune disorders (Gronwall et al., 2012. *Front. Immunol.* 3, 66), while low/absent IgM levels are observed with pathogenic IgG production associated with autoimmune and other diseases (Vas et al., 2013. *Front. Immunol.* 4, 4). The idea of protective autoimmunity in TBI is also supported by other work showing autoantibodies binding to breakdown products of injured neural cells ((Stein et al., 2002, *J. Neuropathol. Exp. Neurol.* 61, 1100-1108). The present disclosure proposes that protective autoimmunity, after TBI, is an evolving concept manifested by CNS IgM production to facilitate repair. APA autoantibody associations with PHH were much stronger with APA than AHA, but they provide an exemplar for work focused on identifying other key autoantibodies facilitating CNS clean-up and repair.

The present disclosure further explored chronic inflammation associated with APA and AHA as well as PHH status to begin to understand the underlying mechanisms that may support an IgM associated autoimmunity response after TBI. After all, immune responses against brain specific antigens and cellular debris must be well regulated to optimize healing over damage. Also, those with post-injury immunosuppression are more vulnerable to infections and impaired healing, which negatively impacts neurological recovery that potentially contributes to maladaptive autoantibody responses (Hazeldine et al., *Front Neurol.* 2015; 6:235; Riegger et al., 2009. *Neuroscience* 158, 1194-1199).

T-lymphocytes are critical to post-injury adaptive immune cytokine production driving autoimmunity (Brait et al., 2010 *J Cereb Blood Flow Metab.* 2010 July; 30(7): 1306-1317). Table 6 indicates IL-7 and Fractalkine have strong positive correlations with APA IgM and AHA IgM. After CNS injury, IL-7 production promotes lymphoproliferation of Th-cells sensitive to circulating self-antigens that produce CNS antibodies (Schluns et al., *Nat Immunol.* 2000; 1(5):426-432; Ernst et al., *Immunity.* 1999; 11(2):173-181). Therefore, those with higher endogenous IL-7 may be better equipped than low IL-7 producers to facilitate a lympho-restorative response after TBI (Guimond et al., 2009. *Nat. Immunol.* 10, 149-157; Lucin, et al., 2009. *J. Neurochem.* 110, 1409-1421; Lundstrom et al., 2012. *Semin. Immunol.* 24, 218-224). Fractalkine is a chemokine that promotes monocyte survival, induces cellular chemotaxis, and is a product of proteolytic cleavage of the CX3CR1 membrane bound receptor (Harrison et al., 1998. *Proc. Natl. Acad. Sci. U.S.A* 95, 10896-10901; Imai et al., 1997. *Cell* 91, 521-530). Cellular immunity is amplified with Fractalkine, and increased circulating Fractalkine is linked to T-cell signaling by sources of local inflammation and infection (Bazan et al., 1997 *Nature* 385, 640-644; Shin et al., 2015 *Immunol. Baltim. Md* 1950 195, 2861-2869). Autoantibody associations with serum IL-7 and Fractalkine in the study implicate cellular immunity as impacting protective autoimmunity and adaptive immunity effects that underlie neuroendocrine dysfunction post-TBI.

The present disclosure also explored if, in addition to autoantibody levels, chronic systemic inflammation is relevant to PHH in men with moderate to severe TBI. Since there were significant associations with IL-7 and Fractalkine to IgM levels, the present disclosure hypothesized that inflammatory markers strongly related to cellular immunity and adaptive immune signaling would be associated with PHH. FIG. 89 demonstrated higher levels of GM CSF in the non-PHH group compared to the PHH group. GM CSF is a pro-inflammatory cytokine implicated in several inflammatory diseases (Campbell et al., 1998, *J. Immunol.* 161, 3639-3644). T cells produce GM-CSF. However, GM-CSF requires fine control to effectively regulate Th1 immune responses. GM CSF overexpression may result in an uncoordinated generalized inflammatory response in the context of T-cells and macrophage recruitment to sites of infection (Gonzalez-Juarrero et al., 2005. *J. Leukoc. Biol.* 77, 914-922; Shi et al., 2006, Cell Res. 16, 126). Although speculative, higher GM-CSF in the non-PHH group may reflect an uncoordinated, generalized innate immune response that does not result in a large prolonged CNS inflammatory burden that otherwise might accompany PHH.

Conversely, FIG. 89 shows sTNFRI, sTNFRII, RANTES and sIL-2Ru levels were all higher in the PHH group than in the non-PHH group. sIL-2Ru is an important contributor to autoimmune diseases and is a potent T cell growth factor (Malek et al., 2010. Immunity 33, 153-165; Morgan et al., 1976. *Science* 193, 1007-1008). RANTES is a chemokine that supports chemotaxis and T-cell expression (Mikolajczyk et al., 2016. *FASEB J. Off. Publ. Fed. Am. Soc. Exp. Biol.* 30, 1987-1999). Elevated sIL-2Ru and RANTES signaling with PHH may indicate CNS T-cell depletion and decreased capacity for neural repair chronically. It is not surprising that sTNFRI and sTNFRII are elevated in the PHH group. sTNFRI is a TNFα receptor that is ubiquitously expressed on all cells and has a death domain (Pandey et al., 2003. *Am. J. Pathol.* 162, 933-941; Sedger et al., *Cytokine Growth Factor Rev.* 2014 August; 25(4):453-72). sTNFRII is only present on T-cells, but both receptors are upregulated during chronic inflammation (Cope et al., 1995. *Immunology* 84, 21-30). Soluble TNFα receptors are formed via proteolytic cleavage on surface receptors upon TNFα activation (Pandey et al., *Am J Pathol.* 2003; 162(3):933-941; Waetzig et al., *The FASEB Journal.* 2004; 19(1):91-93), thus supporting that soluble signaling as a key mechanism underlying the capacity of TNFα as a pro-inflammatory molecule that perpetuates the post injury innate immune response (Suvannavejh et al., 2000. *Cell. Immunol.* 205, 24-33) and impacts adaptive immunity.

Men with PHH were on average older than men without PHH. Since the aging immune system has decreased capacity to respond to infection and other insults, with limited reactive potential in both T cells and B cells (Aspinall et al., *Biochem. Soc. Trans.* 42, 651-656; Frasca et al., 2005. *Semin. Immunol.* 17, 378-384; Pereira et al., 2016. *Front. Immunol.* 7, 445), the present disclosure hypothesized that higher APA IgM levels help protect against PHH incidence, while adjusting for the potentially deleterious effects of age and injury severity on pituitary tissue repair. By testing APA IgM levels in a multivariate analysis, the odds ratio indicated that increases in APA IgM levels protect against PHH prevalence by 52.5%. The present disclosure also saw that increases in age concurrently increase incidence of PHH within the population.

Together, the findings presented here serve as a foundation for development and modeling of risk stratification that considers age and autoantibody levels overtime as post-acute biomarkers predicting neuroendocrine dysfunction with TBI. This type of personalized, biomarker-based approach to susceptibility to secondary conditions after TBI fits well within the Rehabilomics framework for rehabilitation-related research aimed at personalizing treatments that improve health and function for those with disabilities. (Wagner et al., 2000. J. Trauma 49, 404-410; Wagner et al., 2014 Am. J. Phys. Med. Rehabil. 93, 913-916; Wagner et al., 2013 Pathophysiology 20, 39-48). The findings also suggest that more mechanistic studies are warranted that explore the role potentially protective role of autoimmunity after TBI.

Conclusion

In conclusion, the present disclosure reported novel, longitudinal data on APA and AHA levels in the setting of post-traumatic hypopituitarism, specifically PHH. The higher APA IgM levels observed in those without PHH suggest a protective role for IgM class autoantibodies against pituitary dysfunction during the first six months after TBI.

Example 23: Epilepsy and Traumatic Brain Injury

Seizures are the major cause of death in the TBI patient population. Individuals with TBI have a 50-times increased risk for dying from a seizure compared to healthy age, sex, and race-matched controls. The present disclosure have generated prognostic models were generated to predict PTE risk for ~2000 individuals with moderate to severe TBI at both one and two years after injury, including SDH, intraparenchymal fragment, craniotomy, craniectomy, seizure during acute hospitalization, preinjury incarceration. IL-10 levels during acute care and IL-10 genetics can be linked with time to first seizure after TBI. But no studies on chronic inflammatory marker associations with PTE. This example provides that TNFR or IL-7 can be a treatment target in the post-acute or chronic phase and/or serve as a point of stratification for PTE risk.

The time to event (first seizure) epilepsy model was depicted in FIG. 90. It shows Cox Proportional Hazards Regression of IL-7 and sTNFR1 at months 0-6 by time until first seizure through 3-years post-injury. 136 adults with moderate to severe TBI were tested. All biomarkers were standardized. As a result, effect sizes are interpreted as increased risk per 1 standard deviation increase.

A logistic regression model of month 0-6 sgp130 levels and up to three-year seizure event status, was also controlled for age, GCS, subdural hematoma, craniotomy, craniectomy, and depressed skull fracture and is shown in FIG. 91. The base model included covariates only. This model included covariates and month 0-6 sTNFR1 levels, demonstrating 5.6% improvement in area under ROC Curve, a measurement of the model's ability to accurately discriminate seizure status. Individuals in the High sTNFR1 TRAJ experienced a nearly 3.7× increased risk of epilepsy compared to the Low sTNFR1 TRAJ. The data showed that even after adjusting for several known factors impacting PTE, adding sTNFRI to the model substantially improves overall model prediction and indicated that TNF inhibitors could be useful in reducing epileptogenesis after TBI.

Example 24: Neurorecovery as Measured by GOS and DRS

The Glasgow Outcome Scale (GOS) is a widely utilized tool that classifies outcome into five categories: 5=good recovery, 4=moderate disability, 3=severe disability, 2=persistent vegetative state and 1=death. Among survivors, pts often grouped GOS ⅔ vs. GOS group ⅘. GOS (and extended GOS) represents global capacities and impairments in the areas of cognition, behavior, mood, fatigue, sleep and other impairments that contribute to overall neurorecovery. GOS (and GOS-Extended) primary variables for most acute care clinical trials to date, none of which have successfully shown to have broad efficacy value.

Treelet transform analysis was used to generate individual Treelet Cluster (TC) scores for the 5 main clusters. These scores were based on standardized mean inflammatory levels (m0-6) and capture the expression of multiple markers present in the respective cluster. The markers listed here (Adaptive: IL-2, IL-12, Fractalkine, IFNg, IL-21, IL-23; Innate: IL-1b, TNFα, IL-6, MIP-1b, MIP-3a; Allergy: IL-5, IL-13; sReceptors: sIL-2ra, sTNFRII; Chemokines: ITAC, RANTES) belonged to the respective clusters. A TC score >0 (positive) can be interpreted as expression of "above mean levels" of the markers contained in that cluster on average. Treelet scores were calculated as a sum of the (standardized inflammatory mean)×(weight contribution of the inflammatory marker to the cluster). Therefore, an individual had a total of five treelet cluster scores describing their relative states of immunity. FIG. 92 shows increased odds of unfavorable global outcome with elevated soluble receptor & chemokine load.

Disability Rating Scale Score Overview was depicted in FIG. 93. Broad metric with some prognostic capacities included subscales for eye opening, motor response, cognitive abilities for feeding, toileting or grooming, dependence on others and employability.

FIG. 94 showed the linear regression modeling of Disability Rating Scale (DRS) score which ranged from 0 (none) to 29 (extreme vegetative) or 30 (dead). This scale captured disability severity in the following categories: arousal, awareness and responsiveness, cognitive ability for self-care activities, dependence on others, and psychosocial adaptability. A specificity difference was observed: soluble receptors strongly distinguished both global outcome and disability while chemokine levels showed less differentiation when it came to disability severity. Thus, greater disability severity was accompanied by higher soluble receptor load.

Mean sTNFRI levels had a particularly strong and unique discriminatory capacity over IL-7 and other immunity biomarkers in projecting global outcome and disability severity post-TBI. (FIGS. 95A and 95B). The interaction of IL-7xsTNFRI was not significant in the GOS or DRS model, nor IL-7 alone. This further implicated the importance of controlling (i.e. treating) high sTNFRI to mitigate risk for unfavorable global outcome and severity of disability. Also, autoantibody levels did not significantly influence this model.

The soluble receptor driven impact on unfavorable outcome was shown by these unfavorable GOS score Logistic Regression Models (step-wise) in FIG. 96. Higher IL-7 TRAJ was associated with significantly higher adaptive, innate, allergy and chemokine cluster scores., again showing the potential need for dual therapy with a drug like Etanercept when endogenous TNFR1 levels and/or IL-7 levels are high.

Consistent with the statement above, high IL-7 TRAJ was associated with better outcome when controlling for the potential negative effects of exacerbated chemokine signaling and soluble receptor signaling. This model aligns with the understanding of the potentially non-specific capacity of rhIL-7 treatment in elevating all arms of immunity and supports the need for combination therapy with etanercept to contain non-specific effects while allowing for restoration of adaptive immunity. This model progression also demonstrated the overall amplified soluble receptor state that likely drives the relationship between sTNFRI TRAJ group and unfavorable outcome.

Example 25: Biomarkers: Gauging Treatment Effectiveness

Mean testosterone levels by IL7 TRAJ Group membership and by sTNFRI TRAJ Group measurement of 175 subjects were measured. Testosterone levels significantly differ over time via the Friedman test ($p<0.0001$). Repeated measures ANCOVA ($p<0.0031$) showed that low TRAJ group had lower T than high TRAJ group (FIG. 97A). Repeated Measures ANCOVA ($p<0.0001$) showed that high TRAJ group had lower T than low TRAJ group (FIG. 97B). Thus, treatment with rhIL-7 or TNFα inhibitor may influence T levels and neuroendocrine dysfunction after TBI.

Chronic Testosterone Levels by APA IgM TRAJ and AHA IgM TRAJ of 125 subjects were also measured. Testosterone levels significantly differ over time via the Friedman test ($p<0.0001$). Repeated measures ANCOVA ($p=0.0029$) showed that low TRAJ group had lower T than high TRAJ group (FIG. 98A). Repeated measures ANCOVA ($p=0.0002$) showed that low TRAJ group had lower T than high TRAJ group (FIG. 98B). Modifying adaptive immunity (specifically autoimmunity, e.g. AHA and APA Autoantibodies) through treatment with rhIL-7 or TNFα inhibitor may influence T levels and neuroendocrine dysfunction after TBI.

In addition to optimizing levels of sTNFRI ($<1500$ μg/mL) and IL-7 ($>25$ μg/mL) comparable to the ideal TRAJ profiles (low sTNFRI and high IL-7), there are other chronic biological readouts that may inform global recovery, and treatment should work to reduce soluble receptor and chemokine load. Soluble Receptors such as sTNFRII (Control=6106 μg/mL) and sIL-2Ra (Control=444 μg/mL) were measured (FIG. 99A). Chemokines such as ITAC (Control=122 μg/mL) and RANTES (Control=74923 μg/mL) were also measured (FIG. 99B). Interestingly, all TBI outcome groups were lower than RANTES control levels, though higher RANTES was implicated in worse global recovery. NLR was also monitored into the post-acute phase based on the disclosed findings that High NLR is significantly concordant to unfavorable GOS.

Treatment effectiveness was gauged by BDNF levels by TRAJ Groups. BDNF is a protein that affects synaptic plasticity and neurogenesis. Low BDNF is linked to poor memory, depression, and mortality. Increased exercise in rats has been associated with elevated BDNF levels. Given that BDNF is present in lymphocytes, lymphocyte restoration effects from IL-7 influence on AAb, and/or Etanercept treatment, may be a relevant readout. Mean BDNF levels by sTNFRI TRAJ (FIG. 100A) and by APA IgM TRAJ (FIG. 100B) were measured. BDNF levels were elevated in the LOW sTNFRI TRAJ group compared to the high TRAJ group (FIG. 100A). BDNF levels were elevated in the HIGH APA IgM TRAJ group compared to the low TRAJ group (FIG. 100B).

Example 26: Rat Etanercept Trials

For rat Etanercept trials, rats underwent severe CCI or sham surgery. Rats received vehicle, etanercept—either 1 or 3 mg/kg on D1-D3 post injury. Groups included 9 CCI High Dose, 14 CCI VEH and 15 Sham VEH. Behavioral Testing such as motor testing of beam balance and bean walk were performed at DO-D6 post injury. Sucrose preference testing was performed at D7 post-injury.

Significant differences were shown between CCI high dose and CCI vehicle ($p=0.025$), with treated rats returning to baseline one day sooner than vehicle controls (FIG. 101). Two-Way RM ANOVA showed that Interaction: $p<0.0001$, Day: $p<0.0001$, Group: $p<0.0001$, and Subject: $p=0.0175$. Overall Group Post-hoc Comparisons were calculated as: Sham VEH vs CCI VEH: $p=0.0001$, Sham VEH vs CCI High Dose: $p=0.3277$, and CCI VEH vs CCI High Dose: $p=0.0205$. Tukey's Post-hoc Multiple Comparisons (DO, D5, D6 not significant) were also calculated. For D1, Sham VEH vs. CCI VEH: $p=0.0011$, Sham VEH vs. CCI High Dose: $p=0.4251$, and CCI VEH vs. CCI High Dose: $p=0.1046$. For D2, Sham VEH vs. CCI VEH: $p=0.0148$, Sham VEH vs. CCI High Dose: $p=0.8616$, and CCI VEH vs. CCI High Dose: $p=0.0382$. For D3, Sham VEH vs. CCI VEH: $p=0.1309$, Sham VEH vs. CCI High Dose: $p=0.5973$, and CCI VEH vs. CCI High Dose: $p=0.2605$. For D4, Sham VEH vs. CCI VEH: $p=0.6542$, Sham VEH vs. CCI High Dose: $p=0.7582$, and CCI VEH vs. CCI High Dose: $p=0.9882$.

Overall there was no treatment difference with beam walking scores, but CCI treated rats reached full score a day sooner than CCI vehicle (FIG. 102). Two-Way RM ANOVA showed that Interaction: $p<0.0001$, Day: $p<0.0001$, Group: $p<0.0001$, and Subject: $p<0.0001$. Overall Group Post-hoc Comparisons were calculated: Sham VEH vs CCI VEH: $p<0.0001$, Sham VEH vs CCI High Dose: $p<0.0001$, and CCI VEH vs CCI High Dose: $p=0.9730$. Tukey's Post-hoc Multiple Comparisons (DO, not significant) were calculated at different days. For D1, Sham VEH vs. CCI VEH: $p<0.0001$, Sham VEH vs. CCI High Dose: $p=0.0002$, CCI VEH vs. CCI High Dose: $p=0.9916$. For D2, Sham VEH vs. CCI VEH: $p<0.0001$, Sham VEH vs. CCI High Dose: $p=0.0007$, and CCI VEH vs. CCI High Dose: $p=0.9965$. For D3, Sham VEH vs. CCI VEH: $p<0.0001$, Sham VEH vs. CCI High Dose: $p=0.0106$, and CCI VEH vs. CCI High Dose: $p=0.9823$. For D4, Sham VEH vs. CCI VEH: $p=0.0390$, Sham VEH vs. CCI High Dose: $p=0.0489$, and CCI VEH vs. CCI High Dose: $p=0.8393$. For D5, Sham VEH vs. CCI VEH: $p=0.0377$, Sham VEH vs. CCI High Dose: $p=0.4098$, and CCI VEH vs. CCI High Dose: $p=0.3867$. For D6, Sham VEH vs. CCI VEH: $p=0.3660$, Sham VEH vs. CCI High Dose: $p=0.3358$, and CCI VEH vs. CCI High Dose: $p=0.9916$.

The average sucrose preference was also measured in control and different treatment groups (FIG. 103). Significantly higher degree of sucrose preference for CCI high dose treated vs. CCI vehicle ($p<0.02$). One-Way ANOVA had a p value $<0.0001$. The unpaired t-tests were calculated: SHAM/VEH vs CCI/VEH: $p<0.0001$, CCI/VEH vs CCI/High Dose: $p=0.0199$, and CCI/High Dose vs Sham/VEH: $p=0.0092$. Etanercept improved certain components of beam performance, sucrose preference related anhedonia in Rats after experimental TBI.

Example 27: Chronic Systemic Inflammation and Associations with Autoantibody Production after Traumatic Brain Injury Traumatic brain injury (TBI) is associated with long-term complications and persistent functional impairments.

Autoantibodies (AAb) to the pituitary, hypothalamus (APA/AHA) and Glial fibrillary acidic protein (GFAP) following CNS injury are present one-year post-injury, and reduced IgM AAb production increases the risks for persistent hypogonadotropic hypogonadism (PHH) in men with TBI. Given that neuro-recovery is largely driven by adaptive and innate immunity, a panel serum inflammatory marker profiles that are associated with APA/AHA/GFAP IgM AAb may inform on immune responses to neural repair post-injury. Serum levels for inflammatory markers and IgM/IgG APA, AHA and GFAP AAb were evaluated 2 weeks to 12 months post injury for a total number of 163 human subjects with TBI. Group based trajectory (TRAJ) analyses were done to identify distinct subgroups of autoantibody profiles within the human population. High, medium and low TRAJ groupings of AAb levels up to 6 months post-injury were generated.

A Treelet Cluster (TC) Analysis was performed on the inflammatory markers, which algorithmically identified meaningful groups of markers. A cluster weight was generated for each marker based on the adherence to the different clusters. TC1 and TC2 represented the adaptive and innate immune responses respectively. The base ordinal logistic regression modeled how age, sex and Glascow Coma Scale (GCS) informed on AAb production. The final models indicated that TC1 was significantly associated with IgM AAb production, while TC2 did not influence IgM TRAJ as significantly. These data showed that markers involved in adaptive and innate immune responses predicted and were relevant to autoantibody production post-injury.

Anti-inflammatory therapies showed inconclusive results, which addressed the complexity of beneficial and detrimental inflammation post-injury (Ziebell et al., *Neurotherapeutics*. 2010; 7(1):22-30). Despite progress in the neurotrauma field, many individuals who sustain a TBI experience debilitating long-term functional deficits and disabilities (Zaloshnja et al., *J Head Trauma Rehabil*. 2008; 23(6):394-400).

The secondary injury response post-TBI is characterized by both an acute innate response, and an adaptive immune response. Activation of the innate immune response is a major element of the acute secondary injury response to TBI; the self-propagating nature of the innate immune response can be one reason for why inflammation continues to persist long after the acute injury (Simon et al., *Nat Rev Neurol*. 2017; 13(3):171-191). Adaptive immunity also contributes TBI related inflammation. Autoantibody (AAb) production can occur after TBI (Zhang et al., *PloS One*. 2014;9(3); Wang et al., *J Neurotrauma*. 2016; 33(13):1270-1277), and autoantibody production is a significant component of the adaptive autoimmune response. Post-TBI blood samples can contain autoantibodies to brain proteins such as glial fibrillary acidic protein (GFAP) (Wang et al., *J Neurotrauma*. 2016; 33(13):1270-1277). Autoantibody production promotes tissue repair, yet can also facilitates neuroinflammation (Kobeissy et al., *Front Neurol*. 2013; 4:186), and the characterization of autoantibody production after CNS injury may help improve the understanding of TBI pathobiology beyond the acute phase after an injury. Ongoing inflammation chronically after TBI contributes significantly to many types of complications experienced post-injury. Yet, there are no successful therapeutic measures that target specifically the reduction of long-term complications after TBI.

Controlled inflammation may be necessary to clear damaged cells, a process initially mediated by key pro-inflammatory cytokines. Though the chronic elevations of serum inflammatory markers and their association with long-term global outcome in a clinical population with moderate and severe TBI were characterized (Kumar et al., *J Head Trauma Rehabil*. 2015 Nov-Dec;30(6):369-81), the mechanisms of secondary injury related inflammation are not fully understood; more detailed characterization of inflammatory biomarker patterns, including autoantibody production, could lead to identification of the recovery processes and potential novel therapeutic targets.

A significant contributor to post-TBI disability is neuroendocrine dysfunction, including persistent hypogonadotropic hypogonadism (PHH) (Fernandez-Rodriguez et al., *Front Endocrinol*. 2011; 2:25), and research lacks a mechanistic understanding of why neuroendocrine dysfunction occurs so commonly, even in the setting of no other structural damage to the pituitary or hypothalamus after injury. Higher serum autoantibodies to the pituitary (APA) and hypothalamus (AHA) IgG antibodies are associated with pituitary deficits in TBI patients 5 years post-injury (Tanriverdi et al., *Eur J Endocrinol Eur Fed Endocr Soc*. 2008; 159(1):7-13; Tanriverdi et al., *J Neurotrauma*. 2013; 30(16): 1426-1433). These studies suggested that autoantibody production occurs in the context of post-traumatic hypopituitarism. Furthermore, auto-immunity was suggested that it may contribute, at least in part, mechanistically to neuroendocrine dysfunction (Barton et al., *J Head Trauma Rehabil*. 2016 Jul-Aug;31(4):277-87). In order to understand the mechanism for post-injury hypopituitarism, chronic inflammation processes involving the hypothalamus and pituitary gland as well as autoimmune responses involving these brain regions were identified (Kasturi et al., *J Neurotrauma*. 2009; 26(8):1315-1324; Tanriverdi et al., *Eur J Endocrinol*. 2010; 162(5):861-867). But it has been unclear as to the potential neuroendocrine implications in play in response to endocrine tissue specific autoimmunity responses after TBI. While the physiology of PHH and TBI related auto-immunity remains unclear, the present disclosure showed that inflammatory patterns associated with autoimmunity and inflammation, characterized by chronic serum autoantibodies to the pituitary and hypothalamus, may have some influence on PHH risk.

Following TBI centrally derived cytokines including IL-1β, IL-6 and TNFα, can contribute to increased blood-brain barrier (BBB) permeability (Burton et al., *J Neuroinflammation*. 2011; 8:54). BBB disruption occurs rapidly, and may allow for systemic exposure to CNS antigens (Chodobski et al.. *Transl Stroke Res*. 2011; 2(4):492-516), resulting in successive autoantibody production through the adaptive immune response. After spinal cord injury (Riegger et al., *Neuroscience*, 2009:1.58(3):1194-1.199), the adaptive immune response is suppressed, and many individuals experience lymphopenia following the aseptic acute inflammatory response (Thong et al., *Exp Neurobiol*. 2013;22(2)59-67). Suppressed immune responses after injury can facilitate infections and impair wound healing, negatively impact neurological recovery (Riegger et aL., *Neuroscience*. 2009; 158(3):1194-1 199), and can contribute to autoantibody development (Traumatic Brain Injury and Peripheral Immune Suppression: Primer and Prospectus. www.ncbi.nlm.nih.gov/pmc/articles/PMC4633482/).

T-lymphocytes are critical to the post-injury inflammatory response and are a major source of cytokines involved in inflammatory activity (Brait et al., 2010 *J Cereb Blood Flow Metab*. 2010 July; 30(7): 1306-1317), as well as autoantibody production. Adaptive immune response signaling molecules, such as interleukin 7 (IL-7), promotes lymphoproliferation of a T-cell population sensitive to circulating self-antigens that produce CNS antibodies (Schluns et al., *Nat Immunol.* 2000; 1(5):426-432; Ernst et al., *Immunity.* 1999; 11(2):173-181). This process may be protective in nature (Schwartz et al., *Trends Mol Med.* 2001; 7(6):252-258; Schwartz et al., *J Neurol Sci.* 2005;233(1-2):163-166). In this context, some individuals may be better prepared to immunologically generate a lymphoreparative response after TBI than those with reduced adaptive immune function due to factors such as aging and stress (Lucin et al., *J Neurochem.* 2009; 110(5):1409-1421; Gregory et al., *Nat Genet.* 2007; 39(9):1083-1091; Lundstrom et al., *Semin Immunol.* 2012; 24(3):218-224). Furthermore, several inflammatory markers involved in the adaptive immune response whose profiles and patterns post-TBI may be relevant to mechanisms underlying the development of post-TBI autoimmunity (Sutton et al., *Immunity.* 2009; 31(2):331-341).

The present disclosure suggested that patterns and profiles of serum inflammatory associated with APA, AHA and GFAP IgM autoantibody could inform how the inflammatory response post-TBI impacts on neural repair and recovery. GFAP AAbs are a brain-derived autoantigen after TBI and therefore might enhance a persistent autoimmune reaction (Zhang et al., *PloS One.* 2014;9(3)). Furthermore, demonstration of APA and AHA AAbs after head trauma has suggested more involvement in autoimmunity and TBI-induced hypopituitarism (Dubourg et al., *Neurosurg Focus.* 2011;31(5):E2). Lower levels of APA IgM in men with severe TBI were associated with PHH status, suggesting that these antibodies play a protective role in preserving neuroendocrine function post injury. Therefore, this present disclosure examined patterns and profiles of systemic inflammatory markers and their relationship to APA, AHA and GFAP IgM AAb production in a mixed population of men and women after moderate to severe TBI. Autoantibodies, along with inflammation markers, may provide insights in the adaptive and innate immune response and neuroendocrine recovery post TBI.

Methods

Study Design and Population

This was a prospective, longitudinal cohort study of patients who had sustained moderate to severe traumatic brain injuries. The present disclosure recruited (n=163) individuals at the University of Pittsburgh Medical Center (UPMC) level 1 trauma center with severe TBI, defined by the Glasgow Coma Scale <8 at presentation. The analysis included both men and women aged 17 to 85 years old. Demographic and injury information, including age, sex, race, mechanism of injury, and GCS score were obtained from patient records from admission.

Blood samples for this study cohort were collected daily for the first week post injury and then every two weeks for six months after injury (n=933). Samples were centrifuged and stored in a −80° C. freezer until analysis.

APA AHA GFAP ELISA Protocol 96-well plates were coated with bovine hypothalamic lysate. After plate preparation, Il of human serum sample was mixed with 99 ul of start-block buffer, which was then transferred to each well (1:100 dilution) and incubated, at 4° C. overnight with shaking. Plates were then washed 4× with Tris-Buffered saline and Tween® (TBST) 20 wash buffer. Anti-Human IgG/IgM HRP conjugate was added as a 100ul aliquot to each well. Plates were then incubated at 25° C. with shaking for 45 minutes. The plates were then washed again 4× with TBST, 100ul of TMB substrate was added to develop color for 15 minutes. Lastly, 100ul of Stop Solution was added and the plates were read for the yellow color of the final product at 450 nm.

Two standard curves were generated for APA or AHA or GFAP specifically using IDC-a7_Sub,AMD their respective antibody, human IgM or human IgG, specific to them. Standard curves were generated by adding 0, 17, 26, 39, 58.5, 88, 131.5, 198, 296, 444, 666 and 1,000 ng/mL (50 uL) of either purified human IgG or human IgM (Sigma Co.) to the first rows of the ELISA-plate. A 50-factor dilution was applied, using 50 uL of standard for 1 uL of human serum sample. A sample analysis was performed over 2 weeks and calculated intraassay % CV as 5-7% and interassay % CV as 15-20%.

Luminex BeadAssay

Cytokine levels were measured in serum samples (n=933) using a Milliplex Multiplex Luminex bead assay. The Human High Sensitivity T cell Magnetic Bead Panel included interleukin (IL)-10, IL12(p70), IL13, IL-10, IL-2, IL-21, IL-4, IL-23, IL-5, IL-6, IL-7, IL-8, MIP-1α, MIP-10, TNFα, Fractalkine, GM-CSF, ITAC and IFNγ. The intra-assay % CV was generated from the mean of the % CV from 8 results across two different concentrations in a single assay and was <5%. The inter-assay % CV was generated from means of the % CV's across two concentrations of analytes across 6 different assays. The Human Neurodegenerative Disease Magnetic Bead included sICAM-1 (intra- and inter-assay % CV 5.7%), RANTES (intra-assay % CV 4% and inter-assay % CV 4.7%), NCAM (intra-assay % CV 3.5% and inter-assay % CV 4.9%) and sVCAM-1 (intra-assay % CV 2.8 and inter-assay % CV 7.3%). The Human Soluable Cytokine Receptor Magnetic Bead Panel included sCD30, sgp130, sIL1RI, sIL-1RII, sIL-2u, sIL-4R, sIL-6R, sTNFRI, and sTNFRII. The inter-assay % CV was <10% while the inter-assay % CV was <15%. These assays utilized a microsphere processed as an immunoassay tagged with multiple fluorescent labeled markers. In order to observe the specific interleukins, a fluorescence detection laser optic system was used to analyze the binding of each protein on the microsphere. Samples that were undetectable by the assay were assigned levels of 0.0001 µg/mL.

Group Based Trajectory Analysis

In order to assess serum autoantibody profiles longitudinally, group-based trajectory analysis (TRAJ) was utilized (Niyonkuru et al., *J Neurotrauma.* 2013; 30(11):938-945). The group-based trajectory analysis identifies the distinct sub-populations within a cohort to create longitudinal profiles. This data driven methodology assumed that there are a finite number of distinct groups within a population and was used to identify the groups that best fit the data. This method was applied to identify distinct subgroups of autoantibody profiles within the population. Distinct TRAJ groups were comprised of individuals that exhibited similar longitudinal autoantibody characteristics over the 2-week to 26-week period. For this study, IgM and IgG trajectories for APA, AHA and GFAP autoantibodies were generated. Three distinct groups were identified, representing high, medium and low autoantibody profiles over time. TRAJ group formation was conducted using a log transformation of the autoantibody data 2-weeks to 26-weeks post injury.

Statistical Analysis and Treelet Cluster Weights

Statistical analyses were performed using Statistical Analysis Software (SAS) version 9.4 (SAS Institute Inc. 2010. SAS® 9.2 Language Reference: Concepts, Second Edition. Cary, NC: SAS Institute Inc). Cytokine levels collected from multiple serum samples were assessed longitudinally over the 2-26 week time period. Bivariate analyses, including mean and standard error values, were calculated for these cytokines among the generated IgM TRAJ groups for APA and AHA. Inflammatory markers were classified using a form of hierarchal cluster analysis called Treelet Transform, which is a data reduction methodology. Using this approach, the different inflammatory markers were used as components for the Treelet Transform. The most closely correlated 2 inflammatory markers joined the tree first, and then a principle components analysis (PCA) was issued to generate a sum factor of these markers. This sum factor was used again to join the next closest component.

This process was repeated until all the components (inflammatory markers) were joined in a tree. The final product was known as dendrogram, which was a visual representation of the relationships of all the inflammatory cytokines. The vertical line indicated the cut level of the treelet, which was algorithmically generated and used to identify meaningful clusters of related inflammatory markers. The disclosed treelet included four cluster groups, labeled TC1, TC2, TC3 and TC4. TC1 included markers involved in the adaptive immune system, and TC2 indicated markers involved in the pro-inflammatory, innate immune response. Additionally, TC3 represented soluble receptors, and TC4 represented allergy markers. This present disclosure focused on TC1 and TC2 in order to understand the innate and adaptive immune responses regarding autoimmune responses post-TBI. The dendrogram produced cluster weights for each person in the cohort, and these weights were used as a quantitative measure to consider the contribution of these inflammatory markers to IgM TRAJ. Multivariable logistic regression model was used to assess how treelet cluster weights predict IgM autoantibody TRAJ while adjusting for age, gender and GCS score.

Results

Demographic and Sample Characteristics

The cohort included in this study consisted of 163 men and women whose ages ranged from 17 to 78 years old. These individuals all had at least two post-acute blood samples collected over the first 6 months post-injury to be used for autoantibody analysis. Demographic information for this cohort is reported in FIGS. 104A-104C. Mean age was lower across TRAJ groups for AHA/GFAP IgM, such that individuals who were younger fell into higher TRAJ groups with higher autoantibody levels. There was also a significant difference across GFAP IgM TRAJ groups and sex, while this was not the case with APA/AHA IgM. There were no significant differences between TRAJ groups in race, TBI severity, Non-head Injury Severity Scale (ISS), Length of Hospital Stay or Mechanism of Injury. Acute neuroradiology reports from CT scans were available for 90 individuals. However, there were no significant differences among the 3-autoantibody TRAJ groups and CT reported data.

IgM Trajectory Groups

TRAJ analysis of autoantibody levels over time in this cohort revealed three distinct subgroups of individuals with IgM profiles of APA, AHA and GFAP. These groups are denoted as high, medium and low, as graphed in FIGS. 105A-105C. Group-based trajectory analysis (TRAJ) was performed for APA, AHA and GFAP IgM to identify distinct groups with similar chronic autoantibody level profiles up to 6 months post-injury. Three groups were identified for all three analyses, which were labeled as high, medium and low. Autoantibodies differed significantly (p<0.05) across all time points for APA, AHA and GFAP TRAJ groups. For APA IgM TRAJ, there were 32 (20%) individuals in the low group, 60 (37%) individuals in the medium group and 71 (43%) individuals in the high group. For AHA IgM TRAJ, there were 40 (24%) individuals in the low group, 103 (63%) individuals in the medium group and 20 (13%) individuals in the high group. For GFAP IgM TRAJ, there were 19 (12%) individuals in the low group, 76 (46%) individuals in the medium group and 68 (42%) individuals in the high group. Furthermore, the control levels for each autoantibody falls near the medium TRAJ group. APA/AHA/GFAP IgM levels of each TRAJ group were generally stable overtime, and there were significant differences in IgM levels between each TRAJ group at all points across 6 months post-injury (p<0.05) (FIGS. 105A-105C).

IgG Trajectory Groups

TRAJ analysis of autoantibody levels indicated three distinct subgroups of IgG profiles for APA, AHA and GFAP. Similar to the IgM TRAJ groups, the APA and AHA IgG groups were denoted as high, medium and low. For APA IgG TRAJ, there were 50 (31%) people in the low group, 75 people (46%) in the medium group and 38 (23%) people in the high group. For AHA IgG TRAJ, there were 61 people (37%) in the low group, 79 people (49%) in the medium group and 23 (14%) in the high group. The group based TRAJ analysis identified two distinct sub-populations for GFAP IgG TRAJ, which were denoted as high and low. There were 49 individuals (30%) in the low group and 114 individuals (70%) in the high group for GFAP IgG TRAJ.

Treelet Cluster Weight Dendrogram

To classify groups of biomarkers, the treelet cluster analysis was conducted. The dendrogram, shown in FIG. 106, indicated four treelet clusters based on the optimal cut off level. The 4 circles indicated the 4 significant Treelet clusters. The solid vertical line indicated the cute level for which the last branch considered was significant. All markers to the left of the circles were considered cluster components. Reading from left to right, branches that connect first had the strongest correlation, with the next connect branch having the next highest correlation, etc.

Treelet cluster 1 (TC1) represented markers involved in the adaptive immune system. These included Interleukin (IL) 2, IL7, IL12 p70, IL21, IL23, Interferon gamma (IFNg) and Fractalkine. These biological markers were involved in an antigen specific immune response after injury. This secondary response is highly specialized to particular pathogens and has the ability to provide long-lasting protection[33]. Treelet cluster 2 (TC2) indicated markers involved in the pro-inflammatory, innate immune response, which are the markers that participate in the first line of defense after injury. These markers included IL1b, IL6, Tumor necrosis factor alpha (TNFα) and Macrophage inflammatory protein-3 alpha (MIP3a). Additionally, treelet cluster 3 (TC3) represented receptor, including soluble tumor necrosis factor receptor 1 (sTNFRI), including soluble tumor necrosis factor receptor 2 (sTNFRII) and soluble IL2 receptor alpha (IL2Ra). Treelet cluster 4 (TC4) represented markers involved in allergies, including IL5 and IL13. The present disclosure focused on TC1 and TC2 in the hopes to understand the innate and adaptive immune responses with regard to inflammatory cytokines post-TBI.

Treelet Cluster Weight Associations to TRAJ Groups

Additionally, treelet cluster weights varied across trajectory groups. As shown in FIGS. 107A-107F, APA IgM TRAJ was significant associated with TC1 (p=<0.0001), TC2 (p=0.0004) and TC4 (p=0.0343). There were also significant differences of TC1 (p=<0.0001) and TC2 (p=0.0341) weights across AHA IgM TRAJ. For TC2, the medium TRAJ had the highest cluster weights; followed by the high, then low TRAJ groups. TC1 was significantly associated with GFAP IgM TRAJ (p=<0.0001), while TC2 had a trend across GFAP IgM TRAJ (p=0.0537). There was a positive trend in TC1 across TRAJ groups, however TC2 was higher in the medium GFAP IgM TRAJ, followed by the high, then low TRAJ. FIGS. 107A-107F also showed associations of TC cluster weights to APA/AHA/GFAP IgG TRAJ groups. The only significant association was between APA IgG TRAJ and TC2 (p=0.0493).

Ordinal Logistic Regression Model Results

An ordinal logistic regression model was run in order to identify whether inflammatory profiles inform on AAb production. The cluster weights produced by the dendrogram are used in multivariate modeling. The base model included age, sex and Best in 24 Hours Glasgow Coma Scale (GCS) score as covariates to inform APA/AHA/GFAP IgM TRAJ. The disclosed variables of interest were the TC1 and TC2 weights, as they informed on markers associated with the adaptive and innate immune responses. Since there were not strong associations between IgG TRAJ and TC1 and TC2 (FIGS. 107A-107F), the regressions modeled only relationships to IgM TRAJ. All three ordinal logistic regressions were modeled in reference to the high TRAJ group. As shown in FIG. 108, in the final model, with these cluster weights included as covariates, TC1 was significantly associated with APA IgM TRAJ (p=0.0004), while TC2 did not inform APA IgM TRAJ as strongly with only a trend (p=0.0778). For every unit increase of TC1 weight, an individual were at 1.602 times odds of being in the low APA IgM TRAJ group. For every unit increase of TC2, there was a 1.650 times odds of being in the low APA IgM TRAJ group.

FIG. 109 shows results of associations to AHA IgM TRAJ. TC1 was significantly associated with AHA IgM TRAJ (p=<0.0001), however, TC2 remained indicating insignificant associations to AHA IgM TRAK (p=0.1366). The ordinal logistic regression modeled the reference category to high TRAJ membership. Therefore, for every unit increase in TC1 weight, an individual experienced 1.622 odds of being in the high AHA IgM TRAJ group. TC2 experienced higher odds for higher TRAJ group association. GFAP IgM TRAJ associations to TC1 (p=<0.0001) and TC2 (p=0.0729) are shown in FIG. 110. The ordinal logistic regression was modeled in reference to the high TRAJ group, therefore for every unit increase of TC1 weight, there was a 1.868 times odds of being in the higher GFAP IgM TRAJ group.

Furthermore, in order to identify whether including TC1 and TC2 in the final model helped inform AAb production, the AIC statistic was observed. A lower AIC statistic determined a strong model with a better goodness of fit. As shown in FIGS. 108-110, the final model had a lower AIC statistic for APA IgM TRAJ (236.45), AHA IgM TRAJ (209.66) and GFAP IgM TRAJ (217.05) compared to the base models. This suggested that the models with TC1 and TC2 included as covariates had a better goodness of fit for predicting IgM AAb TRAJ.

Discussion

The secondary injury cascades after TBI trigger many pathological responses, including inflammation. Little is known about how inflammation persists over time chronically post injury. Despite growing knowledge about the acute secondary injury mechanisms, less is known about the chronic pathology or persistent complications that follow TBI. The present disclosure carries significant implications for understanding chronic TBI pathologies and begin to characterize the link between the inflammatory response involved in adaptive/innate immune responses and autoantibody production after injury. The treelet clusters examined in the example provides information on specific markers that co-vary together to better inform on autoantibody production and development after injury that helps predicts the neural reparative functions.

The strong association between TCT weights and AAb TRAJ suggested a link between inflammatory markers and AAb production after TBI. The weaker association exhibited by TC2 exemplified the nature of the innate immune response, which consists of initial debris-clean up resulting from injury. The innate immune response occurs before the adaptive immune response, and therefore, innate effects may diminish over the course of 6 months post-injury (Jassam et al., *Neuron.* 2017; 95(6):1246-1265). TRAJ analysis revealed that after TBI individuals can associate with distinct subgroup populations of AAb levels up to 6months post-injury. The present disclosure also showed that in addition to having a bivariate associated with AAb TRAJ membership, TC1 and TC2 increased the goodness of fit for modeling IgM AAb TRAJ group membership. These results may provide important biological insight into the role of prolonged inflammation and autoimmune recovery after TBI.

Neuro-inflammation was linked to injury severity in the acute phase (Buttram et al., *J Neurotrauma.* 2007; 24(11): 1707-1717; Singhal et al., *J Neurotrauma.* 2002; 19(8):929-937; Hensler et al., *J Trauma.* 2002; 52(5):962-970). Blood brain barrier disruption occurs rapidly after TBI and the infiltration of systemic exposure to CNS antigens (Morganti-Kossmann et al., *Injury.* 2007; 38(12):1392-1400). This process activates CNS cells, including astrocytes and microglia which then work to produce various cytokines and chemokines (Feuerstein et al., *Neuro immunomodulation.* 1998;5(3-4):143-159). A major component of the brain's innate immune response is the microglia that can release numerous inflammatory mediators, including cytokines (Rivest, *Nat Rev Immunol.* 2009 June;9(6):429-39). Microglial activation in patients with TBI may indicate the BBB disruption is occurring, contributing to inflammatory responses. Additionally, activated microglia in regions of the brain up to 18 years post injury was identified, suggesting that these pathological responses are responsible for elevated neuroinflammation after TBI (Johnson et al., *Brain J Neurol.* 2013;136(Pt 1):28-42).

In relation to the adaptive immune response, IL-7, a cytokine clustered in TC1, was shown to have an important role in lymphoproliferation to facilitate neuro-repair (Schluns et al., *Nat Immunol.* 2000; 1(5):426-432; Ernst et al., *Immunity.* 1999; 11(2):173-181). Administered recombinant IL-7 (rIL-7) in small clinical studies showed improvements in immunodeficiency. A study using animal sepsis models to induce immunosuppression indicated that rIL-7 administration increased splenic and peripheral node T-cell lymphoproliferation. Furthermore, the administration of rIL-7 indicated a noticeable increase in splenic CD4 T-cells and leukocyte adhesion molecule expression on CD4 and CD8 T-cells (Shindo et al., *Shock.* 2015; 43(4):334-343). IL-7 bioavailability varies among individuals and post-injury innate factors may influence IL-7 production and utilization.

Additionally, CNS cytokines, including IL-1, IL6 and TNFα, which co-vary with TC2, are activators of the hypothalamic pituitary axis, contributing to dysfunctional inflammation post-injury (Sorrells et al., *Brain Behav Immun.* 2007; 21(3):259-272). Under biologically stressful situations, production of these pro-inflammatory markers may increase (Griesbach et al., *Neuroscience*. 2012; 210: 393-402). The balance of pro and anti-inflammation is crucial to understanding the therapeutic implications of neuroinflammation (Jeong et al., *Exp Neurobiol*. 2013; 22(2):59-67).

Characterizing AAb profiles post-injury is important in understanding the complexities of autoimmune responses post-CNS injury. IgM autoantibodies are the most evolutionary conserved antibody and are the earliest isotype to be expressed during immune development (Gronwall et al., *Front Immunol*. 2012; 3:66). IgM AAbs were suggested deriving from B-1 cells and are amplified in environments of pro-inflammatory states to activate mediated anti-inflammatory pathways (Lobo et al., *J Clin Immunol*. 2010;30 Suppl 1:S31-36; Vas et al., *Front Immunol*. 2013; 4:4; Gray et al., *Proc Natl Acad Sci USA*. 2007; 104(35):14080-14085). Higher levels of IgM AAbs work to maintain homeostatic conditions of the immune system while lower levels of IgM AAbs enhance pathogenic IgG production, associated with autoimmune diseases (Gronwall et al., *Front Immunol*. 2012; 3:66). Specifically, IgM antibodies bound to antigens promote phagocytosis, support inflammatory cell recruitment and modulate the adaptive immune response (Kjaer et al., *Mol Immunol*. 2013; 56(4):413-422). Furthermore, higher levels of IgM APA/AHA AAbs were shown linked to reduced risks for persistent hypogonadotropic hypogonadism, a chronic condition that is associated with various functional deficits, including low energy, poor concentration and mood disturbances[12]. Moreover, men with PHH on average were older, showing that aging immunity has a decreased capacity to respond to various assaults (Aspinall et al., 2014; 42(3):651-656).

The present disclosure has implications for furthering the understanding of a wide range of secondary complications resulting from TBI. Prolonged inflammation was shown to have effects on other diseases including fatigue (Klimas et al., *Brain Behav Immun*. 2012; 26(8):1202-1210), seizures (Vezzani et al., *Epilepsy Curr*. 2007;7(1535-7597 (Print)): 45-50), and PHH (Barton et al., *J Head Trauma Rehabil*. 2016 Jul-Aug;31(4):277-87). Since these conditions can persist commonly after TBI, the present disclosure calls attention to investigation of chronic markers and their incidence of these conditions. In conclusion, pro- and anti-inflammatory makers were reported to associate with various sub-populations of autoantibody levels post-TBI. Including markers that associated with autoimmune responses in the dialogue of neuro-repair and regeneration after TBI is important to understanding mechanisms of delayed autoantibody related recovery. Serum inflammatory markers associated with the adaptive and innate immune responses inform on autoantibody production and the present disclosure provides certain understanding how neuroinflammation and repair is facilitated after TBI.

Example 28: Evaluating the Predictive Capacity of the Neutrophil-to-Lymphocyte Ratio and Platelet-to-Lymphocyte Ratio after Traumatic Brain Injury Neurotrauma has become focused on minimizing the long-term consequences of the heterogeneous traumatic brain injury (TBI) patient population. TBI patients are susceptible to various acute and chronic complications while in the hospital, alongside secondary inflammatory biochemical cascades mediated by immune cells. Yet, these conditions have not been well-characterized in terms of predictive biomarkers in TBI. The present disclosure aimed to explore inflammatory biomarker patterns associated with immune cell counts and other unfavorable conditions associated with TBI. Group based trajectory (TRAJ) analyses of neutrophil-to-lymphocyte ratios (NLR) and platelet-to-lymphocyte ratios (PLR) identified low, moderate, and high group TRAJ profiles. TRAJ group memberships were compared to clinical and behavioral variables, CSF and serum inflammatory marker levels, and 6-month GOS and DRS scores, which serve as long-term outcomes of interest. NLR TRAJ was significantly associated with poor GCS, longer hospital length of stay, longer time on mechanical ventilation, unfavorable 6-month GOS, and greater acute infection incidence and risk. NLR TRAJ was also associated with greater incidence of SAH, IVH, DAI, and intra-axial injury. Factors contributing to unfavorable global outcome at 6 months post-TBI were evaluated using logistic regression modeling. NLR TRAJ was also significantly associated with Satisfaction with Life, Percent Back to Normal, and Patient Health Questionnaire-9 scores. PLR TRAJ was significantly associated with age and sex, as well as greater SAH incidence. Both NLR and PLR TRAJ were associated with 6-month PTD status and predicted PTD risk. When considering inflammatory markers, both NLR and PLR TRAJ were associated with MIP-3a, sICAM-1, and IL-5 in the acute phase (day 0 to 5). In the chronic phase (months 0 to 6), both TRAJ groupings were associated with MIP-1b only.

Acutely, NLR TRAJ was uniquely associated with NCAM, IL-10, sIL-6R, sgp130, sIL-2Ra, sIL-1RII, sTNFRI, and sTNFRII, and PLR TRAJ was uniquely associated with the sIL-6R:IL-6 ratio. Chronically, NLR TRAJ was uniquely associated with IL-8, sTNFRI, sTNFRII, sCD30, sIL-6R, sIL-1RII, sTNFRII:sTNFRI ratio, sTNFRI:TNFα ratio, and the sgp130:sIL-6R ratio, whereas PLR TRAJ was uniquely associated with ITAC, sgp130, RANTES, and NCAM. When comparing biomarkers among NLR TRAJs, sgp130, sIL-2Ra, MIP-3a, NCAM, IL-10, sICAM-1, and IL-5 were uniquely associated in the acute phase, whereas MIP-1b, IL-8, sCD30, sTNFRII:sTNFRI, sTNFRI:TNFα, and sgp140:sIL-6R were uniquely associated in the chronic phase after injury. Interestingly, sIL-6R, sIL-1RII, sTNFRI, and sTNFRII were all significantly associated with NLR TRAJ in both the acute and chronic recovery phases. Comparing across PLR TRAJ groups, MIP-3a, sICAM-1, IL-5, and the sIL-6R:IL-6 ratio were all uniquely associated acutely, and ITAC, MIP-1b, sgp130, RANTES, and NCAM were uniquely associated chronically. No shared markers were significantly different during both the acute and chronic time points between PLR TRAJs. These findings suggested the differential capacity of NLR and PLR of predicting clinical outcomes and are informative of the different inflammatory mechanisms at play after TBI that contribute to poor long-term outcomes.

According to the United States Center for Disease Control, traumatic brain injury (TBI) is defined as a mild, moderate, or severe injury that disrupts normal brain functionality by a bump, blow, jolt, or penetrating injury. In 2013, 2.5 million emergency department visits, 282,000 hospitalizations, and 56,000 deaths related to TBI were recorded attributed to various etiologies including, but not limited to, motor vehicle accidents, falls, assaults, and intentional self-harm (Taylor et al., 2017). TBI is a significant public health and socioeconomic concern, with a higher incidence of mortality and chronic disability in those with moderate to severe injuries (U.S. Center for Disease Control and Prevention, 2016). Persistent long-term complications are also present after TBI, which include neuroendocrine dysfunction as well as cognitive, behavioral, and functional deficits.

Systemic acute immunosuppression results from sympathetic nervous system activation and the innate immune response post-injury, which can increase lymphocyte apoptosis when prolonged (Hazeldine et al., *Front Neurol.* 2015; 6:235). Certain studies have found that there is a lack of helper T cell and cytotoxic T cell proliferation in patients with head injuries, leading to an increased risk of developing an infection (Quattrocchi et al., (1991) *Neurological Research,* 13(1), 13-20). Mrakovcic-Sutic et al. also tracked T cells in TBI patients for 7 days after injury and found decreased cytotoxic T cells and natural killer T cells 4 days after the injury. The natural killer T cells remained low after 7 days, related to a lymphopenic immunosuppressed state (Mrakovcic-Sutic et al., (2010) *Scandinavian Journal of Immunology,* 72(1), 57-65). It has also been documented that TBI patients who developed an acute infection have worse outcomes than those who have not acquired an infection (Glance et al., (2011). *Archives of Surgery,* 146(7), 794-801; Kesinger et al., (2015). *The Journal of Trauma and Acute Care Surgery,* 78(2), 396-402). But, the underlying causes and markers of infection associated with poor course of recovery and long-term outcomes after TBI are not well understood, but lymphopenia serves as a major indicator of injury-induced systemic immunosuppression linked to unfavorable aspects of the injury response.

Certain white blood cells may be suppressed following trauma and severe head injury, but neutrophilic leukocytosis, or a state of elevated neutrophils, has also been reported after TBI as a part of the systemic inflammatory response after injury. Neutrophils are the first immune cells recruited to the brain after trauma to perform reparative functions and predominate in the first few days after injury, directed by purines, cytokines, and chemokines. Neutrophils respond rapidly in a non-specific manner as a part of the innate immune response. Santucci et. al and Rovlias et. al found associations between severe head trauma and elevated neutrophil counts after injury (Rovlias et al., *Surg Neurol.* 2001; 55(4):190-196; Santucci et al., (2008) *Western Journal of Emergency Medicine,* 9(2), 81-85). Neutrophilia has also been reported to coincide with blood brain barrier (BBB) breakdown and neurodegeneration, though the relationships between neutrophilia and cytotoxic neuronal death mechanisms are not clear (McKee et al., *Front Immunol.* 2016; 7:556). Neutrophil depletion in mice were reported to reduce edema, microglia activation, tissue loss, and activated caspase-3+cells that contribute to cell death, suggesting the pathogenic nature of these immune cells if activity persists beyond their initial reparative function (Kenne et al., (2012) Journal of Neuroinflammation, 9, 17). The increased oxidative activity of excessive circulating neutrophils can cause further systemic damage and dysfunction and exacerbate secondary local damage (Liao et al., (2013) *PLoS ONE,* 8(7)). Head injury is associated with cortisol and catecholamine increase, which leads to the release of neutrophil stores and acute leukocytosis along with an increase in cell lifespan (Rovlias et al., *Surg Neurol.* 2001; 55(4):190-196). Generally, sustained high levels of neutrophils can contribute to neurodegenerative mechanisms and poor outcome.

The neutrophil-to-lymphocyte ratio (NLR) can serve as a predictor of outcome in critical illness, additionally confirmed in patients with severe TBI. Sustained excessive neutrophil levels were observed along with a group of clinically-lymphopenic individuals in the first week post-injury. The coupling of high neutrophil and low lymphocyte levels contributes to high NLR observed upon admission, exacerbated by sympathetic hypothalamic-pituitary axis activation following trauma. High NLR is associated with unfavorable outcome and mortality at 1 year following head trauma (Chen et al., *J Head Trauma Rehabil.* 2018 Jan/Feb; 33(1):E53-E59). High neutrophils, lower lymphocytes, and high NLRs are predictive of worse outcome 3 months after intracerebral hemorrhage (Lattanzi et al., (2016) *Stroke,* 47(6), 1654-1657). Further, peak NLR in days 1 through 12 served as an independent predictor of unfavorable outcome 1 year after severe TBI (Chen et al. *Neuro crit Care.* 2019 April; 30(2):334-339). High NLR after trauma can be injurious; however, characterization of the biomarkers associated with this patient population has not yet been explored.

The development of coagulopathy and platelet dysfunction follows trauma and brain injury. Normal homeostasis is reliant upon a balance between the mechanisms controlling bleeding and thrombosis, which can be disrupted by the primary injury. Peck et al. found that anticoagulants and antiplatelet agents can adversely affect patient outcomes after TBI, leading to greater in-hospital mortality, especially among older patients (Peck et al., (2014) *The Journal of Trauma and Acute Care Surgery,* 76(2), 431-436). After TBI, platelet aggregation is reduced and can increase hemorrhage risk, further exacerbating the initial injury (Joseph et al., (2014) *The Journal of Trauma and Acute Care Surgery,* 77(3), 417-421; Martin et al., *J Trauma Acute Care Surg.* 2019 April; 86(4):592-600). Further, acute platelet dysfunction is followed by rebound platelet hyper-aggregation, which is temporally associated with the systemic proinflammatory response (Martin et al., (2018) *Neuro critical Care,* 28(3), 330-337). Holzmacher et al. found that platelet dysfunction post-injury has been associated with worse outcomes with patients requiring platelet transfusion having a higher injury severity score (ISS), worse admission computed tomography scores, and a longer hospital length of stay (LOS) (Holzmache et al., (2018) *Brain Injury,* 32(3), 325-330).

TBI patients are reported to have lower venous platelet counts, longer bleeding time, and lower platelet responses to arachidonic acid that make bleeding complications more likely. Neuronal glycosphingolipids induce platelet degranulation and the secretion of neurotransmitters and other proinflammatory factors. There is the potential for interaction of platelets and proinflammatory cytokines in the modulation of coagulation, microthrombosis, and venous thromboembolic events after TBI. The unregulated inflammatory and thrombotic responses are proposed causes of early brain injury and poor clinical outcomes in various contexts, including intracerebral hemorrhage, subarachnoid hemorrhage, and TBI. In combination with the immune response of lymphocytes, the platelet-to-lymphocyte ratio (PLR) may inform the state of inflammation among these concurrent mechanisms. PLR has been implicated in hemorrhage and stroke thus far. SAH comprises a state of systemic inflammation and hypercoagulation combined with lymphopenia, leading to secondary infectious complications. After acute SAH, leukocytes infiltrate, and platelets are also activated. This activity can contribute to the main pathophysiological mechanisms of neuroinflammation and reactive thrombosis, thus impacting neurological outcome while also having systemic effects (Tao et al., (2017) *Neurocritical Care,* 26(3), 393-401). Yet, PLR has not been explored with regard to the post-injury immune response or in association with inflammatory biomarkers in the context of TBI Damaging secondary biochemical cascades result from the biomechanics of TBI (Simon et al., *Nat Rev Neurol.*

2017; 13(3):171-191). Post-traumatic inflammation is a significant component of this response, where controlled inflammation is necessary to clear cellular debris and damage early after injury. The cytokine and chemokine pathways that are upregulated after trauma can remain elevated for long periods of time following the initial injury in both the CNS and periphery (McKee et al., *Front Immunol.* 2016; 7:556). Neuroinflammation can have both beneficial and detrimental effects, which likely differ in the acute and chronic phases post-injury. Acutely, neuroinflammation mobilizes immune cells, glial cells, cytokines, and chemokines toward the injury site to mount an inflammatory response against brain damage. The apoptosis of damaged cells in early inflammation is an essential inflammatory response in injury recovery. Chronically, if not regulated, sustained elevation of certain inflammatory markers can be damaging, contributing to the cytotoxic microenvironment that leads to secondary cell death. This further affects neurological function, cognition, and global outcome. Microglia and astrocytes also suffer functional deficits after TBI, so inflammatory cascades are not always well coordinated. Blood brain barrier compromise also causes irregular immune trafficking.

An important aspect in developing anti-inflammatory based neuroprotective treatments for TBI is minimizing the neurotoxic effects of neuroinflammation while promoting the beneficial and neurotrophic effects (Lozano et al., 2015). Experimental models of inflammation also show that cytokine production and release are correlated with each other. However, little is known of which biomarkers account for patterns of variance among TBI patients relative to controls or which markers have discriminatory predictive capacity among different outcomes after injury.

The concept of inflammatory cytokine patterns associated with neutrophils, lymphocytes, platelets, NLR, or PLR has not yet been explored in the context of TBI. This is an important point because alterations in these cell counts affect cytokine and chemokine levels that play a key role in coordinating the immune response and managing tissue damage after injury. NLR and PLR reflect an individual's proinflammatory and procoagulant status, as well as their lymphopenic status and are more stable than individual blood parameters. The addition of PLR to NLR as a predictive measure in TBI may reflect pulmonary and cardiac injury alongside inflammation-induced secondary injury (Tao et al., (2017) *Neurocritical Care*, 26(3), 393-401). Certain TBI clinical studies are limited in characterizing peripheral and neuroinflammatory cytokine patterns associated with lymphopenia, neutrophilia, platelet dysfunction, infection, and chronic pathology following injury. Moreover, they have not been successful in identifying definitive neuroprotective treatments or post-acute immunotherapies.

The present disclosure aims to address a gap in current research by integrating these concepts together into a single study assessing the predictive capacity of NLR and PLR as an efficient, accessible measure of the patient immune state in relation to early immune cell counts, infection, clinical variables, patient outcomes, and inflammatory profiles. The present disclosure intends to identify markers of infection incidence in the TBI population and characterize cytokine and chemokine patterns accompanying changes in NLR and PLR after TBI and their relation to clinical variables. The present disclosure evaluated both acute cerebrospinal fluid (CSF) and chronic serum marker levels and assessed if and how these markers relate to cell counts, infection, and outcomes. Comparing the relative levels of immune cells and cytokines to their associations with chronic pathology and long-term survivor-based outcomes in the patient population can help to identify risk groups and target groups for immunotherapeutic intervention, as well as discriminate treatment windows to guide interventions in a clinical trial. Overall, the findings contribute to the understanding of immune cell counts and inflammatory biomarkers patterns accompanying TBI and their comparative predictive capacity.

Materials and Methods

Study Protocol

This retrospective cohort study was approved by the University of Pittsburgh Institutional Review Board. All patients were recruited through University of Pittsburgh Medical Center (UPMC) hospitals. Informed consent was obtained from the next of kin. Patients were eligible between ages 16-78 years with a severe TBI based on an admission Glasgow Coma Scale (GCS) score;8 with positive findings of intracranial damage on a head computed tomography (CT) scan, required extraventricular drainage catheter (EVD) for intracranial pressure (ICP) management, and at least two absolute (ABS) lymphocyte, platelet, and neutrophil values reported in the electronic medical records (EMR) available for analysis. A cohort of n=321 individuals with moderate-to-severe closed-head TBI at level 1 trauma center met the study conditions. Individuals were excluded from analysis if they exhibited a penetrating head injury, prolonged cardiac or respiratory arrest at injury (>30 minutes occurring prior to admission), evidence of brain death within the first three days after injury, an Abbreviated Injury Scale (AIS) score of 5 in regions other than head or neck, or history of cancer (malignant neoplasms) or concurrent cancer reported via International Classification of Diseases (ICD)-9 codes upon acute care discharge. Women with TBI were not on hormone replacement or oral contraceptive therapy during the sample collection period.

Participants received standard of care medical treatment consistent with. The Guidelines for the Management of Severe Head Injury, including EVD placement for ICP monitoring and ICP treatment by CSF drainage, central venous and arterial catheter placement, and surgical intervention for decompression of mass lesions as necessary (Brain Trauma Foundation, *J Neurotrauma.* 2007; 24(Suppl 1):S1-106).

Sample Collection and Processing

Acute CSF samples (n=92) were collected passively via EVD placed for clinical care, and samples were collected up to 2 times daily for up to 5 days after injury. After collection, CSF samples were stored at 4° C. until processing. Clinical care issues, such as medical stability, minimal CSF output, or removal from the intensive care unit (ICU), affected the duration over which CSF sample collection occurred. Chronic serum samples (n=204) (~10-20 ml per sample) were drawn at monthly home visits with patients for the first 12 months after injury. Upon collection and centrifugation, all CSF and serum samples were centrifuged, aliquoted, and stored at −80° C. until batch analysis. CSF and serum inflammatory markers were measured using Luminex™ bead array assays (Millipore, Billerica, Massachusetts; Milliplex High Sensitivity 9-plex). Multiplex bead array assays use a microsphere tagged with multiple fluorescent-labelled markers. A fluorescence detection laser optic system was used to simultaneously analyze individual protein binding. Single samples were used for analysis for each Luminex assay. Samples with out of range (low) or undetectable levels were assigned the detection limit (1 ng/ml) of the assay for analysis purposes.

Chronic serum markers measured included the following cytokines and cell-surface markers: interleukin (IL)-1β, IL-2, IL-4, IL-5, IL-6, IL-7, IL-8, IL-10, IL-12p70, IL-13, IL-17a, IL-21, IL-23, interferon (IFN)-γ, granulocyte-macrophage colony-stimulating factor (GM-CSF), tumor necrosis factor (TNF)-α, interferon-inducible T-cell a chemoattractant (ITAC), fractalkine, macrophage inflammatory protein (MIP)-3u, MIP-1α, MIP-1P, soluble TNF receptor (sTNFR)-I, sTNFRII, soluble CD30 (sCD30), soluble glycoprotein 130 (sgpl30), soluble IL-1 receptor I (sIL-1RI), sIL-1RII, soluble IL-2 receptor a (sIL-2Ru), soluble IL-4 receptor (sIL-4R), soluble IL-6 receptor (sIL-6R), soluble intracellular adhesion molecule-I (sICAM-1), soluble vascular adhesion molecule-1 (sVCAM-1), neural cell adhesion molecule (NCAM), and Regulated upon Activation Normal T-cell Expressed and Secreted (RANTES). The acute CSF marker panel excluded IL-7, IL-13, IL-21, IL-23, MIP-1α, sCD30, IFNγ, ITAC, sIL-1RI, sIL-4R, and sVCAM due to different assay configurations.

Demographic and Clinical Variable Abstraction

Cemer's PowerChart and MARS were used to abstract data from patient acute care EMRs. Demographic and clinical variables collected from both personal interview and medical record review included: age, sex, race, body mass index (BMI), best in 24 hours post-injury GCS score, Injury Severity Score (ISS), hospital length of stay, ICU length of stay, rehabilitation length of stay, mechanism of injury (MOI), hospital complications, microbiology test results, time spent on mechanical ventilation, ABS lymphocytes, ABS neutrophils, platelets, behavioral questionnaires, radiological computed tomography (CT) injury type. Acute care data was abstracted for a total of 21 days (day 0-20) after injury for each patient, unless the patient died or was discharged before the end of the time frame. GCS, as assessed by trained clinical ICU staff, serves as a commonly used measure of neurological injury severity based on verbal, motor, and eye responses. MOI was binned into 6 categories: motor vehicle accidents (MVA) by automobile or off-road vehicle, motorcycle accident, bicycle or skateboard accident, fall, assault or fight, and other which includes injury by truck, bus, construction nor industrial vehicle, train, falling object, or other. Trauma research staff abstracted ISS scores, which quantifies overall injury severity across multiple anatomical regions, using the AIS for the three most injured body regions (Baker et al., *J Trauma.* 1974; 14:187-196). Microbiological culture results were used to determine infection status, considered positive if >100,000 colony forming units (CFU) per mL for any particular microorganism present. The highest ABS neutrophil value and lowest ABS lymphocyte and platelet values were abstracted from EMRs in order to calculate daily ratios for NLR and PLR analyses. Presence of the following CT injury types were abstracted from EMRs: subdural hematoma (SDH), subarachnoid hemorrhage (SAH), epidural or extradural hematoma (EDH), intraventricular hemorrhage (IVH), intraparenchymal hemorrhage (IPH), diffuse axonal injury (DAI), contusion, and midline shift. These were categorized into extra-axial hemorrhage and intra-axial hemorrhage. Extra-axial hemorrhage designates the presence of SDH, SAH, or EDH, while intra-axial hemorrhage designates the presence of IVH, IPH, or contusion.

Six Month Outcome Assessments

Individuals with immune cell data were followed up at 6 (76.32% follow-up rate) months post-injury for assessment of global recovery using the Glasgow Outcome Scale (GOS), which served as the primary outcome measure. The GOS measures overall mental and physical recovery to reflect function on a scale ranging from 1-5, with scores corresponding to: 1) dead, 2) vegetative state, 3) severe disability, 4) moderate disability, and 5) good recovery (Jennett et al., *Lancet.* 1975; 1(7905):480-484). Participants' GOS scores were dichotomized into two categories to discriminate outcomes: 1) unfavorable (GOS=1-3) and 2) favorable (GOS=4/5).

The Disability Rating Scale (DRS) scores at 6 (75.39% follow-up rate) months post-injury were also used in assessing individuals in the rehabilitation phase of recovery on: 1) arousal and awareness, 2) cognitive ability to handle self-care functions, 3) physical dependence on others, and 4) psychosocial adaptability for work, housework, or school (Rappaport et al., (1982) *Archives of Physical Medicine and Rehabilitation,* 63(3), 118-123). Scores range from 0-30, where higher scores indicate increasing disability and 30 indicating death. Participants' DRS scores were divided into four categories: 1) partial to no disability (DRS=0-3); 2) moderate to severe disability (DRS=4-14); 3) extreme severe disability to vegetative state (DRS=15-29), or 4) dead (DRS=30).

Secondary Outcome Assessments

Individuals with immune cell data were evaluated for various secondary outcomes after injury. Participants were assessed for post-traumatic depression (PTD) at 6 (38.94% follow-up rate) months post-TBI. The Patient Health Questionnaire (PHQ-9) is a questionnaire for screening, diagnosing, monitoring, and measuring the severity of depression using DSM-IV depression diagnostic criteria. The Total Percent Back-to-Normal question evaluates participants' perception of their recovery compared to before the injury on a scale of 0-100 percent. The Satisfaction with Life questionnaire asks participants to rate their satisfaction with various aspects of their life compared to before the injury on a scale of 0-100. Analysis of these outcomes at 6 months post-TBI helps in assessing perceived quality of life post-injury.

Statistical Analysis

Statistical analyses were performed using SAS™ Version 9.4 (Cary, North Carolina) and R Version 3.5.1 (Vienna, Austria). Descriptive statistics, including mean, median, and standard error of the mean (SE), were computed to describe continuous variables. Frequency measures and percentages were used to assess differences for categorical variables. Non-parametric Mann Whitney or Kruskal Wallis U tests were conducted for continuous variables, and chi-square tests were used for categorical variables. All tests were two-tailed with a significance level set at α=0.05.

Trajectory Analysis

Group-based trajectory (TRAJ) modeling analyzes patterns of change overtime in a chosen dependent variable to create temporal profiles. TRAJ analysis was utilized to characterize distinct patient subpopulations with similar fluctuations in NLR and PLR over the first three weeks post-injury. Trajectory groups were formulated using the SAS Macro PROC TRAJ (Jones et al., (2005) *The European Journal of Neuroscience,* 22(1), 72-78). This assumes that every subject in the same trajectory group exhibits the same dependent variable pattern. NLR and PLR data were ranked to meet the normal distribution requirement for TRAJ modeling. Bayesian Information Criterion (BIC) and posterior subject-specific group probabilities were used as model diagnostic metrics for goodness of fit. Three distinct TRAJ group profiles were identified for both NLR and PLR.

Risk Calculations

Cumulative incidence (CI) is calculated as the number of individuals experiencing a specified event (i.e. positive infection or PTD) divided by the total number of individuals in the population at risk of the event during a specific time frame. Risk calculations quantify measures of association between exposure and undesirable events among groups and compare event occurrence with that of another and were calculated. Risk difference (RD) focuses on the excess risk of an undesirable event in those with the exposure compared with those who do not, calculated by:

$$RD = \text{Cumulative Incidence}_{Exposed} - \text{Cumulative Incidence}_{Unexposed}$$

Percent relative effect (% RE) expresses the percent change in risk in the exposed group compared to the unexposed group, calculated by:

$$\% RE = (RR - 1) * 100, \text{ where } RR = \frac{\text{Cumulative Incidence}_{Exposed}}{\text{Cumulative Incidence}_{Unexposed}}.$$

In determining the exposure and non-exposure groups, the present disclosure first calculated the CI of each TRAJ group for each event and compared these values. The two TRAJs with the highest CIs were grouped together as the risk or exposure group, and the lowest CI TRAJ was determined to be the non-exposure group. The low NLR and PLR TRAJ groups were deemed the non-exposure group. The moderate and high NLR and PLR groups were deemed the exposure group.

Bivariate Analyses

Bivariate analyses compared demographic and clinical variables by low, moderate, and high NLR and PLR TRAJ groups. Outcome variables (i.e. GOS and DRS), acute infection status, PTD status, behavioral outcomes, and acute CSF and chronic serum inflammatory biomarker mean levels were also tested for bivariate associations to TRAJ group memberships. The present disclosure tested ratios of soluble receptors and ratios to their agonist (i.e. sTNFRI:sTNFRII, sgp130:sIL-6R, sIL-6R:IL-6, sIL-2Ra:IL-2, sTNFRI:TNFα, and sTNFRII:TNFα) to represent unfavorable conditions. Transmembrane receptors protease activity cleaves extracellular portions of the receptor to circulate soluble receptors, which are supposedly neuroprotective in binding inflammatory cytokines. Excess levels of soluble receptors, however, can be injurious, and the present disclosure sought to elucidate relevant receptor-cytokine ratios in inflammation after injury.

Multivariate Regression Analyses

To assess the contribution of multiple post-injury components to unfavorable global outcome at 6-months, as well as assess the discriminatory capacity of NLR versus PLR in distinguishing GOS score, multivariate regression modeling was leveraged. Trajectory group membership was designated as the predictor, and the primary outcome of interest was unfavorable GOS score. Trajectory group memberships (for both NLR and PLR) were binned as "risk" (moderate and high TRAJ) and "non-risk" (low TRAJ) groups according to the preliminary bivariate understanding of relationships to outcome. To control for potential effects of confounders, age, gender, and GCS score (best in 24 hours), and infection acquisition during acute care were included as covariate adjustments in the models. Serum biomarker levels associated with TRAJ memberships and global outcome were also investigated as contributors to outcome in the model buildup as presented in FIG. 122.

Results

Trajectory Groupings and Corresponding Immune Cell Counts Following TBI

Group-based TRAJ analyses of both NLR and PLR time-course data yielded 3 groups: low, moderate, and high. Each individual in the study was assigned both an NLR and PLR TRAJ membership. FIG. 111 describes the population based on their 2 memberships to help inform risk groups. The low NLR TRAJ group included 110 patients (33.3%), whereas the moderate NLR TRAJ group included 127 patients (40.1%) and the high NLR TRAJ group included 84 patients (26.7%). The average posterior probabilities for individuals assigned to the low, moderate, and high TRAJ group were 0.91, 0.88, and 0.92, respectively, which suggests an adequate model fit to the data. Mean NLR was compared across NLR TRAJ groups. All NLR TRAJ groups display a general decrease in NLR over time (FIG. 112A). Across low, moderate, and high NLR TRAJ groups, the mean lymphocyte value decreased and mean neutrophil value increased. The moderate NLR TRAJ had the greatest mean platelet value.

The low PLR TRAJ group included 111 patients (34.2%), whereas the moderate PLR TRAJ group included 110 patients (34.2%) and the high PLR TRAJ included 101 patients (31.6%). The average posterior probabilities for individuals assigned to low, moderate, and high TRAJ groups were 0.93, 0.87, and 0.93, respectively, suggesting an adequate model fit. After comparing mean PLR across PLR TRAJ groups, PLR TRAJ groups display a general increase in PLR over time (FIG. 112B). Across low, moderate, and high NLR TRAJ groups, the mean lymphocyte value decreased while the mean neutrophil and platelet values increased.

Bivariate relationships to demographic and clinical variables were assessed by NLR and PLR TRAJ group. The high NLR TRAJ groups exhibited significantly worse initial neurological injury measured by GCS score, longer hospital LOS, and required more days of mechanical ventilation (FIG. 113A). The high NLR TRAJ group had significantly more patients with unfavorable global outcome as measured by GOS at 6 months (FIG. 114A). Trending positive associations were found between rehabilitation LOS with increased NLR. The proportion of each NLR TRAJ with associated unfavorable clinical conditions are represented in FIGS. 115A-115C. NLR TRAJ also significantly differs by incidence of SAH, IVH, DAI, and intra-axial primary injury types. Trending association was found with incidence of contusion (FIG. 121A). Only significant (p<0.05) associations were included due to the larger sample size available for chronic markers. Interestingly, soluble receptor levels became higher in the high NLR TRAJ, compared to acute results.

When comparing variables by PLR TRAJ, the low PLR TRAJ group was significantly older, and the high PLR TRAJ was composed of significantly more men (FIG. 113B). Trending positive associations were found for hospital LOS with increased PLR. Neurological injury measures (GCS), 6-month disability (DRS), or 6-month global outcome (GOS) did not differ significantly by PLR TRAJ (FIG. 114B). PLR TRAJ membership significantly differs by incidence of SAH and has a trending association with EDH incidence (FIG. 120B).

Secondary Outcome Relationships to Trajectory Groups

Behaviorally, the high NLR TRAJ had a greater satisfaction with life as measured by SWLS score, a lower percent back-to-normal, and higher PHQ-9 total score (FIG. 117A). The high NLR TRAJ group had significantly more cases of 6-month PTD (FIG. 114A). The proportion of each NLR TRAJ with PTD represented in FIG. 115D.

Trending positive associations were found for 6-month PTD status with increased PLR (FIG. 116B). Behavioral measures, neurological injury measures (GCS), 6-month disability (DRS), and 6-month global outcome (GOS) did not significantly differ by PLR TRAJ (FIGS. 114B and 117B). The proportion of each PLR TRAJ with PTD is represented in FIG. 115E.

Comparative Risk and Incidence of Acute Infection by Trajectory Group Membership Regarding infection risk, percent relative effect calculations demonstrate that the moderate/high NLR TRAJ group has a 24% greater risk of infection compared to low NLR TRAJ. Risk difference calculations show that there are 11 more cases of infection per 100 people in the moderate/high NLR TRAJ compared to the low NLR TRAJ group. Incidence of infection does not differ significantly by PLR TRAJ group.

Comparative Risk and Incidence of 6-Month PTD by Trajectory Group Membership

With regard to 6-month PTD risk, percent relative effect calculations show that the moderate/high NLR TRAJ group has a 72% greater risk of PTD compared to the low NLR TRAJ. Risk difference calculations show that there are 18 more cases of PTD per 100 people in the moderate/high NLR TRAJ compared to the low NLR TRAJ group. The moderate/high PLR TRAJ also demonstrates a 72% greater risk of PTD compared to the low PLR TRAJ. In the moderate/high PLR TRAJ group, there are 17 more cases of PTD per 100 people compared to the low PLR TRAJ group. These results show that NLR and PLR TRAJ group membership are comparable in predicting risk of 6-month PTD.

Associations with Acute CSF Inflammatory Markers and Trajectory Group Membership In order to begin characterizing how neutrophils, lymphocytes, and platelets influence acute inflammatory profiles in CSF, bivariate comparisons were conducted for individual inflammatory biomarker relationships to NLR and PLR TRAJs. Significant associations were found between NLR and day 0 to 5 mean levels of sIL-6R, sgp130, sIL-2Ra, sIL-1RII, sTNFRI, MIP-3a, NCAM, IL-10, sICAM-1, and IL-5 ($p<0.05$) and trending associations with sTNFRII ($p=0.07$) (FIG. 118A). Levels for each marker tended to be lowest in the moderate NLR TRAJ and higher in either the low or high NLR TRAJ. Relative soluble receptor and cytokine levels by NLR TRAJ are represented in FIGS. 119A and 119B. Trending ($p<0.10$) markers were included due to the smaller sample size of the acute panel. Acutely, soluble receptor levels tended to be higher in the low NLR TRAJ.

For the PLR TRAJ groups, significant associations were found with day 0-5 mean levels of MIP-3a and sICAM-1. Trending relationships were found between PLR TRAJ group and both IL-5 and the sIL-6R-to-IL-6 ratio ($p<0.05$) (FIG. 118B). Lower levels of inflammatory markers were associated with high PLR TRAJ membership, except for the sIL-6R-to-IL-6 ratio which was higher in the high PLR TRAJ group. Relative levels by PLR TRAJ are represented in FIG. 119C.

Associations with Chronic Serum Inflammatory Markers and Trajectory Group Membership To begin characterizing how early neutrophil, lymphocyte, and platelet counts influence chronic inflammatory profiles in blood serum, bivariate comparisons were analyzed between individual mean month 0-6 marker levels and NLR (FIG. 120A) and PLR TRAJs. Significant associations were found between NLR TRAJ and MIP-1b, sTNFRI, sCD30, sIL-6R, sTNFRII, and the sgp130-to-sIL-6R ratio ($p<0.05$). Relative levels are represented in FIG. 121A.

When comparing chronic inflammatory markers by PLR TRAJ, significant associations were found for ITAC, MIP-1b, sgp130, and RANTES ($p<0.05$) (FIG. 120B). Relative levels are represented in FIG. 121B. Only significant ($p<0.05$) associations were included due to the larger sample size available for chronic markers. Marker levels were higher in the high PLR TRAJ, followed by moderate and low TRAJ groups.

Multivariate Models of Unfavorable GOS Score at 6-months Post-TBI

The multivariate models proposed in Table 8 provide a comparative assessment of the discriminatory capacity of NLR and PLR TRAJ in contributing to poor outcome. Risk groups (moderate and high TRAJ) were compared to non-risk (low TRAJ) for both NLR and PLR. A similar finding is shown in Model 1 and 2 for PLR and NLR, as those in the moderate/high TRAJs had significantly greater odds than the low TRAJ of unfavorable outcome, when controlling for covariates including: age, GCS score, gender and infection status. There is slight model improvement with the use of NLR over PLR based on the area under the curve (AUC) statistic capture. This relationship to unfavorable outcome is only significant ($p<0.05$) in the case of NLR TRAJ however. Of note, the model covariates were significantly associated with dichotomized GOS scores, with increased age, lesser GCS score, and female gender associated with worse global outcome. An additional modeling buildup step was taken from Model 2 to incorporate significant bivariate inflammatory findings to NLR TRAJ and global outcome (Model 3). Model 3 shows increased sTNFRI mean levels over the first six months (scaled by a factor of 100), in addition to higher NLR TRAJ membership, are significantly associated with worse GOS score. However, there is limited to no model improvement with the inflammatory component addition. The inclusion of chronic serum sTNFRI tempers the relationship between NLR TRAJ and unfavorable outcome however, implicating this inflammatory profile as a chronic embodiment of acute NLR related pathophysiology to poor TBI outcome.

Discussion

Traumatic brain injury is a noteworthy public health concern and burden without a direct cure. Neurotrauma researchers and clinicians have acknowledged the reality that this injury is heterogeneous in cause, nature, and severity and can happen to a diverse population of people. Thus, focus has shifted toward alleviating symptoms and mitigating long-term injury implications.

Injury-induced immunosuppression during the first week was characteristic of this cohort. The present disclosure observed a rapid decline in lymphocyte counts during the first day, consistently lower levels over the first week, and climbing counts into the second week. This immunosuppressed, lymphopenic state significantly increases one's vulnerability to infection acquisition. However, a lymphopenic state coupled with excessive neutrophil counts (i.e. high NLR) during the acute recovery phase is associated with even greater infection risk. The immune system is then faced with battling infection on top of responding to brain damage and further immune cell dysfunction. Susceptibility to infection after brain injury is immense; therefore, caregivers should focus on vulnerable subpopulations for infection. This contributes to the complexity of the immune response and hinders an individuals' recovery from the initial CNS injury.

NLR in the first three weeks post-injury is associated with factors that account for greater health resource utilization, which include greater infection incidence and risk, longer hospital length of stay, and more time on mechanical ventilation. When considering secondary behavioral outcomes, those in the high NLR TRAJ report being more satisfied with life after the injury compared to moderate and low TRAJ individuals yet describe feeling at a less-than-normal level of function and more severe depressive symptoms than moderate and low TRAJs. High NLR TRAJs also reported more depressive symptoms.

These reports may be attributed to awareness of injury severity. Acute NLR is also predictive of PTD at 6 months post-injury and unfavorable global outcome assessed by GOS, which are influenced by the various biochemical mechanisms at play.

Elevated cytokine expression, such as that of TNFα, from damaged tissue induces the secretion of neutrophil chemoattractants by the choroid plexus epithelium (Szmydynger-Chodobska et al., *J Cereb Blood Flow Metab.* 2009 September;29(9):1503-16). The additional expression of adhesion molecules, such as NCAM and sICAM-1 which were associated with higher NLR TRAJs, facilitates the migration of neutrophils across the BBB or through pial microvessels, contributing to the deleterious elevation of neutrophils (Szmydynger-Chodobska et al., (2016) *PLoS ONE,* 11(12)). The clinical conditions described are mediated by various inflammatory mechanisms that differ temporally and compartmentally. Using acute NLR, the present disclosure can predict long-term global outcomes mediated by inflammatory markers.

Acutely, sTNFRI and sTNFRII levels in CSF are lowest in the high NLR TRAJ, yet, there were elevated levels of these soluble TNFα receptors in the high NLR trajectory group chronically in serum. This group experienced greater incidences of infection and, in turn, were susceptible to programmed inflammatory cell-death termed "necroptosis." This is a protective defense mechanism which kills infected cells via membrane-bound TNFα receptor I (TNFRI) activation. Upon the death of these cells, damage associated molecular patterns (DAMPs) are released and recruit additional immune cells to the center of cell damage or infection. TNFα receptors are widely expressed on immune cells, undergo proteolytic cleavage upon activation, and are released into circulation. Binding of the soluble receptor form to TNFα buffers and limits excessive TNFα bioactivity. Chronic elevation of sTNFRI and sTNFRII may suggest dysregulation of these soluble receptors or ongoing attempts to mitigate further TNFα signaling and a role in poor global outcomes, whereas lower levels acutely may play a neuroprotective role or represent less TNFα signaling has occurred (less soluble receptor byproduct).

Additionally, IL-2 receptor (IL-2R) is expressed on lymphocytes, and the source of its soluble version in circulation is from proteolytic cleavage of this membrane-bound receptor. As a lymphoproliferative cytokine, IL-2 targets lymphocytes to boost cell counts and differentiation. Increased levels could be expected acutely as the immune response strives to rebound from the infection and injury immunosuppression (Skrombolas, D., & Frelinger, J. G. (2014) *Expert Review of Clinical Immunology,* 10(2), 207-217). However, the acute prominence of the soluble receptor may suggest dysregulation of lymphoproliferative mechanisms that contribute to lymphopenia. The acute lymphopenic state and sustained elevation neutrophil presence set the stage for increased infection and subsequent immune signaling complications. The observation of the increased soluble receptor levels of TNFα mean that there are competing mechanisms at play, which are responsible for managing proinflammatory mechanisms like programmed cell death. These findings are meaningful in that the acute immune state has chronic cell signaling implications.

Further, sIL-1RII levels were significantly higher in the high NLR TRAJ both acutely and chronically. Certain studies have demonstrated a pathogenic role for IL-1 in animals, where applying an IL-1 receptor antagonist reduced lesion volumes and improved neurological function (Jones et al., (2005) *The European Journal of Neuroscience,* 22(1), 72-78). This suggests that elevated sIL-1R levels may be implicated in reflecting IL-1 signaling imbalances, worsening the initial injury. Moreover, IL-10 levels were significantly higher in the low NLR TRAJ group. The acute elevation of the anti-inflammatory cytokine IL-10 is associated with monocyte circulation. Its administration prior to injury reduced TNFα expression and improved neurological recovery (Knoblach et al., (1999) *Journal of Neuroimmunology,* 95(1), 115-125). Acute elevation of IL-10, as observed in the favorable outcome TRAJ group, can be neuroprotective, but its failure to act at the periphery may be necessary for more global protective effects.

Platelets are also implicated in mediating the inflammatory response after TBI. PLR was introduced as a potential biomarker since platelets release many inflammatory mediators, such as cytokines and thromboxanes. Dukhinova et al. demonstrated that platelets play an important role in regulating neuroinflammation and neuronal plasticity after acute TBI through a mouse study where the mice lack gangliosides within the neuronal lipid raft responsible for CNS platelet activation. Platelet-derived serotonin and platelet activating factor demonstrated a key role in controlling hemorrhage, neuroinflammation, and induction of plasticity, serving as "danger alarm signals" of neurovascular damage in the CNS. Upon recognition of the neuronal lipid rafts, platelets degranulate and produce inflammatory mediators and other platelet-derived factors (Dukhinova et al., (2018). *Brain, Behavior, and Immunity,* 74, 7-27).

Moreover, the enhancement of platelet production through erythropoietin injections in an animal model demonstrated the neuroprotective effects of platelets in that this resulted in decreased brain edema and improved cognitive function while also reducing the infiltration and activation of inflammatory cells in the injured hemisphere. Furthermore, the erythropoietin treatment increased the expression of anti-inflammatory cytokine IL-10 and decreasing the expression of proinflammatory IL-1P and TNFα in injured brain tissue (Zhou et al., (2017) *Brain and Behavior,* 7(11), e00827). The findings show that age and sex differ significantly by PLR TRAJ, suggesting innate biological differences that contribute to group membership and thus subsequent inflammatory mechanisms as well. Those with high PLR are also at risk of PTD 6 months after TBI. PLR in the first three weeks after injury is informative of additional acute and chronic inflammatory mechanisms at play. Chronically, RANTES was found to be higher in the high PLR TRAJ group. Platelets have been reported to store inflammatory cytokines like RANTES/CCL5. Upon RANTES binding to its CCR5 receptor, the Akt signaling pathway may suppress apoptosis to influence pro-platelet production that may be protective (Machlus et al., (2016) *Blood,* 127(7), 921-926).

Acutely, both NLR and PLR are significantly associated with MIP-3a, sICAM-1, and IL-5. MIP-3a serves as a chemokine for Th17 cell recruitment and guides dendritic cell positioning in tissue. sICAM-1 expression can be induced by cytokines and promotes cell-cell adhesion. IL-5 promotes the activation of eosinophils, which promotes tissue damage in allergic reactions but also promotes B cell proliferation. Having these markers in common suggests a joint role of lymphocytes in mitigating injury through these immune cell interactions. Interestingly, MIP-1b was the only chronic biomarker that was associated with both NLR and PLR. MIP-1b is primarily released from CCL4 cells and targets T cells, dendritic cells, and monocytes and serves as a recruiter for natural killer cells. This suggests that lymphocytes play a common role in mediating immune cell recruitment through these messengers to the injury location but may contribute to injury with prolonged circulation.

Lymphocytes serve as a common denominator between the two ratios used for analysis. Yet, neutrophils and platelets demonstrate associations with different inflammatory markers and primary injury types, and neutrophils serve as a stronger predictor of long-term outcomes. This may be due to the mechanisms lengthening the neutrophil lifespan and facilitating their migration to the location of injury. Neutrophils have the capacity to break down the BBB through the release of metalloproteinases, proteases, TNFα, and ROS. The additional inflammatory cytokines released can facilitate this by inducing a hyperactive state allowing neutrophils to breach the BBB (Scholz et al., (2007). *Medicinal Research Reviews,* 27(3), 401-416). Once entering the CNS, neutrophils can induce neuronal cell death using the same soluble mediators (Nguyen et al., (2007) *Journal of Neurochemistry,* 102(3), 900-912). Neutrophil contributions to CNS damage depend on their localization and state of activation. The extended presence of these damaging mechanisms can intensify the effects of the initial injury, contributing more heavily to poor outcome in comparison to platelets.

This framework has the temporal resolution that is necessary to associate acute cell counts to recovery and long-term outcome. Therefore, the present disclosure suggests NLR and PLR as novel perspectives post-TBI, utilizing early clinical measures to predict a patient's course of recovery, susceptibilities, and long-term patient outcomes. The present disclosure has delineated the relation of early immune cell count relations to clinical conditions and inflammatory profiles contributing to long-term global and behavioral outcomes. Low follow-up rates for secondary outcome measures and acute inflammatory marker panels served as limitations to the present disclosure.

Various publications are cited herein, the contents of which are hereby incorporated by reference in their entireties.

Although the presently disclosed subject matter and its advantages have been described in detail, it should be understood that various changes, substitutions and alterations can be made herein without departing from the spirit and scope of the present disclosure. Moreover, the scope of the present application is not intended to be limited to the particular embodiments of the process, machine, manufacture, and composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods, or steps.

Various patents, patent applications, publications, product descriptions, protocols, and sequence accession numbers are cited throughout this application, the presently disclosed subject matter of which are incorporated herein by reference in their entireties for all purposes.

What is claimed is:

1. A method of treating a traumatic brain injury (TBI)-associated impairment, in a subject that has sustained a TBI, comprising administering to the subject interleukin-7 (IL-7).

2. The method of claim 1, wherein the method comprises an increase in a Glasgow Outcome Scale (GOS) score of the subject,
    wherein the GOS score is assessed at least three distinct time points post-TBI,
    wherein a first time point assessment occurs within 6 months post-TBI,
    wherein a second time point assessment occurs within 12 months post-TBI,
    wherein a third time point assessment occurs within 24 months post-TBI, and
    wherein the GOS score increases from the first time point assessment to the second or third time point assessment.

3. The method of claim 2, wherein the method comprises a reduction in a Disability Rating Scale (DRS) score of the subject,
    wherein the DRS score is assessed at least three distinct time points post-TBI,
    wherein a first time point assessment occurs within 6 months post-TBI,
    wherein a second time point assessment occurs within 12 months post-TBI,
    wherein a third time point assessment occurs within 24 months post-TBI, and
    wherein the DRS score reduces from the first time point assessment to the second or third time point assessment.

4. The method of claim 1, wherein the method comprises an increase in a serum IgM level in the subject,
    wherein the serum IgM level is assessed at least three distinct time points,
    wherein a first time point assessment occurs prior to treatment,
    wherein a second time point assessment occurs within 1 month post-TBI,
    wherein a third time point assessment occurs within 24 months post-TBI, and
    wherein the serum IgM level increases from the first time point assessment to the second or third time point assessment.

5. The method of claim 1, wherein the method comprises an increase in a serum IgM:IgG ratio in the subject,
    wherein the serum IgM:IgG ratio is assessed at least three distinct time points,
    wherein a first time point assessment occurs prior to treatment,
    wherein a second time point assessment occurs within 1 month post-TBI,
    wherein a third time point assessment occurs within 24 months post-TBI, and
    wherein the serum IgM:IgG ratio increases from the first time point assessment to the second or third time point assessment.

6. The method of claim 1, wherein the TBI-associated impairment is selected from the group consisting of cognitive deficits, psychological deficits, somatic symptoms, emotional symptoms, behavioral dysfunctions, physical dysfunctions, and neuroendocrine dysfunction.

7. The method of claim 1, wherein the IL-7 is administered to the subject at the acute stage, at the post-acute stage and/or at the chronic stage of the TBI.

8. The method of claim 1, wherein the IL-7 is a recombinant IL-7.

9. The method of claim 1, wherein the method further comprises administering to the subject etanercept.

10. A method for treating a TBI-associated impairment in a subject that has sustained a TBI, comprising:
   (a) determining a level of soluble tumor necrosis factor receptor (sTNFR) and a level of IL-7 in at least two samples obtained from the subject;
   (b) comparing the level of sTNFR to a reference level of sTNFR and the level of IL-7 to a reference level of IL-7,
   wherein the reference levels of sTNFR and IL-7 are predetermined levels
   wherein the predetermined levels of sTNFR and IL-7 are from (i) a healthy individual or a population of healthy individuals free of the TBI-associated impairment or (ii) the same subject collected at an earlier time point,
   wherein the reference level of IL-7 is about 25 pg/ml, and wherein the reference level of sTNFR is about 1500 pg/ml;
   (c) assigning trajectory group memberships to the subject by assessing the IL-7 and sTNFRI levels of the subject in relation to group-based trajectory analyses derived from a population with TBI,
   wherein if the level of IL-7 is lower than the reference level of the IL-7 the subject is assigned a low IL-7 trajectory group membership,
   wherein if the level of IL-7 is higher than the reference level of the IL-7 the subject is assigned a high IL-7 trajectory group membership,
   wherein if the level of sTNFRI is lower than the reference level of sTNFRI the subject is assigned a low sTNFRI trajectory group membership,
   wherein if the level of sTNFRI is higher than the reference level of sTNFRI the subject is assigned a high sTNFRI trajectory group membership; and
   (c-i) treating the subject with IL-7 if the subject is assigned a low IL-7 trajectory group membership and a low sTNFR trajectory group membership,
   (c-ii) treating the subject with IL-7 and etanercept if the subject is assigned a low IL-7 trajectory group membership and a high sTNFR trajectory group membership; or
   (c-iii) treating the subject with etanercept if the subject is assigned a high IL-7 trajectory group membership and a high sTNFR trajectory group membership.

11. The method of claim 10, wherein the dose of IL-7 is higher in (c-ii) than in (c-i).

* * * * *